(12) United States Patent
Bloch et al.

(10) Patent No.: US 9,388,412 B2
(45) Date of Patent: Jul. 12, 2016

(54) INHIBITORS OF MICRORNAS THAT REGULATE PRODUCTION OF ATRIAL NATRIURETIC PEPTIDE (ANP) AS THERAPEUTICS AND USES THEREOF

(71) Applicant: THE GENERAL HOSPITAL CORPORATION, Boston, MA (US)

(72) Inventors: Kenneth D. Bloch, Chestnut Hill, MA (US); Pankaj Arora, Chestnut Hill, MA (US); Christopher Newton-Cheh, Lexington, MA (US); Thomas J. Wang, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/408,189

(22) PCT Filed: Jun. 14, 2013

(86) PCT No.: PCT/US2013/045925
§ 371 (c)(1),
(2) Date: Dec. 15, 2014

(87) PCT Pub. No.: WO2013/188787
PCT Pub. Date: Dec. 19, 2013

(65) Prior Publication Data
US 2015/0133521 A1    May 14, 2015

Related U.S. Application Data

(60) Provisional application No. 61/660,240, filed on Jun. 15, 2012.

(51) Int. Cl.
| | |
|---|---|
| *A61K 48/00* | (2006.01) |
| *C07H 21/02* | (2006.01) |
| *C07H 21/04* | (2006.01) |
| *C12N 15/113* | (2010.01) |
| *C12N 15/11* | (2006.01) |
| *C12Q 1/68* | (2006.01) |
| *A61K 31/7088* | (2006.01) |
| *A61K 45/06* | (2006.01) |

(52) U.S. Cl.
CPC .......... *C12N 15/113* (2013.01); *A61K 31/7088* (2013.01); *A61K 45/06* (2013.01); *C12N 15/111* (2013.01); *C12Q 1/6883* (2013.01); *A61K 48/00* (2013.01); *C12N 2310/113* (2013.01); *C12N 2320/31* (2013.01); *C12N 2320/34* (2013.01); *C12Q 2600/106* (2013.01); *C12Q 2600/156* (2013.01); *C12Q 2600/178* (2013.01)

(58) Field of Classification Search
CPC .............................. A61K 48/00; C12N 15/113
See application file for complete search history.

(56) References Cited

U.S. PATENT DOCUMENTS

2010/0021914 A1    1/2010   Moller

FOREIGN PATENT DOCUMENTS

WO    WO 2011/026909 A1 *  3/2011    ............. A61K 48/00

OTHER PUBLICATIONS

Cannone et al., "A Genetic Variant of the Atrial Natriuretic Peptide Gene is Associated with Cardiometabilic Protection in the General Community", J. Am. Coll. Cardiol., 58(6), pp. 629-636, 2011.
Database: miRBASE, Ac.No. MI0001448 (miR-425, has-miR-425) and Ac.No. MIMAT0003393 (hsa-miR-425-5p), 2007.
Fedorowski et al., "Orthostatic hypotension and novel blood pressure-associated gene variants: Genetics of Postural Hemodynamics (GPH) Consortium", Eur. Heart J., 33(18), pp. 2331-2341, 2012.
Sethuparthy et al., "MicroRNA target site polymorphisms and human disease", Trends in Genetics, 24(10), pp. 489-497, 2008.

* cited by examiner

*Primary Examiner* — Amy Bowman
(74) *Attorney, Agent, or Firm* — Nixon Peabody LLP

(57) ABSTRACT

The present invention relates to methods, kits and compositions to treat hypertension and other cardiovascular diseases in a subject, in particular, a method of treating or preventing a cardiovascular disease in a subject comprising administering to a subject at least one anti-miR agent to miRNA-425. In some embodiments, an anti-miR agent is a small molecule or an oligonucleotide complementary to at least part of the miR-425 of SEQ ID NO: 1, or an anti-miR complementary to at least part of the miRNA seed sequence AUGACA (SEQ ID NO: 2). Another aspect of the present invention relates to methods, kits and compositions to treat low blood pressure in a subject comprising administering a composition comprising a miR-425 agent to decrease ANP levels in the subject. Other aspects of the present invention relates to assays, methods and systems to identify a subject at risk of hypertension, or identifying a subject suitable to administration of an anti-miR-425 agent for treatment of hypertension, the assay comprising assessing if a subject is homozygous or heterozygous for the major (A) allele of rs5068 SNP, and/or assaying for levels of miR-425 and/or assaying for levels of NT-proANP and/or levels of ANP in the plasma of a subject.

13 Claims, 16 Drawing Sheets

US 9,388,412 B2

INHIBITORS OF MICRORNAS THAT REGULATE PRODUCTION OF ATRIAL NATRIURETIC PEPTIDE (ANP) AS THERAPEUTICS AND USES THEREOF

CROSS REFERENCE TO RELATED APPLICATIONS

This Application is a 35 U.S.C. 371 National Phase Entry Application of International Application No. PCT/US2013/045925 filed Jun. 14, 2013, which designates the U.S., and which claims benefit under 35 U.S.C. §119(e) of U.S. Provisional Application No. 61/660,240 filed on Jun. 15, 2012, the contents of each of which are incorporated herein by reference in their entireties.

GOVERNMENT SUPPORT

The invention was made with Government Support under National Institute of Health Grant Nos. R01-HL098283 and 1 UL1-RR025758-01. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jun. 13, 2013, is named 030258-074601-PCT_SL.txt and is 18,435 bytes in size.

FIELD OF THE INVENTION

The present invention relates generally to methods to treat cardiovascular diseases by using an inhibitor of the miR-425 and in alternative embodiments to treat subjects with low blood pressure with an miR-425 agent. Other aspects relates to compositions, methods and kits comprising inhibitors of miR-425 or miR-425 agents, and methods, assays and arrays to assess a subject amenable to treatment with an inhibitor of miR-425 use in a method to inhibit metastasis of cancer cells in a subject.

BACKGROUND OF THE INVENTION

The average U.S. adult consumes nearly 10 g of salt per day, far in excess of the limit recommended by the Departments of Agriculture and Health and Human Services.[1,2] High salt intake has been linked to hypertension and cardiovascular disease.[3,4] Randomized clinical trials demonstrate that reducing salt intake substantially lowers this risk.[5] It has been estimated that a 3 g reduction of daily salt intake would save an estimated 44,000 to 92,000 lives annually in the U.S.[6]

The natriuretic peptide system plays a central role in the response to salt intake. Synthesized by the heart, atrial natriuretic peptide (ANP) and B-type natriuretic peptide (BNP) promote natriuresis, diuresis, and vasodilation. In animals, deficient ANP signaling results in salt-sensitive hypertension, adverse cardiac remodeling, and premature mortality.[7,8] Evidence from population genetic studies suggests that variation in plasma natriuretic peptides may alter susceptibility to cardiovascular disease in humans as well. Common genetic polymorphisms in the chromosome 1 region containing NPPA and NPPB, which encode the ANP and BNP propeptides, respectively, are associated with circulating natriuretic peptide levels.[9] Large-scale epidemiologic studies have established that the same variants are associated with blood pressure with, for example, a 15% lower risk of hypertension in carriers of the rs5068 minor allele.[9,10]

Genetic studies have appeal because they avoid the reverse causation that can be observed with non-genetic associations. However, as with all complex traits, the majority of blood pressure-related variants are non-coding, and there are typically many partially correlated variants due to linkage disequilibrium. These factors increase the difficulty of identifying a causal variant and the mechanism by which it acts. Indeed, although genome-wide association studies (GWASs) have yielded a long list of candidate single nucleotide polymorphisms (SNPs) for blood pressure, the only genetic variants, for which a mechanism has been established, are rare mutations in families with Mendelian forms of hypertension or hypotension.[11]

More than 30% of adults in the US have hypertension, and hypertension is an important risk factor for myocardial infarction, stroke, and heart failure (Go, et al., Circulation 127:143-152.5). Seventy-five percent of adults with hypertension are taking antihypertensive medications, but target blood pressures are attained in only 53%. It is estimated that, in 2010, ~3% of Americans over the age of 18 had heart failure, and about 50% of patients diagnosed with heart failure die within 5 years (Roger et al., Circulation 125:e2-e2206). The 2010 health care costs associated with treating hypertension and heart failure (including those related to lost productivity) were estimated to be 93.5 and 34.4 billion dollars, respectively (Heidenreich, et al., Circulation 123:933-944.). These data strongly indicate that it is necessary to elucidate the mechanisms responsible for hypertension and demonstrate the need to develop novel treatment strategies for the effective treatment of hypertension and heart failure (HF).

SUMMARY OF THE INVENTION

The present invention relates to methods to treat or prevent cardiovascular diseases and disorders in a subject, in particular the present invention relates to a method of treating and/or preventing cardiovascular diseases and disorders, for example, high blood pressure, hypertension, hypertrophy, heart failure (HF), metabolic syndrome, stroke or renal failure, or any combination thereof, comprising administering an anti-miR agent, e.g., an anti-miR to a miRNA-425 (SEQ ID NO: 1) to a subject. In some embodiments, the present invention relates to a method of increasing atrial natriuric peptide (ANP) in a subject by administering to the subject an anti-miR agent to a miRNA-425. In some embodiments, the method to increase ANP in a subject comprises administering an agent which inhibits the expression of miRNA-425 in the subject. In some embodiments, the subject to whom is administered an anti-miR agent, e.g., an anti-miR to a miRNA-425 has, or has been identified to be homozygous for the major "A" allele (e.g., is AA) of the single nucleotide polymorphism (SNP) rs5068 (A/G). In some embodiments, the subject to whom is administered an anti-miR agent, e.g., an anti-miR to a miRNA-425 has, or has been identified to be heterozygous for the major "A" allele (e.g., is AG) of the single nucleotide polymorphism (SNP) rs5068 (A/G).

The SNP rs5068 (A/G) is located in the 3' untranslated region (UTR) of the NPPA gene. It has been reported that small non-coding RNAs (microRNAs) play a role in post-transcriptional regulation of gene expression by binding to 3' UTRs.[12,13] The inventors demonstrated herein that a minor (G) allele of rs5068 affects plasma natriuretic peptide (ANP) levels, and that absence of this minor variant (G), e.g., subjects homozygous for the major A allele (e.g., AA subjects) have lower levels of ANP which is regulated by microRNA binding. Accordingly, the inventors have discovered that minor allele (G) carriers have resistance to the inhibitory effect of mRNA binding, in particular, the binding of miR-425. Accordingly, subjects that have the G allele of rs5068 are not affected by the miR-425-mediated inhibition of expression from the NPPA gene, and thus have a decrease in the production of the ANP peptide. For example, the inventors demonstrate herein that miR-425 binds to, and represses, the production of ANP in AA homozygous rs5068 subjects, and can repress half the expression of ANP levels in AG (heterozygous) rs5068 subjects. Herein, the inventors demonstrated using a series of genotype-directed studies and selecting individuals on the basis of rs5068 genotype, the effect of genotype (e.g., AA or AG) of rs5068 on the subjects' physiologic response to salt. In addition, the inventors demonstrated in vitro the association of rs5068 with ANP levels. The inventors demonstrate that binding of the miR-425 microRNA to the 3'UTR mRNA sequence of ANP requires complementarity of a seed sequence starting from positions 2-7 of the 5'end of the miRNA (SEQ ID NO: 2).

Accordingly, one aspect of the present invention relates to a method of treating or preventing a cardiovascular disease in a subject which comprises administering to the subject a pharmaceutical composition comprising an effective amount of at least one anti-miR agent to miRNA-425 (SEQ ID NO: 2), e.g., an anti-miR agent such as the anti-miR of SEQ ID NO: 1, wherein the anti-miR agent binds to and inhibits miRNA-425 in the subject. In some embodiments, an anti-miR complementary to at least part of the miR-425 sequence of SEQ ID NO: 1, or at least part of the miR-425 miRNA seed sequence SEQ ID NO: 2 (AUGACA). In some embodiments, an anti-miR-425 agent as disclosed herein is useful to treat one or more diseases selected from the group consisting of congestive heart failure, hypertension, systemic hypertension (thereby preventing the development of myocardial infarction, congestive heart failure (CHF), renal failure, and stroke), pulmonary hypertension, acute kidney injury, modulating inflammatory responses (either positively or negatively), lipolysis, obesity, diabetes mellitus, reducing intraocular pressure (preventing blindness in glaucoma, reducing ischemia-reperfusion (I/R) injury, (including spinal cord I/R injury and cardiac FR injury), preventing atrial fibrillation, liver failure, liver fibrosis, ascites, anasarca, cirrhosis, cancer, promoting angiogenesis, or weight loss.

In some embodiments, the method comprises administering a pharmaceutical composition comprising an anti-miR-425 agent, e.g., a small molecule which inhibits the function of miR-425 or an oligonucleotide anti-miR of miR-425, where an oligonucleotide anti-miR-425 agent is oligonucleotide complementary to at least part of the miR-425 of SEQ ID NO: 1, or an anti-miR complementary to at least part of the miR-425 miRNA seed sequence AUGACA (SEQ ID NO: 2). In some embodiments, an anti-miR-425 agent is an anti-miR (or anti-miR) of miR-425, such as an oligonucleotide of TTACTGTGCTAGTGAGGGCAACT (SEQ ID NO: 3) or a homologue or variant thereof. In some embodiments, where an anti-miR-425 is an oligonucleotide, such as an anti-miR which is complementary, at least in part, of the miR-425 sequence of SEQ ID NO: 1, or at least part of the miR-425 miRNA seed sequence SEQ ID NO: 2, the anti-miR-425 agent is encoded by a nucleic acid construct.

In some embodiments, an anti-miR-425 agent as disclosed herein can be, for example a small molecule, nucleic acid, nucleic acid analogue, aptamer, ribozyme, peptide, protein, antibody, or variants and fragments thereof. In some embodiments, a nucleic acid agent can be DNA, RNA, nucleic acid analogue, peptide nucleic acid (PNA), pseudo-complementary PNA (pcPNA), locked nucleic acid (LNA) or analogue thereof, and in embodiments where the nucleic acid agent is RNA, the RNA can be a small inhibitory RNA (RNAi), siRNA, microRNA, shRNA, miRNA and analogues and homologues and variants thereof effective in gene silencing. In some embodiments, the anti-miR-425 agent is a LNA oligonucleotide which is complementary to, or complementary to at least part of the miR-425 sequence of SEQ ID NO: 1, or at least part of the miR-425 miRNA seed sequence SEQ ID NO: 2.

In some embodiments, an anti-miR-425 agent is a Tiny LNA oligonucleotide which is complementary to the entire miR-425 miRNA seed sequence SEQ ID NO: 2, which stops miRNA interference at the seed sequence by blocking the binding of the miRNA-425-RISC complex to the mRNA NPPA transcript, thus allowing translation of the NPPA gene to occur. Tiny LNAs have been demonstrated to be effective to inhibit miRNA mediated gene suppression in vivo (Obad et al, Nature Genetics, 2011; 43; 371-378, which is incorporated herein in its entirety by reference).

In some embodiments, an anti-miR-425 agent is an antagomir, fully 2'-O-methoxyethyl (2'-MOE), 2'-F/MOE mixmer, LNA/DNA mixmer, a tiny LNA or a combination thereof, which are complementary to, or complementary in part, to the miRNA seed sequence SEQ ID NO: 2. As used herein, the term "tiny LNA" refers to a short, e.g., 6, 7, 8, 9, 10, 11 or 12-mer oligonucleotide that is comprised entirely of locked nucleic acid monomers. Tiny LNAs are described in Obad et al., (Nature Genetics, 2010, 43(4): 371-380, content of which is incorporated herein by reference. In some embodiments, the tiny LNA comprises phosphorothioate inter-sugar linkages at all positions. In some embodiments, the tiny LNA is 8 nucleotides in length and comprises phosphorothioate inter-sugar linkages at all positions. In some embodiments, the tiny LNA comprises a nucleotide sequence complementary to the seed sequence of miRNA-425 (SEQ ID NO: 2).

In some embodiments, administration an anti-miR-425 agent, e.g., an anti-miR complementary to, or complementary in part, to miRNA seed sequence SEQ ID NO: 2 is prophylactic administration and in alternative embodiments, administration is therapeutic administration. In some embodiments, the methods and compositions as disclosed herein can be administered to a subject, where the subject is, for example, a mammal such as a human.

Another aspect of the present invention relates to a method of inhibiting or preventing hypertension or a symptom thereof in a subject in need thereof, the method comprising administering to the subject an effective amount of an inhibitor of miRNA-425 activity. Another aspect of the present invention relates to a method of inhibiting or preventing hypertension or a symptom thereof in a subject in need thereof, the method comprising administering to a subject determined to homozygous (AA) or heterozygous (AG) for A allele for the single nucleotide polymorphism (SNP) rs5068 (A/G) an effective amount of an inhibitor of miRNA-425 activity. In some embodiments, the anti-miR-425 inhibitor is an oligonucleotide, or an anti-miR, antagomir, ribozyme, or siRNA. In some embodiments, the anti-miR-425 inhibitor comprises a nucleotide sequence that is complementary to at least a portion of the pre-miRNA-425 nucleic acid sequence of: GAAAGCGCUUUGGAAUGACAC-GAUCACUCCCGUUGAGUGGGCAC-CCGAGAAGCCAUCGGG AAUGUCGUGUCCGC-CCAGUGCUCUUUC (SEQ ID No: 13). In some embodiments, the anti-miR-425 inhibitor comprises a nucleotide sequence that is complementary to at least a portion nucleic acid sequence AAUGACACGAUCACUCCCG- UUGA (SEQ ID NO: 1), or a nucleotide sequence that is complementary to nucleic acid sequence AUGACA (SEQ ID NO: 2).

In some embodiments, an oligonucleotide anti-miR-425 agent comprises a modification selected from the group consisting of nucleobase modifications, sugar modifications, inter-sugar linkage modifications, backbone modifications, and any combinations thereof. In some embodiments, an oligonucleotide anti-miR-425 agent comprises a ligand. In some embodiments, an oligonucleotide anti-miR-425 agent is about 11 to about 30 nucleotides in length. In some embodiments, an oligonucleotide anti-miR-425 agent comprises is single-stranded. In some embodiments, an oligonucleotide anti-miR-425 agent is formulated in a lipid delivery vehicle, e.g., liposomes, lipid particles, other compositions used for oligonucleotide delivery. In some embodiments, an anti-miR-425 agent is encoded by an expression vector. In some embodiments, an anti-miR-425 agent comprises the nucleotide sequence TTACTGTGCTAGTGAGGGCAACT (SEQ ID NO: 3). In some embodiments, an anti-miR-425 agent decrease the amount of miRNA-425 in a cell relative to a control or reference level, e.g., a reference level of miRNA-425 which is the mean circulating plasma miR-425 level from a group of subjects AA for rs5068 (e.g., about 0.8 pg/L after a high-salt diet or 2.8 pg/L after a week of low-salt diet).

In some embodiments, an anti-miR-425 agent increases expression of atrial natriuretic peptide (ANP) or a nucleic acid encoding ANP in a cell relative to a control or reference level, for example decreases a nucleic acid encoding ANP is mRNA. In some embodiments, a subject is homozygous AA or heterozygous AG for a single nucleotide polymorphism (SNP) of ANP gene, wherein the SNP is rs5068 (A/G).

In some embodiments, the method further comprises selecting a subject for treatment for hypertension before onset of said administering, comprising assaying a biological sample from the subject for single nucleotide polymorphism of SNP rs5068 (A/G) and selecting the subject who is homozygous (AA) or heterozygous (AG) for the major allele (A) for the SNP rs5068 (A/G). In some embodiments, the method further comprises co-administering an anti-miR-425 agent with an additional therapeutic agent, wherein the therapeutic agent is for treatment of hypertension, for example, co-administering an anti-miR-425 agent with a therapeutic agent such as an ANP (which activates cGMP synthesis) and an inhibitor of cGMP metabolism. In some embodiments, an inhibitor of cGMP metabolism is a phosphodiesterase inhibitor, such as for example, but not limited to, PDE1, PDE2, PDE3, PDE4, PDE5 etc., which inhibit cGMP metabolism and/or production. In some embodiments, a therapeutic agent administered in combination with an anti-miR-425 agent is selected from the group consisting of statins, diuretics, adrenergic receptor antagonists, PDE5 inhibitors, calcium channel blockers, renin inhibitors, ACE inhibitors, angiotensin II receptor antagonists, aldosterone antagonists, vasodilators; alpha-2-agonists, and any combination thereof. Other therapeutic agents which can be co-administered include, but are not limited to, bumetanide; ethacrynic acid; furosemide; torsemide; epitizide; hydrochlorothiazide; chlorothiazide; bendroflumethiazide; indapamide; chlorthalidone; metolazone; amiloride; triamterene; spironolactone; atenolol; metoprolol; nadolol; oxprenolol; pindolol; propranolol; timolol; doxazosin; phentolamine; indoramin; phenoxybenzamine; prazosin; terazosin; tolazoline; bucindolol; carvedilol; labetalol; amlodipine; felodipine; isradipine; lercanidipine; nicardipine; nifedipine; nimodipine; nitrendipine; diltiazem; verapamil; Aliskiren; captopril; enalapril; fosinopril; lisinopril; perindopril; quinapril; ramipril; trandolapril; benazepril; candesartan; eprosartan; irbesartan; losartan; olmesartan; telmisartan; valsartan; eplerenone; spironolactone; sodium nitroprusside; hydralazine; hydralazine derivatives; Clonidine; Guanabenz; Methyldopa; Moxonidine; Guanethidine; Reserpine; atorvastatin; fluvastatin; lovastatin; pitavastatin; pravastatin; rosuvastatin; simvastatin; nitrates, and any combinations thereof.

In some embodiments, an anti-miR-425 agent can be administered with other anti-miRs which target miRNA's which decrease the expression from the NPPA gene and/or the NPRA gene (which expresses the ANP receptor) and/or NPRB gene (which express the BNP receptor). In alternative embodiments, an anti-miR-425 agent can be administered with a miRNA agent, which for example, targets and reduces the gene expression of a gene which, in turn, results in an increase in the expression from the NPPA gene and/or the NPRA gene (which expresses the ANP receptor) and/or NPRB gene (which expresses the BNP receptor). In some embodiments, an anti-miR-425 agent as disclosed herein can be administered with mRNA or other nucleic acid sequences, e.g., modified mRNA, which increase the expression from the NPPA gene and/or the NPRA gene (which expresses the ANP receptor) and/or NPRB gene (which expresses the BNP receptor) and/or increase expression of proteins which regulate blood pressure.

Another aspect of the present invention relate to an isolated oligonucleotide which can be used as an anti-miR-425 agent comprising a nucleotide sequence complementary to at least a portion of the pre-miRNA-425 nucleic acid sequence of: GAAAGCGCUUUGGAAUGACAC-GAUCACUCCCGUUGAGUGGGCAC-CCGAGAAGCCAUCGGG AAUGUCGUGUCCGC-CCAGUGCUCUUUC (SEQ ID NO: 13). In some embodiments, the isolated oligonucleotide comprises a nucleotide sequence that is complementary to at least a portion nucleic acid sequence AAUGACACGAUCACUCCCG-UUGA (SEQ ID NO: 1) or alternatively, can comprise a nucleotide sequence that is complementary to nucleic acid sequence AUGACA (SEQ ID NO: 2). In some embodiments, an anti-miR-425 agent as disclosed herein is from about 10 to about 35 nucleotides in length. In some embodiments, an anti-miR-425 agent as disclosed herein comprises a modification selected from the group consisting of nucleobase modifications, sugar modifications, inter-sugar linkage modifications, backbone modifications, and any combinations thereof. In some embodiments, an anti-miR-425 agent comprises a ligand. In some embodiments, an anti-miR-425 agent as disclosed herein inhibits the activity of miRNA-425 in a cell, e.g., reduces the amount of, or inhibits the activity of miRNA-425 in a cell, or decreases the miR-425-mediated inhibition of expression from the NPPA gene and thus decreases miR-425-mediated inhibition of ANP production. Accordingly, in some embodiments, an anti-miR-425 agent as disclosed herein is increases the production of atrial natriuretic peptide (ANP) or a nucleic acid encoding ANP in a cell, e.g., increases gene expression from the NPPA gene from a subject which comprises the A allele of SNP rs5068 (A/G). In some embodiments, an anti-miR-425 agent comprises the nucleic acid sequence TTACTGTGCTAGTGAGGGCAACT (SEQ ID NO: 3) or a variant thereof.

Another aspect of the present invention relates to a method of treating a subject having a high blood pressure, hypertension, obesity or a cardiovascular disease, comprising administering a pharmaceutically effective amount of an anti-miR-425 agent to a subject having high blood pressure, hypertension or a cardiovascular disease and determined to show the plasma expression of miR-425 which is at least the same as or increased relative to a control level, and wherein the subject is not administered an anti-miR-425 agent if the plasma expression of miR-425 from the subject was determined to be less than the control level.

Another aspect of the present invention relates to a method of determining if a subject is responsive to an anti-miR-425 agent comprising assaying a blood sample for at least one copy of the adenine (A) allele at rs5068 SNP (homozygotes or heterozygotes), wherein the subject is responsive to an anti-miR-425 agent where at least one copy of the adenine (A) allele at rs5068 SNP is present. In some embodiments, the method further comprises administering an anti-miR-425 agent to the subject if at least one copy of the adenine (A) at rs5068 SNP are present (e.g., the subject is homozygous AA or heterozygous AG). Another aspect of the present invention relates to an assay to determine if a subject is at risk of a cardiovascular disease or disorder, the assay comprising: contacting a biological sample obtained from the subject with at least one probe to detect the levels of miR-425, wherein the level of miR-425 above a predefined reference miR-425 level identifies a subject who would be predicted to be at risk of a cardiovascular disease or disorder. In some embodiments, the predefined reference level of miR-425 is the circulating plasma level of a subject who is homozygous or heterozygous at the G allele for rs5068 loci, e.g., about above 0.8 pg/L. In some embodiments, a predefined reference level of miR-425 in the plasma of a subject who is homozygous for the A allele for rs5068 is about 2-4 pg/L after a high-salt diet or 11-2 pg/L after a week of low-salt diet (as demonstrated in FIG. 12), In some embodiments, a predefined reference level of miRNA-425 in the plasma of a subject who is heterozygous for the A allele (e.g., AG) for the rs5068 loci is between 0.5-4 pg/L for a subject on a high or low salt diet, as demonstrated herein in FIG. 12. In some embodiments, the probe comprises a detectable label or means of generating a detectable signal. In some embodiments, the subject has a cardiovascular disease, for example selected from the group consisting of: heart failure, myocardial infarction, or stable coronary artery disease.

Another aspect of the present invention relates to an assay comprising: (a) subjecting a test sample from a human subject diagnosed of having a cardiovascular disease or disorder to determine if treatment with an anti-miR-425 agent would be effective, to at least one genotyping assay that determines the genotype of the rs5068 loci, (b) determining the genotype of the rs5068 loci, (c) selecting a treatment regimen with an anti-miR-425 agent when at least one adenine "A" allele at position 647 of SEQ ID NO: 12 is present, or when the subject is homozygous (AA) or heterozygous (AG) at the rs5068 loci, and not selecting a treatment regimen where there the adenine "A" allele occurs at position 647 of SEQ ID NO: 12 is absent, or when the subject is homozygous for the minor G allele at the rs5068 loci (e.g., GG subjects).

Another aspect of the present invention relates to a pharmaceutical composition comprising an isolated anti-miR-425 oligonucleotide agent as disclosed herein and a pharmaceutically acceptable carrier.

Conversely, another aspect of the present invention relates to a method of decreasing atrial natriuretic peptide (ANP) in a subject in need thereof comprising administering to the subject a composition comprising miRNA-425 (SEQ ID NO: 1) or a homologue thereof. In some embodiments, a homologue or variant of miR-425 encompassed for use binds to the miR-425 miRNA target sequence SEQ ID NO: 8 or SEQ ID NO: 9 in the 3' UTR of the NPPA gene. In such embodiments, a method of decreasing ANP in a subject is useful in treating subjects in need thereof, e.g., for subjects with low blood pressure and associated disorders. In some embodiments, a miR-425 (e.g., SEQ ID NO: 1) or variant thereof which binds to the miRNA target sequence SEQ ID NO:8 is administered to a subject whom has been identified as having at least one A allele at the rs5068 loci, e.g., a AA or AG subject. In alternative embodiments, a modified miR-425 which binds to the "G" allele miRNA target sequence of SEQ ID NO: 9 in the 3'UTR of the NPPA gene is administered to a subject who has been identified to have at least one G allele at the rs5068 loci (e.g., GG or AG subjects). In some embodiments, a subject, e.g., a AG heterozygous subject is administered a miR-425 of SEQ ID NO: 1 and/or a variant miRNA which binds to SEQ ID NO: 8, in combination with a modified miR-425 which binds to the miR target sequence SEQ ID NO: 9. In some embodiments, administration of a miR-425, or mimetic thereof is administered to a subject to treat any one or a combination of inhibiting angiogenesis, low blood pressure, increased endothelial permeability, or orthostatic hypotension.

In some embodiments, where a miR-425 is administered to a subject, (e.g., to a subject with low blood pressure, or where it is desirable to increase blood pressure in a subject) an miR-425 miRNA can be a pri-miRNA, pre-miRNA, mature miRNA or a fragment or variant thereof effective in gene silencing the 3'UTR of the ANP mRNA. In some embodiments, the miR-425 comprises SEQ ID NO: 1 or a fragment or variant or homologue thereof effective in gene silencing the 3' UTR of the NPPA gene, and/or binds to the miR-425 target sequence SEQ ID NO: 8. In alternative embodiments, miR-425 homologues can be used, or a fragment thereof effective in gene silencing the 3'UTR of NPPA mRNA, in particular, effective at binding to the "A" major allele miRNA target sequence of 5'ATGACAC-3' (SEQ ID NO: 8), where a subject is homozygous AA or heterozygous AG for the major allele of rs5068, or where the miR-425 homologue is effective at binding the "G" minor allele miRNA target sequence of 5'GTGACAC-3' (SEQ ID NO: 9), where a subject is heterozygous (AG) or homozygous (GG) for the minor allele of rs5068. In other embodiments, the miR-425 is an RNA interference-inducing (RNAi) molecule including, but not limited to, a siRNA, dsRNA, stRNA, shRNA and gene silencing variants thereof. In alternative embodiments the miR-425 is an agent which binds and inhibits an RNA transcript comprising a miR-425 target sequence. Examples of such agents include, but are not limited to an anti-miR, small molecule, protein, antibody, aptamer, ribozyme, nucleic acid or nucleic acid analogue. Accordingly, the present invention provides for methods to decrease ANP levels in a subject in need of increasing blood pressure, e.g., a subject with low blood pressure, in shock etc., by administering to a subject a miR-425 or variant thereof which binds to the miRNA target sequence of SEQ ID NO: 8, (e.g., for administration to an AA or AG rs50668 subject) or a modified miR-425 which binds to the miRNA target sequence SEQ ID NO: 9 (e.g., (e.g., for administration to an AA or AG rs50668 subject).

Another aspect of the present invention relates to a method of inhibiting angiogenesis, or preventing or inhibiting hypotension (e.g., low blood pressure), for example, orthostatic hypotension, or a symptom thereof in a subject in need thereof, the method comprising administering to the subject an effective amount of miR-425 agent, or a mimetic thereof.

Another aspect of the present invention relates to a method of inhibiting angiogenesis, or preventing or inhibiting hypotension (e.g., low blood pressure), for example, orthostatic hypotension, or a symptom thereof in a subject in need thereof, the method comprising administering to a subject determined to heterozygous (e.g., AG) or homozygous (AA)

for A allele for the single nucleotide polymorphism (SNP) rs5068 (A/G) an effective amount of a miR-425 agent, or a mimetic thereof.

In alternative embodiments, a modified miR-425 agent as disclosed herein which binds to the "G" allele miRNA target sequence of SEQ ID NO: 9 in the 3'UTR of the NPPA can be used for the treatment of low blood pressure in a subject who is heterozygous (e.g., AG) or homozygous (GG) for G allele at the rs5068 loci.

In some embodiments, a miR-425 agent comprises at least a portion of nucleic acid sequence GAAAGCGCUUUG-GAAUGACACGAUCACUCCCG-UUGAGUGGGCACCCGAGAAGCCAUCGGG AAU-GUCGUGUCCGCCCAGUGCUCUUUC (SEQ ID NO. 13). In some embodiments, an miR-425 agent comprises at least a portion nucleic acid sequence AAUGACACGAUCACUC-CCGUUGA (SEQ ID NO: 1). In some embodiments, an miR-425 agent comprises at least nucleic acid sequence AUGACA (SEQ ID NO:2). In some embodiments, a miR-425 agent comprises a modification selected from the group consisting of nucleobase modifications, sugar modifications, inter-sugar linkage modifications, backbone modifications, and any combinations thereof. In some embodiments, a miR-425 agent comprises a ligand. In some embodiments, a miR-425 agent is from about 11 to about 30 nucleotides in length. In some embodiments, a miR-425 agent is single-stranded. In some embodiments, an miR-425 agent is formulated in a lipid delivery vehicle, e.g., liposomes, lipid particles, other compositions used for oligonucleotide delivery. In some embodiments, a miR-425 agent is encoded by an expression vector. In some embodiments, a miR-425 agent decreases the amount of NPPA mRNA in a cell relative to a control or reference level and/or decrease the expression of atrial natriuretic peptide (ANP) or a nucleic acid encoding ANP in a cell relative to a control or reference level, e.g., where ANP mRNA expression levels are decreased. In some embodiments, an miR-425 agent is administered to a subject who is homozygous AA or heterozygous AG for the SNP rs5068. In some embodiments, a modified miR-425 agent which recognizes SEQ ID NO: 9 in the 3'UTR of NPPA gene is administered to a subject who is heterozygous AG or homozygous minor (GG) for the rs5068 SNP. In some embodiments, the methods further comprise selecting a subject for treatment for inhibiting angiogenesis or preventing or inhibiting orthostatic hypotension before onset of said administering, comprising assaying a biological sample from the subject for single nucleotide polymorphism of SNP rs5068 (A/G) and selecting the subject who is heterozygous AG or homozygous for AA allele of SNP rs5068 (A/G). In some embodiments, the method further comprises co-administering a therapeutic agent, wherein the therapeutic agent is for treatment for inhibiting angiogenesis or orthostatic hypotension.

In all aspects of the invention as disclosed herein, an anti-miR-425 agent (e.g., an anti-miR complementary to, in part, to the miR-425 of SEQ ID NO: 1, or complementary to at least in part the miRNA seed sequence SEQ ID NO: 2) and/or a miR-425 agent can further comprise a binding moiety and a targeting moiety. In some embodiments the binding moiety binds the anti-miR-425 agent, or miR-425 to the targeting moiety. In some embodiments, a targeting moiety is a cell surface receptor ligand or antigen-binding fragment thereof, for example a cell surface receptor or ligand which is expressed on cells expressing NPPA gene or combinations or antigen binding fragments thereof. In some embodiments, a targeting moiety targets an anti-miR-425 agent, or miR-425 to cells expressing the NPPA gene, e.g., cardiac cells and cells the heart atrium and ventricle.

In some embodiments, a targeting moiety useful in the methods as disclosed herein is an antibody, for example an antibody including not just complete or full length antibodies, but also antibody derivatives, such as a single chain antibody, a Fab portion of an antibody or a (Fab')$_2$ segment. In some embodiments, a binding moiety useful in the methods as disclosed herein is a protein or a nucleic acid binding domain of a protein, and in some embodiments the binding moiety is fused to the carboxyl terminus of the targeting moiety, and in some embodiments, the binding moiety is the protein protamine or nucleic acid binding fragment of protamine.

In some embodiments, an anti-miR-425 agent, (e.g., a small molecule inhibitor of miR-425 or an anti-miR complementary to, or complementary in part, to the miR-425 sequence of SEQ ID NO: 1, or complementary at least part of the miRNA seed sequence SEQ ID NO: 2) is encoded by a nucleic acid in a vector, for example, a plasmid, cosmid, phagemid, or virus or variants thereof, and in some embodiments the anti-miR-425 agent, e.g., anti-miR of miR-425 is operatively linked to a promoter. In some embodiments, the vector further comprises one or more in vivo expression elements for expression in human cells, such as a promoter or enhancer and combinations thereof.

In some embodiments, administration of an anti-miR-425 agent, e.g., a small molecule inhibitor of miR-425 or an anti-miR complementary to, or complementary in part, to the miR-425 sequence of SEQ ID NO: 1, or complementary at least part of the miRNA seed sequence SEQ ID NO: 2 can be intravenous, intradermal, intramuscular, intraarterial, intralesional, percutaneous, subcutaneous, or by aerosol administration, or combinations thereof. In some embodiments, administration is prophylactic administration, and in alternative embodiments, administration is therapeutic administration. Anitmirs have been effective in vivo to block miRNA mediated gene suppression when administered a variety of ways, in particular, intravenous, subcutaneous, interperatenial (i.p) and other administration routes. In some embodiments, where the anti-miR-425 agent is a locked nucleic acid (LNA), the LNA is administered to a subject intravenously, for example at a dose of about 10 mg/kg, or at least about 2 mg/kg, or at about at least 5 mg/kg, or at least about 10 mg/kg. Intravenous administration of LNA has been demonstrated to be effective to inhibit miRNA mediated gene suppression in vivo (Obad et al, Nature Genetics, 2011; 43; 371-378, which is incorporated herein in its entirety by reference).

In some embodiments, the methods and compositions as disclosed herein can be administered to a subject, where the subject is, for example, a mammal such as a human.

Another aspect of the present invention relates to a kit comprising an anti-miR-425 oligonucleotide as disclosed herein, e.g., for the treatment of a subject with a hypertension, or a cardiovascular disease or disorder as disclosed herein. Another aspect of the present invention relates to a kit comprising an miR-425 oligonucleotide as disclosed herein, e.g., for the treatment of a subject with, for example, low blood pressure (e.g., a subject suffering orthostatic hypotension), or to inhibit angiogenesis, etc.

Another aspect of the present invention relates to an assay comprising: (a) measuring or quantifying the amount of miR-425 in a biological sample obtained from a subject; and (b) comparing the measured or quantified amount of miR-425 with a reference value, and if the amount of miR-425 is increased relative to the reference value, (c) identifying the subject as having an increased probability of having hypertension (e.g., high blood pressure) or cardiovascular disease. Accordingly, one aspect of the present invention relates to measuring circulating miR-425 levels (e.g., in the plasma) of the subject as a biomarker for a cardiovascular disease. In some embodiments, the present invention also encompasses measuring the level of circulating miR-425 in a subject who is homozygous (AA) or heterozygous (AG) at the rs5068 loci to assess the effect of salt in their diet, e.g., to assess if the subject is maintaining a low salt diet.

Another aspect of the present invention relates to an assay comprising: (a) contacting a biological sample obtained from a subject with a detectable antibody specific for miR-425 or detectable nucleic acid for miR-425; (b) washing the sample to remove unbound antibody or unbound nucleic acid; (c) measuring the intensity of the signal from the bound, detectable antibody or bound detectable nucleic acid; (d) comparing the measured intensity of the signal with a reference value and if the measured intensity is increased relative to the reference value; and (e) identifying the subject as having an increased probability of having high blood pressure or cardiovascular disease.

Another aspect of the present invention relates to a system for obtaining data from at least one test sample obtained from at least one subject, the system comprising: (a) a determination module configured to receive said at least one test sample and perform at least one analysis on said at least one test sample to determine the presence or absence of at least one of the following conditions: (i) an expression of NT-proANP and/or ANP mRNA is smaller than a pre-determined level; (ii) expression of miR-425 is greater than a pre-determined standard; (iii) at least one copy of a single nucleotide polymorphism (SNP) at position 647 of SEQ ID NO: 12 comprises an adenine "A" allele, or its complement thereof comprises a thymine "T" allele; (b) a storage device configured to store data output from said determination module; and (c) a display module for displaying a content based in part on the data output from said determination module, wherein the content comprises a signal indicative of the presence of at least one of these conditions determined by the determination module, or a signal indicative of the absence of at least one of these conditions determined by the determination module.

In some embodiments, the system as disclosed herein provides for the content displayed on the display module to further comprise a signal indicative of the subject being recommended to receive a particular treatment regimen, for example, a signal that a subject is recommended a treatment with a composition comprising an anti-miR-425 agent (e.g., for the treatment of hypertension) where the content from the display module produces a signal indicative of at least one of: (i) the expression of NT-proANP and/or ANP and/or ANP mRNA is smaller than a pre-determined level (e.g., smaller than an level of a GG minor homozygous level); (ii) the expression of miR-425 is at least the same as, or greater than a pre-determined standard (e.g., greater than a GG homozygous level); (iii) the presence of at least one copy of single nucleotide polymorphism (SNP) at position 647 of SEQ ID NO: 12 comprises an adenine "A" allele, or its complement thereof comprises a thymine "T" allele (e.g., the subject is homozygous AA or heterozygous AG at the rs5068 loci). In alternative embodiments, a subject is not recommended a treatment with a composition comprising an anti-miR-425 agent where the content from the display module produces a signal indicative of at least one of: (i) the expression of NT-proANP and/or ANP peptide or ANP mRNA is at least the same as, or higher than a pre-determined level; (ii) the expression of miR-425 is lower than a pre-determined standard; (iii) or the absence of an A allele of single nucleotide polymorphism (SNP) at position 647 of SEQ ID NO: 12 and/or the presence of at least one two copies of the "G" allele at position 647 of SEQ ID NO: 12, or its complement thereof comprises a thymine "C" allele (e.g., the subject is homozygous minor GG at the rs5068 loci).

In some embodiments, the system as disclosed herein provides for the content displayed on the display module to further comprise a signal indicative of the subject being recommended to receive a particular treatment regimen, for example, a signal that a subject is recommended a treatment with a composition comprising an miR-425 agent (e.g., for the treatment of low blood pressure) where the content from the display module produces a signal indicative of at least one of: (i) the expression of NT-proANP and/or ANP and/or ANP mRNA is above than a pre-determined level; (ii) the expression of miR-425 is lower than a pre-determined standard; (iii) the presence of at least one copy of single nucleotide polymorphism (SNP) at position 647 of SEQ ID NO: 12 comprises an adenine "A" allele, or its complement thereof comprises a thymine "T" allele (e.g., the subject is homozygous AA or heterozygous AG at the rs5068 loci). In alternative embodiments, a subject is not recommended a treatment with a composition comprising an miR-425 agent where the content from the display module produces a signal indicative of at least one of: (i) the expression of NT-proANP and/or ANP peptide or ANP mRNA is at least the same as, or higher than a pre-determined level; (ii) the expression of miR-425 is higher than a pre-determined standard; (iii) or the absence of an A allele of single nucleotide polymorphism (SNP) at position 647 of SEQ ID NO: 12 (e.g., the subject is homozygous minor GG at the rs5068 loci and is not either AG or AA).

In the methods, systems and assays as disclosed herein, in some embodiments, the biological sample is a tissue samples, such as blood sample, e.g., plasma sample. In some embodiments of the methods, systems and assays as disclosed herein miR-425 miRNA levels can be determined by any methods known by persons of ordinary skill in the art. For example, miR-425 miRNA levels can be determined using a nucleic acid probe in, for example, Northern blot analysis, PCR, RT-PCR or quantitative RT-PCR. Examples of a nucleic acid probe useful in the methods as disclosed herein in the Examples, include a nucleic acid probe corresponding to SEQ ID NO: 2 or a nucleic acid probe which specifically hybridizes to SEQ ID NO: 1 or SEQ ID NO: 2, where such nucleic acid probes can be used in Northern blot analysis, PCR, RT-PCR, quantitative RT-PCR and other methods to determine expression levels of nucleic acids in a biological sample. Any means to analyze a miRNA expression profile known by persons of ordinary skill in the art can be used in the methods as disclosed herein, for example by microarray assay.

BRIEF DESCRIPTION OF DRAWINGS

FIG. 1A shows the effect of dietary sodium and genotype on plasma Nt-proANP levels at baseline (p=0.016 for overall genotype effect and p<0.001 for diet). FIG. 1B shows the effect of genotype and dietary sodium on plasma Nt-proANP levels during saline challenge, after one week of a low-salt diet. FIG. 1C shows the effect of genotype and dietary sodium on plasma Nt-proANP levels during saline challenge, after one week of a high-salt diet (P=0.018 for genotype effect, P<0.001 for diet and saline effects). FIG. 1C demonstrates that GG subjects (n=3) have higher plasma Nt-proANP levels as compared to the levels of AA (n=23) and AG (n=8) subjects, where AA subjects have the lowest level of NT-proANP levels, demonstrating the greatest effect of miR-425-mediated inhibition of gene expression from the NPPA gene. AA=homozygous for the major A allele. AG=heterozygous subjects, with one copy of the major A allele, and one copy of the minor G allele, GG=homozygous subjects for the minor (G) allele.

FIG. 3A show miR-425 reduces activity of the NPPA major A allele-luciferase reporter (major-LUC) but not the NPPA minor G allele-luciferase reporter (minor-LUC). FIG. 3B shows that anti-miR-425 increases activity of the NPPA major A allele (major-LUC construct) but not the NPPA minor G allele (minor-LUC construct). FIG. 3C shows a modified miR-425 targeting the NPPA 3'UTR minor (G) allele reduces activity of the NPPA minor G allele (minor-LUC construct) but not the NPPA major (A) allele (major-LUC construct). FIG. 3D shows modified miR-425 resulting in perfect match for NPPA 3'UTR rs5068 minor allele reduces activity of the NPPA minor G allele-luciferase reporter but not the NPPA major A allele-luciferase reporter.

FIG. 5A shows relative NPPA mRNA levels (normalized to 18S ribosomal RNA levels in control and miR-425 transfected cardiomyocytes. FIG. 5B shows the concentrations of Nt-proANP immunoreactivity in the cell supernatant of control and miR-425 transfected cardiomyocytes. Data are expressed as mean±SEM (n=4)

FIG. 6A shows the effect of genotype on the change in plasma cGMP levels induced by saline challenge after one week on a low-salt diet. FIG. 6B shows the effect of the genotype on the change in plasma cGMP levels induced by saline challenge after one week on a high-salt diet. (p=0.03 for difference by genotype, p<0.001 for effect of saline).

FIG. 7A shows the effect of genotype and dietary sodium on plasma Nt-proBNP levels during saline challenge, after one week of a low-salt diet. FIG. 7B shows the effect of genotype and dietary sodium on plasma Nt-proBNP levels during saline challenge, after one week of a high-salt diet. (P=0.5 for genotype effect, P<0.001 for diet and saline effects).

FIG. 8A shows the effect of genotype and dietary sodium on plasma BNP levels during saline challenge, after one week of a low-salt diet. FIG. 8B shows the effect of genotype and dietary sodium on plasma BNP levels during saline challenge, after one week of a high-salt diet (P=0.6 for genotype effect, P<0.001 for diet and saline effects).

FIG. 15A show that ANP levels are higher in post-bypass surgery subjects and increase with time after saline infusion, and that ANP levels follow a similar projectory of increase, but starting at a lower level for pre-bypass subjects. FIG. 15B show that Nt-proANP levels are higher in post-bypass surgery subjects and increase to a lesser degree with time after saline infusion as compared to saline infusion of pre-bypass subjects.

DESCRIPTION OF THE INVENTION

Figure 1A:
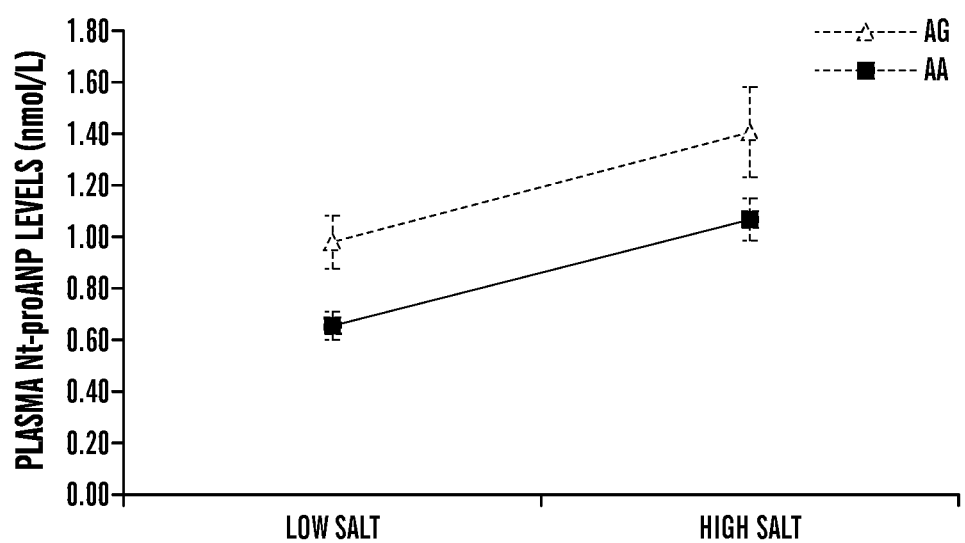
FIG. 1A-1C shows samples for measurement of plasma Nt-proANP levels were obtained at baseline and at 0, 1, 2, 3, 4, 5, 6, 7 and 8 hours (h) after the start of saline infusion. AA denotes rs5068 major homozygote, and AG denotes rs5068 heterozygote.

In accordance with the present invention, the inventors have discovered that subjects homozygous for the major allele (A) of rs5068 (A/G) have increased miR-425 levels and decreased ANP levels as compared to subjects whom are heterozygous (e.g., AG heterozygous subjects). The inventors have discovered that miR-425 binds to a target region of the 3'UTR of the NPPA gene which is the location of the rs5068 SNP, and that miR-425 binds to a target region comprising the A allele of the rs5068 SNP resulting in repression of ANP expression. Accordingly, in some embodiments an anti-miR to miR-425 can be administered to AA (major homozygotes) or AG (heterozygotes) rs5068 SNP subjects to decrease miR-425 function and thus elevate ANP levels in such subjects. It is expected that because the miR-425 binds to the A allele of the rs5068 SNP in the 3'UTR of the NPPA gene, an anti-miR to miR-425 will be twice as effective in inhibiting miR-425-mediated suppression of NPPA in subjects homozygous AA as compared to subject heterozygous AG for the rs5068 SNP.

Accordingly, the present invention general relates to a method to treat a cardiovascular disease or disorder comprising administering a pharmaceutical composition comprising an anti-miR-425 agent, e.g., anti-miR of miR-425, where an anti-miR-425 agent is complementary to, at least part of the miR-425 sequence of SEQ ID NO: 1, or at least part of the miR-425 miRNA seed sequence SEQ ID NO: 2. In some embodiments, an anti-miR-425 agent is an anti-miR (or anti-miR) of miR-425, such as an oligonucleotide of TTACTGT-GCTAGTGAGGGCAACT (SEQ ID NO: 3) or a homologue thereof.

DEFINITIONS

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein, the term "ANP" refers to atrial natriuretic peptide (ANP), and is also known as atrial natriuretic factor (ANF), atrial natriuretic hormone (ANH), Cardionatrine, Cardiodilatine (CDD) or atriopeptin, and is a protein hormone secreted by heart muscle cells that functions as a vasodilator and a potent mediator of natriuresis. ANP is expressed from the NPPA (natriuretic peptide A) gene. ANP is involved in the homeostatic control of body water, sodium, potassium and fat (adipose tissue). ANP is released by muscle cells in the upper chambers (atria) of the heart (atrial myocytes) in response to high blood pressure. ANP acts to reduce the water, sodium and adipose loads on the circulatory system, thereby reducing blood pressure. ANP is produced, stored, and released mainly by cardiac myocytes of the atria of the heart. Synthesis of ANP also takes place in the ventricles, brain, suprarenal glands, and renal glands. ANP is released in response to atrial stretch and a variety of other signals induced by hypervolemia, exercise, or caloric restriction. ANP is constitutively expressed in the ventricles in response to stress induced by increased afterload (e.g. increased ventricular pressure from aortic stenosis) or injury (e.g. myocardial infarction). The ANP gene has 3 exons and 2 introns; it codes 151-amino acid preproANP protein. Cleaving the 25-amino acid N-terminal signal sequence results in pro-ANP. Pro-ANP is cleaved by the serin protease corin, into ANP (the 28-amino acid C-terminal terminal fragment) and NT-proANP (the N-terminal fragment). Accordingly, ANP is a 28-amino acid peptide corresponding to amino acids 124-151 of accession number NP_006163.1. The accession number NP_006163.1 corresponds to the ANP pre-proprotein, which includes a signal peptide (amino acids 1-25) and the proprotein (amino acids 26-151). ANP is closely related to BNP (brain natriuretic peptide) and CNP (C-type natriuretic peptide).

As used herein, the term "NT-proANP" refers to the N-terminal atrial natriuretic peptide and is the N-terminal fragment (proANP$_{1-30}$ fragment) as a result from cleavage of the proANP protein (proANP$_{1-126}$) to NT-proANP and ANP. The 126-amino acid peptide atrial natriuretic peptide pro-hormone (proANP$_{1-126}$) is synthesized and stored in atrial myocyte. Upon distension of the cardiac atria, proANP$_{1-126}$ is cleaved and equimolar amounts of the 28-amino acid ANP protein (e.g., C-terminal fragment proANP$_{99-126}$) and an N-terminal fragment (proANP$_{1-98}$) which are secreted from the atria. Whereas ANP is rapidly removed from the circulation, the N-terminal fragments, such as the proANP$_{1-30}$ fragment (Nt-proANP), which is also termed long-acting natriuretic peptide and has strong salt-excreting properties itself, are stable and remain in the circulation at manifold higher concentrations than ANP. Nt-proANP measured in peripheral plasma is therefore less prone to fluctuation and may thus be a more reliable measure of atrial ANP secretion than peripheral plasma concentration of ANP itself.

As used herein, the term "NPPA gene" refers to the natriuretic peptide A gene which encodes the pre-proANP peptide. The human NPPA gene expresses the mRNA identified by accession number: NM_006172.3 which is 856 bp in length, and includes a signal peptide (nucleic acids 100-174 of NM_006172.3) and the ANP pro-protein (nucleic acids 175-552 of NM_006172.3), which includes the mature ANP peptide (nucleic acids 175-375 of NM_006172.3).

As used herein, the term "BNP" refers to B-type natriuretic peptide, also known as Basic natriuretic peptide or GC-B, and is a 32 amino acid polypeptide secreted by the ventricles of the heart in response to excessive stretching of heart muscle cells (e.g., cardiomyocytes). The release of BNP is modulated by calcium ions. BNP is secreted along with a 76 amino acid N-terminal fragment (NT-proBNP) which is biologically inactive. BNP binds to and activates the atrial natriuretic factor receptors NPRA, and to a lesser extent NPRB, in a fashion similar to atrial natriuretic peptide (ANP) but with 10-fold lower affinity. The biological half-life of BNP, however, is twice as long as that of ANP, and that of NT-proBNP is even longer. BNP is encoded as a pre-proprotein by the NPPB gene, corresponding to accession number NM_002521.2.

As used herein, the term "miR-425" refers to a nucleic acid or an agent which has a minimum biological activity of binding to (or hybridizing to) the 3' UTR of the NPPA gene, in particular binding to and hybridizing to residues 23-29 of SEQ ID NO: 7, which comprise the major A allele of the rs5068 SNP. In particular, the miR-425 corresponds to nucleic acid AAUGACACGAUCACUCCCGUUGA (SEQ ID NO: 1) and inhibiting the expression of a gene comprising the miR-425 target sequence, where the target sequence is 5'-ATGACAC' (SEQ ID NO: 8), which is the A allele of rs5068. A miR-425 can be assessed for its ability to bind to and inhibit the target sequence SEQ ID NO:8 using the luciferase assay as disclosed herein in the Examples, for example by using the pMIR-REPORT™ luciferase reporter vector with a major (A) allele of rs5068 in the 3'UTR of the NPPA exon 3 gene sequence. The term "anti-miR-425 agent" herein refers to any agent which binds to, at least part of the miR-425 sequence of SEQ ID NO: 1, or at least part of the miR-425 miRNA seed sequence SEQ ID NO: 2 (AUGACA) and also encompasses an "anti-miR-425 mimetic" and means an agent which binds to and inhibits the miR-425 nucleic acid of SEQ ID NO: 1. In this context, an anti-miR-425 agent can be any agent or RNA interference-inducing molecule, for example but not limited to unmodified and modified double stranded (ds) RNA molecules including, short-temporal RNA (stRNA), small interfering RNA (siRNA), short-hairpin RNA (shRNA), microRNA (miRNA), double-stranded RNA (dsRNA). Alternatively, an anti-miR-425 agent can be a small molecule, protein, aptamer, nucleic acid analogue, antibody etc. that binds to the miRNA seed sequence SEQ ID NO: 2 and/or inhibits miR-425 activity (e.g., an anti-miR complementary to at least part of the miR-425 sequence of SEQ ID NO: 1, or at least part of the miR-425 miRNA seed sequence SEQ ID NO: 2). The terms "same activity" or "same function" as used in reference to the same activity or function of an anti-miR-425 agent means an anti-miR-425 agent molecule which can bind to at least part of the miRNA seed sequence AUGACA (SEQ ID NO: 2) or at least part of the miR-425 sequence of SEQ ID NO: 1, and/or inhibit miR-425 with at least 80% of the efficiency, or greater efficiency, as the anti-miR of SEQ ID NO: 3, as assessed using, for example, the luciferase assay as disclosed herein in the Examples.

The terms "microRNA" or "miRNA" or "mir" or "miR" are used interchangeably herein, are endogenous RNAs, some of which are known to regulate the expression of protein-coding genes at the posttranscriptional level. As used herein, the term "microRNA" refers to any type of micro-interfering RNA, including but not limited to, endogenous microRNA and artificial microRNA. Typically, endogenous microRNA are small RNAs encoded in the genome which are capable of modulating the productive utilization of mRNA. A mature miRNA is a single-stranded RNA molecule of about 21-23 nucleotides in length which is complementary to a target sequence, and hybridizes to the target RNA sequence to inhibit expression of a gene which encodes a miRNA target sequence. miRNAs themselves are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression. MicroRNA sequences have been described in publications such as, Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into the precursor molecule.

A mature miRNA is produced as a result of a series of miRNA maturation steps; first a gene encoding the miRNA is transcribed. The gene encoding the miRNA is typically much longer than the processed mature miRNA molecule; miRNAs are first transcribed as primary transcripts or "pri-miRNA" with a cap and poly-A tail, which is subsequently processed to short, about 70-nucleotide "stem-loop structures" known as "pre-miRNA" in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). This complex is responsible for the gene silencing observed due to miRNA expression and RNA interference. The pathway is different for miRNAs derived from intronic stem-loops; these are processed by Drosha but not by Dicer. In some instances, a given region of DNA and its complementary strand can both function as templates to give rise to at least two miRNAs. Mature miRNAs can direct the cleavage of mRNA or they can interfere with translation of the mRNA, either of which results in reduced protein accumulation, rendering miRNAs capable of modulating gene expression and related cellular activities.

The term "pri-miRNA" refers to a precursor to a mature miRNA molecule which comprises; (i) a microRNA sequence and (ii) stem-loop component which are both flanked (i.e. surrounded on each side) by "microRNA flanking sequences", where each flanking sequence typically ends in either a cap or poly-A tail. A pri-microRNA, (also referred to as large RNA precursors), are composed of any type of nucleic acid based molecule capable of accommodating the microRNA flanking sequences and the microRNA sequence. Examples of pri-miRNAs and the individual components of such precursors (flanking sequences and microRNA sequence) are provided herein. The nucleotide sequence of the pri-miRNA precursor and its stem-loop components can vary widely. In one aspect a pre-miRNA molecule can be an isolated nucleic acid; including microRNA flanking sequences and comprising a stem-loop structure and a microRNA sequence incorporated therein. A pri-miRNA molecule can be processed in vivo or in vitro to an intermediate species caller "pre-miRNA", which is further processed to produce a mature miRNA.

The term "pre-miRNA" refers to the intermediate miRNA species in the processing of a pri-miRNA to mature miRNA, where pri-miRNA is processed to pre-miRNA in the nucleus, whereupon pre-miRNA translocates to the cytoplasm where it undergoes additional processing in the cytoplasm to form mature miRNA. Pre-miRNAs are generally about 70 nucleotides long, but can be less than 70 nucleotides or more than 70 nucleotides.

The term "microRNA flanking sequence" as used herein refers to nucleotide sequences including microRNA processing elements. MicroRNA processing elements are the minimal nucleic acid sequences which contribute to the production of mature miRNA from precursor microRNA. Often these elements are located within a 40 nucleotide sequence that flanks a microRNA stem-loop structure. In some instances the microRNA processing elements are found within a stretch of nucleotide sequences of between 5 and 4,000 nucleotides in length that flank a microRNA stem-loop structure. Thus, in some embodiments the flanking sequences are 5-4,000 nucleotides in length. As a result, the length of the precursor molecule can be, in some instances at least about 150 nucleotides or 270 nucleotides in length. The total length of the precursor molecule, however, can be greater or less than these values. In other embodiments the minimal length of the microRNA flanking sequence is 10, 20, 30, 40, 50, 60, 70, 80, 90, 100, 150, 200 and any integer there between. In other embodiments the maximal length of the microRNA flanking sequence is 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900 4,000 and any integer there between.

MicroRNA flanking sequences can be native microRNA flanking sequences or artificial microRNA flanking sequences. A native microRNA flanking sequence is a nucleotide sequence that is ordinarily associated in naturally existing systems with microRNA sequences, i.e., these sequences are found within the genomic sequences surrounding the minimal microRNA hairpin in vivo. Artificial microRNA flanking sequences are nucleotides sequences that are not found to be flanking to microRNA sequences in naturally existing systems. microRNA flanking sequences within the pri-miRNA molecule can flank one or both sides of the stem-loop structure encompassing the microRNA sequence. Thus, one end (i.e., 5') of the stem-loop structure can be adjacent to a single flanking sequence and the other end (i.e., 3') of the stem-loop structure cannot be adjacent to a flanking sequence. Preferred structures have flanking sequences on both ends of the stem-loop structure. The flanking sequences can be directly adjacent to one or both ends of the stem-loop structure or can be connected to the stem-loop structure through a linker, additional nucleotides or other molecules.

A "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. The actual primary sequence of nucleotides within the stem-loop structure is not critical to the practice of the invention as long as the secondary structure is present. As is known in the art, the secondary structure does not require exact base-pairing. Thus, the stem can include one or more base mismatches. Alternatively, the base-pairing can be exact, i.e. not include any mismatches. In some instances the precursor microRNA molecule can include more than one stem-loop structure. The multiple stem-loop structures can be linked to one another through a linker, such as, for example, a nucleic acid linker or by a microRNA flanking sequence or other molecule or some combination thereof.

Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways. As used herein, the term "miRNA mimetic" refers to an artificial miRNA or RNAi (RNA interference molecule) which is flanked by the stem-loop like structures of a pri-miRNA.

The term "artificial microRNA" includes any type of RNA sequence, other than endogenous microRNA, which is capable of modulating the productive utilization of mRNA. For instance, the term artificial microRNA also encompasses a nucleic acid sequence which would be previously identified as siRNA, where the siRNA is incorporated into a vector and surrounded by miRNA flanking sequences as described herein.

As used herein, "double stranded RNA" or "dsRNA" refers to RNA molecules that are comprised of two substantially complementary strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

As used herein, "gene silencing" or "gene silenced" by a miRNA and/or RNA interference molecule "refers to a decrease in the mRNA level in a cell for a target gene by at least about 5%, at least about 10%, at least about 20%, at least about 30%, at least about 40%, at least about 50%, at least about 60%, at least about 70%, at least about 80%, at least about 90%, at least about 95%, at least about 99% up to and including 100%, and any integer in between of the mRNA level found in the cell without the presence of the miRNA or RNA interference molecule. In one preferred embodiment, the mRNA levels are decreased by at least about 70%, at least about 80%, at least about 90%, at least about 95%, at least about 99%, up to and including 100% and any integer in between 5% and 100%."

The term "reduced" or "reduce" as used herein generally means a decrease by a statistically significant amount. However, for avoidance of doubt, "reduced" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The term "increased" or "increase" as used herein generally means an increase by a statically significant amount; for the avoidance of any doubt, "increased" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "tissue" refers to a group or layer of similarly specialized cells which together perform certain special functions. The term "tissue-specific" refers to a source of cells from a specific tissue.

As used herein a "siRNA" refers to a nucleic acid that forms a double stranded RNA, which double stranded RNA has the ability to reduce or inhibit expression of a particular gene or target gene when the siRNA is expressed in the same cell as the gene or target gene. The double stranded RNA siRNA can be formed by the complementary strands. The complementary portions of the siRNA that hybridize to form the double stranded molecule typically have substantial or complete identity. In one embodiment, a siRNA refers to a nucleic acid that has substantial or complete identity to sequence of a target gene and forms a double stranded RNA. The sequence of the siRNA can correspond to the full length target gene, or to a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The term "biological sample" as used herein means a sample of biological tissue or fluid that comprises nucleic acids. Such samples include, but are not limited to, tissue isolated from animals. Biological samples can also include sections of tissues such as biopsy and autopsy samples, frozen sections taken for histologic purposes, blood, plasma, serum, sputum, stool, tears, mucus, hair, and skin. Biological samples also include explants and primary and/or transformed cell cultures derived from patient tissues. A biological sample can be provided by removing a sample of cells from an animal, but can also be accomplished by using previously isolated cells (e.g., isolated by another person, at another time, and/or for another purpose), or by performing the methods as disclosed herein in vivo. Archival tissues, such as those having treatment or outcome history can also be used.

The term "tissue" is intended to include, blood, blood preparations such as plasma and serum, bones, joints, muscles, smooth muscles, and organs.

The terms "disease" or "disorder" are used interchangeably herein, and refer to any alteration in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, indisposition or affliction.

The terms "subject" and "individual" are used interchangeably herein, and refer to an animal, for example a human, to whom treatment, including prophylactic treatment, with a pharmaceutical composition as disclosed herein, is provided. The term "subject" as used herein refers to human and non-human animals. The term "non-human animals" includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term 'effective amount" as used herein refers to the amount of therapeutic agent of pharmaceutical composition to alleviate at least one of the symptoms of the disease or disorder.

The term "gene" as used herein refers to a genomic gene comprising transcriptional and/or translational regulatory sequences and/or a coding region and/or non-translated sequences (e.g., introns, 5'- and 3'-untranslated sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "nucleic acid" or "oligonucleotide" or "polynucleotide" used herein means at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe that can hybridize to the target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

A nucleic acid will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog can be located for example at the 5'-end and/or the 3'-end of the nucleic acid molecule. Representative examples of nucleotide analogs can be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenines and guanosines modified at the 8-position, e.g. 8-bromo guanosine; deaza nucleotides, e.g. 7 deaza-adenine; O- and N-alkylated nucleotides, e.g. N6-methyl adenine are suitable. The 2' OH— group can be replaced by a group selected from H, OR, R, halo, SH, SR, NH2, NHR, NR2 or CN, wherein R is C-C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

The term "probe" as used herein refers to an oligonucleotide capable of binding to a target nucleic acid of complementary sequence through one or more types of chemical bonds, usually through complementary base pairing, usually through hydrogen bond formation. Probes can bind target sequences lacking complete complementarily with the probe sequence depending upon the stringency of the hybridization conditions. There can be any number of base pair mismatches which will interfere with hybridization between the target sequence and single stranded target nucleic acids, but a probe will bind a selected target specifically, i.e. to the substantial exclusion of non-target nucleic acids under at least one set of conditions. A probe can be single stranded or partially single and partially double stranded. A probe will generally be detectably labeled or carry a moiety that permits signal detection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more typically less than about 0.01, and most typically less than about 0.001.

The term "variant" as used in the context of anti-miR-425 agent, e.g., an anti-miR of miR-425 variant means a modified anti-miR with at least on of the following; altered nucleic acid sequence, such as insertions, deletions, substitutions, fragments of at least 5 nucleic acids, modification of the nucleic acids or nucleic acid analogues as compared to the wild type anti-miR of SEQ ID NO:3 or a modified nucleic acid which is complementary to at least part of the miR-425 sequence of SEQ ID NO: 1, or at least part of the miR-425 miRNA seed sequence SEQ ID NO: 2.

As used herein, the terms "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see below) are identical, with appropriate nucleotide insertions or deletions or amino-acid insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. The term "substantially homologous" refers to sequences that are at least 90%, at least 95% identical, at least 97% identical or at least 99% identical. Homologous sequences can be the same functional gene in different species.

Determination of homologs of the genes or peptides of the present invention can be easily ascertained by the skilled artisan. The terms "homology", "identity" and "similarity"

refer to the degree of sequence similarity between two peptides or between two optimally aligned nucleic acid molecules. Homology and identity can each be determined by comparing a position in each sequence which can be aligned for purposes of comparison. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectfully. A sequence which is "unrelated" or "non-homologous" shares less than 40% identity, though preferably less than 25% identity with a sequence of the present application.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G. U. or 1) or residue occurs in both sequences to yield the number of matched positions, dividing the number of matched positions by the total number of positions in the comparison window (i.e., the window size), and multiplying the result by 100 to yield the percentage of sequence identity.

The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the; percentage of sequence identity is calculated by comparing the reference sequence to the sequence which can include deletions or additions which total 20 percent or less of the reference sequence over the comparison window. The reference sequence can be a subset of a larger sequence. The term "similarity", when used to describe a polypeptide, is determined by comparing the amino acid sequence and the conserved amino acid substitutes of one polypeptide to the sequence of a second polypeptide.

The term "vectors" refers to a nucleic acid molecule capable of transporting another nucleic acid to which it has been linked; a plasmid is a species of the genus encompassed by "vector". The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA loops which, in their vector form are not bound to the chromosome, and typically comprise entities for stable or transient expression or the encoded DNA. Other expression vectors can be used in the methods as disclosed herein for example, but are not limited to, plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self replicating extrachromosomal vectors or vectors which integrates into a host genome.

As used herein, the terms "treat" or "treatment" or "treating" as used herein in reference to use of an anti-miR-425 agent for the treatment of a cardiovascular disease or disorder refers to therapeutic treatment, wherein the object is to prevent or slow the development of the disease, such as slow down the development of a cardiac disorder, or reducing at least one adverse effect or symptom of a cardiovascular condition, disease or disorder, i.e., any disorder characterized by insufficient or undesired cardiac function. Adverse effects or symptoms of cardiac disorders are well-known in the art and include, but are not limited to, dyspnea, chest pain, palpitations, dizziness, syncope, edema, cyanosis, pallor, fatigue and death. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with a cardiac condition, as well as those likely to develop a cardiac condition due to genetic susceptibility or other factors such as weight, diet and health. In some embodiments, the term to treat also encompasses preventative measures and/or prophylactic treatment, which includes administering a pharmaceutical composition as disclosed herein to prevent the onset of a disease or disorder.

In some embodiment, the term "treating" when used in reference to a treatment of a cardiovascular disease or disorder is used to refer to the reduction of a symptom and/or a biochemical marker of a cardiovascular disease or disorder, for example a reduction in at least one biochemical marker of a cardiovascular disease by at least about 10% would be considered an effective treatment. Examples of such biochemical markers of cardiovascular disease include a reduction of, for example, creatine phosphokinase (CPK), aspartate aminotransferase (AST), lactate dehydrogenase (LDH) in the blood, and/or a decrease in a symptom of cardiovascular disease and/or an improvement in blood flow and cardiac function as determined by someone of ordinary skill in the art as measured by electrocardiogram (ECG or EKG), or echocardiogram (heart ultrasound), Doppler ultrasound and nuclear medicine imaging. A reduction in a symptom of a cardiovascular disease by at least about 10% would also be considered effective treatment by the methods as disclosed herein. As alternative examples, a reduction in a symptom of cardiovascular disease, for example a reduction of at least one of the following; dyspnea, chest pain, palpitations, dizziness, syncope, edema, cyanosis etc. by at least about 10% or a cessation of such systems, or a reduction in the size one such symptom of a cardiovascular disease by at least about 10% would also be considered as affective treatments by the methods as disclosed herein. In some embodiments, it is preferred, but not required that the therapeutic agent actually eliminate the cardiovascular disease or disorder, rather just reduce a symptom to a manageable extent.

Subjects amenable to treatment with an anti-miR-425 agent according to the methods as disclosed herein can be identified by any method to diagnose high blood pressure, e.g., using a blood pressure cuff). Methods of diagnosing these conditions are well known by persons of ordinary skill in the art. By way of non-limiting example, myocardial infarction can be diagnosed by (i) blood tests to detect levels of creatine phosphokinase (CPK), aspartate aminotransferase (AST), lactate dehydrogenase (LDH) and other enzymes released during myocardial infarction; (ii) electrocardiogram (ECG or EKG) which is a graphic recordation of cardiac activity, either on paper or a computer monitor. An ECG can be beneficial in detecting disease and/or damage; (iii) echocardiogram (heart ultrasound) used to investigate congenital heart disease and assessing abnormalities of the heart wall, including functional abnormalities of the heart wall, valves and blood vessels; (iv) Doppler ultrasound can be used to measure blood flow across a heart valve; (v) nuclear medicine imaging (also referred to as radionuclide scanning in the art) allows visualization of the anatomy and function of an organ, and can be used to detect coronary artery disease, myocardial infarction, valve disease, heart transplant rejection, check the effectiveness of bypass surgery, or to select patients for angioplasty or coronary bypass graft.

The term "effective amount" as used herein refers to the amount of therapeutic agent of pharmaceutical composition to alleviate at least one or more symptom of the disease or disorder, and relates to a sufficient amount of pharmacological composition to provide the desired effect. With reference to the treatment of, for example, a cardiovascular condition or disease in a subject, the term "effective amount" refers to the amount that is safe and sufficient to prevent or delay the development or a cardiovascular disease or disorder. The amount can thus cure or cause the cardiovascular disease or disorder to go into remission, slow the course of cardiovascular disease progression, slow or inhibit a symptom of a cardiovascular disease or disorder, slow or inhibit the establishment of secondary symptoms of a cardiovascular disease or disorder or inhibit the development of a secondary symptom of a cardiovascular disease or disorder. The effective amount for the treatment of the cardiovascular disease or disorder depends on the type of cardiovascular disease to be treated, the severity of the symptoms, the subject being treated, the age and general condition of the subject, the mode of administration and so forth. Thus, it is not possible to specify the exact "effective amount". However, for any given case, an appropriate "effective amount" can be determined by one of ordinary skill in the art using only routine experimentation. The efficacy of treatment can be judged by an ordinarily skilled practitioner, for example, efficacy can be assessed in animal models of a cardiovascular disease or disorder as discussed herein, for example treatment of a rodent with acute myocardial infarction or ischemia-reperfusion injury, and any treatment or administration of the compositions or formulations that leads to a decrease of at least one symptom of the cardiovascular disease or disorder as disclosed herein, for example, increased heart ejection fraction, decreased rate of heart failure, decreased infarct size, decreased associated morbidity (pulmonary edema, renal failure, arrhythmias) improved exercise tolerance or other quality of life measures, and decreased mortality indicates effective treatment. In embodiments where the compositions are used for the treatment of a cardiovascular disease or disorder, the efficacy of the composition can be judged using an experimental animal model of cardiovascular disease, e.g., animal models of ischemia-reperfusion injury (Headrick J P, Am J Physiol Heart circ Physiol 285; H1797; 2003) and animal models acute myocardial infarction. (Yang Z, Am J Physiol Heart Circ. Physiol 282:H949:2002; Guo Y, J Mol Cell Cardiol 33; 825-830, 2001). When using an experimental animal model, efficacy of treatment is evidenced when a reduction in a symptom of the cardiovascular disease or disorder, for example, a reduction in one or more symptom of dyspnea, chest pain, palpitations, dizziness, syncope, edema, cyanosis, pallor, fatigue and high blood pressure which occurs earlier in treated, versus untreated animals. By "earlier" is meant that a decrease occurs at least 5% earlier, but preferably more, e.g., one day earlier, two days earlier, 3 days earlier, or more.

The phrase "therapeutically effective amount" as used herein, e.g., of an anti-miR-425 agent or miRNA-425 agent as disclosed herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically significant reduction in a symptom or clinical marker associated with a cardiovascular disease or disorder, or hypertension or associated diseases.

A therapeutically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, that the total daily usage of the compositions and formulations as disclosed herein will be decided by the attending physician within the scope of sound medical judgment. The exact amount required will vary depending on factors such as the type of disease being treated.

As used herein, the phrase "cardiovascular condition, disease or disorder" is intended to include all disorders characterized by insufficient, undesired or abnormal cardiac function, e.g. hypertension, ischemic heart disease, hypertensive heart disease and pulmonary hypertensive heart disease, valvular disease, congenital heart disease and any condition which leads to congestive heart failure in a subject, particularly a human subject. Insufficient or abnormal cardiac function can be the result of disease, injury and/or aging. By way of background, a response to myocardial injury follows a well-defined path in which some cells die while others enter a state of hibernation where they are not yet dead but are dysfunctional. This is followed by infiltration of inflammatory cells, deposition of collagen as part of scarring, all of which happen in parallel with in-growth of new blood vessels and a degree of continued cell death. As used herein, the term "ischemia" refers to any localized tissue ischemia due to reduction of the inflow of blood. The term "myocardial ischemia" refers to circulatory disturbances caused by coronary atherosclerosis and/or inadequate oxygen supply to the myocardium. For example, an acute myocardial infarction represents an irreversible ischemic insult to myocardial tissue. This insult results in an occlusive (e.g., thrombotic or embolic) event in the coronary circulation and produces an environment in which the myocardial metabolic demands exceed the supply of oxygen to the myocardial tissue.

The terms "coronary artery disease" and "acute coronary syndrome" as used interchangeably herein, and refer to myocardial infarction refer to a cardiovascular condition, disease or disorder, include all disorders characterized by insufficient, undesired or abnormal cardiac function, e.g. ischemic heart disease, hypertensive heart disease and pulmonary hypertensive heart disease, valvular disease, congenital heart disease and any condition which leads to congestive heart failure in a subject, particularly a human subject. Insufficient or abnormal cardiac function can be the result of disease, injury and/or aging. By way of background, a response to myocardial injury follows a well-defined path in which some cells die while others enter a state of hibernation where they are not yet dead but are dysfunctional. This is followed by infiltration of inflammatory cells, deposition of collagen as part of scarring, all of which happen in parallel with in-growth of new blood vessels and a degree of continued cell death.

As used herein, the term "ischemia" refers to any localized tissue ischemia due to reduction of the inflow of blood. The term "myocardial ischemia" refers to circulatory disturbances caused by coronary atherosclerosis and/or inadequate oxygen supply to the myocardium. For example, an acute myocardial infarction represents an irreversible ischemic insult to myocardial tissue. This insult results in an occlusive (e.g., thrombotic or embolic) event in the coronary circulation and produces an environment in which the myocardial metabolic demands exceed the supply of oxygen to the myocardial tissue.

The term "hypertension" is also referred to as "HTN" or "high blood pressure" or "arterial hypertension" refers to a medical condition in which the blood pressure in the arteries is elevated. This requires the heart to work harder than normal to circulate blood through the blood vessels. Blood pressure is summarised by two measurements, systolic and diastolic, which depend on whether the heart muscle is contracting (systole) or relaxed between beats (diastole) and equate to a maximum and minimum pressure, respectively. Normal blood pressure at rest is within the range of 100-140 mmHg systolic (top reading) and 60-90 mmHg diastolic (bottom reading). High blood pressure is said to be present if it is persistently at or above 140/90 mmHg Without wishing to be bound by theory, hypertension is classified as either primary (essential) hypertension or secondary hypertension; about 90-95% of cases are categorized as "primary hypertension" which means high blood pressure with no obvious underlying medical cause. The remaining 5-10% of cases (secondary hypertension) are caused by other conditions that affect the kidneys, arteries, heart or endocrine system. Hypertension is a major risk factor for stroke, myocardial infarction (heart attacks), heart failure or chronic heart failure (CHF), aneurysms of the arteries (e.g. aortic aneurysm), peripheral arterial disease and is a cause of chronic kidney disease. Even moderate elevation of arterial blood pressure is associated with a shortened life expectancy. Dietary and lifestyle changes can improve blood pressure control and decrease the risk of associated health complications, although drug treatment is often necessary in people for whom lifestyle changes prove ineffective or insufficient.

The term "hypotension" as used herein refers to low blood pressure, especially in the arteries of the systemic circulation. Blood pressure is the force of blood pushing against the walls of the arteries as the heart pumps out blood. Hypotension is generally considered to be systolic blood pressure less than 90 millimeters of mercury (mm Hg) or diastolic less than 60 mm Hg. Hypotension is the opposite of hypertension, which is high blood pressure. For many people, low blood pressure can cause dizziness and fainting or indicate serious heart, endocrine or neurological disorders. Severely low blood pressure can deprive the brain and other vital organs of oxygen and nutrients, leading to a life-threatening condition called shock.

The term "orthostatic hypotension" as used herein is also known as postural hypotension, orthostasis, and refers to a form of hypotension in which a person's blood pressure suddenly falls when standing up or stretching. Medically it is defined as a fall in systolic blood pressure of at least 20 mm Hg and diastolic blood pressure of at least 10 mm Hg when a person assumes a standing position. The symptom is caused by blood pooling in the lower extremities upon a change in body position.

As used herein, the terms "administering," and "introducing" are used interchangeably herein and refer to the placement of the therapeutic agents as disclosed herein into a subject by a method or route which results in delivering of such agent(s) at a desired site. The compounds can be administered by any appropriate route which results in an effective treatment in the subject, including topical administration.

The phrases "parenteral administration" and "administered parenterally" as used herein mean modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration therapeutic compositions other than directly into a tumor such that it enters the animal's system and, thus, is subject to metabolism and other like processes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent or encapsulating material, involved in maintaining the activity of or carrying or transporting the subject agents from one organ, or portion of the body, to another organ, or portion of the body. In addition to being "pharmaceutically acceptable" as that term is defined herein, each carrier must also be "acceptable" in the sense of being compatible with the other ingredients of the formulation. The pharmaceutical formulation contains a compound of the invention in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, targeted delivery composition of the invention is formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the invention in combination with one or more pharmaceutically acceptable ingredients. The carrier can be in the form of a solid, semi-solid or liquid diluent, cream or a capsule.

The terms "composition" or "pharmaceutical composition" used interchangeably herein refer to compositions or formulations that usually comprise an excipient, such as a pharmaceutically acceptable carrier that is conventional in the art and that is suitable for administration to mammals, and preferably humans or human cells. Such compositions can be specifically formulated for administration via one or more of a number of routes, including but not limited to, oral, ocular parenteral, intravenous, intraarterial, subcutaneous, intranasal, sublingual, intraspinal, intracerebroventricular, and the like. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) *Remington: The Science and Practice of Pharmacy with Facts and Comparisons,* 21st Ed.

The term "agent" refers to any entity which is normally not present or not present at the levels being administered to a cell, tissue or subject. Agent can be selected from a group comprising: chemicals; small molecules; nucleic acid sequences; nucleic acid analogues; proteins; peptides; aptamers; antibodies; or functional fragments thereof. A nucleic acid sequence can be RNA or DNA, and can be single or double stranded, and can be selected from a group comprising: nucleic acid encoding a protein of interest; oligonucleotides; and nucleic acid analogues; for example peptide-nucleic acid (PNA), pseudo-complementary PNA (pc-PNA), locked nucleic acid (LNA), etc. Such nucleic acid sequences include, but are not limited to nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The articles "a" and "an" are used herein to refer to one or to more than one (i.e., to at least one) of the grammatical object of the article. By way of example, "an element" means one element or more than one element.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following examples, but the scope of the invention should not be limited thereto.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Anti-miR-425 Agents

The inventors herein demonstrate that miR-425 binds to, and represses, the production of ANP in AA homozygous rs5068 subjects. Accordingly, subjects that are homozygous for the major A allele (e.g., AA subjects) have lower levels of ANP which is regulated by miRNA-425 binding. The inventors also demonstrate that miR-425 repress approximately 50% of the expression of ANP levels in AG (heterozygous) rs5068 subjects. Additionally, it was also discovered that subjects that are homozygous for the minor (G) allele of rs5068 are not affected by miR-425 (e.g., effectively have resistance to the inhibitory effect of miRNA-425), and thus are not affected by miR-425-mediated inhibition of gene expression from the NPPA gene. Accordingly, subjects homozygous for the minor allele (e.g., are GG) do not have a decrease in production of the ANP peptide.

Accordingly, the inventors demonstrate that inhibitors to miRNA-425 can be used for increasing ANP in subjects having at least one A allele at the rs5068 loci Inhibitors of miRNA-425 are referred to herein as "anti-miR-425 agents" or anti-miR to miR-425. In alternative embodiments, miRNA-425 can be used to decrease ANP levels in subjects in need thereof, e.g., subjects with low blood pressure or subjects suffering from shock and the like.

The terms "anti-miR," "anti-miR agent," "antimir" "microRNA inhibitor" or "miR inhibitor" is synonymous and refers to any agent which interferes with the function of the target miRNA. In some embodiments, an anti-miR is an oligonucleotide or modified oligonucleotide that interferes with the activity of a specific miRNA, e.g., miR-425. In some embodiments, an anti-miR can also be a small molecule which interferes with the miR binding to the miRNA target binding sequence (e.g., SEQ ID NO: 8 or SEQ ID NO: 9) or a small molecule which decreases expression of the miR. In some embodiments, where an anti-miR is an oligonucleotide, an anti-miR can adopt a variety of configurations including single stranded, double stranded (RNA/RNA or RNA/DNA duplexes), and hairpin designs, in general, microRNA inhibitors comprise one or more sequences or portions of sequences that are complementary or partially complementary with the mature strand (or strands) of the miRNA to be targeted, in addition, the miRNA inhibitor can also comprise additional sequences located 5' and 3' to the sequence that is the reverse complement of the mature miRNA. The additional sequences can be the reverse complements of the sequences that are adjacent to the mature miRNA in the pri-miRNA from which the mature miRNA is derived, or the additional sequences can be arbitrary sequences (having a mixture of A, G, C, U, or dT). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. MicroRNA inhibitors, when double stranded, can include mismatches between nucleotides on opposite strands. Furthermore, microRNA inhibitors can be linked to conjugate moieties in order to facilitate uptake of the inhibitor into a cell.

Anti-miR-425 Agents

For example, encompassed in the methods of the present invention is the use of any anti-miR-425 agent which binds to the miR-425 of SEQ ID NO: 1 or to at least part of the seed sequence SEQ ID NO:2 and inhibits miR-425 mediated suppression of NPPA gene expression by the inhibiting the binding of miR-425 to the 3'UTR coding region of the NPPA mRNA. An anti-miR-425 agent can be a small molecule or oligonucleotide which inhibits binding of the miR-425 to SEQ ID NO: 8 in the 3'UTR of the NPPA gene, or alternatively, inhibits the expression of the miR-425 molecule. Such an anti-miR-425 agent which inhibits binding of the miR-425 to SEQ ID NO: 8 are useful to increase ANP levels in a subject whom is either AA or AG for the rs5068 SNP. In alternative embodiments, an anti-miR which inhibits a miRNA which binds to the miRNA target site of SEQ ID NO: 9, (e.g., the G variant of the rs5068 SNP) is also encompassed for use in the present invention, e.g., to increase ANP levels in a subject whom is either AG or GG for the rs5068 SNP.

An anti-miR agent encompassed for use in the methods, compositions and kits as disclosed herein is a nucleic acid, or analogue or mimetic thereof which is complementary to at least part of the miR-425 sequence of SEQ ID NO: 1, or at least part of the miR-425 miRNA seed sequence SEQ ID NO: 2. In some embodiments, an anti-miR agent to miRNA-425 is an anti-miR of SEQ ID NO: 3 or homologue or variant thereof.

In some embodiments, an anti-miR-425 agent is an anti-miR which is complementary to, or in part, to the miRNA seed sequence AUGACA (SEQ ID NO: 2). In some embodiments, an anti-miR-425 agent is an anti-miR (or anti-miR) of miR-425, such as an oligonucleotide of TTACTGTGCTAGT-GAGGGCAACT (SEQ ID NO: 3) or a homologue thereof. In some embodiments, where an anti-miR-425 is an oligonucleotide, such as an anti-miR which is complementary, at least in part, to the miRNA seed sequence is encoded SEQ ID NO: 2, the anti-miR-425 agent is encoded by a nucleic acid construct.

As discussed herein, encompassed for use in the methods, compositions and kits herein are anti-miR-425 agents which can be any or a combination of RNA interference molecules, for example anti-miRs, oligonucleotides, LNA, miRNA, siRNA, shRNA, or proteins, small molecules, nucleic acids, nucleic acid analogues, aptamers, antibodies, peptides and variants and analogues thereof. In some embodiments, where the anti-miR-425 agent is an antibody, the antibody can be a recombinant antibody, humanized antibody, chimeric antibody, modified antibody, monoclonal antibody, polyclonal antibody, miniantibody, dimeric miniantibody, minibody, diabody or tribody or antigen-binding variants, analogues or modified versions thereof.

In some embodiments, an anti-miR-425 agent can be RNA-interference or RNA interference molecules, including, but not limited to double-stranded RNA, such as siRNA, double-stranded DNA or single-stranded DNA. In some embodiments, an anti-miR-425 agent is a single-stranded RNA (ssRNA), a form of RNA endogenously found in eukaryotic cells as the product of DNA transcription. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme.

Numerous specific siRNA molecules have been designed that have been shown to inhibit gene expression (Ratcliff et al. Science 276:1558-1560, 1997; Waterhouse et al. Nature 411: 834-842, 2001). In addition, specific siRNA molecules have been shown to inhibit, for example, HIV-1 entry to a cell by targeting the host CD4 protein expression in target cells thereby reducing the entry sites for HIV-1 which targets cells expressing CD4 (Novina et al. Nature Medicine, 8:681-686, 2002). Short interfering RNA have further been designed and successfully used to silence expression of Fas to reduce Fas-mediated apoptosis in vivo (Song et al. Nature Medicine 9:347-351, 2003).

It has been shown in plants that longer, about 24-26 nt siRNA, correlates with systemic silencing and methylation of homologous DNA. Conversely, the about 21-22 nt short siRNA class correlates with mRNA degradation but not with systemic signaling or methylation (Hamilton et al. EMBO J. 2002 Sep. 2; 21(17):4671-9). These findings reveal an unexpected level of complexity in the RNA silencing pathway in plants that may also apply in animals. In higher order eukaryotes, DNA is methylated at cytosines located 5' to guanosine in the CpG dinucleotide. This modification has important regulatory effects on gene expression, especially when involving CpG-rich areas known as CpG islands, located in the promoter regions of many genes. While almost all gene-associated islands are protected from methylation on autosomal chromosomes, extensive methylation of CpG islands has been associated with transcriptional inactivation of selected imprinted genes and genes on the inactive X-chromosomes of females. Aberrant methylation of normally unmethylated CpG islands has been documented as a relatively frequent event in immortalized and transformed cells and has been associated with transcriptional inactivation of defined tumor suppressor genes in human cancers. In this last situation, promoter region hypermethylation stands as an alternative to coding region mutations in eliminating tumor suppression gene function (Herman, et al.). The use of siRNA molecules for directing methylation of a target gene is described in U.S. Provisional Application No. 60/447,013, filed Feb. 13, 2003, referred to in U.S. Patent Application Publication No. 20040091918.

It is also known that the RNA interference does not have to match perfectly to its target sequence. Preferably, however, the 5' and middle part of the antisense (guide) strand of the siRNA is perfectly complementary to the target nucleic acid sequence.

The RNA interference-inducing molecule functioning as miR-425 mimetics according to the present invention includes RNA molecules that have natural or modified nucleotides, natural ribose sugars or modified sugars and natural or modified phosphate backbone.

Accordingly, the RNA interference-inducing molecules functioning as a miR-425 mimetic includes, but are not limited to, unmodified and modified double stranded (ds) RNA molecules including short-temporal RNA (stRNA), small interfering RNA (siRNA), short-hairpin RNA (shRNA), microRNA (miRNA), and double-stranded RNA (dsRNA), (see, e.g. Baulcombe, Science 297:2002-2003, 2002). The dsRNA molecules, e.g. siRNA, also may contain 3' overhangs, preferably 3'UU or 3'TT overhangs. In one embodiment, the siRNA molecules do not include RNA molecules that comprise ssRNA greater than about 30-40 bases, about 40-50 bases, about 50 bases or more. In one embodiment, the siRNA molecules have a double stranded structure. In one embodiment, the siRNA molecules are double stranded for more than about 25%, more than about 50%, more than about 60%, more than about 70%, more than about 80% or more than about 90% of their length.

In some embodiments, an anti-miR-425 agent is any agent which binds to the miRNA seed sequence of SEQ ID NO: 2, and inhibits the activity of miR-425. In some embodiments, an anti-miR-425 agent is an anti-miR, which is complementary at least in part, to the miRNA seed sequence SEQ ID NO: 2, as shown in FIG. 6. In such embodiments, these agents can be an RNA interference-inducing molecule, including, but not limited to unmodified and modified double stranded (ds) RNA molecules including, short-temporal RNA (stRNA), small interfering RNA (siRNA), short-hairpin RNA (shRNA), microRNA (miRNA), and double-stranded RNA (dsRNA). In other embodiments, the agents may be any small molecule, protein, aptamer, nucleic acid analogue, antibody etc. that binds to the miRNA miR-425 of SEQ ID NO: 1, or the miR-425 seed sequence of SEQ ID NO: 2, to inhibit the interference activity of miR-425.

The miRNA and RNA interference molecules according to the present invention can be produced using any known techniques such as direct chemical synthesis, through processing of longer double stranded RNAs by exposure to recombinant Dicer protein or *Drosophila* embryo lysates, through an in vitro system derived from S2 cells, using phage RNA polymerase, RNA-dependent RNA polymerase, and DNA based vectors. Use of cell lysates or in vitro processing may further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.).

Examples of methods of preparing such RNA interference are shown, for example in an International Patent application Nos. PCT/US03/34424 and PCT/US03/34686 the contents and references of which are herein incorporated by reference in their entirety.

Various specific siRNA and miRNA molecules have been described and additional molecules can be easily designed by one skilled in the art. For example, the miRNA Database at http://www.sanger.ac.uk/Software/Rfam/mirna/index.shtml provides a useful source to identify additional miRNAs useful according to the present invention (Griffiths-Jones S. NAR, 2004, 32, Database Issue, D109-D111; Ambros V, Bartel B, Bartel D P, Burge C B, Carrington J C, Chen X, Dreyfuss G, Eddy S R, Griffiths-Jones S, Marshall M, Matzke M, Ruvkun G, Tuschl T. RNA, 2003, 9(3), 277-279).

The miRNA and RNA interference as described herein also includes RNA molecules having one or more non-natural nucleotides, i.e. nucleotides other than adenine "A", guanine "G", uracil "U", or cytosine "C", a modified nucleotide residue or a derivative or analog of a natural nucleotide are also useful. Any modified residue, derivative or analog may be used to the extent that it does not eliminate or substantially reduce (by at least 50%) RNAi activity of the dsRNA. For example, the activity a miRNA or RNAi molecule with the modified residue can be compared with the activity of a miRNA or RNAi molecule with the same nucleic acid sequence without the modified residue in an assay for gene silencing the target gene. If the miRNA or RNAi with the modified residue(s) has an efficiency of gene silencing which is the same, greater or a least half as efficient as the miRNA or RNAi without the modification, the modified mRNA or RNAi is useful in the methods and compositions as disclosed herein. Examples of modified residues, derivatives or analogues include, but are not limited to, aminoallyl UTP, pseudo-UTP, 5-I-UTP, 5-I-CTP, 5-Br-UTP, alpha-S ATP, alpha-S CTP, alpha-S GTP, alpha-S UTP, 4-thio UTP, 2-thio-CTP, 2'NH2 UTP, 2'NH$_2$ CTP, and 2'F UTP. Such modified nucleotides include, but are not limited to, aminoallyl uridine, pseudo-uridine, 5-I-uridine, 5-I-cytidine, 5-Br-uridine, alpha-S adenine, alpha-S cytidine, alpha-S guanosine, alpha-S uridine, 4-thio uridine, 2-thio-cytidine, 2'NH2 uridine, 2'NH2 cytidine, and 2' F uridine, including the free pho (NTP) RNA molecules as well as all other useful forms of the nucleotides.

RNA interference as referred to herein additionally includes RNA molecules which contain modifications in the ribose sugars, as well as modifications in the "phosphate backbone" of the nucleotide chain. For example, siRNA or miRNA molecules containing D-arabinofuranosyl structures in place of the naturally-occurring D-ribonucleosides found in RNA can be used in RNA interference according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotides and molecules similar to the oligonucleotides containing 2'-O-methyl ribose, arabinose and particularly D-arabinose (U.S. Pat. No. 5,177,196). Also, phosphorothioate linkages can be used to stabilize the siRNA and miRNA molecules (U.S. Pat. No. 5,177,196). siRNA and miRNA molecules having various "tails" covalently attached to either their 3'- or to their 5'-ends, or to both, are also been known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

MiRNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the compositions and methods disclosed herein. Anti-miRs can be used to efficiently silence endogenous miRNAs by forming duplexes comprising the anti-miR and endogenous miRNA, thereby preventing miRNA-induced gene silencing.

In some embodiments, the anti-miR is an antagomir. In some embodiment, the anti-miR is a ribozyme that can cleave the target microRNA.

Antagomirs:

Antagomirs are anti-miRs that harbor various modifications for RNAse protection and pharmacologic properties, such as enhanced tissue and cellular uptake. They differ from normal RNA by, for example, complete 2'-O-methylation of sugar, phosphorothioate intersugar linkage and, for example, a cholesterol-moiety at 3'-end. In some embodiments, antagomir comprises a 2'-O-methylmodification at all nucleotides, a cholesterol moiety at 3'-end, two phsophorothioate intersugar linkages at the first two positions at the 5'-end and four phosphorothioate linkages at the 3'-end of the molecule. Antagomirs can be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety.

Ribozymes:

Ribozymes are oligonucleotides having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes can be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

The anti-miR oligonucleotide can comprise a nucleic acid sequence that is complementary to at least a portion of a pre-miRNA-425 nucleic acid sequence (e.g. a portion of nucleic acid sequence GAAAGCGCUUUGGAAUGACAC-GAUCACUCCCGUUGAGUGGGCAC-CCGAGAAGCCAUCGGG AAUGUCGUGUCCGC-CCAGUGCUCUUUC (SEQ ID No. 13). An anti-miR oligonucleotide can be at least 75% (e.g., 80%, 85%, 90%, 91%, 92%, 93%, 94%, 95%, 96%, 97%, 98%, 99%, or 100% (i.e. completely complementary)) complementary over a sequence comprising at least 6 (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more) consecutive nucleotides of sequence of SEQ ID NO: 13.

In some embodiments, the anti-miR oligonucleotide comprises a nucleotide sequence that is complementary to at least a portion of miRNA-425 nucleic acid sequence AAUGA-CACGAUCACUCCCGUUGA (SEQ ID NO: 1 The anti-miR oligonucleotide can be at least 75% (e.g., 80%, 85%, 90%, 91%, 92%, 93%, 94%, 95%, 96%, 97%, 98%, 99%, or 100% (i.e. completely complementary)) over a sequence comprising at least 6 (e.g., 6, 7, 8, 9, 10, 11, 12, 13, 14, 15, 16, 17, 18, 19, 20, 21, 22, or 23) consecutive nucleotides of sequence of SEQ ID NO: 1.

The method of claim 4, wherein the inhibitor comprises a nucleotide sequence that is complementary to nucleic acid sequence AUGACA (SEQ ID NO: 2).

As used herein, the term "oligonucleotide" refers to a polymer or an oligomer of nucleotide or nucleoside monomers consisting of naturally occurring bases, sugars and intersugar linkages. The term "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The oligonucleotide can be single-stranded or double-stranded. A single-stranded oligonucleotide can have double-stranded regions and a double-stranded oligonucleotide can have single-stranded regions. The oligonucleotide can have a hairpin structure or have a dumbbell structure. The oligonucleotide can be, e.g., wherein the 5'end of the oligonucleotide is linked to the 3' end of the oligonucleotide.

The oligonucleotides described herein can comprise any oligonucleotide modification described herein and below. In some embodiments, the oligonucleotide comprises at least one modification. In some embodiments, the modification is selected from the group consisting of a sugar modification, a non-phosphodiester inter-sugar (or inter-nucleoside) linkage, nucleobase modification, and ligand conjugation.

In some embodiments, the oligonucleotide comprises at least two different modifications selected from the group consisting of a sugar modification, a non-phosphodiester inter-sugar linkage, nucleobase modification, and ligand conjugation. In some embodiments, the at least two different modifications are present in the same subunit of the oligonucleotide, e.g. present in the same nucleotide.

As used herein, an oligonucleotide can be of any length. In some embodiments, oligonucleotides can range from about 6 to 100 nucleotides in length. In various related embodiments, the oligonucleotide can range in length from about 10 to about 50 nucleotides, from about 10 to about 35 nucleotides, from about 15 to about 30 nucleotides, from about 20 to about 30 nucleotides in length. In some embodiments, oligonucleotide is from about 8 to about 39 nucleotides in length. In some embodiments, the oligonucleotide is 10 to 25 nucleotides in length (e.g., 10, 11, 12, 13, 14, 15, 16, 18, 19, 20, 21, 22, 23, or 24 nucleotides in length). In some embodiments the oligonucleotide is 25-30 nucleotides. In some embodiments, the single-stranded oligonucleotide is 15 to 29 nucleotides in length. In some other embodiments, the oligonucleotide is from about 18 to about 25 nucleotides in length. In some embodiments, the oligonucleotide is about 23 nucleotides in length.

The oligonucleotide can be completely DNA, completely RNA, or comprise both RNA and DNA nucleotides. It is to be understood that when the oligonucleotide is completely DNA, RNA or a mix of both, the oligonucleotide can comprise one or more oligonucleotide modifications described herein.

An oligonucleotide can be a chimeric oligonucleotide. As used herein, a "chimeric" oligonucleotide" or "chimera" refers to an oligonucleotide which contains two or more chemically distinct regions, each made up of at least one monomer unit, i.e., a modified or unmodified nucleotide in the case of an oligonucleotide. Chimeric oligonucleotides can be described as having a particular motif. In some embodiments, the motifs include, but are not limited to, an alternating motif, a gapped motif, a hemi-mer motif, a uniformly fully modified motif and a positionally modified motif. As used herein, the phrase "chemically distinct region" refers to an oligonucleotide region which is different from other regions by having a modification that is not present elsewhere in the oligonucleotide or by not having a modification that is present elsewhere in the oligonucleotide. An oligonucleotide can comprise two or more chemically distinct regions. As used herein, a region that comprises no modifications is also considered chemically distinct.

A chemically distinct region can be repeated within an oligonucleotide. Thus, a pattern of chemically distinct regions in an oligonucleotide can be realized such that a first chemically distinct region is followed by one or more second chemically distinct regions. This sequence of chemically distinct regions can be repeated one or more times. Preferably, the sequence is repeated more than one time. Both strands of a double-stranded oligonucleotides can comprise these sequences. Each chemically distinct region can actually comprise as little as a single nucleotide. In some embodiments, each chemically distinct region comprises 1, 2, 3, 4, 5, 6, 7, 8, 9, 10, 11, 12, 13, 14, 15, 16, 17 or 18 nucleotides.

In some embodiments, alternating nucleotides comprise the same modification, e.g. all the odd number nucleotides in a strand have the same modification and/or all the even number nucleotides in a strand have the similar modification to the first strand. In some embodiments, all the odd number nucleotides in an oligonucleotide have the same modification and all the even numbered nucleotides have a modification that is not present in the odd number nucleotides and vice versa.

When the oligonucleotide is double-stranded and both strands of the double-stranded oligonucleotide comprise the alternating modification patterns, nucleotides of one strand can be complementary in position to nucleotides of the second strand which are similarly modified. In an alternative embodiment, there is a phase shift between the patterns of modifications of the first strand, respectively, relative to the pattern of similar modifications of the second strand. Preferably, the shift is such that the similarly modified nucleotides of the first strand and second strand are not in complementary position to each other. In some embodiments, the first strand has an alternating modification pattern wherein alternating nucleotides comprise a 2'-modification, e.g., 2'-O-Methyl modification. In some embodiments, the first strand comprises an alternating 2'-O-Methyl modification and the second strand comprises an alternating 2'-fluoro modification. In other embodiments, both strands of a double-stranded oligonucleotide comprise alternating 2'-O-methyl modifications. When both strands of a double-stranded oligonucleotide comprise alternating 2'-O-methyl modifications, such 2'-modified nucleotides can be in complementary position in the duplex region. Alternatively, such 2'-modified nucleotides may not be in complementary positions in the duplex region.

In some embodiments, the oligonucleotide comprises two chemically distinct regions, wherein each region is 1-10 nucleotides in length.

In other embodiments, the oligonucleotide comprises three chemically distinct regions. The middle region is about 5-15, (e.g., 5, 6, 7, 8, 9, 10, 11, 12, 13, 14 or 15) nucleotide in length and each flanking or wing region is independently 1-10 (e.g., 1, 2, 3, 4, 5, 6, 7, 8, 9 or 10) nucleotides in length. All three regions can have different modifications or the wing regions can be similarly modified to each other. In some embodiments, the wing regions are of equal length, e.g. 1, 2, 3, 4, 5, 6, 7, 8, 9 or 10 nucleotides long.

As used herein the term "alternating motif" refers to an oligonucleotide comprising at least two different chemically distinct regions that alternate for essentially the entire sequence of the oligonucleotide. In an alternating motif length of each region is independent of the length of other regions.

As used herein, the term "uniformly fully modified motif" refers to an oligonucleotide wherein all nucleotides in the oligonucleotide have at least one modification that is the same.

As used herein, the term "hemi-mer motif" refers to an oligonucleotide having two chemically distinct regions, wherein one region is at the 5' end of the oligonucleotide and the other region is at the 3 end of the oligonucleotide. In some embodiments, length of each chemically distinct region is independently 1 nucleotide to 1 nucleotide less than the length of the oligonucleotide.

As used herein the term "gapped motif" refers to an oligonucleotide having three chemically distinct regions. In some embodiments, the gapped motif is a symmetric gapped motif, wherein the two outer chemically distinct regions (wing regions) are identically modified. In another embodiment, the gapped motif is an asymmetric gaped motif in that the three regions are chemically distinct from each other As used herein the term "positionally modified motif" refers to an oligonucleotide having three or more chemically distinct regions. Positionally modified oligonucleotides are distinguished from gapped motifs, hemi-mer motifs, block-mer motifs and alternating motifs because the pattern of regional substitution defined by any positional motif does not fit into the definition provided herein for one of these other motifs. The term positionally modified oligomeric compound includes many different specific substitution patterns.

In some embodiments, oligonucleotide comprises two or more chemically distinct regions and has a structure as described in International Application No. PCT/US09/038433, filed Mar. 26, 2009, content of which is incorporated herein by reference in its entirety. In some embodiments, the single-stranded oligonucleotide has a ZXY structure, such as is described in International Application No. PCT/US2004/07070 filed on Mar. 8, 2004, content of which is incorporated herein by reference in its entirety.

In some embodiments, the anti-miR oligonucleotide comprises 2'-MOE modifications at all positions and phosphorothioate inter-sugar linkages at all positions.

In some embodiments, the anti-miR comprises a mix of 2'-F and 2'-MOE modified nucleotides.

In some embodiments, the anti-miR comprises at least 1 (e.g., 1, 2, 3, 4, or 5) 2'-F modified nucleotides at the 5' end (i.e., the first 1, 2, 3, 4, or 5 nucleotides at the 5' end are 2'-F modified nucleotides).

In some embodiments, the anti-miR comprises at least 1 (e.g., 1, 2, 3, 4, or 5) 2'-F modified nucleotides at the 3' end (i.e., the first 1, 2, 3, 4, or 5 nucleotides at the 3' end are 2'-F modified nucleotides).

In some embodiments, the anti-miR comprises, independently, at least 1 (e.g., 1, 2, 3, 4, or 5) 2'-F modified nucleotides at the 5' end and at the 3' end and 2'-MOE modified nucleotides at all other positions.

In some embodiments, the anti-miR comprises two 2'-F modified nucleotides at the 5' end and at the 3' end and 2'-MOE modified nucleotides at all other positions, e.g., a 2'-F/2'-MOE mixmer.

In some embodiments, the anti-miR comprises two 2'-F modified nucleotides at the 5' end and at the 3' end, 2'-MOE modified nucleotides at all other positions, and phosphorothioate inter-sugar linkages at all positions.

In some embodiments, the anti-miR comprises a mix of LNA and DNA monomers, e.g., a LNA/DNA mixmer. The LNA and DNA monomers can be arranged in any pattern. In some embodiments, the LNA and DNA monomers are arranged in an alternative pattern, e.g., a LNA monomer followed by a DNA monomer. This alternating pattern can be repeated for the full length of the anti-miR.

The oligonucleotide can hybridize to a complementary RNA, e.g., mRNA, pre-mRNA, microRNA, or pre-microRNA and reduce the activity, expression, or amount of the complementary RNA, e.g., target RNA. This can be by reducing access of the translation machinery to the target RNA transcript, thereby preventing protein synthesis. The oligonucleotide can induce cleavage of the complementary RNA by an enzyme, such RISC mediated cleavage or RNase H and thus reducing the amount of the target RNA. The oligonucleotide itself can cleave the complementary RNA, e.g., a ribozyme, RISC mediated cleavage or RNase H and thus reducing the amount of the target RNA. The oligonucleotide, by hybridizing to the target RNA, can inhibit binding of the target RNA to another complementary strand.

By "target sequence" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, mammal, or plant.

In some embodiments, the target sequence is a nucleic acid encoding, expressing or comprising the nucleotide sequence of pre-miRNA-425, e.g., SEQ ID NO: 13. In some embodiments, the target sequence is a nucleic acid encoding, expressing or comprising the nucleotide sequence of miR-425, e.g., SEQ ID NO: 1. In some embodiments, the target sequence is a nucleic acid encoding, expressing or comprising the nucleotide sequence of miR-425 seed sequence, e.g., SEQ ID NO: 2.

By "specifically hybridizable" and "complementary" is meant that a first nucleic acid strand can form hydrogen bond(s) with a second nucleic acid strand by either traditional Watson-Crick or other non-traditional types. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other. "Substantial complementarity" refers to polynucleotide strands exhibiting 90% or greater complementarity, excluding regions of the polynucleotide strands, such as overhangs, that are selected so as to be non-complementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 1, 2, 3, 4, or 5 nucleotides.

miR-425 Agents

In some embodiments, where the miR-425 is administered to a subject, (e.g., to a subject with low blood pressure, or where it is desirable to increase blood pressure in a subject, e.g., a subject suffering from severe shock) a miR-425 miRNA can be a pri-miRNA, pre-miRNA, mature miRNA or a fragment or variant thereof effective in gene silencing the 3'UTR of the ANP mRNA. In some embodiments, the miR-425 comprises SEQ ID NO: 1 or a fragment or homologue thereof effective in gene silencing. In alternative embodiments, miR-425 homologues can be used, or a fragment thereof effective in gene silencing the 3'UTR of NPPA mRNA, in particular, effective at binding to the "A" major allele miRNA target sequence of 5'ATGACAC-3' (SEQ ID NO: 8), where a subject is homozygous AA for the major allele of rs5068. In some embodiments, a miR-425 homologue which is effective at binding the "G" minor allele miRNA in the target sequence of 5'GTGACAC-3' (SEQ ID NO: 9) can be used to reduce ANP levels by gene silencing the 3'URT of the NPPA gene in a subject is heterozygous (AG) or homozygous (GG) for the minor allele of rs5068. In other embodiments, the miR-425 is an RNA interference-inducing (RNAi) molecule including, but not limited to, a siRNA, dsRNA, stRNA, shRNA and gene silencing variants thereof. In alternative embodiments the miR-425 is an agent which binds and inhibits an RNA transcript comprising a miR-425 target sequence. Examples of such agents include, but are not limited to an anti-miR, small molecule, protein, antibody, aptamer, ribozyme, nucleic acid or nucleic acid analogue.

MicroRNAs (also referred to as miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

MicroRNAs have also been implicated in modulation of pathogens in hosts. For example, see Jopling, C. L., et al., *Science* (2005) vol. 309, pp 1577-1581. Without wishing to be bound by theory, administration of a microRNA, microRNA mimic, and/or anti microRNA oligonucleotide, leads to modulation of pathogen viability, growth, development, and/or replication. In some embodiments, the oligonucleotide is a microRNA, microRNA mimic, and/or anti microRNA, wherein microRNA is a host microRNA (miRNA).

Methods of making and stabilizing miRNAs for therapeutic use are well known in the art, and are discussed in Broderick et al., Gene Therapy, 2011; 18; 1104-1110, which is incorporated herein in its entirety by reference. Broderick et al., also discusses methods of artificially inhibiting miRNAs, suitable for generating anti-miR-425 agents as disclosed herein.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; "*The microRNA Registry*" Griffiths-Jones S. NAR, 2004, 32, Database Issue, D109-D111; and also on the worldwide web at microrna.dot.sanger.dot.ac.dot.uk/sequences/.

miRNA Mimics:

miRNA mimics represent a class of molecules that can be used to imitate the gene modulating activity of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs).

In one design, miRNA mimics are double stranded molecules (e.g., with a duplex region of between about 16 and about 31 nucleotides in length) and contain one or more sequences that have identity with the mature strand of a given miRNA. Double-stranded miRNA mimics have designs similar to as described above for double-stranded oligonucleotides.

In some embodiments, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

Supermirs:

A supermir refers to an oligonucleotide, e.g., single stranded, double-stranded or partially double-stranded, which has a nucleotide sequence that is substantially identical to an miRNA and that is antisense with respect to its target. This term includes oligonucleotides which comprise at least one non-naturally-occurring portion which functions similarly. In a preferred embodiment, the supermir does not include a sense strand, and in another preferred embodiment, the supermir does not self-hybridize to a significant extent. A supermir featured in the invention can have secondary structure, but it is substantially single-stranded under physiological conditions. A supermir that is substantially single-stranded is single-stranded to the extent that less than about 50% (e.g., less than about 40%, 30%, 20%, 10%, or 5%) of the supermir is duplexed with itself. The supermir can include a hairpin segment, e.g., sequence, preferably at the 3' end can self hybridize and form a duplex region, e.g., a duplex region of at least 1, 2, 3, or 4 and preferably less than 8, 7, 6, or 5 nucleotides, e.g., 5 nucleotides. The duplexed region can be connected by a linker, e.g., a nucleotide linker, e.g., 3, 4, 5, or 6 dTs, e.g., modified dTs. In another embodiment the supermir is duplexed with a shorter oligo, e.g., of 5, 6, 7, 8, 9, or 10 nucleotides in length, e.g., at one or both of the 3' and 5' end or at one end and in the non-terminal or middle of the supermir.

Oligonucleotide Modifications

In some embodiments, anti-miR-425 agents and miR-425 agents for use in the aspects of the invention as disclosed herein can include oligonucleotide modifications. Unmodified oligonucleotides can be less than optimal in some applications, e.g., unmodified oligonucleotides can be prone to degradation by e.g., cellular nucleases. However, chemical modifications to one or more of the subunits of oligonucleotide can confer improved properties, e.g., can render oligonucleotides more stable to nucleases. Typical oligonucleotide modifications can include one or more of: (i) alteration, e.g., replacement, of one or both of the non-linking phosphate oxygens and/or of one or more of the linking phosphate oxygens in the phosphodiester intersugar linkage; (ii) alteration, e.g., replacement, of a constituent of the ribose sugar, e.g., of the 2' hydroxyl on the ribose sugar; (iii) wholesale replacement of the phosphate moiety with "dephospho" linkers; (iv) modification or replacement of a naturally occurring base with a non-natural base; (v) replacement or modification of the ribose-phosphate backbone, e.g. peptide nucleic acid (PNA); (vi) modification of the 3' end or 5' end of the oligonucleotide, e.g., removal, modification or replacement of a terminal phosphate group or conjugation of a moiety, e.g., conjugation of a ligand, to either the 3' or 5' end of oligonucleotide; and (vii) modification of the sugar, e.g., six membered rings.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule. As described below, modifications, e.g., those described herein, can be provided as asymmetrical modifications.

A modification described herein can be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

Modifications of Phosphate Group:

The phosphate group in the intersugar linkage can be modified by replacing one of the oxygens with a different substituent. One result of this modification to RNA phosphate intersugar linkages can be increased resistance of the oligonucleotide to nucleolytic breakdown. Examples of modified phosphate groups include phosphorothioate, phosphoroselenates, borano phosphates, borano phosphate esters, hydrogen phosphonates, phosphoroamidates, alkyl or aryl phosphonates and phosphotriesters. In some embodiments, one of the non-bridging phosphate oxygen atoms in the intersugar linkage can be replaced by any of the following: S, Se, $BR_3$ (R is hydrogen, alkyl, aryl), C (i.e. an alkyl group, an aryl group, etc. . . . ), H, NR (R is hydrogen, optionally substituted alkyl, aryl), or OR (R is optionally substituted alkyl or aryl). The phosphorus atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligonucleotides diastereomers. Thus, while not wishing to be bound by theory, modifications to both non-bridging oxygens, which eliminate the chiral center, e.g. phosphorodithioate formation, can be desirable in that they cannot produce diastereomer mixtures. Thus, the non-bridging oxygens can be independently any one of O, S, Se, B, C, H, N, or OR (R is alkyl or aryl).

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either one of the linking oxygens or at both linking oxygens.

When the bridging oxygen is the 3'-oxygen of a nucleoside, replacement with carbon is preferred. When the bridging oxygen is the 5'-oxygen of a nucleoside, replacement with nitrogen is preferred.

Modified phosphate linkages where at least one of the oxygen linked to the phosphate has been replaced or the phosphate group has been replaced by a non-phosphorous group, are also referred to as "non-phosphodiester intersugar linkage" or "non-phosphodiester linker."

Replacement of the Phosphate Group:

The phosphate group can be replaced by non-phosphorus containing connectors, e.g. dephospho linkers. Dephospho linkers are also referred to as non-phosphodiester linkers herein. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include, but are not limited to, amides (for example amide-3 (3'-$CH_2$—C(=O)—N(H)-5') and amide-4 (3'-$CH_2$—N(H)—C(=O)-5')), hydroxylamino, siloxane (dialkylsiloxxane), carboxamide, carbonate, carboxymethyl, carbamate, carboxylate ester, thioether, ethylene oxide linker, sulfide, sulfonate, sulfonamide, sulfonate ester, thioformacetal (3'-S—$CH_2$—O-5'), formacetal (3'-O—$CH_2$—O-5'), oxime, methyleneimino, methykenecarbonylamino, methylenemethylimino (MMI, 3'-$CH_2$—N($CH_3$)—O-5'), methylenehydrazo, methylenedimethylhydrazo, methyleneoxymethylimino, ethers (C3'-O—C5'), thioethers (C3'-S—C5'), thioacetamido (C3'-N(H)—C(=O)—$CH_2$—S—C5', C3'-O—P(O)—O—SS—C5', C3'-$CH_2$—NH—NH—C5', 3'-NHP(O)($OCH_3$)—O-5' and 3'-NHP(O)($OCH_3$)—O-5' and nonionic linkages containing mixed N, O, S and $CH_2$ component parts. See for example, Carbohydrate Modifications in Antisense Research; Y. S. Sanghvi and P. D. Cook Eds. ACS Symposium Series 580; Chapters 3 and 4, (pp. 40-65). Preferred embodiments include methylenemethylimino (MMI), methylenecarbonylamino, amides, carbamate and ethylene oxide linker.

One skilled in the art is well aware that in certain instances replacement of a non-bridging oxygen can lead to enhanced cleavage of the intersugar linkage by the neighboring 2'-OH, thus in many instances, a modification of a non-bridging oxygen can necessitate modification of 2'-OH, e.g., a modification that does not participate in cleavage of the neighboring intersugar linkage, e.g., arabinose sugar, 2'-O-alkyl, 2'-F, LNA and ENA.

Preferred non-phosphodiester intersugar linkages include phosphorothioates, phosphorothioates with an at least 1%, 5%, 10%, 20%, 30%, 40%, 50%, 60%, 70%, 80%, 90% 95% or more enantiomeric excess of Sp isomer, phosphorothioates with an at least 1%, 5%, 10%, 20%, 30%, 40%, 50%, 60%, 70%, 80%, 90% 95% or more enantiomeric excess of Rp isomer, phosphorodithioates, phsophotriesters, aminoalkylphosphotrioesters, alkyl-phosphonaters (e.g., methyl-phosphonate), selenophosphates, phosphoramidates (e.g., N-alkylphosphoramidate), and boranophosphonates.

Replacement of Ribophosphate Backbone:

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the morpholino, cyclobutyl, pyrrolidine, peptide nucleic acid (PNA), aminoethylglycyl PNA (aegPNA) and backnone-extended pyrrolidine PNA (bepPNA) nucleoside surrogates. In some embodiments, the oligonucleotide is a peptide nucleic acid, e.g., the ribophosphate backbone of the oligonucleotide is completely replaced by peptide nucleic acid (PNA).

Sugar Modifications:

An oligonucleotide can include modification of all or some of the sugar groups of the nucleic acid. For example, the 2' position (H, DNA; or OH, RNA) can be modified with a number of different "oxy" or "deoxy" substituents. While not being bound by theory, enhanced stability is expected since the 2'-hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O($CH_2CH_2O$)$_n$$CH_2CH_2$OR, n=1-50; "locked" nucleic acids (LNA) in which the oxygen at the 2' position is connected by ($CH_2$)$_n$, wherein n=1-4, to the 4' carbon of the same ribose sugar, preferably n is 1 (LNA) or 2 (ENA); O-AMINE or O—($CH_2$)$_n$AMINE (n=1-10, AMINE=$NH_2$; alkylamino, dialkylamino, heterocyclyl, arylamino, diaryl amino, heteroaryl amino, diheteroaryl amino, ethylene diamine or polyamino); and O—$CH_2CH_2$(N$CH_2CH_2$N$Me_2$)$_2$.

Examples of "deoxy" modifications include halo (e.g., fluoro); amino (e.g. $NH_2$; alkylamino, dialkylamino, heterocyclyl, arylamino, diaryl amino, heteroaryl amino, diheteroaryl amino, or amino acid); NH($CH_2CH_2$NH)$_n$$CH_2CH_2$-AMINE (AMINE=$NH_2$; alkylamino, dialkylamino, heterocyclyl, arylamino, diaryl amino, heteroaryl amino, or diheteroaryl amino); —NHC(O)R (R=alkyl, cycloalkyl, aryl, aralkyl, heteroaryl or sugar); cyano; mercapto; alkyl-thioalkyl; thioalkoxy; thioalkyl; alkyl; cycloalkyl; aryl; alkenyl and alkynyl, which can be optionally substituted with e.g., amino functionality.

The sugar group can also contain one or more carbons that possess the opposite stereochemical configuration than that of the corresponding carbon in the ribose sugar. Thus, an oligonucleotide can include nucleotides containing e.g., arabinose, as the sugar. Similarly, a modification at the 2' position can be present in the arabinose configuration The term "arabinose configuration" refers to the placement of a substituent on the C2' of ribose in the same configuration as the 2'-OH is in the arabinose.

A nucleotide can have an alpha linkage at the 1' position on the sugar, e.g., alpha-nucleosides. The monomer can also have the opposite configuration at the 4'-position, e.g., C5' and H4' or substituents replacing them are interchanged with each other. When the C5' and H4' or substituents replacing them are interchanged with each other, the sugar is said to be modified at the 4' position.

Oligonucleotides can also include abasic sugars, i.e., monomers which lack a nucleobase at C-1' or has other chemical groups in place of a nucleobase at C1'. See for example U.S. Pat. No. 5,998,203, contents of which are herein incorporated in their entirety. These abasic sugars can also be further containing modifications at one or more of the constituent sugar atoms. Oligonucleotides can also contain one or more sugars that are the L isomer, e.g. L-nucleosides. Modification to the sugar group can also include replacement of the 4'-O with a sulfur, optionally substituted nitrogen or CH$_2$ group. In some embodiments, linkage between C1' and nucleobase is in the a configuration.

Oligonucleotide modifications can also include acyclic nucleotides, wherein a C—C bonds between ribose carbons (e.g., C1'-C2', C2'-C3', C3'-C4', C4'-O4', C1'-O4') is absent and/or at least one of ribose carbons or oxygen (e.g., C1', C2', C3', C4' or O4') are independently or in combination absent from the nucleotide. In some embodiments, acyclic nucleotide is

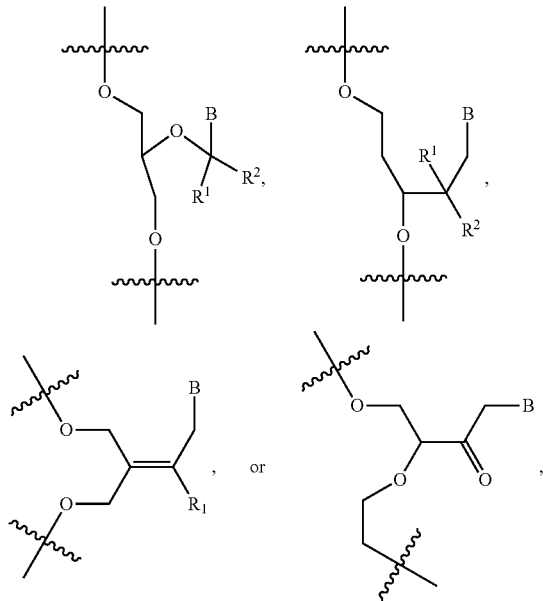

wherein B is a modified or unmodified nucleobase, R$_1$ and R$_2$ independently are H, halogen, OR$_3$, or alkyl; and R$_3$ is H, alkyl, cycloalkyl, aryl, aralkyl, heteroaryl or sugar).

Preferred sugar modifications are 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA), 2'-O—CH$_2$CH$_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP), and 2'-O-dimethylaminoethyloxyethyl (2'-O-DMAEOE).

It is to be understood that when a particular nucleotide is linked through its 2'-position to the next nucleotide, the sugar modifications described herein can be placed at the 3'-position of the sugar for that particular nucleotide, e.g., the nucleotide that is linked through its 2'-position. A modification at the 3' position can be present in the xylose configuration. The term "xylose configuration" refers to the placement of a substituent on the C3' of ribose in the same configuration as the 3'-OH is in the xylose sugar.

The hydrogen attached to C4' and/or C1' can be replaced by a straight- or branched-optionally substituted alkyl, optionally substituted alkenyl, optionally substituted alkynyl, wherein backbone of the alkyl, alkenyl and alkynyl can contain one or more of O, S, S(O), SO$_2$, N(R'), C(O), N(R')C(O)O, OC(O)N(R'), CH(R'), phosphorous containing linkage, optionally substituted aryl, optionally substituted heteroaryl, optionally substituted heterocyclic or optionally substituted cycloalkyl, where R' is hydrogen, halogen, alkyl, alkenyl, alkynyl, alkoxy, aryl, heteroaryl, cyclyl, or heterocyclyl, each of which can be optionally substituted. In some embodiments, the hydrogen attached to the C4' of the 5' terminal nucleotide is replaced.

In some embodiments, C4' and C5' together form an optionally substituted heterocyclic, preferably comprising at least one —PX(Y)—, wherein X is H, OH, OM, SH, optionally substituted alkyl, optionally substituted alkoxy, optionally substituted alkylthio, optionally substituted alkylamino or optionally substituted dialkylamino, where M is independently for each occurrence an alki metal or transition metal with an overall charge of +1; and Y is O, S, or NR', where R' is hydrogen, optionally substituted aliphatic. Preferably this modification is at the 5 terminal of the oligonucleotide.

Nucleobase Modifications:

Adenine, cytosine, guanine, thymine and uracil are the most common bases (or nucleobases) found in nucleic acids. These bases can be modified or replaced to provide oligonucleotides having improved properties. For example, nuclease resistant oligonucleotides can be prepared with these bases or with synthetic and natural nucleobases (e.g., inosine, xanthine, hypoxanthine, nubularine, isoguanisine, or tubercidine) and any one of the above modifications. Alternatively, substituted or modified analogs of any of the above bases and "universal bases" can be employed. When a natural base is replaced by a non-natural and/or universal base, the nucleotide is said to comprise a modified nucleobase and/or a nucleobase modification herein. Modified nucleobase and/or nucleobase modifications also include natural, non-natural and universal bases, which comprise conjugated moieties, e.g. a ligand described herein. Preferred conjugate moieties for conjugation with nucleobases include cationic amino groups which can be conjugated to the nucleobase via an appropriate alkyl, alkenyl or a linker with an amide linkage.

An oligonucleotide can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as inosine, xanthine, hypoxanthine, nubularine, isoguanisine, tubercidine, 2-(halo)adenine, 2-(alkyl)adenine, 2-(propyl)adenine, 2-(amino)adenine, 2-(aminoalkyll)adenine, 2-(aminopropyl)adenine, 2-(methylthio)-N$^6$-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, N$^6$-(isopentyl)adenine, N$^6$-(methyl)adenine, N$^6$,N$^6$-(dimethyl)adenine, 2-(alkyl)guanine, 2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, N$^4$-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)

uracil, 5-(alkynyl)uracil, 5-(allylamino)uracil, 5-(aminoallyl)uracil, 5-(aminoalkyl)uracil, 5-(guanidiniumalkyl)uracil, 5-(1,3-diazole-1-alkyl)uracil, 5-(cyanoalkyl) uracil, 5-(dialkylaminoalkyl)uracil, 5-(dimethylaminoalkyl) uracil, 5-(halo)uracil, 5-(methoxy)uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl) uracil, 5-(trifluoromethyl)uracil, 6-(azo)uracil, dihydrouracil, $N^3$-(methyl)uracil, 5-uracil (i.e., pseudouracil), 2-(thio) pseudouracil, 4-(thio)pseudouracil, 2,4-(dithio) psuedouracil, 5-(alkyl)pseudouracil, 5-(methyl) pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio) pseudouracil, 5-(methyl)-2,4-(dithio)pseudouracil, 1-substituted pseudouracil, 1-substituted 2(thio)-pseudouracil, 1-substituted 4-(thio)pseudouracil, 1-substituted 2,4-(dithio) pseudouracil, 1-(aminocarbonylethylenyl)-pseudouracil, 1-(aminocarbonylethylenyl)-2(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylaminocarbonylethylenyl)-2(thio)-pseudouracil, 1-(aminoalkylaminocarbonylethylenyl)-4-(thio)pseudouracil, 1-(aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5-nitroindole, 3-nitropyrrole, 6-(aza) pyrimidine, 2-(amino)purine, 2,6-(diamino)purine, 5-substituted pyrimidines, $N^2$-substituted purines, $N^6$-substituted purines, $O^6$-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof. Alternatively, substituted or modified analogs of any of the above bases and "universal bases" can be employed.

As used herein, a universal nucleobase is any modified or nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylinolyl, 4,6-dimethylindolyl, phenyl, napthalenyl, anthracenyl, phenanthracenyl, pyrenyl, stilbenyl, tetracenyl, pentacenyl, and structural derivatives thereof (see for example, Loakes, 2001, *Nucleic Acids Research*, 29, 2437-2447).

Further nucleobases include those disclosed in U.S. Pat. No. 3,687,808; those disclosed in International Application No. PCT/US09/038425, filed Mar. 26, 2009; those disclosed in the Concise Encyclopedia Of Polymer Science And Engineering, pages 858-859, Kroschwitz, J. I., ed. John Wiley & Sons, 1990; those disclosed by English et al., Angewandte Chemie, International Edition, 1991, 30, 613; those disclosed in Modified Nucleosides in Biochemistry, Biotechnology and Medicine, Herdewijin, P. Ed. Wiley-VCH, 2008; and those disclosed by Sanghvi, Y. S., Chapter 15, dsRNA Research and Applications, pages 289-302, Crooke, S. T. and Lebleu, B., Eds., CRC Press, 1993. Contents of all of the above are herein incorporated by reference.

Terminal Modifications:

In vivo applications of oligonucleotides can be limited due to presence of nucleases in the serum and/or blood. Thus in certain instances it is preferable to modify the 3', 5' or both ends of an oligonucleotide to make the oligonucleotide resistant against exonucleases. In some embodiments, the oligonucleotide comprises a cap structure at 3' (3'-cap), 5' (5'-cap) or both ends. In some embodiments, oligonucleotide comprises a 3'-cap. In another embodiment, oligonucleotide comprises a 5'-cap. In yet another embodiment, oligonucleotide comprises both a 3' cap and a 5' cap. It is to be understood that when an oligonucleotide comprises both a 3' cap and a 5' cap, such caps can be same or they can be different.

As used herein, "cap structure" refers to chemical modifications, which have been incorporated at either terminus of oligonucleotide. See for example U.S. Pat. No. 5,998,203 and International Patent Publication WO03/70918, contents of which are herein incorporated in their entireties.

Exemplary 5'-caps include, but are not limited to, ligands, 5'-5'-inverted nucleotide, 5'-5'-inverted abasic nucleotide residue, 2'-5' linkage, 5'-amino, 5'-amino-alkyl phosphate, 5'-hexylphosphate, 5'-aminohexyl phosphate, bridging and/or non-bridging 5'-phosphoramidate, bridging and/or non-bridging 5'-phosphorothioate and/or 5'-phosphorodithioate, bridging or non bridging 5'-methylphosphonate, non-phosphodiester intersugar linkage between the end two nucleotides, 4',5'-methylene nucleotide, I-(beta-D-erythrofuranosyl) nucleotide, 4'-thio nucleotide, carbocyclic nucleotide, 1,5-anhydrohexitol nucleotide, L-nucleotides, alpha-nucleotides, modified nucleobase nucleotide, phosphorodithioate linkage, threo-pentofuranosyl nucleotide, acyclic nucleotide, acyclic 3,4-dihydroxybutyl nucleotide, acyclic 3,5-dihydroxypentyl nucleotide, 5'-mercapto nucleotide and 5'-1,4-butanediol phosphate.

Exemplary 3'-caps include, but are not limited to, ligands, 3'-3'-inverted nucleotide, 3'-3'-inverted abasic nucleotide residue, 3'-2'-inverted nucleotide moiety, 3'-2'-inverted abasic moiety, 2'-5'-linkage, 3'-amino, 3'-amino-alkyl phosphate, 3'-hexylphosphate, 3'-aminohexyl phosphate, bridging and/or non-bridging 3'-phosphoramidate, bridging and/or non-bridging 3'-phosphorothioate and/or 3'-phosphorodithioate, bridging or non bridging 3'-methylphosphonate, non-phosphodiester intersugar linkage between the end two nucleotides, I-(beta-D-erythrofuranosyl) nucleotide, 4'-thio nucleotide, carbocyclic nucleotide, 1,5-anhydrohexitol nucleotide, L-nucleotides, alpha-nucleotides, modified nucleobase nucleotide, phosphorodithioate linkage, threo-pentofuranosyl nucleotide, acyclic nucleotide, acyclic 3,4-dihydroxybutyl nucleotide, acyclic 3,5-dihydroxypentyl nucleotide, and 3'-1,4-butanediol phosphate. For more details see Beaucage and Iyer, 1993, *Tetrahedron* 49, 1925, incorporated by reference herein.

Other 3' and/or 5' caps amenable to the invention are described in U.S. Provisional Application No. 61/223,665, filed Jul. 7, 2009, contents of which are herein incorporated in their entirety.

The 3' and/or 5' ends of an oligonucleotide can also be conjugated to other functional molecular entities such as labeling moieties, e.g., fluorophore (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

Terminal modifications useful for modulating activity include modification of the 5' end with phosphate or phosphate analogs. For example, in some embodiments the 5' end of the oligonucleotide can be phosphorylated or includes a phosphoryl analog at the 5' terminus. The 5'-phosphate modifications can include those which are compatible with RISC mediated gene silencing. Modifications at the 5'-terminal end can also be useful in stimulating or inhibiting the immune system of a subject. In some embodiments, the 5'-end of the oligonucleotide comprises the modification

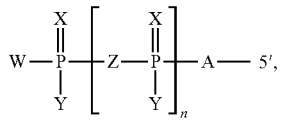

wherein W, X and Y are each independently selected from the group consisting of O, OR (R is hydrogen, alkyl, aryl), S, Se, BR$_3$ (R is hydrogen, alkyl, aryl), BH$_3^-$, C (i.e. an alkyl group, an aryl group, etc. . . . ), H, NR$_2$ (R is hydrogen, alkyl, aryl), or OR (R is hydrogen, alkyl or aryl); A and Z are each independently for each occurrence absent, O, S, CH$_2$, NR (R is hydrogen, alkyl, aryl), or optionally substituted alkylene, wherein backbone of the alkylene can comprise one or more of O, S, SS and NR (R is hydrogen, alkyl, aryl) internally and/or at the end; and n is 0-2. In some embodiments n is 1 or 2. It is understood that A is replacing the oxygen linked to 5' carbon of sugar.

In some embodiments, one or both hydrogen on C5' of the 5'-terminal nucleotides can be replaced with a halogen, e.g., F.

Exemplary 5'-modifications include, but are not limited to, 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); 5'-alpha-thiotriphosphate; 5'-beta-thiotriphosphate; 5'-gamma-thiotriphosphate; 5'-phosphoramidates ((HO)$_2$(O)P—NH-5', (HO)(NH$_2$)(O)P—O-5'). Other 5'-modification include 5'-alkylphosphonates (R(OH)(O)P—O-5', R=alkyl, e.g., methyl, ethyl, isopropyl, propyl, etc. . . . ), 5'-alkyletherphosphonates (R(OH)(O)P—O-5', R=alkylether, e.g., methoxymethyl (CH$_2$OMe), ethoxymethyl, etc. . . . ). Other exemplary 5'-modifications include where Z is optionally substituted alkyl at least once, e.g., ((HO)$_2$(X)P—O[—(CH$_2$)$_a$—O—P(X)(OH)—O]$_b$-5', ((HO)2(X)P—O[—(CH$_2$)$_a$—P(X)(OH)—O]$_b$-5', ((HO)2(X)P—[—(CH$_2$)$_a$—O—P(X)(OH)—O]$_b$-5'; dialkyl terminal phosphates and phosphate mimics: HO[—(CH$_2$)$_a$—O—P(X)(OH)—O]$_b$-5', H$_2$N[—(CH$_2$)$_a$—O—P(X)(OH)—O]$_b$-5', H[—(CH$_2$)$_a$—O—P(X)(OH)—O]$_b$-5', Me$_2$N[—(CH$_2$)$_a$—O—P(X)(OH)—O]$_b$-5', HO[—(CH$_2$)$_a$—P(X)(OH)—O]$_b$-5', H$_2$N[—(CH$_2$)$_a$—P(X)(OH)—O]$_b$-5', H[—(CH$_2$)$_a$—P(X)(OH)—O]$_b$-5', Me$_2$N[—(CH$_2$)$_a$—P(X)(OH)—O]$_b$-5', wherein a and b are each independently 1-10. Other embodiments include replacement of oxygen and/or sulfur with BH$_3$, BH$_3^-$ and/or Se.

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include targeting ligands. Terminal modifications can also be useful for cross-linking an oligonucleotide to another moiety; modifications useful for this include mitomycin C, psoralen, and derivatives thereof.

Ligands:

A wide variety of entities, e.g., ligands, can be coupled to the oligonucleotides described herein. Ligands can include naturally occurring molecules, or recombinant or synthetic molecules. Exemplary ligands include, but are not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG]$_2$, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g., steroids, bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., a helical cell-permeation agent).

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic) is a molecule capable of folding into a defined three-dimensional structure similar to a natural peptide. The peptide or peptidomimetic ligand can be about 5-50 amino acids long, e.g., about 5, 10, 15, 20, 25, 30, 35, 40, 45, or 50 amino acids long.

Exemplary amphipathic peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, H$_2$A peptides, Xenopus peptides, esculentinis-1, and caerins.

As used herein, the term "endosomolytic ligand" refers to molecules having endosomolytic properties. Endosomolytic ligands promote the lysis of and/or transport of the composition of the invention, or its components, from the cellular compartments such as the endosome, lysosome, endoplasmic reticulum (ER), golgi apparatus, microtubule, peroxisome, or other vesicular bodies within the cell, to the cytoplasm of the cell. Some exemplary endosomolytic ligands include, but are not limited to, imidazoles, poly or oligoimidazoles, linear or branched polyethyleneimines (PEIs), linear and brached polyamines, e.g. spermine, cationic linear and branched polyamines, polycarboxylates, polycations, masked oligo or poly cations or anions, acetals, polyacetals, ketals/polyketals, orthoesters, linear or branched polymers with masked or unmasked cationic or anionic charges, dendrimers with masked or unmasked cationic or anionic charges, polyanionic peptides, polyanionic peptidomimetics, pH-sensitive peptides, natural and synthetic fusogenic lipids, natural and synthetic cationic lipids.

Exemplary endosomolytic/fusogenic peptides include, but are not limited to,

```
                                              SEQ ID NO: 14,
AALEALAEALEALAEALEALAEAAAAGGC (GALA);

SEQ ID NO: 15,
AALAEALAEALAEALAEALAEALAAAAGGC (EALA);

SEQ ID NO: 16,
ALEALAEALEALAEA;

SEQ ID NO: 17,
GLFEAIEGFIENGWEGMIWDYG (INF-7);

SEQ ID NO: 18,
GLFGAIAGFIENGWEGMIDGWYG (Inf HA-2);

SEQ ID NO: 19,
GLFEAIEGFIENGWEGMIDGWYGCGLFEAIEGFIENGWEGMID GWYGC
(diINF-7);

SEQ ID NO: 20,
GLFEAIEGFIENGWEGMIDGGCGLFEAIEGFIENGWEGMIDGGC
(diINF-3);

SEQ ID NO: 21,
GLFGALAEALAEALAEHLAEALAEALEALAAGGSC (GLF);

SEQ ID NO: 22,
GLFEAIEGFIENGWEGLAEALAEALEALAAGGSC (GALA-INF3);

SEQ ID NO: 23,
GLF EAI EGFI ENGW EGnI DG K GLF EAI EGFI ENGW
EGnI DG (INF-5, n is norleucine);

SEQ ID NO: 24,
LFEALLELLESLWELLLEA (JTS-1);

SEQ ID NO: 25,
GLFKALLKLLKSLWKLLLKA (ppTG1);

SEQ ID NO: 26,
GLFRALLRLLRSLWRLLLRA (ppTG20);

SEQ ID NO: 27,
WEAKLAKALAKALAKHLAKALAKALKACEA (KALA);

SEQ ID NO: 28,
GLFFEAIAEFIEGGWEGLIEGC (HA);

SEQ ID NO: 29,
GIGAVLKVLTTGLPALISWIKRKRQQ (Melittin);

SEQ ID NO: 30,
H$_5$WYG;
and

SEQ ID NO: 31,
CHK$_6$HC.
```

Without wishing to be bound by theory, fusogenic lipids fuse with and consequently destabilize a membrane. Fusogenic lipids usually have small head groups and unsaturated acyl chains. Exemplary fusogenic lipids include, but are not limited to, 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine.

Synthetic polymers with endosomolytic activity amenable to the present invention are described in U.S. Pat. App. Pub. Nos. 2009/0048410; 2009/0023890; 2008/0287630; 2008/0287628; 2008/0281044; 2008/0281041; 2008/0269450; 2007/0105804; 2007/0036865; and 2004/0198687, content of all of is incorporated herein by reference in its entirety.

Exemplary cell permeation peptides include, but are not limited to,

```
                                          SEQ ID NO: 32,
RQIKIWFQNRRMKWKK (penetratin);

SEQ ID NO: 33,
GRKKRRQRRRPPQC (Tat fragment 48-60);

SEQ ID NO: 34,
GALFLGWLGAAGSTMGAWSQPKKKRKV (signal sequence
based peptide);

SEQ ID NO: 35,
LLIILRRRIRKQAHAHSK (PVEC);

SEQ ID NO: 36,
GWTLNSAGYLLKINLKALAALAKKIL (transportan);

SEQ ID NO: 37,
KLALKLALKALKAALKLA (amphiphilic model peptide);

SEQ ID NO: 38,
RRRRRRRRR (Arg9);

SEQ ID NO: 39,
KFFKFFKFFK (Bacterial cell wall permeating
peptide);

SEQ ID NO: 40,
LLGDFFRKSKEKIGKEFKRIVQRIKDFLRNLVPRTES (LL-37);

SEQ ID NO: 41,
SWLSKTAKKLENSAKKRISEGIAIAIQGGPR (cecropin P1);

SEQ ID NO: 42,
ACYCRIPACIAGERRYGTCIYQGRLWAFCC (α-defensin)

SEQ ID NO: 43,
DHYNCVSSGGQCLYSACPIFTKIQGTCYRGKAKCCK
(β-defensin);

SEQ ID NO: 44,
RRRPRPPYLPRPRPPPFFPPRLPPRIPPGFPPRFPPRFPGK
R-NH2 (PR-39);

SEQ ID NO: 45,
ILPWKWPWWPWRR-NH2 (indolicidin);

SEQ ID NO: 46,
AAVALLPAVLLALLAP (RFGF);

SEQ ID NO: 47,
AALLPVLLAAP (RFGF analogue);
and

SEQ ID NO: 48,
RKCRIVVIRVCR (bactenecin).
```

Exemplary cationic groups include, but are not limited to, protonated amino groups, derived from e.g., O-AMINE (AMINE=NH$_2$; alkylamino, dialkylamino, heterocyclyl, arylamino, diaryl amino, heteroaryl amino, or diheteroaryl amino, ethylene diamine, polyamino); aminoalkoxy, e.g., O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino); amino (e.g. NH$_2$; alkylamino, dialkylamino, heterocyclyl, arylamino, diaryl amino, heteroaryl amino, diheteroaryl amino, or amino acid); and NH(CH$_2$CH$_2$NH)$_n$CH$_2$CH$_2$-AMINE (AMINE=NH$_2$; alkylamino, dialkylamino, heterocyclyl, arylamino, diaryl amino, heteroaryl amino, or diheteroaryl amino).

As used herein the term "targeting ligand" refers to any molecule that provides an enhanced affinity for a selected target, e.g., a cell, cell type, tissue, organ, region of the body, or a compartment, e.g., a cellular, tissue or organ compartment. Some exemplary targeting ligands include, but are not limited to, antibodies, antigens, folates, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands.

Carbohydrate based targeting ligands include, but are not limited to, D-galactose, multivalent galactose, N-acetyl-D-galactose (GalNAc), multivalent GalNAc, e.g. GalNAc2 and GalNAc3; D-mannose, multivalent mannose, multivalent lactose, N-acetyl-galactosamine, N-acetyl-gulucosamine, multivalent fucose, glycosylated polyaminoacids and lectins. The term multivalent indicates that more than one monosaccharide unit is present. Such monosaccharide subunits can be linked to each other through glycosidic linkages or linked to a scaffold molecule.

A number of folate and folate analogs amenable to the present invention as ligands are described in U.S. Pat. Nos. 2,816,110; 51410,104; 5,552,545; 6,335,434 and 7,128,893, contents of which are herein incorporated in their entireties by reference.

As used herein, the terms "PK modulating ligand" and "PK modulator" refers to molecules which can modulate the pharmacokinetics of the oligoncucleotide. Some exemplary PK modulator include, but are not limited to, lipophilic molecules, bile acids, sterols, phospholipid analogues, peptides, protein binding agents, vitamins, fatty acids, phenoxazine, aspirin, naproxen, ibuprofen, suprofen, ketoprofen, (S)-(+)-pranoprofen, carprofen, PEGs, biotin, and transthyretia-binding ligands (e.g., tetraiidothyroacetic acid, 2, 4, 6-triiodophenol and flufenamic acid). Oligonucleotides that comprise a number of phosphorothioate intersugar linkages are also known to bind to serum protein, thus short oligonucleotides, e.g. oligonucleotides of comprising from about 5 to 30 nucleotides (e.g., 5 to 25 nulceotides, preferably 5 to 20 nucleotides, e.g., 5, 6, 7, 8, 9, 10, 11, 12, 13, 14, 15, 16, 17, 18, 19, or 20 nucleotides), and that comprise a plurality of phosphorothioate linkages in the backbone are also amenable to the present invention as ligands (e.g. as PK modulating ligands). The PK modulating oligonucleotide can comprise at least 3, 4, 5, 6, 7, 8, 9, 10, 11, 12, 13, 14, 15 or more phosphorothioate and/or phosphorodithioate linkages. In some embodiments, all internucleotide linkages in PK modulating oligonucleotide are phosphorothioate and/or phosphorodithioates linkages. In addition, aptamers that bind serum components (e.g. serum proteins) are also amenable to the present invention as PK modulating ligands. Binding to serum components (e.g. serum proteins) can be predicted from albumin binding assays, such as those described in Oravcova, et al., Journal of Chromatography B (1996), 677: 1-27.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. When two or more ligands are present, the ligand can be on opposite ends of an oligonucleotide. In preferred embodiments, the ligand is attached to the oligonucleotides via an intervening tether/linker. The ligand or tethered ligand can be present on a monomer when said monomer is incorporated into the growing strand. In some embodiments, the ligand can be incorporated via coupling to a "precursor" monomer after said "precursor" monomer has been incorporated into the growing strand. For example, a monomer having, e.g., an amino-terminated tether (i.e., having no associated ligand), e.g., monomer-linker-NH$_2$ can be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction can be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. When a ligand is conjugated to a nucleobase, the preferred position is one that does not interfere with hybridization, i.e., does not interfere with the hydrogen bonding interactions needed for base pairing.

Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligomeric compounds. Generally, an oligomeric compound is attached to a conjugate moiety by contacting a reactive group (e.g., OH, SH, amine, carboxyl, aldehyde, and the like) on the oligomeric compound with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254, 469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; 6,559,279; content all of which is incorporated by reference in its entirety.

Ligand Carriers:

In some embodiments, the ligands, e.g. endosomolytic ligands, targeting ligands or other ligands, are linked to a monomer which is then incorporated into the growing oligonucleotide strand during chemical synthesis. Such monomers are also referred to as carrier monomers herein. The carrier monomer is a cyclic group or acyclic group; preferably, the cyclic group is selected from the group consisting of pyrrolidinyl, pyrazolinyl, pyrazolidinyl, imidazolinyl, imidazolidinyl, piperidinyl, piperazinyl, [1,3]-dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone. In some embodiments, the cyclic carrier monomer is based on pyrrolidinyl such as 4-hydroxyproline or a derivative thereof.

Exemplary ligands and ligand conjugated monomers amenable to the invention are described in U.S. patent application Ser. No. 10/916,185, filed Aug. 10, 2004; Ser. No. 10/946,873, filed Sep. 21, 2004; Ser. No. 10/985,426, filed Nov. 9, 2004; Ser. No. 10/833,934, filed Aug. 3, 2007; Ser. No. 11/115,989 filed Apr. 27, 2005, Ser. No. 11/119,533, filed Apr. 29, 2005; Ser. No. 11/197,753, filed Aug. 4, 2005; Ser. No. 11/944,227, filed Nov. 21, 2007; Ser. No. 12/328,528, filed Dec. 4, 2008; and Ser. No. 12/328,537, filed Dec. 4, 2008, contents which are herein incorporated in their entireties by reference for all purposes. Ligands and ligand conjugated monomers amenable to the invention are also described in International Application Nos. PCT/US04/001461, filed Jan. 21, 2004; PCT/US04/010586, filed Apr. 5, 2004; PCT/US04/011255, filed Apr. 9, 2005; PCT/US05/014472, filed Apr. 27, 2005; PCT/US05/015305, filed Apr. 29, 2005; PCT/US05/027722, filed Aug. 4, 2005; PCT/US08/061289, filed Apr. 23, 2008; PCT/US08/071576, filed Jul. 30, 2008; PCT/US08/085574, filed Dec. 4, 2008 and PCT/US09/40274, filed Apr. 10, 2009, contents which are herein incorporated in their entireties by reference for all purposes.

Linkers:

In some embodiments, the covalent linkages between the oligonucleotide and other components, e.g. a ligand or a ligand carrying monomer can be mediated by a linker. This linker can be cleavable linker or non-cleavable linker, depending on the application. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In some embodiments, a cleavable linker can be used to release the oligonucleotide after transport to the desired target. The intended nature of the conjugation or coupling interaction, or the desired biological effect, will determine the choice of linker group.

As used herein, the term "linker" means an organic moiety that connects two parts of a compound. Linkers typically comprise a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylherероaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In some embodiments, the linker is a branched linker. The branchpoint of the branched linker may be at least trivalent, but can be a tetravalent, pentavalent or hexavalent atom, or a group presenting such multiple valencies. In some embodiments, the branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branchpoint is glycerol or derivative thereof.

Cleavable Linking Groups:

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions)

Exemplary cleavable linking groups include, but are not limited to, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid celavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where $R^A$ and $R^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleaveable in an acidic environment with a pH of about 6.5 or lower (e.g., about 6.5, 6.0, 5.5, 5.0, or lower), or by agents such as enzymes that can act as a general acid.

General References:

General references for oligonucleotide modification are discussed below. The anti-miR-425 and miR-425 agents and oligonucleotides used in accordance with this invention can be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotides: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta,* 1995, 78, 486-504; Beaucage, S. L. and Iyer, R. P., Tetrahedron, 1992, 48, 2223-2311 and Beaucage, S. L. and Iyer, R. P., *Tetrahedron,* 1993, 49, 6123-6194, or references referred to therein. Modification described in WO 00/44895, WO01/75164, or WO02/44321 can be used herein. The disclosure of all publications, patents, and published patent applications listed herein are hereby incorporated by reference.

Modification of the Phosphate Group References:

The preparation of phosphinate oligonucleotides is described in U.S. Pat. No. 5,508,270. The preparation of alkyl phosphonate oligonucleotides is described in U.S. Pat. No. 4,469,863. The preparation of phosphoramidite oligonucleotides is described in U.S. Pat. No. 5,256,775 or U.S. Pat. No. 5,366,878. The preparation of phosphotriester oligonucleotides is described in U.S. Pat. No. 5,023,243. The preparation of boranophosphate oligonucleotide is described in U.S. Pat. Nos. 5,130,302 and 5,177,198. The preparation of 3'-Deoxy-3'-amino phosphoramidate oligonucleotides is described in U.S. Pat. No. 5,476,925. 3'-Deoxy-3'-methylenephosphonate oligonucleotides is described in An, H, et al. *J. Org. Chem.* 2001, 66, 2789-2801. Preparation of sulfur bridged nucleotides is described in Sproat et al. *Nucleosides Nucleotides* 1988, 7, 651 and Crosstick et al. *Tetrahedron Lett.* 1989, 30, 4693.

Replacement of the Phosphate Group References:

Methylenemethylimino linked oligonucleosides, also identified herein as MMI linked oligonucleosides, methylenedimethylhydrazo linked oligonucleosides, also identified herein as MDH linked oligonucleosides, and methylenecarbonylamino linked oligonucleosides, also identified herein as amide-3 linked oligonucleosides, and methyleneaminocarbonyl linked oligonucleosides, also identified herein as amide-4 linked oligonucleosides as well as mixed intersugar linkage compounds having, as for instance, alternating MMI and PO or PS linkages can be prepared as is described in U.S. Pat. Nos. 5,378,825, 5,386,023, 5,489,677 and in International Application Nos. PCT/US92/04294 and PCT/US92/04305 (published as WO 92/20822 WO and 92/20823, respectively). Formacetal and thioformacetal linked oligonucleosides can be prepared as is described in U.S. Pat. Nos. 5,264,562 and 5,264,564. Ethylene oxide linked oligonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 1 1972, 1991. Carbamate replacements are described in Stirchak, E. P. Nucleic Acids Res. 1989, 17, 6129.

Replacement of the Phosphate-Ribose Backbone References:

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They can also be prepared in accordance with U.S. Pat. No. 5,539,083.

Sugar Modification References:

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, *J. Acc. Chem. Res.* 1999, 32, 301-310).

Modifications of Nucleobases References:

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference in its entirety.

Terminal Modification References:

Terminal modifications are described in Manoharan, M. et al. *Antisense and Nucleic Acid Drug Development* 12, 103-128 (2002) and references therein.

Placement of Modifications within an Oligonucleotide (e.g., Placement within an Anti-miR-425 or miR-425 Agent)

As oligonucleotides (e.g., anti-miR-425 or miR-425 agent) can be are polymers of subunits or monomers, many of the modifications described herein can occur at a position which is repeated within an oligonucleotide, e.g., a modification of a nucleobase, a sugar, a phosphate moiety, or the non-bridging oxygen of a phosphate moiety. It is not necessary for all positions in a given oligonucleotide to be uniformly modified, and in fact more than one of the aforementioned modifications can be incorporated in a single oligonucleotide or even at a single nucleoside within an oligonucleotide.

In some cases the modification will occur at all of the subject positions in the oligonucleotide but in many, and in fact in most cases it will not. By way of example, a modification can occur at a 3' or 5' terminus position, can occur in the internal region, can occur in 3', 5' or both terminal regions, e.g. at a position on a termus nucleotide or in the last 2, 3, 4, 5, 6, 7, 8, 9, or 10 nucleotides of an oligonucleotide. In some embodiments, the terminus nucleotide does not comprise a modification.

In some embodiments, the terminus nucleotide or the last 2, 3, 4, 5, 6, 7, 8, 9, or 10 nucleotides of at least one end of the oligonucleotide all comprise at least one modification. In some embodiments, the modification is same. In some embodiments, the terminus nucleotide or the last 2, 3, 4, 5, 6, 7, 8, 9, or 10 nucleotides at both ends of the oligonucleotide all comprise at least one modification. It is to be understood that type of modification and number of modified nucleotides on one end of the oligonucleotide is independent of type of modification and number of modified nucleotides on the other end of the oligonucleotide.

When the oligonucleotide is double-stranded or partially double-stranded, a modification can occur in the double strand region, the single strand region, or in both the double- and single-stranded regions. In some embodiments, a modification described herein does not occur in the region corresponding to the target cleavage site region. For example, a phosphorothioate modification at a non-bridging oxygen position can occur at one or both termini, can occur in a terminal regions, e.g., at a position on a terminal nucleotide or in the last 2, 3, 4, 5, 6, 7, 8, 9, or 10 nucleotides of a strand, or can occur in double strand and single strand regions, particularly at termini.

Some modifications can preferably be included on an oligonucleotide at a particular location, e.g., at an internal position of a strand, or on the 5' or 3' end of an oligonucleotide. A preferred location of a modification on an oligonucleotide, can confer preferred properties on the oligonucleotide. For example, preferred locations of particular modifications can confer increased resistance to endonuclease or exonuclease activity.

Production of Anti-miR-425 Agents and Mimetics Thereof

In some embodiments, the oligonucleotide compounds (e.g., anti-miR-425 or miR-425 agents) as disclosed herein can be prepared using solution-phase or solid-phase organic synthesis, or enzymatically by methods known in the art. Organic synthesis offers the advantage that the oligonucleotide strands comprising non-natural or modified nucleotides can be easily prepared. Any other means for such synthesis known in the art can additionally or alternatively be employed. It is also known to use similar techniques to prepare other oligonucleotides, such as the phosphorothioates, phosphorodithioates and alkylated derivatives. The double-stranded oligonucleotide compounds of the invention can be prepared using a two-step procedure. First, the individual strands of the double-stranded molecule are prepared separately. Then, the component strands are annealed.

MicroRNAs have also been implicated in modulation of pathogens in hosts. For example, see Jopling, C. L., et al., *Science* (2005) vol. 309, pp 1577-1581.

Regardless of the method of synthesis, the oligonucleotide can be prepared in a solution (e.g., an aqueous and/or organic solution) that is appropriate for formulation. For example, the oligonucleotide preparation can be precipitated and redissolved in pure double-distilled water, and lyophilized. The dried oligonucleotide can then be resuspended in a solution appropriate for the intended formulation process.

Teachings regarding the synthesis of particular modified oligonucleotides can be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having beta-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups can be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262, 241, and 5,459,255, drawn to, inter alia, methods of synthesizing 2'-fluoro-oligonucleotides.

Additionally, in some embodiments, miRNA can be isolated from cells or tissues, recombinantly produced, or synthesized in vitro by a variety of techniques well known to one of ordinary skill in the art. In one approach, miRNA is isolated from cells or tissues.

Techniques for isolating miRNA from cells or tissues are well known to one of ordinary skill in the art. For example, miRNA can be isolated from total RNA using the miRNA isolation kit from Ambion, Inc. Another technique utilizes the flashPAGE Fractionator System (Ambion, Inc.) for PAGE purification of small nucleic acids.

The miRNA can be obtained by preparing a recombinant version thereof (i.e., by using the techniques of genetic engineering to produce a recombinant nucleic acid which can then be isolated or purified by techniques well known to one of ordinary skill in the art). This approach involves growing a culture of host cells in a suitable culture medium, and purifying the miRNA from the cells or the culture in which the cells are grown. For example, the methods include a process for producing a miRNA in which a host cell, containing a suitable expression vector that includes a nucleic acid encoding a miRNA, is cultured under conditions that allow expression of the encoded miRNA. The miRNA can be recovered from the culture, from the culture medium or from a lysate prepared from the host cells, and further purified. The host cell can be a higher eukaryotic host cell such as a mammalian cell, a lower eukaryotic host cell such as a yeast cell, or the host cell can be a prokaryotic cell such as a bacterial cell. Introduction of a vector containing the nucleic acid encoding the miRNA into the host cell can be effected by calcium phosphate transfection, DEAE-dextran mediated transfection, or electroporation (Davis, L. et al., Basic Methods in Molecular Biology (1986)).

Any host/vector system can be used to express one or more of the miRNAs. These include, but are not limited to, eukaryotic hosts such as HeLa cells and yeast, as well as prokaryotic host such as *E. coli* and *B. subtilis*. An anti-miR-425 agent, e.g., anti-miR can be expressed in mammalian cells, yeast, bacteria, or other cells where the anti-miR-425 agent, e.g., anti-miR is under the control of an appropriate promoter. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989). In the preferred embodiment, the miRNA is expressed in mammalian cells. Examples of mammalian expression systems include C127, monkey COS cells, Chinese Hamster Ovary (CHO) cells, human kidney 293 cells, human epidermal A43 1 cells, human Colo205 cells, 3T3 cells, CV-1 cells, other transformed primate cell lines, normal diploid cells, cell strains derived from in vitro culture of primary tissue, primary explants, HeLa cells, mouse L cells, BILK, HL-60, U937, HaK or Jurkat cells.

Mammalian expression vectors will comprise an origin of replication, a suitable promoter, polyadenylation site, transcriptional termination sequences, and 5' flanking non-transcribed sequences. DNA sequences derived from the SV40 viral genome, for example, SV40 origin, early promoter, enhancer, splice, and polyadenylation sites may be used to provide the required non-transcribed genetic elements. Potentially suitable yeast strains include *Saccharomyces cer-* evsiae, *Schizosaccharomyces pombe, Klayveromyces* strains, *Candida*, or any yeast strain capable of expressing miRNA. Potentially suitable bacterial strains include *Escherichia coli, Bacillus subtilis, Salmonella typhimurium*, or any bacterial strain capable of expressing miRNA.

In another approach, genomic DNA encoding an anti-miR-425 agent, e.g., anti-miR is isolated, the genomic DNA is expressed in a mammalian expression system, and RNA is purified and modified as necessary for administration to a patient. In some embodiments, a miR-425 (e.g., to decrease ANP levels in a subject) is in the form of a pre-miRNA, which can be modified as desired (i.e. for increased stability or cellular uptake).

Knowledge of DNA sequences of miRNA allows for modification of cells to permit or increase expression of an endogenous miRNA. Cells can be modified (e.g., by homologous recombination) to provide increased miRNA expression by replacing, in whole or in part, the naturally occurring promoter with all or part of a heterologous promoter so that the cells express the miRNA at higher levels. The heterologous promoter is inserted in such a manner that it is operatively linked to the desired miRNA encoding sequences. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems. Cells also may be; engineered to express an endogenous gene comprising the miRNA under the control of inducible regulatory elements, in which case the regulatory sequences of the endogenous gene may be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al. The miRNA may be prepared by culturing transformed host cells under culture conditions suitable to express the miRNA. The resulting expressed miRNA may then be purified from such culture (i.e., from culture medium or cell extracts) using known purification processes, such as gel filtration and ion exchange chromatography. The purification of the miRNA may also include an affinity column containing agents which will bind to the protein; one or more column steps over such affinity resins as concanavalin A-agarose, Heparin-Toyopearl™ or Cibacrom blue 3GA Sepharose™; one or more steps involving hydrophobic interaction chromatography using such resins as phenyl ether, butyl ether, or propyl ether; immunoaffnity chromatography, or complementary cDNA affinity chromatography.

The miRNA can also be expressed as a product of transgenic animals, which are characterized by somatic or germ cells containing a nucleotide sequence encoding the miRNA. A vector containing DNA encoding miRNA and appropriate regulatory elements can be inserted in the germ line of animals using homologous recombination (Capecchi, Science t 244:1288-1292 (1989)), such that they express the miRNA. Transgenic animals, preferably non-human mammals, are produced using methods as described in U.S. Pat. No. 5,489,743 to Robinson, et al., and PCT Publication No. WO 94/28122 by Ontario Cancer Institute. miRNA can be isolated from cells or tissue isolated from transgenic animals as discussed above.

In one approach, the miRNA can be obtained synthetically, for example, by chemically synthesizing a nucleic acid by any method of synthesis known to the skilled artisan. The synthesized miRNA can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In some circumstances, for example, where increased nuclease stability is desired, nucleic acids having nucleic acid analogs and/or modified internucleoside linkages may be preferred. Nucleic acids containing modified internucleoside linkages can also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH2-S—CH2), diinethylene-sulfoxide (—CH2-SO—CH2), dimethylene-sulfone (—CH2-SO2-CH2), 2'-O-alkyl, and 2'-deoxy-2'-fluoro' phosphorothioate internucleoside linkages are well known in the art (see Uhlmann et al., 1990, Chem. Rev. 90:543-584; Schneider et al., 1990, Tetrahedron Lett. 31:335 and references cited therein). U.S. Pat. Nos. 5,614,617 and 5,223,618 to Cook, et al., U.S. Pat. No. 5,714,606 to Acevedo, et al, U.S. Pat. No. 5,378,825 to Cook, et al., U.S. Pat. Nos. 5,672,697 and 5,466, 786 to Buhr, et al., U.S. Pat. No. 5,777,092 to Cook, et al., U.S. Pat. No. 5,602,240 to De Mesmacker, et al., U.S. Pat. No. 5,610,289 to Cook, et al. and U.S. Pat. No. 5,858,988 to Wang, also describe nucleic acid analogs for enhanced nuclease stability and cellular uptake.

Oligonucleotide Formulations:

A formulated oligonucleotide composition can assume a variety of states. In some examples, the composition can be at least partially crystalline, uniformly crystalline, and/or anhydrous (e.g., less than 80, 50, 30, 20, or 10% water). In another example, the oligonucleotide is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a micro particle as can be appropriate for a crystalline composition). Generally, the oligonucleotide composition is formulated in a manner that is compatible with the intended method of administration.

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An oligonucleotide preparation can be formulated in combination with another agent, e.g., another therapeutic agent or an agent that stabilizes the oligonucleotide, e.g., a protein that complex with oligonucleotide to form an oligonucleotide-protein compelx Still other agents include chelators, e.g., EDTA (e.g., to remove divalent cations such as $Mg^{2+}$), salts, DNAse inhibitors, RNAse inhibitors (e.g., a broad specificity RNAse inhibitor such as RNAsin) and so forth.

In some embodiments, the oligonucleotide preparation includes at least a second therapeutic agent (e.g., an agent other than RNA or DNA). Exemplary therapeutic agents that can formulated with an oligonucleotide preparation include, but are not limited to, those found in *Harrison's Principles of Internal Medicine*, $17^{th}$ Edition, 2008, McGraw-Hill N.Y., N.Y.; Physicians Desk Reference, $63^{rd}$ Edition, 2008, Thomson Reuters, N.Y., N.Y.; Goodman & Gilman's The Pharmacological Basis of Therapeutics, $11^{th}$ Edition, 2005, McGraw-Hill N.Y., N.Y.; United States Pharmacopeia, The National Formulary, USP-32 NF-27, 2008, U.S. Pharmacopeia, Rockville, Md., the complete contents of all of which are incorporated herein by reference.

In some embodiments, the second therapeutic agent is an anti-hypertension agent or anti-hypertensive.

Exemplary Oligonucleotide Formulations

Liposomes:

The oligonucleotides of the invention (e.g., anti-miR-425 or miR-425 agent) can be formulated in liposomes. As used herein, a liposome is a structure having lipid-containing membranes enclosing an aqueous interior. Liposomes can have one or more lipid membranes. In some embodiments, liposomes have an average diameter of less than about 100 nm More preferred embodiments provide liposomes having an average diameter from about 30-70 nm and most preferably about 40-60 nm Oligolamellar large vesicles and multilamellar vesicles have multiple, usually concentric, membrane layers and are typically larger than 100 nm Liposomes with several nonconcentric membranes, i.e., several smaller vesicles contained within a larger vesicle, are termed multivesicular vesicles.

Liposomes can further comprise one or more additional lipids and/or other components such as sterols, e.g., cholesterol. Additional lipids can be included in the liposome compositions for a variety of purposes, such as to prevent lipid oxidation, to stabilize the bilayer, to reduce aggregation during formation or to attach ligands onto the liposome surface. Any of a number of additional lipids and/or other components can be present, including amphipathic, neutral, cationic, anionic lipids, and programmable fusion lipids. Such lipids and/or components can be used alone or in combination. One or more components of the liposome can comprise a ligand, e.g., a targeting ligand.

Liposome compositions can be prepared by a variety of methods that are known in the art. See e.g., U.S. Pat. Nos. 4,235,871; 4,737,323; 4,897,355 and 5,171,678; published International Applications WO 96/14057 and WO 96/37194; Feigner, P. L. et al., *Proc. Natl. Acad. Sci.*, USA (1987) 8:7413-7417, Bangham, et al. *M. Mol. Biol.* (1965) 23:238, Olson, et al. *Biochim. Biophys. Acta* (1979) 557:9, Szoka, et al. *Proc. Natl. Acad. Sci.* (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol.* (1984) 115:757.

Micelles and Other Membranous Formulations:

In some embodiments, the oligonucleotides (e.g., anti-miR-425 or miR-425 agent) as disclosed herein can be prepared and formulated as micelles. As used herein, "micelles" are a particular type of molecular assembly in which amphipathic molecules are arranged in a spherical structure such that all hydrophobic portions on the molecules are directed inward, leaving the hydrophilic portions in contact with the surrounding aqueous phase. The converse arrangement exists if the environment is hydrophobic.

In some embodiments, the formulations comprises micelles formed from an oligonucleotide of the invention and at least one amphiphilic carrier, in which the micelles have an average diameter of less than about 100 nm, preferably. More preferred embodiments provide micelles having an average diameter less than about 50 nm, and even more preferred embodiments provide micelles having an average diameter less than about 30 nm, or even less than about 20 nm.

Micelle formulations can be prepared by mixing an aqueous solution of the oligonucleotide composition, an alkali metal $C_8$ to $C_{22}$ alkyl sulphate, and an amphiphilic carrier. The amphiphilic carrier can be added at the same time or after addition of the alkali metal alkyl sulphate. Micelles will form with substantially any kind of mixing of the ingredients but vigorous mixing in order to provide smaller size micelles.

Emulsions:

In some embodiments, the oligonucleotides (e.g., anti-miR-425 or miR-425 agent) as disclosed herein can be prepared and formulated as emulsions. As used herein, "emulsion" is a heterogenous system of one liquid dispersed in another in the form of droplets. Emulsions are often biphasic systems comprising two immiscible liquid phases intimately mixed and dispersed with each other. Either of the phases of the emulsion can be a semisolid or a solid, as is the case of emulsion-style ointment bases and creams. The oligonucleotide can be present as a solution in either the aqueous phase, oily phase or itself as a separate phase.

In some embodiments, the compositions are formulated as microemulsions. As used herein, "microemulsion" refers to a system of water, oil and amphiphile which is a single optically isotropic and thermodynamically stable liquid solution. Microemuslions also include thermodynamically stable, isotropically clear dispersions of two immiscible liquids that are stabilized by interfacial films of surface-active molecules.

The application of emulsion formulations via dermatological, oral and parenteral routes and methods for their manufacture have been reviewed in the literature, for example see Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., volume 1, p. 245; and Block, in Pharmaceutical Dosage Forms, Lieberman, Rieger and Banker (Eds.), 1988, Marcel Dekker, Inc., New York, N.Y., volume 1, p. 335, contents of which are herein incorporated by reference in their entirety.

Lipid Particles:

In some embodiments, the oligonucleotides (e.g., anti-miR-425 or miR-425 agent) as disclosed herein can be prepared and formulated as lipid particles, e.g., formulated lipid particles (FLiPs) comprising (a) an oligonucleotide of the invention, where said oligonucleotide has been conjugated to a lipophile and (b) at least one lipid component, for example an emulsion, liposome, isolated lipoprotein, reconstituted lipoprotein or phospholipid, to which the conjugated oligonucleotide has been aggregated, admixed or associated. The stoichiometry of oligonucleotide to the lipid component can be 1:1. Alternatively the stoichiometry can be 1:many, many:1 or many:many, where many is two or more.

The FLiP can comprise triacylglycerols, phospholipids, glycerol and one or several lipid-binding proteins aggregated, admixed or associated via a lipophilic linker molecule with an oligonucleotide. Surprisingly, it has been found that due to said one or several lipid-binding proteins in combination with the above mentioned lipids, the FLiPs show affinity to liver, gut, kidney, steroidogenic organs, heart, lung and/or muscle tissue. These FLiPs can therefore serve as carrier for oligonucleotides to these tissues. For example, lipid-conjugated oligonucleotides, e.g., cholesterol-conjugated oligonucleotides, bind to HDL and LDL lipoprotein particles which mediate cellular uptake upon binding to their respective receptors thus directing oligonucleotide delivery into liver, gut, kidney and steroidogenic organs, see Wolfrum et al. Nature Biotech. (2007), 25:1145-1157.

The FLiP can be a lipid particle comprising 15-25% triacylglycerol, about 0.5-2% phospholipids and 1-3% glycerol, and one or several lipid-binding proteins. FLiPs can be a lipid particle having about 15-25% triacylglycerol, about 1-2% phospholipids, about 2-3% glycerol, and one or several lipid-binding proteins. In some embodiments, the lipid particle comprises about 20% triacylglycerol, about 1.2% phospholipids and about 2.25% glycerol, and one or several lipid-binding proteins.

Another suitable lipid component for FLiPs is lipoproteins, for example isolated lipoproteins or more preferably reconstituted lipoprotieins. Exemplary lipoproteins include chylomicrons, VLDL (Very Low Density Lipoproteins), IDL (Intermediate Density Lipoproteins), LDL (Low Density Lipoproteins) and HDL (High Density Lipoproteins). Methods of producing reconstituted lipoproteins are known in the art, for example see A. Jones, Experimental Lung Res. 6, 255-270 (1984), U.S. Pat. Nos. 4,643,988 and 5,128,318, PCT publication WO87/02062, Canadian Pat. No. 2,138,925. Other methods of producing reconstituted lipoproteins, especially for apolipoproteins A-I, A-II, A-IV, apoC and apoE have been described in A. Jonas, Methods in Enzymology 128, 553-582 (1986) and G. Franceschini et al. J. Biol. Chem., 260(30), 16321-25 (1985).

One preferred lipid component for FLiP is Intralipid. Intralipid® is a brand name for the first safe fat emulsion for human use. Intralipid® 20% (a 20% intravenous fat emulsion) is made up of 20% soybean oil, 1.2% egg yolk phospholipids, 2.25% glycerin, and water for injection. It is further within the present invention that other suitable oils, such as saflower oil, can serve to produce the lipid component of the FLiP.

FLiP can range in size from about 20-50 nm or about 30-50 nm, e.g., about 35 nm or about 40 nm. In some embodiments, the FLiP has a particle size of at least about 100 nm FLiPs can alternatively be between about 100-150 nm, e.g., about 110 nm, about 120 nm, about 130 nm, or about 140 nm, whether characterized as liposome- or emulsion-based. Multiple FLiPs can also be aggregated and delivered together, therefore the size can be larger than 100 nm.

The process for making the lipid particles comprises the steps of: (a) mixing a lipid components with one or several lipophile (e.g. cholesterol) conjugated oligonucleotides that can be chemically modified; and (b) fractionating this mixture. In some embodiments, the process comprises the additional step of selecting the fraction with particle size of 30-50 nm, preferably of about 40 nm in size.

Some exemplary lipid particle formulations amenable to the invention are described in U.S. patent application Ser. No. 12/412,206, filed Mar. 26, 2009, contents of which are herein incorporated by reference in their entirety.

Yeast Cell Wall Particles:

In some embodiments, the oligonucleotides (e.g., anti-miR-425 or miR-425 agent) as disclosed herein are formulated in yeast cell wall particles ("YCWP"). A yeast cell wall particle comprises an extracted yeast cell wall exterior and a core, the core comprising a payload (e.g., oligonucleotides). Exterior of the particle comprises yeast glucans (e.g. beta glucans, beta-1,3-glucans, beta-1,6-glucans), yeast mannans, or combinations thereof. Yeast cell wall particles are typically spherical particles about 1-4 µm in diameter.

Preparation of yeast cell wall particles is known in the art, and is described, for example in U.S. Pat. Nos. 4,992,540; 5,082,936; 5,028,703; 5,032,401; 5,322,841; 5,401,727; 5,504,079; 5,607,677; 5,741,495; 5,830,463; 5,968,811; 6,444,448; and 6,476,003, U.S. Pat. App. Pub. Nos. 2003/0216346 and 2004/0014715, and Int. App. Pub. No. WO 2002/12348, contents of which are herein incorporated by reference in their entirety. Applications of yeast cell like particles for drug delivery are described, for example in U.S. Pat. Nos. 5,032,401; 5,607,677; 5,741,495; and 5,830,463; and U.S. Pat. Pub Nos. 2005/0281781 and 2008/0044438, contents of which are herein incorporated by reference in their entirety. U.S. Pat. App. Pub. No. 2009/0226528, contents of which are herein incorporated by reference, describes formulation of nucleic acids with yeast cell wall particles for delivery of oligonucleotide to cells.

Additional exemplary formulations for oligonucleotides are described in U.S. Pat. Nos. 4,897,355; 4,394,448; 4,235,871; 4,231,877; 4,224,179; 4,753,788; 4,673,567; 4,247,411; 4,814,270; 5,567,434; 5,552,157; 5,565,213; 5,738,868; 5,795,587; 5,922,859; and 6,077,663, Int. App. Nos. PCT/US07/079203, filed Sep. 21, 2007; PCT/US07/080331, filed Oct. 3, 2007; U.S. patent application Ser. No. 12/123,922, filed May 28, 2008; U.S. Pat. Pub. Nos. 2006/0240093 and 2007/0135372 and U.S. Provisional App. Nos. 61/018,616, filed Jan. 2, 2008; 61/039,748, filed Mar. 26, 2008; 61/045,228, filed Apr. 15, 2008; 61/047,087, filed Apr. 22, 2008; 61/051,528, filed May 21, 2008; and 61/113,179 (filed Nov. 10, 2008), contents of which are herein incorporated by reference in their entirety. Behr (1994) Bioconjugate Chem. 5:382-389, and Lewis et al. (1996) PNAS 93:3176-3181), also describe formulations for oligonucleotides that are amenable to the invention, contents of which are herein incorporated by reference in their entirety.

Pharmaceutical Compositions Comprising Oligonucleotides:

In another aspect, provided herein are pharmaceutically acceptable compositions which comprise a therapeutically-effective amount of one or more of the oligonucleotides (e.g., anti-miR-425 or miR-425 agent) as disclosed herein, formulated together with one or more pharmaceutically acceptable carriers (additives) and/or diluents.

Stratagies for delivery of miRNA's and anti-miRs are known by persons of ordinary skill in the art and are encompassed for use in the delivery of anti-miR-425 agents and miR-425 agents as disclosed herein. Delivery of miRNAs are discussed in, for example, Broderick et al., Gene Therapy, 2011, 18; 1104-1110, which is incorporated herein in its entirety by reference. In some embodiments, anti-miR-425 agents and miR-425 agents as disclosed herein can be modified to comprise 2'O-methyl, 2' O-methyloxyethyl or 2-fluoro modified nucleotides. In some embodiments, antagomirs are 2'-O-methyl oligonucleotides conjugated to cholesterol at their 3' ends, and contain phosphorothioate linkages between nucleotides at both ends in place of natural phosphate linkages. In some embodiments, the anti-miR-425 agents and miR-425 agents as disclosed herein can be formulated in lipid nanoparticles, for example, lipid vesicles containing therapeutic RNA. The formulated lipid bilayer encapsulates the therapeutic RNA, delivering it to cells and promoting fusion with the phospholipid bilayer of cell membranes. Individual lipids within the vesicle bilayer can contain ionizable head groups that will disrupt the endosome at low pH to release the therapeutic RNA to the cytoplasm.

In some embodiments, anti-miR-425 agents and miR-425 agents as disclosed herein can be formulated as golden lipid nanoparticles for therapeutic delivery, e.g., as disclosed in 2012/0128777, 2012/0244075 and 2013/0011339, and in Shi et al., *Solid lipid nanoparticles loaded with anti-microRNA oligonucleotides (AMOs) for suppression of microRNA-21 functions in human lung cancer cells*, Pharm Res, 2012; 29(1); 97-109, which are incorporated herein in its entirety by reference.

Figure 5A:
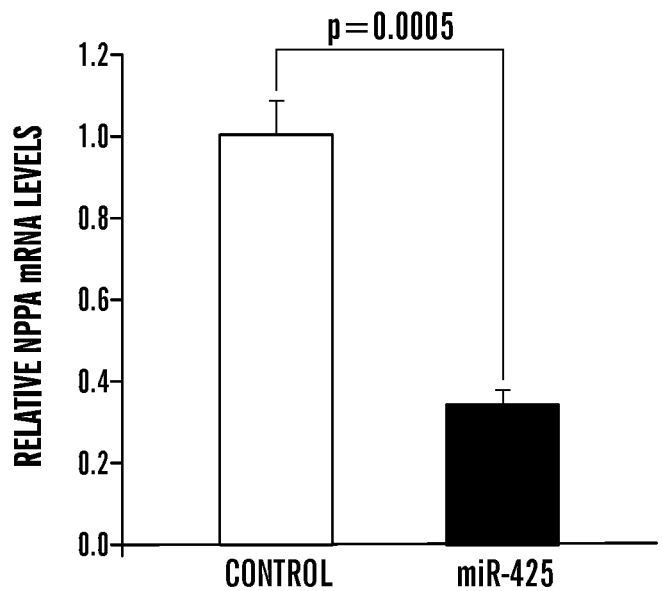
FIG. 5A-5B miR-425 transfection reduces NPPA mRNA levels and secretion of Nt-proANP immunoreactivity in human cardiomyocytes derived from induced pluripotent stem (iPS) cells. Cardiomyocytes (~4×10⁵/well) were transfected with miR-425 or a control miR. Twenty-four hours later, cells were washed and incubated in 1 ml of media. After an additional 48 hours, cells and media were harvested.
Figure 5B:
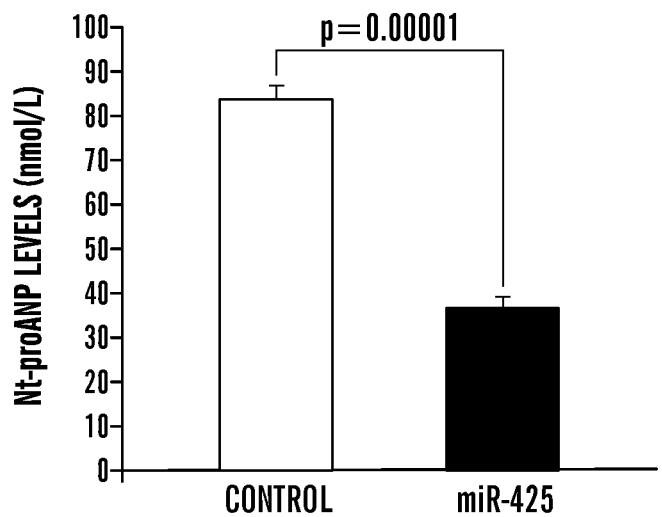

In some embodiments, chemical modifications that improve the stability, biodistribution and delivery of anti-miR-425 agents and miR-425 agents is encompassed, for example as disclosed in FIG. 5 in Broderick et al., Gene Therapy, 2011, 18; 1104-1110.

As described in detail below, the pharmaceutical compositions can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Determination of a therapeutically effective amount is well within the capability of those skilled in the art. Generally, a therapeutically effective amount can vary with the subject's history, age, condition, sex, as well as the severity and type of the medical condition in the subject, and administration of other agents alleviate the disease or disorder to be treated.

The amount of oligonucleotide which can be combined with a carrier material to produce a single dosage form will generally be that amount of the compound which produces a therapeutic effect. Generally out of one hundred percent, this amount will range from about 0.1% to 99% of oligonucleotide, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the 1050 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage can be determined by a physician and adjusted, as necessary, to suit observed effects of the treatment. Generally, the compositions are administered so that oligonucleotide is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. Examples of dosing schedules are administration once a week, twice a week, three times a week, daily, twice daily, three times daily or four or more times daily.

Combinations of Anti-miR-425 Agents or miR-425 with Additional Agents

In some embodiments, the oligonucleotides (e.g., anti-miR-425 or miR-425 agent) as disclosed herein, can be administrated to a subject in combination with a pharmaceutically active agent, e.g., a second therapeutic agent. Exemplary pharmaceutically active compound include, but are not limited to, those found in Harrison's Principles of Internal Medicine, 13$^{th}$ Edition, Eds. T. R. Harrison et al. McGraw-Hill N.Y., N.Y.; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; and United States Pharmacopeia, The National Formulary, USP XII NF XVII, 1990, the complete contents of all of which are incorporated herein by reference.

In some embodiments, where an anit-miR-425 agent is being administered, a second therapeutic agent is an anti-hypertension agent or anti-hypertensive. Anti-hypertensives are a class of drugs that are used to treat hypertension (high blood pressure). Antihypertensive therapy seeks to prevent the complications of high blood pressure, such as stroke and myocardial infarction. Exemplary types of anti-hypertension agents include, but are not limited to, statins, diuretics, adrenergic receptor antagonists, calcium channel blockers, renin inhibitors, ACE inhibitors, angiotensin II receptor antagonists, aldosterone antagonists, vasodilators; alpha-2-agonists, and any combination thereof.

Exemplary anti-hypertension agents include, but are not limited to, bumetanide; ethacrynic acid; furosemide; torsemide; epitizide; hydrochlorothiazide; chlorothiazide; bendroflumethiazide; indapamide; chlorthalidone; metolazone; amiloride; triamterene; spironolactone; atenolol; metoprolol; nadolol; oxprenolol; pindolol; propranolol; timolol; doxazosin; phentolamine; indoramin; phenoxybenzamine; prazosin; terazosin; tolazoline; bucindolol; carvedilol; labetalol; amlodipine; felodipine; isradipine; lercanidipine; nicardipine; nifedipine; nimodipine; nitrendipine; diltiazem; verapamil; Aliskiren; captopril; enalapril; fosinopril; lisinopril; perindopril; quinapril; ramipril; trandolapril; benazepril; candesartan; eprosartan; irbesartan; losartan; olmesartan; telmisartan; valsartan; eplerenone; spironolactone; sodium nitroprusside; hydralazine; hydralazine derivatives; Clonidine; Guanabenz; Methyldopa; Moxonidine; Guanethidine; Reserpine; atorvastatin; fluvastatin; lovastatin; pitavastatin; pravastatin; rosuvastatin; simvastatin; and any combinations thereof.

In some embodiments, an anti-miR-425 can be administered in combination with, or sequentially to, ANP and/or BNP, or ANP or BNP mimetics, for example, but not limited to nesiritide or ANP, or an agent which has substantially the same function as endogenous ANP, or mimic the effects of natriuretic peptides.

In some embodiments, an anti-miR-425 can be administered in combination, or sequentially to (either before or after) administration of the anti-miR with a PDE-5 inhibitor, or other agent which increases endogenous cGMP, which is a secondary messenger for ANP. In some embodiments, a PDE-5 inhibitor is selected from the group consisting of: drug tadalafil (CIALIS™, ADCIRCA™), sildenafil (VIAGRA™), sildenafil citrate, zaprinast, LASSBio596, E-4010, and vardenafil, or a combination thereof. In some embodiments, examples of PDE5 inhibitors which can be used include, without limitation, pyrimidine and pyrimidinone derivatives, such as the compounds described in U.S. Pat. Nos. 6,677,335, 6,458,951, 6,251,904, 6,787,548, 5,294, 612, 5,250,534, 6,469,012, WO 94/28902, WO96/16657, EP0702555, and Eddahibi, Br. J. Pharmacol., 125(4): 681688 (1988); griseolic acid derivatives, such as the compounds disclosed in U.S. Pat. No. 4,460,765; 1-arylnaphthalene ligands, such as those described in Ukita, J. Med. Chem. 42(7): 1293-1305 (1999); quinazoline derivatives, such as 4-[[3',4'-(methylenedioxy)benzyl]amino]-6-methoxyquinazoline) and compounds described in U.S. Pat. Nos. 3,932,407, 4,146,718, and RE31,617; pyrroloquinolones and pyrrolopyridinones, such as those described in U.S. Pat. Nos. 6,686,349, 6,635,638, 6,818,646, US20050113402; carboline derivatives, such the compounds described in U.S. Pat. Nos. 6,492,358, 6,462,047, 6,821,975, 6,306,870, 6,117,881, 6,043,252, 3,819,631, US20030166641, WO 97/43287, Daugan et al, J Med. Chem, 46(21):4533-42 (2003), and Daugan et al, J Med. Chem, 9; 46(21):4525-32 (2003); imidazo derivatives, such as the compounds disclosed in U.S. Pat. Nos. 6,130,333, 6,566,360, 6,362,178, 6,582,351, US20050070541, and US20040067945; and compounds described in U.S. Pat. Nos. 6,825,197, 6,943, 166, 5,981,527, 6,576,644, 5,859,009, 6,943,253, 6,864,253, 5,869,516, 5,488,055, 6,140,329, 5,859,006, 6,143,777, WO 96/16644, WO 01/19802, WO 96/26940, Dunn, Org. Proc. Res. Dev, 9: 88-97 (2005), and Bi et al, Bioorg Med Chem. Lett, 11(18): 2461-4 (2001). Content of all of the above is incorporated herein by reference in its entirety.

Additional exemplary PDE5 inhibitors include, but are not limited to, zaprinast; MY-5445; dipyridamole; sulindac sulfone; vinpocetine; FR229934; 1-methyl-3-isobutyl-8-(methylamino)xanthine; furazlocillin; Sch-51866; E4021; GF-196960; IC-351; T-1032; sildenafil; tadalafil; vardenafil; DMPPO; RX-RA-69; KT-734; SKF-96231; ER-21355; BF/GP-385; NM-702; PLX650; PLX134; PLX369; PLX788; vesnarinone; sildenafil or a related compound disclosed in U.S. Pat. Nos. 5,346,901, 5,250,534, or 6,469,012; tadalafil or a related compound disclosed in U.S. Pat. Nos. 5,859,006, 6,140,329, 6,821,975, or 6,943,166; or vardenafil or a related compound disclosed in U.S. Pat. No. 6,362,178. Content of all of the above is incorporated herein by reference in its entirety.

The anti-miR to miR-425 and the pharmaceutically active agent can be administrated to the subject in the same pharmaceutical composition or in different pharmaceutical compositions (at the same time or at different times).

Delivery of Anti-miR-425 Agents and miRNAs

In one embodiment, a vector encoding an anti-miR-425 agent, e.g., anti-miR is delivered into a specific target cell. Nucleic acid sequences necessary for expression in prokaryotes usually include a promoter, an operator (optional), often along with other sequences. Eukaryotic cells are known to utilize promoters, enhancers, and termination and polyadenylation signals.

One can also use localization sequences to deliver the released an anti-miR-425 agent, e.g., anti-miR intracellularly to a cell compartment of interest. Typically, the delivery system first binds to a specific receptor on the cell. Thereafter, the targeted cell internalizes the delivery system, which is bound to the cell. For example, membrane proteins on the cell surface, including receptors and antigens can be internalized by receptor mediated endocytosis after interaction with the ligand to the receptor or antibodies. (Dautry-Varsat, A., et al., Sci. Am. 250:52-58 (1984)). This endocytic process is exploited by the present delivery system. Because this process may damage an anti-miR-425 agent, e.g., anti-miR interference molecules, for example anti-miR-425 siRNA agent or, anti-miR as it is being internalized, it may be desirable to use a segment containing multiple repeats of the RNA interference-inducing molecule of interest. One can also include sequences or moieties that disrupt endosomes and lysosomes. See, e.g., Cristiano, R. J., et al., Proc. Natl. Acad. Sci. USA 90:11548-11552 (1993); Wagner, E., et al., Proc. Natl. Acad. Sci. USA 89:6099-6103 (1992); Cotten, M., et al., Proc. Natl. Acad. Sci. USA 89:6094-6098 (1992).

In some embodiments, an anti-miR-425 agent, e.g., anti-miR are complexed with desired targeting moieties by mixing an anti-miR-425 agent, e.g., anti-miR RNA interference molecules with the targeting moiety in the presence of complexing agents. Examples of such complexing agents include, but are not limited to, poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. In some embodiments, the complexing agents include chitosan, N-trimethylchitosan, poly-L-lysine, polyhistidine, polyornithine, polyspermines, protamine, polyvinylpyridine, polythiodiethylaminomethyl-ethylene P(TDAE), polyaminostyrene (e.g. p-amino), poly (methylcyanoacrylate), poly(ethylcyanoacrylate), poly(butylcyanoacrylate), poly(isobutylcyanoacrylate), poly (isohexylcynaoacrylate), DEAE-methacrylate, DEAE-hexylacrylate, DEAE-acrylamide, DE AE-albumin and DEAE-dextran, polymethylacrylate, polyhexylacrylate, poly (D,L-lactic acid), poly(DL-lactic-co-glycolic acid (PLGA), alginate, and polyethyleneglycol (PEG), and polyethylenimine.

In alternative embodiments, an anti-miR-425 agent, e.g., anti-miR complexing agent is protamine or an RNA-binding domain, such as an siRNA-binding fragment or nucleic acid binding fragment of protamine. Protamine is a polycationic peptide with molecular weight about 4000-4500 Da. Protamine is a small basic nucleic acid binding protein, which serves to condense the animal's genomic DNA for packaging into the restrictive volume of a sperm head (Warrant, R. W., et al., Nature 271:130-135 (1978); Krawetz, S. A., et al., Genomics 5:639-645 (1989)). The positive charges of the protamine can strongly interact with negative charges of the phosphate backbone of nucleic acid, such as RNA, resulting in a neutral and stable interference RNA-protamine complex.

In one embodiment, the protamine fragment is encoded by a nucleic acid sequence disclosed in International Patent Application: PCT/US05/029111, which is incorporated herein in its entirety by reference. The methods, reagents and references that describe a preparation of a nucleic acid-protamine complex in detail are disclosed in the U.S. Patent Application Publication Nos. US2002/0132990 and US2004/0023902, and are herein incorporated by reference in their entirety.

Targeting an Anti-miR-425 Agent, or Anti-miR to miR-425

In another embodiment of the invention an anti-miR-425 agent as disclosed herein are targeted to specific cells, for example cells expressing either the miR-425 and/or cells expressing the NPPA mRNA in order to avoid any potential undesired side effects of anti-miR-425 agent. However, the fact that miR-425 is present in the plasma of subjects, it is not essential to have the anti-miR-425 agent targeted to any particular cell, as an anti-miR-425 present in the plasma will have effect at inhibiting the effect of miR-425 circulating in the blood. In some embodiments, where the anti-miR-425 agent is an anti-miR, the anti-miR can be fused to a cell targeting moiety or protein, as disclosed in the International Patent Application PCT/US05/029,111 which is incorporated herein in its entirety by reference.

In such embodiments, the target moiety specifically brings the delivery system to the target cell. The particular target moiety for delivering the interference RNAs, such as anti-miRs complementary to at least part of the miR-425 sequence of SEQ ID NO: 1, or at least part of the miR-425 miRNA seed sequence SEQ ID NO: 2 can be determined empirically based upon the present disclosure and depending upon the target cell.

In some embodiments of the present invention, an anti-miR complementary to at least part of the miR-425 sequence of SEQ ID NO: 1, or at least part of the miR-425 miRNA seed sequence SEQ ID NO: 2 can be delivered to a limited number of cells thereby limiting, for example, potential side effects of therapies using the anti-miR-425 agent. The particular cell surface targets that are chosen for the targeting moiety will depend upon the target cell. Cells can be specifically targeted, for example, by use of antibodies against unique proteins, lipids or carbohydrates that are present on the cell surface. A skilled artisan can readily determine such molecules based on the general knowledge in the art.

The strategy for choosing the targeting moiety is very adaptable. For example, any cell-specific antigen, including proteins, carbohydrates and lipids can be used to create an antibody that can be used to target the anti-miR-425 agent, e.g., an anti-miR complementary to at least part of the miR-425 sequence of SEQ ID NO: 1, or at least part of the miR-425 miRNA seed sequence SEQ ID NO: 2 to a specific cell type according to the methods described herein.

In some embodiments, a binding domain is used to complex the targeting moiety to an anti-miR-425 agent, e.g., anti-miR. In some embodiments, the binding domain is selected from the nucleic acid binding domains present in proteins selected from the group consisting of GCN4, Fos, Jun, TFIIS, FMRI, yeast protein HX, Vigillin, Merl, bacterial polynucleotide phosphorylase, ribosomal protein S3, and heat shock protein.

Treating a Subject with an Anti-miR-425 Agent

In some embodiments, an anti-miR-425 agent as disclosed herein is administered to a subject in a pharmaceutical composition where the subject has a high blood pressure, or a cardiovascular disease or disorder, or hypertension. The administration may be a treatment and/or prophylaxis for any one of high blood pressure, hypertension and the like.

In some embodiments, the methods described herein encompass administering a pharmaceutical composition to a subject comprising an anti-miR-425 agent to a subject, for example, where the subject has normal or high levels of a miR-425 above a predefined reference level. In some embodiments, an anti-miR-425 agent is administered to a subject who does not have circulating levels of miR-425 above a pre-defined level, where the anti-miR-425 agent is administered in a location where miR-425 is expressed, e.g., but not limited to, the atrium and ventricle regions of the heart. In some embodiments, the anti-miR-425 is a small molecule which inhibits the function of miR-425 and/or inhibits the expression of miR-425, and in some embodiments, an anti-miR-425 is an oligonucleotide which inhibits the function of miR-425 and/or inhibits the expression of miR-425. In some embodiments, an oligonucleotide anti-miR binds to any region of miR-425 to inhibit its binding to the miRNA target region on the 3'UTR of the NPPA gene. In some embodiments, an oligonucleotide anti-miR binds to at least part of the seed sequence SEQ ID NO: 2 on the miR-425 molecule. In such embodiments, an oligonucleotide anti-miR-425 is a Tiny LNA as disclosed herein.

In another aspect of the present invention, the methods described herein encompass administering a pharmaceutical composition comprising an anti-miR-425 agent, e.g., an oligonucleotide complementary to at least part of the miR-425 of SEQ ID NO: 1, or an anti-miR complementary to at least part of the miRNA seed sequence SEQ ID NO:2 to a subject, where the subject has high levels of miR-425 above a pre-defined reference level, and/or is homozygous for the major A (AA) allele of rs5068 SNP, or heterozygous (AG).

Effective, safe dosages can be experimentally determined in model organisms and in human trials by methods well known to one of ordinary skill in the art. The anti-miR-425 agent in a pharmaceutical composition can be administered alone or in combination with adjuvant therapy such as, but not limited to, decreased stress, increased exercise, healthier diet, as well as administration with other therapeutic agents well known in the art to treat hypertension and high-blood pressure, such as, but not limited to include thiazide diuretics, beta blockers, angiotensin converting enzyme (ACE) inhibitors, and calcium channel. In some embodiments, a dose of an anti-miR-425 agent is determined by an ordinary physician or one of ordinary skill in the art when the subject is also administered an adjuvant therapy. In some embodiments, a dose of an anti-miR-425 agent is determined by an ordinary physician or one of ordinary skill in the art when the subject is not administered an adjuvant therapy, for example, a test dose with an anti-miR-425 agent is administered to a subject and its efficacy can be determined by measuring the level of circulating miR-425 and/or at least one symptom of hypertension or high blood pressure measured (e.g., blood pressure can be measured using a blood pressure cuff) and depending on the effect of the anti-miR-425 agent, the dose of the anti-miR-425 agent can be modified accordingly based on the efficacy and/or any adverse side effects.

Subjects Amenable to Treatment with an Anti-miR-425 Agent

One aspect as disclosed herein relates to use of an anti-miR-425 in methods for treating any type of disease or disorder in which it is desirable to increase ANP levels. These include, for example, diseases where ANP is reduced, or where ANP is not expressed at high levels and contributes to the disease pathology and/or progression of the disease, such as high blood pressure, hypertension and the like. These also include diseases in which ANP may be elevated but in which augmented ANP levels may have therapeutic benefit. For example, in some embodiments, subjects with heart failure where ANP levels are high, can benefit from increased ANP or BNP levels, and thus are amenable to administration of an anti-miR-425 agent as disclosed herein.

The invention provides methods for the treatment of any disease or disorder characterized by low levels of ANP. In some embodiments, the disease is a cardiovascular disease or disorder, such as but not limited to any one or a combination of high blood, hypertension, heart failure, congestive heart failure, left ventriclar hypertrophy, metabolic syndrome, stroke and renal failure. Hypertension is a leading cause of human cardiovascular morbidity and mortality, with a prevalence rate of 25-30% of the adult Caucasian population of the United States (JNC Report, 1985) Pulmonary hypertension is a pathological condition in which the pulmonary arterial pressure rises above normal levels and may cause sequelae of haemodynamic changes that can become life threatening. Symptoms of pulmonary hypertension include shortness of breath with minimal exertion, fatigue, dizzy spells and fainting. When pulmonary hypertension occurs in the absence of a known cause, it is referred to as idiopathic pulmonary arterial hypertension (previously referred to as primary pulmonary hypertension). Idiopathic pulmonary arterial hypertension is rare, occurring in about two per million people worldwide. Secondary hypertension is much more common occurring as a result of other medical conditions, including congestive heart failure, chronic hypoxic lung disorder, including chronic obstructive pulmonary disease, inflammatory or collagen vascular diseases such as scleroderma and systemic lupus erythematosus, congenital heart diseases associated with left to right shunting and pulmonary thromboembolism.

In some embodiments, the present invention relates to use of an anti-miR-425 agent as disclosed herein, for the treatment cardiovascular disorders and/or congenital heart disease in a subject. In some embodiments, an anti-miR-425 agent as disclosed herein can be used to treat any one or a combination of disorders selected from the group consisting of congestive heart failure, hypertension, systemic hypertension (thereby preventing the development of myocardial infarction, chronic heart failure (CHF), renal failure, and stroke), pulmonary hypertension, acute kidney injury, modulating inflammatory responses (either positively or negatively), lipolysis, obesity, diabetes mellitus, reducing intraocular pressure (preventing blindness in glaucoma, reducing ischemia-reperfusion (I/R) injury, (including spinal cord I/R injury and cardiac FR injury), preventing atrial fibrillation, liver failure, liver fibrosis, cirrhosis, cancer, promote angiogenesis, weight loss.

In some embodiments, circulating miR-425 levels can be used to assess a subject with a specific heart failure phenotype referred to as preserved ejection fraction (HpEF aka Diastolic Heart failure) which is reported to be a "heterogenous subtype" of heart failure. Previous researchers have concerns of using elevated plasma concentrations of natriuretic peptides as a patient selection criterion in HFpEF trials (I-PRESERVE Trial, Anand et al Circulation: Heart failure 2011). Accordingly, in some embodiments the methods and assays as disclosed herein to measure circulating miR-425 can be useful for providing clinical care in these subset of patients with a heart failure phenotype having preserved ejection fraction (e.g., subjects with symptomatic HFpEF). Accordingly, circulating miR-425 levels can be used to determine a "low" natriuretic peptide concentration in a patient with symptomatic HFpEF.

In one embodiment of the invention relates to a method of treating a circulatory disorder comprising administering an effective amount of a composition comprising an anti-miR-425 agent, e.g., an anti-miR complementary to at least part of the miR-425 sequence of SEQ ID NO: 1, or at least part of the miR-425 miRNA seed sequence SEQ ID NO: 2 as disclosed herein to a subject with a circulatory disorder. In a further embodiment, the invention provides a method for treating hypertension (e.g., high blood pressure), comprising administering a composition comprising an anti-miR-425 agent, e.g., an anti-miR complementary to at least part of the miR-425 sequence of SEQ ID NO: 1, or at least part of the miR-425 miRNA seed sequence SEQ ID NO: 2.

In one embodiment of the above methods, the subject is a human and the composition comprising an anti-miR-425 agent, e.g., an anti-miR complementary to at least part of the miR-425 sequence of SEQ ID NO: 1, or at least part of the miR-425 miRNA seed sequence SEQ ID NO: 2 is useful to treat circulatory disorder is selected from the group consisting of cardiomyopathy, myocardial infarction, and congenital heart disease. In some embodiments, the circulatory disorder is a myocardial infarction. The present invention is also directed to a method of treating circulatory damage in the heart or peripheral vasculature which occurs as a consequence of genetic defect, physical injury, environmental insult or damage from a stroke, heart attack or cardiovascular disease (most often due to ischemia) in a subject, the method comprising administering an anti-miR-425 agent, e.g., an anti-miR complementary to at least part of the miR-425 sequence of SEQ ID NO: 1, or at least part of the miR-425 miRNA seed sequence SEQ ID NO: 2 to a subject. Medical indications for such treatment include treatment of acute and chronic heart conditions of various kinds, such as coronary heart disease, cardiomyopathy, endocarditis, congenital cardiovascular defects, and congestive heart failure. Efficacy of treatment can be monitored by clinically accepted criteria, such as an improvement in developed pressure, systolic pressure, end diastolic pressure, patient mobility, and quality of life.

The methods as disclosed herein comprising administering an anti-miR-425 agent, e.g., a small molecule or an anti-miR complementary to at least part of the miR-425 sequence of SEQ ID NO: 1, or at least part of the miR-425 miRNA seed sequence SEQ ID NO: 2 can be used to treat a wide variety of diseases including, but not limited to essential hypertension, hypertension associated with end stage renal failure, hypertension associated with pregnancy (preeclampsia), salt sensitivity hypertension, type II diabetes hypertension, hypertension associated with alcohol abuse, obesity associated hypertension, systolic hypertension in elderly, asthma, allergies, migraine headache, gastrointestinal motility disorders, Alzheimer's disease, senile dementia, angina pectoris, premature labor, cerebrovascular diseases, and convulsive epilepsy. The methods are also suited for treatment of essential hypertension and intra-ocular hypertension.

The pharmaceutical compositions and dosage forms of an anti-miR-425 agent, e.g., a small molecule or an anti-miR complementary to at least part of the miR-425 sequence of SEQ ID NO: 1, or at least part of the miR-425 miRNA seed sequence SEQ ID NO: 2 may be used for treating a wide variety of disease states which involve one or more forms of cardiovascular, cerebrovascular, and intraocular dysfunction. The anti-miR-425 agents as disclosed herein generally possess a broad spectrum of cardiovascular and cerebrovascular activities including increasing ANP levels. The invention compositions can therefore be beneficially used in treating cardiovascular disorders, cerebrovascular disorders.

In one embodiment, administration of an anti-miR-425 agent, e.g., an anti-miR provides a safe, highly effective method for treating severe hypertension and may offer an alternative to side effects associated with other antihypertensive drugs (e.g., nitrendipine). The present invention relies on inhibiting the repression of the NPPA mRNA by the miRNA-425, and is useful for treatment or prevention of hypertension, while simultaneously reducing many of the undesirable side effects (e.g., headache, nausea) associated with other known anti-hypertensive drugs.

In particular, an anti-miR-425 agent, e.g., an anti-miR complementary to at least part of the miR-425 sequence of SEQ ID NO: 1, or at least part of the miR-425 miRNA seed sequence SEQ ID NO: 2 as disclosed herein are useful in the treatment of essential hypertension and/or various secondary hypertensive conditions (e.g., end stage renal hypertension, pregnancy associated hypertension such as preeclampsia, hypertension associated with type II diabetes, salt sensitivity hypertension, hypertension associated with alcohol abuse, hypertension associated with obesity, and systolic hypertension in the elderly).

Treatment of hypertension using an anti-miR-425 agent as disclosed herein typically involves first diagnosing the hypertensive condition and whether treatment with an anti-miR-425 agent is appropriate; administration of an anti-miR-425 agent, e.g., an anti-miR complementary to at least part of the miR-425 sequence of SEQ ID NO: 1, or at least part of the miR-425 miRNA seed sequence SEQ ID NO: 2 alone or in combination with one or more other drug(s) in a therapeutic regimen, monitoring response of the subject, and, if necessary, altering/optimizing dosage/treatment regimen.

Methods of diagnosing essential or secondary hypertension are well known to those of skill in the art (see, e.g., Isselbacher et al. (1994) Harrison's Principles of Internal Medicine, 13.sup.th Ed., McGraw-Hill, Inc., New York). Physical examination and laboratory tests are directed at (1) uncovering correctable secondary forms of hypertension; (2) establishing a pretreament baseline, (3) assessing factors which may influence the type or therapy or which may be adversely modified by therapy, (4) determining if target organ damage is present and (5) determining whether other risk factors for the development or arteriosclerotic cardiovascular diseases are present.

In some embodiments, a subject amenable to treatment with an anti-miR-425 agent as disclosed herein has normal or high levels of miR-425. In some embodiments, a subject is screened for the presence or amount of miR-425 in a biological sample from the subject, e.g., a blood or plasma sample from the subject according to the methods and assays as disclosed herein. In some embodiments, a level of miR-425 above a pre-defined standard level (e.g., reference level) indicates a subject is amenable to treatment with an anti-miR-425 agent, e.g., an anti-miR complementary to at least part of the miR-425 sequence of SEQ ID NO: 1, or at least part of the miR-425 miRNA seed sequence SEQ ID NO: 2 as disclosed herein. In some embodiments, a subject can be screened for the presence of one or two copies of the major A allele of rs5068 SNP, and where a subject is homozygous for the A allele (e.g., is AA), or heterozygous (AG) for rs5068, the subject is amenable to be administered an anti-miR-425 agent, e.g., an anti-miR small molecule, or oligonucleotide complementary to at least part of the miR-425 sequence of SEQ ID NO: 1, or at least part of the miR-425 miRNA seed sequence SEQ ID NO: 2. If a subject is screened for the alleles rs5068, and found to not to have an A allele (e.g., the subject is homozygous GG), the subject is not administered an anti-miR-425 agent as disclosed herein, but can be administered other therapeutic agents for treatment of hypertension and high blood pressure.

In the event treatment with an anti-miR-425 agent is indicated, an anti-miR-425 agent, e.g., an anti-miR complementary to at least part of the miR-425 sequence of SEQ ID NO: 1, or at least part of the miR-425 miRNA seed sequence SEQ ID NO: 2 as disclosed herein can be administered to the subject organism (e.g., patient) alone or in combination with other medications or medicaments (e.g., other anti-hypertensives such as diuretics, antiadrenergic agents, angiotensin-converting enzyme (ACE) inhibitors, other calcium channel antagonists (e.g., nifedipine, amlodipine, verapamil, diltiazem, etc.), or other pharmacological agents) as described below. The subject will be monitored and evaluated according to standard methods in the art and dosages adjusted accordingly.

In one method an anti-miR-425 agent, e.g., an anti-miR complementary to at least part of the miR-425 sequence of SEQ ID NO: 1, or at least part of the miR-425 miRNA seed sequence SEQ ID NO: 2 can be administered to an individual suffering from hypertension. For example, a composition comprising an anti-miR-425 agent, e.g., an anti-miR complementary to at least part of the miR-425 sequence of SEQ ID NO: 1, or at least part of the miR-425 miRNA seed sequence SEQ ID NO: 2 and a pharmaceutically acceptable excipient is administered therapeutically to an individual to reduce or ameliorate hypertension. In another embodiment, an anti-miR-425 agent as disclosed herein—can be administered prophylactically to reduce the probability of occurrence of hypertension or to mitigate and/or prevent the onset of hypertension associated pathologies (e.g., stroke, kidney failure, etc.).

In some embodiments, compositions comprising an anti-miR-425 agent can be used for the treatment of angina pectoris. Angina Pectoris results from the narrowing of the coronary arteries and subsequent reduction in blood supply to the myocardium. Total obstruction of these arteries lead to myocardial infarction. Accordingly, in one embodiment, an anti-miR-425 agent as disclosed herein can be used in the treatment of angina pectoris and myocardial infarction. For example, ANP can prevent adverse LV remodeling and thereby preventing the development of congestive heart failure.

As discussed herein, in some embodiments, an anti-miR-425 agent as disclosed herein can be used to treat any one or a combination of disorders selected from the group consisting of congestive heart failure, hypertension, systemic hypertension (thereby preventing the development of myocardial infarction, chronic heart failure (CHF), renal failure, and stroke), pulmonary hypertension, acute kidney injury, modulating inflammatory responses (either positively or negatively), lipolysis, obesity, diabetes mellitus, reducing intraocular pressure (preventing blindness in glaucoma, reducing ischemia-reperfusion (I/R) injury, (including spinal cord I/R injury and cardiac I/R injury), preventing atrial fibrillation, liver failure, liver fibrosis, cirrhosis, cancer, promote angiogenesis, weight loss.

In some embodiments, an anti-miR-425 agent as disclosed herein can be used in a therapeutic treatment for any one or more of the following disorders; congestive heart failure (CHF) (Kobayashi D, et al., Human atrial natriuretic peptide treatment for acute heart failure: a systematic review of efficacy and mortality. Can J Cardiol; 28:102-9.), systemic hypertension—thereby preventing the development of myocardial infarction, CHF, renal failure, and stroke, pulmonary hypertension, acute kidney injury (Nigwekar et al., Atrial natriuretic peptide for preventing and treating acute kidney injury. Cochrane Database Syst Rev 2009:CD006028.), modulating inflammatory responses (either positively or negatively) (Casserly et al. The role of natriuretic peptides in inflammation and immunity Recent Pat Inflamm Allergy Drug Discov; 4:90-104), lipolysis (enhancing breakdown of adipose tissue), obesity (Birkenfeld et al., Atrial natriuretic peptide induces postprandial lipid oxidation in humans. Diabetes 2008; 57:3199-204; Lafontan et al., Control of lipolysis by natriuretic peptides and cyclic GMP. Trends Endocrinol Metab 2008; 19:130-7), diabetes mellitus by enhancing insulin secretion in response to glucose (Ropero et al., The atrial natriuretic peptide and guanylyl cyclase-A system modulates pancreatic beta-cell function. Endocrinology; 151:3665-74), reducing intraocular pressure (and thereby preventing blindness in glaucoma, where topical administration of anti-miR-425 would be beneficial), (Wolfensberger et al., Evidence for a new role of natriuretic peptides: control of intraocular pressure. Br J Ophthalmol 1994; 78:446-8), reducing ischemia-reprefusion (FR) injury, including spinal cord I/R injury 8 and cardiac FR injury (Gerczuk P Z, Kloner R A. An update on cardioprotection: a review of the latest adjunctive therapies to limit myocardial infarction size in clinical trials. J Am Coll Cardiol; 59:969-78); preventing atrial fibrillation—NPPA gene mutations are a cause of familial atrial fibrillation (Perrin et al., The role of atrial natriuretic peptide in modulating cardiac electrophysiology. Heart Rhythm; 9:610-5), liver fibrosis (Ishigaki et al., Continuous intravenous infusion of atrial natriuretic peptide (ANP) prevented liver fibrosis in rat. Biochem Biophys Res Commun 2009; 378:354-9), cirrhosis, disorders associated with cirrhosis, treatment of ascites associated with cirrhosis, cancer (e.g., inhibit cancer cell growth (Vesely D L. Metabolic targets of cardiac hormones' therapeutic anti-cancer effects. Curr Pharm Des; 16:1159-66.); promote angiogenesis; weight loss (e.g., by enhancing brown adipocyte phenotype and energy expenditure (decreasing weight) (Bordicchia et al., Cardiac natriuretic peptides act via p38 MAPK to induce the brown fat thermogenic program in mouse and human adipocytes. J Clin Invest; 122:1022-36)).

In alternative embodiments, an anti-miR-425 agent as disclosed herein can be used in a prophylactic treatment any one of the following diseases and disorders; congestive heart failure (CHF) (Kobayashi D, et al., Human atrial natriuretic peptide treatment for acute heart failure: a systematic review of efficacy and mortality. Can J Cardiol; 28:102-9.), systemic hypertension—thereby preventing the development of myocardial infarction, CHF, renal failure, and stroke, pulmonary hypertension, acute kidney injury (Nigwekar et al., Atrial natriuretic peptide for preventing and treating acute kidney injury. Cochrane Database Syst Rev 2009:CD006028.), modulating inflammatory responses (either positively or negatively) (Casserly et al., The role of natriuretic peptides in inflammation and immunity Recent Pat Inflamm Allergy Drug Discov; 4:90-104), lipolysis (enhancing breakdown of adipose tissue), obesity (Birkenfeld et al., Atrial natriuretic peptide induces postprandial lipid oxidation in humans. Diabetes 2008; 57:3199-204; Lafontan et al., Control of lipolysis by natriuretic peptides and cyclic GMP. Trends Endocrinol Metab 2008; 19:130-7)., diabetes mellitus by enhancing insulin secretion in response to glucose (Ropero et al., The atrial natriuretic peptide and guanylyl cyclase-A system modulates pancreatic beta-cell function. Endocrinology; 151:3665-74), reducing intraocular pressure (and thereby preventing blindness in glaucoma, where topical administration of anti-miR-425 would be beneficial), (Wolfensberger et al., Evidence for a new role of natriuretic peptides: control of intraocular pressure. Br J Ophthalmol 1994; 78:446-8), reducing ischemia-reprefusion (I/R) injury, including spinal cord I/R injury 8 and cardiac FR injury (Gerczuk P Z, Kloner R A. An update on cardioprotection: a review of the latest adjunctive therapies to limit myocardial infarction size in clinical trials. J Am Coll Cardiol; 59:969-78); preventing atrial fibrillation—NPPA gene mutations are a cause of familial atrial fibrillation (Perrin et al., The role of atrial natriuretic peptide in modulating cardiac electrophysiology. Heart Rhythm; 9:610-5), liver fibrosis (Ishigaki et al., Continuous intravenous infusion of atrial natriuretic peptide (ANP) prevented liver fibrosis in rat. Biochem Biophys Res Commun 2009; 378:354-9), cirrhosis, disorders associated with cirrhosis, treatment of ascites associated with cirrhosis, cancer (e.g., inhibit cancer cell growth (Vesely D L. Metabolic targets of cardiac hormones' therapeutic anti-cancer effects. Curr Pharm Des; 16:1159-66.); promote angiogenesis; weight loss (e.g., by enhancing brown adipocyte phenotype and energy expenditure (decreasing weight) (Bordicchia et al., Cardiac natriuretic peptides act via p38 MAPK to induce the brown fat thermogenic program in mouse and human adipocytes. J Clin Invest; 122:1022-36))

In some embodiments, addition, an anti-miR-425 agent, e.g., an anti-miR complementary to at least part of the miR-425 sequence of SEQ ID NO: 1, or at least part of the miR-425 miRNA seed sequence SEQ ID NO: 2 can be used for prophylactic treatment of high blood pressure. There are hereditary conditions and/or environmental situations (e.g. stress, diet and high Body Mass index (BMI) and obesity) known in the art that predispose an individual to developing high blood pressure and/or heart failure. Under these circumstances, it may be beneficial to treat these individuals with therapeutically effective doses an anti-miR-425 agent, e.g., anti-miR to reduce the risk of developing high blood pressure, heart failure or other cardiovascular diseases and conditions as disclosed herein.

In some embodiments, an anti-miR-425 agent as disclosed herein is administered to a subject identified to be at risk of a cardiovascular disease or disorder identified by cardiovascular biomarkers, such as but not limited to CRP, creatine phosphokinase (CPK), aspartate aminotransferase (AST), lactate dehydrogenase (LDH) in the blood, or a symptom of cardiovascular disease as determined by someone of ordinary skill in the art as measured by electrocardiogram (ECG or EKG), or echocardiogram (heart ultrasound). In some embodiments, a subject at risk of cardiovascular disease is identified by the presence of one or more biomarkers such as, but not limited to cardiac troponins, C-reactive protein (CRP), ANP, BNP, adrenomedullin, copeptin NT-proBNP, NT-proANP, mid-regional-proANP, Galectin-3, ST-2, GDF-15 and others, which are well known by persons of ordinary skill in the art.

In one embodiment, an anti-miR-425 agent, e.g., an anti-miR complementary to at least part of the miR-425 sequence of SEQ ID NO: 1, or at least part of the miR-425 miRNA seed sequence SEQ ID NO: 2 in a suitable formulation may be administered to a subject who has a family history of high blood pressure, or to a subject who has a genetic predisposition for high blood pressure. In other embodiments, an anti-miR-425 agent, e.g., anti-miR in a suitable formulation is administered to a subject who has reached a particular age, or to a subject more likely to get high blood pressure. In yet other embodiments, an anti-miR-425 agent, e.g., anti-miR in a suitable formulation is administered to subjects who exhibit symptoms of high blood pressure. In still other embodiments, an anti-miR-425 agent, e.g., anti-miR in a suitable formulation may be administered to a subject as a preventive measure. In some embodiments, an anti-miR-425 agent, e.g., anti-miR in a suitable formulation may be administered to a subject based on demographics or epidemiological studies, or to a subject in a particular field or career, e.g., high-stress working environments, or fields and careers where it is desirable subject maintain a low blood pressure.

In addition to subjects being identified as being homozygous for the major allele (e.g., AA) for the rs5068 SNP according to the methods and assays as disclosed herein, other subjects amenable to treatment with anti-miR-425 agents can be identified according to the methods disclosed in U.S. Pat. No. 5,998,145, which is incorporated herein by reference.

In some embodiments, subject amenable to treatment with the anti-miR-425 agents as disclosed herein have a blood pressure of above 120/80 mm Hg, above 115/75 mm Hg, where the risk of cardiovascular disease begins to increase. In some embodiments, subject amenable to treatment with the anti-miR-425 agents as disclosed herein have pre-hypertension, where their Prehypertension. Prehypertension is a systolic pressure ranges from 120 to 139 mm Hg or a diastolic pressure ranges from 80 to 89 mm Hg. In some embodiments, subject amenable to treatment with the anti-miR-425 agents as disclosed herein have stage 1 or Stage 2 hypertension, where subjects with stage 1 hypertension have a systolic pressure ranging from about 90-100 mm Hg to about 159 mm Hg or a diastolic pressure ranging from 90 to 99 mm Hg, and subjects with stage 2 hypertension have a systolic pressure of 160 mm Hg or higher or a diastolic pressure of 100 mm Hg or higher.

Subjects Amenable to Treatment with miR-425 or a Mimetic Thereof

In some embodiments, the present invention relates to a method of decreasing atrial natriuric peptide (ANP) in a subject in need thereof, comprising administering to the subject a composition comprising miR-425 (SEQ ID NO: 1) or a mimetic or homologue thereof to a subject. In some embodiments, a subject in need thereof is a subject who needs an increase in blood pressure. In such embodiments, the method of decreasing ANP in a subject who has high levels of ANP is useful for treating low blood pressure and associated disorders, e.g., shock. In some embodiments, administration of a miR-425, or mimetic thereof is administered to a subject to treat any one or a combination of inhibiting angiogenesis, low blood pressure, increased endothelial permeability, orthostatic hypotension.

In some embodiments, a homologue or variant of miR-425 encompassed for use binds to the miR-425 miRNA target sequence SEQ ID NO: 8 or SEQ ID NO: 9 in the 3' UTR of the NPPA gene. In such embodiments, the method of decreasing ANP in a subject is useful for treating low blood pressure and associated disorders as disclosed herein. In some embodiments, a miR-425 (e.g., SEQ ID NO: 1) or variant thereof which binds to the miRNA target sequence SEQ ID NO:8 is administered to a subject whom has been identified as having at least one A allele of rs5068 SNP, e.g., a AA or AG subject. In alternative embodiments, a modified miR-425 which binds to the "G" allele miRNA target sequence of SEQ ID NO: 9 in the 3'UTR of the NPPA gene is administered to a subject who has been identified to have at least one G allele or rs5068 SNP (e.g., GG or AG subjects). In some embodiments, a subject, e.g., a AG heterozygous subject is administered a miR-425 of SEQ ID NO: 1 and/or a variant miRNA which binds to SEQ ID NO: 8, in combination with a modified miR-425 which binds to the miR target sequence SEQ ID NO: 9. In some embodiments, administration of a miR-425, or mimetic thereof is administered to a subject to treat any one or a combination of inhibiting angiogenesis, low blood pressure, increased endothelial permeability, or orthostatic hypotension.

In some embodiments, a miR-425 agent, or modified miR-425 agent or mimetic thereof can be administered to a subject to treat a subject where there is leakage of the plasma into the extravascular space (increased endothelial permeability). (Kuhn M. Endothelial actions of atrial and B-type natriuretic peptides. Br J Pharmacol; 166:522-31.) In alternative embodiments, a miR-425 agent, or mimetic or homologue thereof can be administered to a subject in need of decreasing ANP levels in a subject, for example a subject where it is desirable to inhibit angiogenesis (Kong X, Wang X, Xu W, et al. Natriuretic peptide receptor a as a novel anticancer target. Cancer Res 2008; 68:249-56.), or a subject with orthostatic hypotension. In particular, there has been an association of the rs5068 variant with orthostatic hypotension 17 (Tunny et al., Inappropriately elevated levels of atrial natriuretic peptide may contribute to the pathophysiology of orthostatic hypotension. Clin Exp Pharmacol Physiol 1992; 19:283-6; Fedorowski A, et al., Orthostatic hypotension and novel blood pressure-associated gene variants: Genetics of Postural Hemodynamics (GPH) Consortium. Eur Heart J.)

Administration

In one aspect, the invention provides methods of administering any, or a combination of anti-miR-425 agents or miR-425 agents as disclosed herein to a subject. When administered, an anti-miR-425 or miR-425 agent is administered to the subject in a therapeutically effective, pharmaceutically acceptable amount as a pharmaceutically acceptable formulation.

A therapeutically effective amount can be determined on an individual basis and will be based, at least in part, on consideration of the species of mammal, the mammal's age, sex, size, and health; the compound and/or composition used, the type of delivery system used; the time of administration relative to the severity of the disease; and whether a single, multiple, or controlled-release dose regimen is employed. A therapeutically effective amount can be determined by one of ordinary skill in the art employing such factors and using no more than routine experimentation.

In administering the anti-miR-425 or miR-425 agent according to the systems and methods of the invention to a subject, dosing amounts, dosing schedules, routes of administration, and the like may be selected so as to affect known activities of these systems and methods. Dosage may be adjusted appropriately to achieve desired drug levels, local or systemic, depending upon the mode of administration. The doses may be given in one or several administrations per day. As one example, if daily doses are required, daily doses may be from about 0.01 mg/kg/day to about 1000 mg/kg/day, and in some embodiments, from about 0.1 to about 100 mg/kg/day or from about 1 mg/kg/day to about 10 mg/kg/day. Parenteral administration, in some cases, may be from one to several orders of magnitude lower dose per day, as compared to oral doses. For example, the dosage of an active compound of anti-miR-425 or miR-425 agent when parenterally administered may be between about 0.1 micrograms/kg/day to about 10 mg/kg/day, and in some embodiments, from about 1 microgram/kg/day to about 1 mg/kg/day or from about 0.01 mg/kg/day to about 0.1 mg/kg/day. In some embodiments, the concentration of the active compound(s), if administered systemically, is at a dose of about 1.0 mg to about 2000 mg for an adult of kg body weight, per day. In other embodiments, the dose is about 10 mg to about 1000 mg/70 kg/day. In yet other embodiments, the dose is about 100 mg to about 500 mg/70 kg/day. Preferably, the concentration, if applied topically, is about 0.1 mg to about 500 mg/gm of ointment or other base, more preferably about 1.0 mg to about 100 mg/gm of base, and most preferably, about 30 mg to about 70 mg/gm of base. The specific concentration partially depends upon the particular composition used, as some are more effective than others. The dosage concentration of a composition comprising an anti-miR-425 or miR-425 agent actually administered is dependent at least in part upon the particular physiological response being treated, the final concentration of composition that is desired at the site of action, the method of administration, the efficacy of the particular composition, the longevity of the particular composition, and the timing of administration relative to the severity of the disease. Preferably, the dosage form is such that it does not substantially deleteriously affect the mammal. The dosage can be determined by one of ordinary skill in the art employing such factors and using no more than routine experimentation. In the event that the response of a particular subject is insufficient at such doses, even higher doses (or effectively higher doses by a different, more localized delivery route) may be employed to the extent that subject tolerance permits. Multiple doses per day are also contemplated in some cases to achieve appropriate systemic levels within the subject or within the active site of the subject. In some cases, dosing amounts, dosing schedules, routes of administration, and the like may be selected as described herein, whereby therapeutically effective levels for the treatment of cancer are provided.

In certain embodiments where high blood pressure, heart failure or other cardiovascular disorder is being treated, an anti-miR-425 agent, e.g., anti-miR as disclosed herein can be administered to a subject who has a family history cardiovascular disorder, e.g., a family history of any one or a combination of high blood pressure, heart failure, hypotrophy (e.g., left ventricle hypotrophy), or to a subject who has a genetic predisposition for cardiovascular disease, e.g., heart failure, high blood pressure and the like. In other embodiments, an anti-miR-425 agent, e.g., anti-miR can be administered to a subject who has reached a particular age, or to a subject more likely to get high blood pressure or heart failure. In yet other embodiments, an anti-miR-425 agent, e.g., anti-miR can be administered to subjects who exhibit symptoms of high blood pressure or heart failure. In still other embodiments, the composition may be administered to a subject as a preventive measure.

In some embodiments, an anti-miR-425 or miR-425 agent may be administered to a subject based on demographics or epidemiological studies, or to a subject in a particular field or career (e.g., a high stress career or career where low blood pressure is important). In some embodiments, an anti-miR-425 agent, e.g., anti-miR can be administered to a subject that has had a prior therapy for a cardiovascular disease.

In some embodiments an anti-miR-425 agent, e.g., anti-miR as disclosed herein can be administered to a subject who has renal failure, obesity or a risk of renal failure and/or obesity.

In some embodiments, an miR-425 agent is administered to a subject who has low blood pressure, or has had a prior history of low blood pressure, or is in need of elevating their blood pressure (e.g., after a surgery etc.).

Administration of an anti-miR-425 or miR-425 agent as disclosed herein to a subject may be accomplished by any medically acceptable method which allows the composition to reach its target. The particular mode selected will depend of course, upon factors such as those previously described, for example, the particular composition, the severity of the state of the subject being treated, the dosage required for therapeutic efficacy, etc. As used herein, a "medically acceptable" mode of treatment is a mode able to produce effective levels of the active compound(s) of the composition within the subject without causing clinically unacceptable adverse effects.

The methods to deliver an anti-miR-425 or miR-425 thereof to the cell or subject useful in the present invention are well known in the art, and include chemical transfection using lipid-based, amine based and polymer based techniques, viral vectors and combinations thereof (see, for example, products from Ambion Inc., Austin, Tex.; and Novagen, EMD Biosciences, Inc, an Affiliate of Merck KGaA, Darmstadt, Germany).

Other described ways to deliver an anti-miR-425 or miR-425 is from vectors, such as lentiviral constructs, and introducing siRNA molecules into cells using electroporation. However, feline FIV lentivirus vectors which are based on the feline immunodeficiency virus (FIV) retrovirus and the HIV lentivirus vector system, which is based on the human immunodeficiency virus (HIV), carry with them problems related to permanent integration. Electroporation is also useful in the present invention, although it is generally only used to deliver siRNAs into cells in vitro.

The target cell types to which anti-miR-425 agents, e.g., anti-miRs complementary to the miRNA seed sequence SEQ ID NO:2 or miR-425 agents can be delivered using the methods of the invention include heart cells, such as cardiomyocytes and cardiac fibroblasts, neuronal tissues, prostate cells and other cells which express either miR-425 and/or NPPA gene.

In one embodiment, the nucleic acid encoding an anti-miR-425 agent, (e.g., anti-miR which is complementary at least in part to the miRNA seed sequence SEQ ID NO:2) or miR-425 agent is present on a vector. These vectors include a sequence encoding an anti-miR-425 agent, e.g., anti-miR and in vivo expression elements. In some embodiments, these vectors include a sequence encoding an anti-miR-425 or miR-425 and in vivo expression elements such that the an anti-miR-425 agent, e.g., anti-miR is expressed and processed in vivo. In another embodiment, these vectors include a sequence encoding an anti-miR-425 agent, e.g., anti-miR and in vivo expression elements, where the anti-miR-425 agent is first processed to produce the stem-loop precursor miRNA molecule, which can be processed to produce anti-miR which is complementary at least in part to the miRNA seed sequence SEQ ID NO:2.

In some embodiments, an anti-miR-425 or miR-425 can be delivered in vivo and in vitro. The in vivo delivery as used herein means delivery an anti-miR-425 or miR-425 into a living subject, including human. The in vitro delivery as used herein means delivery of an anti-miR-425 or miR-425 into cells and organs outside a living subject.

Vectors include, but are not limited to, plasmids, cosmids, phagemids, viruses, other vehicles derived from viral or bacterial sources that have been manipulated by the insertion or incorporation of the nucleic acid sequences for producing the microRNA, and free nucleic acid fragments which can be attached to these nucleic acid sequences. Viral and retroviral vectors are a preferred type of vector and include, but are not limited to, nucleic acid sequences from the following viruses: retroviruses, such as: Moloney murine leukemia virus; Murine stem cell virus, Harvey murine sarcoma virus; marine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; and RNA viruses such as any retrovirus. One of skill in the art can readily employ other vectors known in the art.

Viral vectors are generally based on non-cytopathic eukaryotic viruses in which non-essential genes have been replaced with the nucleic acid sequence of interest. Non-cytopathic viruses include retroviruses, the life cycle of which involves reverse transcription of genomic viral RNA into DNA with subsequent proviral integration into host cellular DNA.

Retroviruses have been approved for human gene therapy trials. Genetically altered retroviral expression vectors have general utility for the high efficiency transduction of nucleic acids in viva. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular L Biology," vol. 7, Humana Press, Inc., Cliffton, N.J. (1991).

In some embodiments the "in vivo expression elements" are any regulatory nucleotide sequence, such as a promoter sequence or promoter-enhancer combination, which facilitates the efficient expression of the nucleic acid to produce the microRNA. The in vivo expression element may, for example, be a mammalian or viral promoter, such as a constitutive or inducible promoter and/or a tissue specific promoter. Examples of which are well known to one of ordinary skill in the art. Constitutive mammalian promoters include, but are not limited to, polymerase promoters as well as the promoters for the following genes: hypoxanthine phosphoribosyl transferase (HPTR), adenine deaminase, pyruvate kinase, and beta.-actin. Exemplary viral promoters which function constitutively in eukaryotic cells include, but are not limited to, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. Inducible promoters are expressed in the presence of an inducing agent and include, but are not limited to, metal-inducible promoters and steroid-regulated promoters. For example, the metallothionein promoter is induced to promote transcription in the presence of certain metal ions. Other inducible promoters are known to those of ordinary skill in the art.

Examples of tissue-specific promoters include, but are not limited to, the promoter for creatine kinase, which has been used to direct expression in muscle and cardiac tissue and immunoglobulin heavy or light chain promoters for expression in B cells. Other tissue specific promoters include the human smooth muscle alpha-actin promoter. Exemplary tissue-specific expression elements for the liver include but are not limited to HMG-COA reductase promoter, sterol regulatory element 1, phosphoenol pyruvate carboxy kinase (PEPCK) promoter, human C-reactive protein (CRP) promoter, human glucokinase promoter, cholesterol L 7-alpha hydroylase (CYP-7) promoter, beta-galactosidase alpha-2,6 sialylkansferase promoter, insulin-like growth factor binding protein (IGFBP-1) promoter, aldolase B promoter, human transferrin promoter, and collagen type I promoter. Exemplary tissue-specific expression elements for the prostate include but are not limited to the prostatic acid phosphatase (PAP) promoter, prostatic secretory protein of 94 (PSP 94) promoter, prostate specific antigen complex promoter, and human glandular kallikrein gene promoter (hgt-1). Exemplary tissue-specific expression elements for gastric tissue include but are not limited to the human $H^+/K^+$-ATPase alpha subunit promoter. Exemplary tissue-specific expression elements for the pancreas include but are not limited to pancreatitis associated protein promoter (PAP), elastase 1 transcriptional enhancer, pancreas specific amylase and elastase enhancer promoter, and pancreatic cholesterol esterase gene promoter. Exemplary tissue-specific expression elements for the endometrium include, but are not limited to, the uteroglobin promoter. Exemplary tissue-specific expression elements for adrenal cells include, but are not limited to, cholesterol side-chain cleavage (SCC) promoter. Exemplary tissue-specific expression elements for the general nervous system include, but are not limited to, gamma-gamma enolase (neuron-specific enolase, NSE) promoter. Exemplary tissue-specific expression elements for the brain include, but are not limited to, the neurofilament heavy chain (NF—H) promoter. Exemplary tissue-specific expression elements for lymphocytes include, but are not limited to, the human CGL-1/granzyme B promoter, the terminal deoxy transferase (TdT), lambda 5, VpreB, and lck (lymphocyte specific tyrosine protein kinase p561ck) promoter, the humans CD2 promoter and its 3' transcriptional enhancer, and the human NK and T cell specific activation (NKG5) promoter. Exemplary tissue-specific expression elements for the colon include, but are not limited to, pp60c-src tyrosine kinase promoter, organ-specific neoantigens (OSNs) promoter, and colon specific antigen-P promoter.

Other elements aiding specificity of expression in a tissue of interest can include secretion leader sequences, enhancers, nuclear localization signals, endosmolytic peptides, etc. Preferably, these elements are derived from the tissue of interest to aid specificity. In general, the in vivo expression element shall include, as necessary, 5' non-transcribing and 5' non-translating sequences involved with the initiation of transcription. They optionally include enhancer sequences or upstream activator sequences.

An anti-miR-425 or miR-425 either alone or expressed as a viral vector, or complexed to targeting moieties can be delivered using any delivery system such as topical administration, subcutaneous, intramuscular, intraperitoneal, intrathecal and intravenous injections, catheters for delivering an anti-miR-425 or miR-425 into, for example, a specific organ, such as heart.

A pharmaceutically acceptable carrier as used herein means any pharmaceutically acceptable means to mix and/or deliver an anti-miR-425 agent, e.g., anti-miR which is complementary at least in part to the miRNA seed sequence SEQ ID NO:2 or miR-425 agent either alone or complexed to targeting moieties to a subject, or in combination with one or more pharmaceutically acceptable ingredients.

In the preparation of pharmaceutical formulations containing an anti-miR-425 or miR-425, either alone or complexed to targeting moieties of the present invention in the form of dosage units for oral administration the compound selected may be mixed with solid, powdered ingredients, such as lactose, saccharose, sorbitol, mannitol, starch, arnylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules may be prepared with capsules containing a mixture of the active compound or compounds of the invention in vegetable oil, fat, or other suitable vehicle for soft gelatin capsules. Hard gelatin capsules may contain granules of the active compound. Hard gelatin capsules may also contain an anti-miR-425 or miR-425 either alone or complexed to targeting moieties in combination with solid powdered ingredients such as lactose, saccharose, sorbitol, mannitol, potato starch, corn starch, arnylopectin, cellulose derivatives or gelatin.

Dosage units for rectal or vaginal administration may be prepared (i) in the form of suppositories which contain the active substance, i.e. an anti-miR-425 or miR-425, either alone or complexed to targeting moieties, mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain coloring agents, flavoring agents, saccharin and carboxymethyl cellulose or other thickening agents. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The methods of the present invention to also encompass delivery an anti-miR-425 or miR-425, either alone or complexed to targeting moieties orally in granular form including sprayed dried particles, or complexed to form micro or nanoparticles.

The subject or individual as referred to herein and throughout the specification includes mammals, such as murine, specifically mice and rats, bovine, and primates, such as human.

Other formulations for oral administration of anti-miR-425 or miR-425 for use with the invention include solutions or suspensions in aqueous or non-aqueous liquids such as a syrup, an elixir, or an emulsion. In another set of embodiments, an anti-miR-425 or miR-425 may be used to fortify a food or a beverage.

Injections can be e.g., intravenous, intratumoral, intradermal, subcutaneous, intramuscular, or interperitoneal. The composition can be injected interdermally for treatment or prevention of infectious disease, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

In some embodiments, an anti-miR-425 agent, e.g., anti-miR and/or nucleic acid encoding such, for example vectors are provided in a manner which enables tissue-specific uptake of the agent and/or nucleic acid delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

An anti-miR-425 or miR-425 as disclosed herein may also be delivered using a bioerodible or bioresorbable implant by way of diffusion, or more preferably, by degradation of the polymeric matrix. Exemplary synthetic polymers which can be used to form the biodegradable delivery system include: polyamides, polycarbonates, polyalkylenes, s polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, lo hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), i poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic; acid and glycolic acid, polyanhydrides, poly(ortho)esters, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifcations routinely made by those skilled in the art), albumin and other hydrophilic proteins, zein and other prolamines and 2s hydrophobic proteins, copolymers and mixtures thereof. In general, these materials degrade either by enzymatic hydrolysis or exposure to water in vivo, by surface or bulk erosion. Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, C. P. Pathak and J. A. Hubell in Macromolecules, (1993) i 26:581-587, the teachings of which are incorporated herein, polyhyaluronic acids, casein, gelatin, glutin, polyanhydrides, polyacrylic acid, alginate, chitosan, poly(methyl I methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In certain embodiments of the invention, the administration of an anti-miR-425 or miR-425 as disclosed herein may be designed so as to result in sequential exposures to the composition over a certain time period, for example, hours, days, weeks, months or years. This may be accomplished, for example, by repeated administrations of an anti-miR-425 or miR-425 of the invention by one of the methods described above, or by a sustained or controlled release delivery system in which an anti-miR-425 or miR-425 are delivered over a prolonged period without repeated administrations. Administration of an anti-miR-425 or miR-425 using such a delivery system may be, for example, by oral dosage forms, bolus injections, transdermal patches or subcutaneous implants. Maintaining a substantially constant concentration of the composition may be preferred in some cases.

Other delivery systems suitable for use with the present invention include time release, delayed release, sustained release, or controlled release delivery systems. Such systems may avoid repeated administrations in many cases, increasing convenience to; the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neukal fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the composition is contained in a form within a matrix (for example, as described in U.S. Pat. Nos. 4,452,775, 4,675,189, 5,736,152, 4,667,014, 4,748,034 and -29 5,239,660), or diffusional systems in which an active component controls the release rate I (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, s the system may allow sustained or controlled release of the composition to occur, for example, through control of the diffusion or erosion/degradation rate of the formulation containing the composition. In addition, a pump-based hardware delivery system may be used to deliver one or more embodiments of the invention.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by a tonically-coated microcapsule with a microcapsule core degrading enzyme. Examples of systems in which release of the inhibitor is gradual and continuous include, e.g., erosional Is systems in which the composition is contained in a forth within a matrix and effusional systems in which the composition permeates at a controlled rate, e.g., through a polymer. Such sustained release systems can be e.g., in the form of pellets, or capsules.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an tonically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some; embodiments of the invention. "Long-term release," as used herein, means that the implant containing an anti-miR-425 agent, e.g., anti-miR are constructed and arranged to deliver therapeutically effective levels of the composition for at least 30 or 45 days, and preferably at least 60 or days, or even longer in some cases. Long-term release implants are well known to those of ordinary skill in the art, and include some of the release systems described above.

In some embodiments, an anti-miR-425 agent, e.g., anti-miR of the invention may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers that may be used with the active compound. For example, if the formulation is a liquid, the carrier may be a solvent, partial solvent, or non-solvent, and may be aqueous or organically based. Examples of suitable formulation ingredients –30 include diluents such as calcium carbonate, sodium carbonate, lactose, kaolin, calcium I phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric lo acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Preparations include sterile aqueous or nonaqueous solutions, suspensions and; emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or all-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. In addition, so sterile, fixed oils are conventionally employed as a solvent or suspending medium. For i this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa. Those of skill in the art can readily determine the various parameters for preparing and formulating the compositions of the invention without resort to undue experimentation.

In some embodiments, the present invention encompasses an anti-miR-425 agent, e.g., anti-miR complementary to, or complementary in part, to miRNA seed sequence SEQ ID NO: 2 or an miR-425 agent as disclosed herein in association or contact with a suitable carrier, which may constitute one or more accessory ingredients. The final compositions may be prepared by any suitable technique, for example, by uniformly and intimately bringing the composition into association with a liquid carrier, a finely divided solid carrier or both, optionally with one or more formulation ingredients as previously described, and then, if necessary, shaping the product. In some embodiments, the compositions of the present invention may be present as pharmaceutically acceptable salts. The term "pharmaceutically acceptable salts" includes salts of the composition, prepared in combination with, for example, acids or bases, depending on the particular compounds found within the composition and the treatment modality desired. Pharmaceutically acceptable salts can be prepared as; alkaline metal salts, such as lithium, sodium, or potassium salts, or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like.

Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable acids include amino acids such as arginate, aspartate, glutamate, and the like.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the anti-miR-425 agent and/or miR-425 miRNA employed and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising one or more nucleic acids are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the nucleic acids at various concentrations, e.g., as applied to the mass and overall health of the patient. Administration can be accomplished via single or divided doses.

In vitro models can be used to determine the effective doses of the nucleic acids as a potential hypertension treatments. In vivo models are the preferred models to determine the effective doses of an anti-miR-425 agent, e.g., anti-miR described above as potential cardiovascular disease therapies, e.g., for the treatment of high blood pressure, chronic heart failure and the like. Suitable in vivo models include, but are not limited to, mice, rat, non-human primates, rabbit, guinea pig, pig. In some embodiments, the anti-miR-425 agent can be assessed in a human cellular model expressing ANP as disclosed in Ma et al., 2011; AJP, 301; H2006-H2017 "High-purity human-induced pluripotent stem cell-derived cardiomyocytes; electrophysiological properties of action potentials and ionic currents", which is incorporated herein in its entirety by reference. Alternatively, an animal model (e.g., rodent, porcrine, or monkey) expressing the human NPPA gene including the 3' UTR is encompassed for use in assessing the effective dose of an anti-miR-425 agent as disclosed herein to knockdown miR-425 and increase ANP respectively.

In some embodiments, a human cell line expressing ANP can be used, as well as cardiomyocytes differentiated from human iPS cells or ES cells as disclosed herein in the Examples. In some embodiments, the iPS cells are obtained from subjects who are AA homozygous or AG heterozygous for the rs5068 SNP. Such cells are commercially available from suppliers such as Cellular Dynamics or iCell.

An anti-miR-425 agent or anti-miR-425 agent can be assessed in other animal models, such as transgenic mouse models. The inventors have developed a transgenic mouse model which expresses miR-425 (data not shown) which can be used to assess the effect of an anti-miR-425 agent, e.g., the effect of an anti-miR-425 agent on knock down of miR-425 agent in vivo can be tested. In some embodiments, dogs can be used to assess the effect of an anti-miR-425 agent, which have a mature miR-425 sequence similar to human miR-425 sequence. Primate models can also be used. For example, chimpanzees and monkeys have a similar miR-425 target sequence to human miR-425 target sequence of SEQ ID NO: 8, and thus are suitable to be used in animal models of miR-425 agents to decrease ANP levels, or alternatively to assess anti-miR-425 agents as disclosed herein. Mouse and rats have differences of 2 base pairs in the miR-425 target sequence, and accordingly transgenic mouse and rat models where these bases have been substituted to resemble the human miR-425 target sequence of SEQ ID NO:8 are also encompassed for assessing anti-miR-425 agents and miR-425 agents as disclosed herein.

In determining the effective amount of an anti-miR-425 agent, e.g., an anti-miR complementary to at least part of the miR-425 sequence of SEQ ID NO: 1, or at least part of the miR-425 miRNA seed sequence SEQ ID NO: 2 to be administered in the treatment of a cardiovascular disease, the physician can evaluate circulating plasma levels of miR-425, by the methods as disclosed herein, as well as formulation toxicities, and progression of the disease.

The dose an anti-miR-425 or miR-425 administered to a 70 kilogram subject is typically in the range equivalent to dosages of currently-used therapeutic antisense oligonucleotides such as Vikavene (fomivirsen sodium injection) which is approved by the FDA for treatment of cytomegaloviral RNA, adjusted for the altered activity or serum half-life of the relevant composition.

In some embodiments, an anti-miR-425 agent, an anti-miR complementary to at least part of the miR-425 sequence of SEQ ID NO: 1, or at least part of the miR-425 miRNA seed sequence SEQ ID NO: 2 or miR-425 agent as disclosed herein can supplement the treatment of any known additional therapy, including, but not limited to, antibody administration, vaccine administration, administration of cytotoxic agents, natural amino acid polypeptides, nucleic acids, nucleotide analogues, and biologic response modifiers. In some embodiments, an additional therapy for concurrent administration with an miR-425 agent is, for example, surgery, chemotherapy, radiotherapy, thermotherapy, immunotherapy, hormone therapy and laser therapy. Two or more combined compounds may be used together or sequentially with an anti-miR-425 or miR-425. In some embodiments, an anti-miR-425 or miR-425 can be administered before the additional therapy, after the additional therapy or at the same time as the additional therapy. In some embodiments, an anti-miR-425 or miR-425 agent are administered a plurality of times, and in other embodiments, the additional therapies are also administered a plurality of times.

In some embodiments, an anti-miR-425 agent can also be administered in therapeutically effective amounts as a portion of an anti-high blood pressure cocktail. An anti-high blood pressure cocktail is a mixture, for example of a least one an anti-miR-425 agent as disclosed herein with one or more additional agents to treat high-blood pressure, in addition to a pharmaceutically acceptable carrier for delivery. High blood pressure agents that are well known in the art and can be used as a treatment in combination with one or more anti-miR-425 agents, e.g., anti-miR as described herein include, but are not limited to: thiazide diuretics, beta blockers, angiotensin converting enzyme (ACE) inhibitors, angiotension II receptor blockers, calcium channel blockers and renin inhibitors (Aliskiren (Tekturna), alpha blockers, alpha-beta blockers, central-acting agents and vasodilators.

In some embodiments, an anti-miR-425 agent as disclosed herein can be administered alone or in combination with an additional therapeutic agent, such as a therapeutic agent is selected from the group consisting of bumetanide; ethacrynic acid; furosemide; torsemide; epitizide; hydrochlorothiazide; chlorothiazide; bendroflumethiazide; indapamide; chlorthalidone; metolazone; amiloride; triamterene; spironolactone; atenolol; metoprolol; nadolol; oxprenolol; pindolol; propranolol; timolol; doxazosin; phentolamine; indoramin; phenoxybenzamine; prazosin; terazosin; tolazoline; bucindolol; carvedilol; labetalol; amlodipine; felodipine; isradipine; lercanidipine; nicardipine; nifedipine; nimodipine; nitrendipine; diltiazem; verapamil; Aliskiren; captopril; enalapril; fosinopril; lisinopril; perindopril; quinapril; ramipril; trandolapril; benazepril; candesartan; eprosartan; irbesartan; losartan; olmesartan; telmisartan; valsartan; eplerenone; spironolactone; sodium nitroprusside; hydralazine; hydralazine derivatives; Clonidine; Guanabenz; Methyldopa; Moxonidine; Guanethidine; Reserpine; atorvastatin; fluvastatin; lovastatin; pitavastatin; pravastatin; rosuvastatin; simvastatin; and any combinations thereof In some embodiments, a pharmaceutical composition comprising an anti-miR-425 agent can be administered to a subject alone or in combination with agents which inhibit the degredation of ANP, for example, but not limited to inhibitors of neutral endopeptidases including OMAPATRILAT™, or ANP clearance by the clearance receptor. As discussed herein, a comprising an anti-miR-425 agent can be administered to a subject alone or in combination with a PDE-5 inhibitor (e.g., but not limited to sildenafil or tadalafil) which increase cGMP, which is the secondary messenger for ANP.

In certain embodiments, the pharmaceutical compositions comprising an anti-miR-425 agent, e.g., an anti-miR complementary to at least part of the miR-425 sequence of SEQ ID NO: 1, or at least part of the miR-425 miRNA seed sequence SEQ ID NO: 2, for example, pharmaceutical compositions comprising an anti-miR-425 agent, e.g., anti-miR can optionally further comprise one or more additional therapies or agents. In certain embodiments, the additional agent or agents are agents for treatment of heart failure or hypertension. In some embodiments, the therapeutic agents include, but are not limited to thiazide diuretics, beta blockers, angiotensin converting enzyme (ACE) inhibitors, angiotension II receptor blockers, calcium channel blockers and renin inhibitors (Aliskiren (Tekturna), alpha blockers, alpha-beta blockers, central-acting agents and vasodilators.

Other therapeutic agents which can be administered in combination with an anti-miR-425 agent as disclosed herein is a mecamylamine agent, its stereoisomers together as the racemic mixture and as purified separate enantiomers, analogs, the free base, and/or salts thereof. Mecamylamine can be obtained according to the methods and processes described in U.S. Pat. No. 5,986,142, incorporated herein by reference for its teaching regarding method of producing mecamylamine Purified exo-S-mecamylamine and exo-R- mecamylamine can be obtained according to methods discussed in U.S. Pat. No. 7,101,916, and references cited therein, also incorporated herein by reference for their teaching regarding the production of purified mecamylamine enantiomers.

ACE inhibitors which can be administered in combination with an anti-miR-425 agent as disclosed herein include, but are not limited to, benazepril, captopril, ceronapril, enalapril, fosinopril, imidapril, lisinopril, moexipril, quinapril, ramipril, trandolapril, perindopril, and zofenopril. This list is not intended to be limiting, and other compounds known in the art as ACE inhibitors may also be used.

AT2 Inhibitors which can be administered in combination with an anti-miR-425 agent as disclosed herein include, but are not limited to, azilsartan, candesartan, losartan, irbesartan, eprosartan, olmesartan, tasosartan, telmisartan, valsartan, and zolarsartan. Below are representative estimated starting dosages and dosing ranges for selected AT2 inhibitors: andesartan: starting dose 16 mg once daily; dosing range 8 to 32 mg once daily rbesartan: starting dose 150 mg once daily; dosing range 150 to 300 mg once daily losartan: starting dose 50 mg once daily; dosing range 25 to 100 mg once daily telmisartan: starting dose 40 mg once daily; dosing range 20 to 80 mg once daily valsartan: starting dose 80 mg once daily; dosing range 80 to 320 mg once daily Source: Kaplan, N. M., Am Fam Physician 60:1185-90 (1999), herein incorporated by reference with regard to such dosages and ranges.

Renin antagonists/inhibitors which can be administered in combination with an anti-miR-425 agent as disclosed herein include, include those taught in US Published Application, Publication No. 2008/0119557 A1, incorporated herein by reference for its teaching of renin inhibitors and method of obtaining such compounds. In some embodiments, a renin antagonist is aliskiren. [0038] In addition to the aforementioned compounds, renin inhibitors useful according to the present invention include, but are not limited to, ditekiren, enalkiren, remikiren, terlakiren, and zankiren.

One example of a further therapeutic agent which can be administered in combination with an anti-miR-425 agent includes calcium channel blockers, namely compounds which work by blocking voltage-sensitive calcium channels in the heart and in the blood vessels. Calcium levels do not increase as much in the cells when stimulated, leading to less contraction. This decreases total peripheral resistance by dilating the blood vessels, and decreases cardiac output by lowering the force of contraction. Because resistance and output drop, so does blood pressure. With lowered blood pressure, the heart does not have to work as hard; this can ease problems with cardiomyopathy and coronary disease. Unlike with beta-blockers, the heart is still responsive to sympathetic nervous system stimulation, so blood pressure can be maintained more effectively. Calcium channel blockers useful in the present invention include dihydropyridine calcium channel blockers including amlodipine, felodipine, nicardipine, nifedipine, nimodipine, nisoldipine, nitrendipine, lacidipine, and lercanidipine; phenylalkylamine calcium channel blockers including verapamil and gallopamil; benzothiazepine calcium channel blockers including diltiazem; and other calcium channel blockers such as menthol.

Additionally, an anti-miR-425 agent as disclosed herein can be used in combination with any one or a combination of one or more of the following agents; anti-hyperlipidemic agents; anti-dyslipidemic agents; plasma HDL-raising agents; anti-hypercholesterolemic agents, including, but not limited to, cholesterol-uptake inhibitors; cholesterol biosynthesis inhibitors, e.g., HMG-CoA reductase inhibitors (also referred to as statins, such as lovastatin, simvastatin, pravastatin, fluvastatin, rosuvastatin, pitavastatin, and atorvastatin); HMG-CoA synthase inhibitors; squalene epoxidase inhibitors or squalene synthetase inhibitors (also known as squalene synthase inhibitors); acyl-coenzyme A cholesterol acyltransferase (ACAT) inhibitors, including, but not limited to, melinamide; probucol; nicotinic acid and the salts thereof; niacinamide; cholesterol absorption inhibitors, including, but not limited to, P-sitosterol or ezetimibe; bile acid sequestrant anion exchange resins, including, but not limited to cholestyramine, colestipol, colesevelam or dialkylaminoalkyl derivatives of a cross-linked dextran; LDL receptor inducers; fibrates, including, but not limited to, clofibrate, bezafibrate, fenofibrate and gemfibrozil; vitamin B6 (also known as pyridoxine) and the pharmaceutically acceptable salts thereof, such as the HCl salt; vitamin B12 (also known as cyanocobalamin); vitamin B3 (also known as nicotinic acid and niacinamide, supra); anti-oxidant vitamins, including, but not limited to, vitamin C and E and betacarotene; platelet aggregation inhibitors, including, but not limited to, fibrinogen receptor antagonists, i.e., glycoprotein IIb/IIIa fibrinogen receptor antagonists; hormones, including but not limited to, estrogen; insulin; ion exchange resins; omega-3 oils; benfluorex; ethyl icosapentate; and amlodipine; appetite-suppressing agents or anti-obesity agents including, but not limited to, insulin sensitizers, protein tyrosine phosphatase-1B (PTP-1 B) inhibitors, dipeptidyl peptidase IV (DPP-IV) inhibitors, insulin or insulin mimetics, sequestrants, nicotinyl alcohol, nicotinic acid, PPARα agonists, PPARγ agonists including, but not limited to thiazolidinediones, including but not limited to rosiglitazone, troglitazone and pioglitazone; PPARα/γ dual agonists, inhibitors of cholesterol absorption, acyl CoA: cholesterol acyltransferase inhibitors, anti-oxidants, anti-obesity compounds, neuropeptide Y5 inhibitors, β3 adrenergic receptor agonists, ileal bile acid transporter inhibitors, anti-inflammatories, including NSAIDs and COX-2 selective inhibitors; insulin; sulfonylureas, including but not limited to chlorpropamide, glipizide, glyburide, and glimepiride; biguanides, including but not limited to metformin; alpha-glucosidase inhibitors, including, but not limited to, acarbose and meglitol; cannabinoid antagonists, including, but not limited to rimonabant; camptothecin and camptothecin derivatives, D-phenylalanine derivatives; meglitinides; diuretics including, but not limited to, methyclothiazide, hydroflumethiazide, metolazone, chlorothiazide, methyclothiazide, hydrochlorothiazide, quinethazone, chlorthalidone, trichlormethiazide, bendroflumethiazide, polythiazide, hydroflumethiazide, spironolactone, triamterene, amiloride, bumetanide, torsemide, ethacrynic acid, furosemide; beta-blockers including, but not limited to acebutolol, atenolol, betaxolol, bisoprolol, carteolol, metoprolol, nadolol, pindolol, propranolol, and timolol; vasodilators including, but not limited to, nitric oxide, hydralazine, and prostacyclin; alpha blockers including, but not limited to, doxazosin, prazosin and terazosin; alpha 2 agonists including, but not limited to clonidine and guanfacine; curcumin, gugulipid, garlic, vitamin E, soy, soluble fiber, fish oil, green tea, carnitine, chromium, coenzyme Q10, anti-oxidant vitamins, grape seed extract, pantothine, red yeast rice, and royal jelly; NNR ligands (such as varenicline), antioxidants (such as free radical scavenging agents), antibacterial agents (such as penicillin antibiotics), antiviral agents (such as nucleoside analogs, like zidovudine and acyclovir), anticoagulants (such as warfarin), anti-inflammatory agents (such as NSAIDs), anti-pyretics, analgesics, anesthetics (such as used in surgery), acetylcholinesterase inhibitors (such as donepezil and galantamine), antipsychotics (such as haloperidol, clozapine, olanzapine, and quetiapine), immuno-suppressants (such as cyclosporin and methotrexate), neuroprotective agents, steroids (such as steroid hormones), corticosteroids (such as dexamethasone, predisone, and hydrocortisone), vitamins, minerals, nutraceuticals, anti-depressants (such as imipramine, fluoxetine, paroxetine, escitalopram, sertraline, venlafaxine, and duloxetine), anxiolytics (such as alprazolam and buspirone), anticonvulsants (such as phenytoin and gabapentin), vasodilators (such as prazosin and sildenafil), mood stabilizers (such as valproate and aripiprazole), anti-cancer drugs (such as antiproliferatives), antihypertensive agents (such as atenolol, clonidine, amlopidine, verapamil, and olmesartan), laxatives, stool softeners, diuretics (such as furosemide), anti-spasmotics (such as dicyclomine), anti-dyskinetic agents, and anti-ulcer medications (such as esomeprazole), PDE5 inhibitor (e.g., sildenafil, preferably sildenafil citrate).

Systems to Identify Subjects Amenable to Treatment with an Anti-miR-425 Agent

Another aspect of the present invention relates to a method, system and assay to identify subjects amenable to treatment with an anti-miR-425 agent as disclosed herein. In one embodiment, the present invention provides for an assay which enables one to measure, or quantify, the amount of miR-425 in a biological sample, e.g., a blood or plasma sample, obtained from a subject; and compare the measured, or quantified amount, of miR-425 with a reference value, and if the amount of miR-425 is increased relative to the reference value, the subject is identified as having an increased probability of having, or at risk of having high blood pressure, hypertension or cardiovascular disease. In such embodiments, the subject can be administered an anti-miR-425 agent as disclosed herein. In some embodiments, subjects with normal or high levels (e.g., above a predefined reference value) of miR-424 are amenable to treatment with an anti-miR-425 agent as disclosed herein, or where it is desirable to increase ANP levels in the subject.

Accordingly, one aspect of the present invention relates to an assay comprising: (a) contacting a biological sample obtained from a subject with a detectable antibody specific for miR-425 or detectable nucleic acid complementary to at least part of miR-425; (b) washing the sample to remove unbound antibody or unbound nucleic acid; (c) measuring the intensity of the signal from the bound, detectable antibody or bound detectable nucleic acid; (d) comparing the measured intensity of the signal with a reference value and if the measured intensity is normal and/or increased relative to the reference value; the subject is identified as having an increased probability of having high blood pressure or cardiovascular disease. In some embodiments, the reference value is the signal of bound antibody or bound nucleic acid in a sample from a subject with low blood pressure, or a subject or a pool of subjects which are heterozygous AG for the rs5068 SNP.

Another aspect of the present invention relates to a system for obtaining data from at least one test sample obtained from at least one subject, the system comprising: (a) a determination module configured to receive said at least one test sample and perform at least one analysis on said at least one test sample to determine the presence or absence of at least one of the following conditions: (i) the level of expression of NT-proANP or ANP mRNA is smaller than a pre-determined level; (ii) expression of miR-425 is greater than a pre-determined standard; (iii) at least one copy of a single nucleotide polymorphism (SNP) at position 647 of SEQ ID NO: 12 comprises a adenine "A" allele, or its complement thereof comprises a thymine "T" allele; (b) a storage device configured to store data output from said determination module; and (c) a display module for displaying a content based in part on the data output from said determination module, wherein the content comprises a signal indicative of the presence of at least one of these conditions determined by the determination module, or a signal indicative of the absence of at least one of these conditions determined by the determination module. In some embodiments, the level of miRNA is determined with the levels of one or more other biomarkers, such as, but not limited to NT-proANP, NT-proBNP, cardiac troponins, C-reactive protein (CRP), ANP, BNP, adrenomedullin, copeptin, mid-regional-proANP, Galectin-3, ST-2, GDF-15 and other biomarkers, which are well known by persons of ordinary skill in the art.

In some embodiments, the nucleic acid sequence encoding NPPA is SEQ ID NO: 12 (NM_006172.3) which is as follows:

```
  1 gagacaggga cagacgtagg ccaagagagg ggaaccagag aggaaccaga ggggagagac
 61 agagcagcaa gcagtggatt gctccttgac gacgccagca tgagctcctt ctccaccacc
121 accgtgagct tcctcctttt actggcattc cagctcctag gtcagaccag agctaatccc
181 atgtacaatg ccgtgtccaa cgcagacctg atggatttca agaatttgct ggaccatttg
241 gaagaaaaga tgcctttaga agatgaggtc gtgccccac aagtgctcag tgagccgaat
301 gaagaagcgg gggctgctct cagcccctc cctgaggtgc ctccctggac cggggaagtc
361 agcccagccc agagagatgg aggtgccctc gggcggggcc cctgggactc ctctgatcga
421 tctgccctcc taaaaagcaa gctgagggcg ctgctcactg cccctcggag cctgcggaga
481 tccagctgct tcgggggcag gatggacagg attggagccc agagcggact gggctgtaac
541 agcttccggt actgaagata acagccaggg aggacaagca gggctgggcc tagggacaga
601 ctgcaagagg ctcctgtccc ctggggtctc tgctgcattt gtgtcatctt gttgccatgg
661 agttgtgatc atcccatcta agctgcagct tcctgtcaac acttctcaca tcttatgcta
721 actgtagata aagtggtttg atggtgactt cctcgcctct cccacccat gcattaaatt
781 ttaaggtaga acctcacctg ttactgaaag tggtttgaaa gtgaataaac ttcagcacca
841 tggacagaag acaaaaaa
```

Accordingly, as this is the nucleic acid encoding for NPPA mRNA, position 647(T) of SEQ ID NO: 12 (shown in bold, underline) shows the major allele for the rs5068 SNP (the corresponding mRNA shows the complementary "U" allele). The complementary genomic DNA sequence of SEQ ID NO: 12 encoding for the NPPA gene will show the adenine (A) major allele.

In some embodiments, the content displayed from the display module of the system as disclosed herein can further comprise a signal indicative of the subject being recommended to receive a particular treatment regimen, for example, if the subject has one or more of the above conditions, a signal is produced to recommend the subject be administered a composition comprising an anti-miR-425 agent as disclosed herein, for example, an anti-miR complementary to at least part of miR-425 of SEQ ID NO: 1, or at least in part complementary to miRNA seed sequence SEQ ID NO: 2.

In some embodiments, the subject is recommended a treatment with a composition comprising an anti-miR-425 agent where the content from the display module produces a signal indicative of at least one of: (a) the expression of NT-proANP or ANP mRNA is smaller than a pre-determined level; (b) the expression of miR-425 is greater than a pre-determined standard; (c) the presence of at least one copy of single nucleotide polymorphism (SNP) at position 647 of SEQ ID NO: 12 comprises a adenine "A" allele, or its complement thereof comprises a thymine "T" allele (e.g., the subject is AA or AG for rs5068 SNP). It is envisioned that while subjects AA homozygous for rs5068 SNP are likely to have a full response to an anti-miR-425 agent which inhibits miR-425-mediated ANP suppression. Similarly, a subject who is AG heterozygous for rs5068 SNP will show a partial response (e.g., typically a 50% response) to an anti-miR-425 agent as compared to the efficacy of response from a AA heterozygous rs5068 subject.

In some embodiments, a subject is not recommended for treatment with a composition comprising an anti-miR-425 agent where the content from the display module produces a signal indicative of at least one of: (a) the expression of NT-proANP or ANP mRNA is less than a pre-determined level; (b) the expression of miR-425 is lower than a pre-determined standard; (c) the presence of at two copies of single nucleotide polymorphism (SNP) at position 647 of SEQ ID NO: 12 comprises an guanine "G" allele or its complement thereof of "C" (e.g., the subject is GG for rs5068 SNP).

In some embodiments, a predetermined level of expression of NT-proANP or ANP is the level of NT-proANP or ANP expression from a subject, or a representative pool of subjects who are homozygous GG for rs5068 SNP. In some embodiments, a pre-determined standard of expression of miR-425 is the level of miR-425 expression from a subject or a representative pool or cohort of subjects who are homozygous GG for rs5068 SNP.

Another embodiment of the present invention relates to a method of treating a subject having at least one or a combination of high blood pressure, hypertension, obesity, renal failure or a cardiovascular disease, comprising administering a pharmaceutically effective amount of an anti-miR-425 agent to a subject having high blood pressure, hypertension, obesity, renal failure, stress, or a cardiovascular disease and determined to show the plasma expression of miR-425 levels which is increased relative to a control (e.g., pre-determined standard miR-425 expression level), and wherein the subject is not administered an anti-miR-425 agent if the plasma expression of miR-425 from the subject is determined to be less than, or equal to that of a subject or a representative pool of subjects who are homozygous GG for rs5068 SNP.

Another embodiment of the present invention relates to a method of determining if a subject is responsive to an anti-miR-425 agent comprising assaying a blood sample for at least one copy of the A allele of the rs5068 SNP (e.g., AA homozygotes, or AG heteozygotes). In some embodiments, an anti-miR-425 agent is administered to the subject if two copies of the A allele of the rs5068 SNP are detected (e.g., AA homozygotes). In some embodiments, an anti-miR-425 agent is administered to the subject if one copies of the A allele of the rs5068 SNP are detected (e.g., AG heterozygotes). In some embodiments, the efficacy of an anti-miR-425 agent and/or miR-425 agent as disclosed herein can be assessed in a AA or AG subject by measuring the levels of circulating ANP or NT-proANP in the plasma, were the efficacy of an anti-miR-425 can be assessed by an increase in ANP and/or NT-proANP in the plasma, and the efficacy of an miR-425 agent can be assessed by a decrease in ANP and/or NT-proANP levels in the plasma.

Computer Systems

In some embodiments, the methods and assay can be carried out in an automated and/or high-throughput system. One aspect of the present invention relates to a computerized system for processing the assays as disclosed herein and identifying any one of the following: (i) the level of expression of NT-proANP or ANP mRNA is smaller than a pre-determined level; (ii) expression of miR-425 is greater than a pre-determined standard; (iii) at least one copy of a single nucleotide polymorphism (SNP) at position 647 of SEQ ID NO: 12 comprises an adenine "A" allele, or its complement thereof comprises a thymine "T" allele in a biological sample from the subject, and/or (iv) the level of expression of NPPA mRNA in circulating cells, (e.g., lymphocytes) is smaller than a pre-determined level.

In some embodiments, a computer system can include: (a) at least one memory containing at least one computer program adapted to control the operation of the computer system to implement a method that includes: (i) receiving data of the level of expression or intensity of signal of measured NT-proANP or ANP mRNA (ii) generating a report of intensity of expression or intensity of signal of measured NT-proANP or ANP mRNA in a biological sample and optionally a reference level for NT-proANP or ANP mRNA signal intensity; and (b) at least one processor for executing the computer program.

In some embodiments, a computer system can include: (a) at least one memory containing at least one computer program adapted to control the operation of the computer system to implement a method that includes: (i) receiving data of the level of expression or intensity of signal of measured miR-425 levels (ii) generating a report of intensity of expression or intensity of signal of measured miR-425 levels in a biological sample and optionally a reference level for miR-425 level signal intensity; and (b) at least one processor for executing the computer program.

In some embodiments, a computer system can include: (a) at least one memory containing at least one computer program adapted to control the operation of the computer system to implement a method that includes: (i) receiving data of the signal intensity if there is an A (adenine) nucleic acid present at position 647 of SEQ ID NO: 12 (ii) generating a report of signal intensity measured if there is an A (adenine) at position 647 of SEQ ID NO: 12 and optionally a reference signal intensity level for 2 copies of an A at nucleic acid present at position (e.g., homozygous AA for rs5068 SNP), or optionally a reference signal intensity for 1 copy of A at position 647 of SEQ ID NO: 12 (e.g., heterogyous AG for rs5068 SNP) or optionally a reference signal intensity for zero copies of A at position 647 of SEQ ID NO: 12 (e.g., homozygous for GG for rs5068 SNP); and (b) at least one processor for executing the computer program.

Another aspect of the present invention relates to a computer readable medium comprising instructions, such as computer programs and software, for controlling a computer system to process the data from signal intensity of one or more of (i) the level of expression of NT-proANP or ANP mRNA; (ii) miR-425 expression level; (iii) presence of an adenine "A" allele, or its complement thereof comprises a thymine "T" allele at the rs5068 SNP and generate a report of the presence or absence, or amount of (i) the expression of NT-proANP or ANP mRNA; (ii) miR-425 expression; (iii) an adenine "A" allele, or its complement thereof comprises a thymine "T" allele at the rs5068 SNP.

The computer system can include one or more general or special purpose processors and associated memory, including volatile and non-volatile memory devices. The computer system memory can store software or computer programs for controlling the operation of the computer system to make a special purpose computer system according to the invention or to implement a system to perform the methods and analysis according to the invention.

In some embodiments, a computer system can include, for example, an Intel or AMD x86 based single or multi-core central processing unit (CPU), an ARM processor or similar computer processor for processing the data. The CPU or microprocessor can be any conventional general purpose single- or multi-chip microprocessor such as an Intel and AMD processor, a SPARC processor, or an ARM processor. In addition, the microprocessor may be any conventional or special purpose microprocessor such as a digital signal processor or a graphics processor. The microprocessor typically has conventional address lines, conventional data lines, and one or more conventional control lines. As described below, the software according to the invention can be executed on dedicated system or on a general purpose computer having a DOS, CPM, Windows, Unix, Linix or other operating system. The system can include non-volatile memory, such as disk memory and solid state memory for storing computer programs, software and data and volatile memory, such as high speed ram for executing programs and software.

Computer-readable physical storage media useful in various embodiments of the invention can include any physical computer-readable storage medium, e.g., solid state memory (such as flash memory), magnetic and optical computer-readable storage media and devices, and memory that uses other persistent storage technologies. In some embodiments, a computer readable media can be any tangible media that allows computer programs and data to be accessed by a computer. Computer readable media can include volatile and non-volatile, removable and non-removable tangible media implemented in any method or technology capable of storing information such as computer readable instructions, program modules, programs, data, data structures, and database information. In some embodiments of the invention, computer readable media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks), Blue-ray, USB drives, micro-SD drives, or other optical storage media, magnetic cassettes, magnetic tape, magnetic disk storage or other magnetic storage media, other types of volatile and non-volatile memory, and any other tangible medium which can be used to store information and which can read by a computer including and any suitable combination of the foregoing.

The present invention can be implemented on a stand-alone computer or as part of a networked computer system. In a stand-alone computer, all the software and data can reside on local memory devices, for example an optical disk or flash memory device can be used to store the computer software for implementing the invention as well as the data. In alternative embodiments, the software or the data or both can be accessed through a network connection to remote devices. In one embodiment, the invention can use a client-server environment over a network, e.g., a public network such as the internet or a private network to connect to data and resources stored in remote and/or centrally located locations. In this embodiment, a server such as a web server can provide access, either open access, pay as you go or subscription based access to the information provided according to the invention. In a client server environment, a client computer executing a client software or program, such as a web browser, connects to the server over the network. The client software provides a user interface for a user of the invention to input data and information and receive access to data and information. The client software can be viewed on a local computer display or other output device and can allow the user to input information, such as by using a computer keyboard, mouse or other input device. The server executes one or more computer programs that receives data input through the client software, processes data according to the invention and outputs data to the user, as well as provide access to local and remote computer resources. For example, the user interface can include a graphical user interface comprising an access element, such as a text box, that permits entry of data from the assay, e.g., the data from a positive reference cancer cell, as well as a display element that can provide a graphical read out of the results of a comparison with a cancer cell with a known metastatic potential or invasive capacity, or data sets transmitted to or made available by a processor following execution of the instructions encoded on a computer-readable medium.

Embodiments of the invention also provide for systems (and computer readable medium providing instructions for causing computer systems) to perform a method for determining quality assurance of a pluripotent stem cell population according to the methods as disclosed herein.

In some embodiments of the invention, the computer system software can include one or more functional modules, which can be defined by computer executable instructions recorded on computer readable media and which cause a computer to perform, when executed, a method according to one or more embodiments of the invention. The modules can be segregated by function for the sake of clarity, however, it should be understood that the modules need not correspond to discreet blocks of code and the described functions can be carried out by the execution of various software code portions stored on various media and executed at various times. Furthermore, it should be appreciated that the modules can perform other functions, thus the modules are not limited to having any particular function or set of functions. In some embodiments, functional modules are, for example, but are not limited to, an array module, a determination module, a storage module, a reference comparison module, a normalization module, and a display module to display the results (e.g., the invasive potential of the test cancer cell population). The functional modules can be executed using one or multiple computers, and by using one or multiple computer networks.

The information embodied on one or more computer-readable media can include data, computer software or programs, and program instructions, that, as a result of being executed by a computer, transform the computer to special purpose machine and can cause the computer to perform one or more of the functions described herein. Such instructions can be originally written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied can reside on one or more of the components of a computer system or a network of computer systems according to the invention.

In some embodiments, a computer-readable media can be transportable such that the instructions stored thereon can be loaded onto any computer resource to implement the aspects of the present invention discussed herein. In addition, it should be appreciated that the instructions stored on computer readable media are not limited to instructions embodied as part of an application program running on a host computer. Rather, the instructions may be embodied as any type of computer code (e.g., object code, software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

In some embodiments, a system as disclosed herein, can receive data of intensity of expression of NT pro-ANP or ANP mRNA, or miR-425 expression from any method of determining the level of expression. Where the quantity to be measured is protein expression, the system as disclosed herein can be configured to receive data from an automated protein analysis systems, for example, using immunoassay, for example western blot analysis or ELISA, or a high through-put protein detection method, for example but are not limited to automated immunohistochemistry apparatus, for example, robotically automated immunodetection apparatus which in an automated system can perform immunohistochemistry procedure and detect intensity of immunostaining, such as intensity of an antibody staining of the substrates and produce output data. Examples of such automated immunohistochemistry apparatus are commercially available, and can be readily adapted to automatically detect the level of protein expression in the assay as disclosed herein, and include, for example but not limited to such Autostainers 360, 480, 720 and Labvision PT module machines from LabVision Corporation, which are disclosed in U.S. Pat. Nos. 7,435,383; 6,998,270; 6,746,851, 6,735,531; 6,349,264; and 5,839; 091 which are incorporated herein in their entirety by reference. Other commercially available automated immunohistochemistry instruments are also encompassed for use in the present invention, for example, but not are limited BOND™ Automated Immunohistochemistry & In Situ Hybridization System, Automate slide loader from GTI vision. Automated analysis of immunohistochemistry can be performed by commercially available systems such as, for example, IHC Scorer and Path EX, which can be combined with the Applied spectral Images (ASI) CytoLab view, also available from GTI vision or Applied Spectral Imaging (ASI) which can all be integrated into data sharing systems such as, for example, Laboratory Information System (LIS), which incorporates Picture Archive Communication System (PACS), also available from Applied Spectral Imaging (ASI) (see world-wideweb: spectral-imaging.com). Other a determination module can be an automated immunohistochemistry systems such as NexES® automated immunohistochemistry (IHC) slide staining system or BenchMark® LT automated IHC instrument from Ventana Discovery SA, which can be combined with VIAS™ image analysis system also available Ventana Discovery. BioGenex Super Sensitive MultiLink® Detection Systems, in either manual or automated protocols can also be used as the detection module, preferably using the BioGenex Automated Staining Systems. Such systems can be combined with a BioGenex automated staining systems, the i6000™ (and its predecessor, the OptiMax® Plus), which is geared for the Clinical Diagnostics lab, and the GenoMx 6000™, for Drug Discovery labs. Both systems BioGenex systems perform "All-in-One, All-at-Once" functions for cell and tissue testing, such as Immunohistochemistry (IHC) and In Situ Hybridization (ISH).

In some embodiments, a system as disclosed herein, can receive data of intensity of protein expression of NT-proANP from an automated ELISA system (e.g. DSX® or DS2® form Dynax, Chantilly, Va. or the ENEASYSTEM III®, Triturus®, The Mago® Plus); Densitometers (e.g. X-Rite-508-Spectro Densitometer®, The HYRYS™ 2 densitometer); automated Fluorescence in situ hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACS-Vantage SE, Becton Dickinson); radio isotope analyzers (e.g. scintillation counters), or adapted systems thereof for detecting cells on the separated substrates as disclosed herein.

In some embodiments, a system as disclosed herein, can receive data can receive data of intensity of mRNA expression of ANP or miR-425 from any method of determining gene or nucleic acid expression. In some embodiments, the system as disclosed herein can be configured to receive data from an automated gene expression analysis system, e.g., an automated protein expression analysis including but not limited Mass Spectrometry systems including MALDI-TOF, or Matrix Assisted Laser Desorption Ionization—Time of Flight systems; SELDI-TOF-MS ProteinChip array profiling systems, e.g. Machines with Ciphergen Protein Biology System II™ software; systems for analyzing gene expression data (see for example U.S. 2003/0194711); systems for array based expression analysis, for example HT array systems and cartridge array systems available from Affymetrix (Santa Clara, Calif. 95051) AutoLoader, Complete GeneChip® Instrument System, Fluidics Station 450, Hybridization Oven 645, QC Toolbox Software Kit, Scanner 3000 7G, Scanner 3000 7G plus Targeted Genotyping System, Scanner 3000 7G Whole-Genome Association System, GeneTitan™ Instrument, GeneChip® Array Station, HT Array.

In some embodiments of the present invention, an automated gene expression analysis system can record the data electronically or digitally, annotated and retrieved from databases including, but not limited to GenBank (NCBI) protein and DNA databases such as genome, ESTs, SNPS, Traces, Celara, Ventor Reads, Watson reads, HGTS, etc.; Swiss Institute of Bioinformatics databases, such as ENZYME, PROSITE, SWISS-2DPAGE, Swiss-Prot and TrEMBL databases; the Melanie software package or the ExPASy WWW server, etc., the SWISS-MODEL, Swiss-Shop and other network-based computational tools; the Comprehensive Microbial Resource database (The institute of Genomic Research). The resulting information can be stored in a relational data base that may be employed to determine homologies between the reference data or genes or proteins within and among genomes.

In some embodiments, a system as disclosed herein, can receive data can receive data from an allele-specific PCR. The term "allele-specific PCR" refers to PCR techniques where the primer pairs are chosen such that amplification is dependent upon the input template nucleic acid containing the polymorphism of interest. In such embodiments, primer pairs are chosen such that at least one primer is an allele-specific oligonucleotide primer. In some sub-embodiments of the present invention, allele-specific primers are chosen so that amplification creates a restriction site, facilitating identification of a polymorphic site. In other embodiments of the present invention, amplification of the target polynucleotide is by multiplex PCR (Wallace et al. (PCT Application WO89/10414)). Through the use of multiplex PCR, a multiplicity of regions of a target polynucleotide can be amplified simultaneously. This is particularly advantageous in embodiments where more than one SNP is to be detected.

In another embodiment, multiplex PCR procedures using allele-specific primers can be used to simultaneously amplify multiple regions of a target nucleic acid (PCT Application WO89/10414), enabling amplification only if a particular allele is present in a sample. Other embodiments using alternative primer-guided nucleotide incorporation procedures for assaying polymorphic sites in DNA can be used, and have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Nat. Acad. Sci. (U.S.A.) 88:1143-1147 (1991); Bajaj et al. (U.S. Pat. No. 5,846,710); Prezant, T. R. et al., Hum Mutat. 1: 159-164 (1992); Ugozzoli, L. et al., GATA 9:107-112 47 (1992); Nyrén, P. et al., Anal. Biochem. 208:171-175 (1993)).

Other known nucleic acid amplification procedures include transcription-based amplification systems (Malek, L. T. et al., U.S. Pat. No. 5,130,238; Davey, C. et al., European Patent Application 329,822; Schuster et al.) U.S. Pat. No. 5,169,766; Miller, H. I. et al., PCT-Application WO89/06700; Kwoh, D. et al., Proc. Natl. Acad. Sci. (U.S.A.) 86:1173 Z1989); Gingeras, T. R. et al., PCT Application WO88/10315)), or isothermal amplification methods (Walker, G. T. et al., Proc. Natl. 4cad Sci. (U.S.A) 89:392-396 (1992)) can also be used.

In some embodiments, a system as disclosed herein, can receive data from any genotyping assay known by persons of ordinary skill in the art, including, but not limited to, those disclosed in U.S. Pat. No. 6,472,157; U.S. Patent Application Publications 20020016293, 20030099960, 20040203034; WO 0180896, all of which are hereby incorporated by reference, or by linkage disequilibrium, restriction fragment length polymorphism" (RFLP) analysis, single strand conformational polymorphism (SSCP), RNaseI for mismatch detection, SNP mapping (Davis et al, Methods Mol Biology, 2006; 351; 75-92); Nanogen Nano Chip, (keen-Kim et al, 2006; Expert Rev Mol Diagnostic, 6; 287-294); Rolling circle amplification (RCA) combined with circularable oligonucleotide probes (c-probes) for the detection of nucleic acids (Zhang et al, 2006: 363; 61-70), luminex XMAP system for detecting multiple SNPs in a single reaction vessel (Dunbar S A, Clin Chim Acta, 2006; 363; 71-82; Dunbar et al, Methods Mol Med, 2005; 114:147-1471), enzymatic mutation detection methods (Yeung et al, Biotechniques, 2005; 38; 749-758), matrix-assisted laser desorption ionization/time-of-flight (MALDI-TOF) mass spectrometric (MS) analysis, long-range PCR (LR-PCR), genotype assays disclosed in Kwok, Hum Mut 2002; 9; 315-323 and Kwok, Annu Rev Genomic Hum Genetics, 2001; 2; 235-58, (which are incorporated herein in their entirety by reference), INVADER® Assay (Gut et al, Hum Mutat, 2001; 17:475-92, Shi et al, Clin Chem, 2001, 47, 164-92, and Olivier et al, Mutat Res, 2005; 573:103-110), the method utilizing FLAP endonucleases (U.S. Pat. No. 6,706,476) and the SNPlex genoptying systems (Tobler et al, J. Biomol Tech, 2005; 16; 398-406) and other such genotyping assays known to one of ordinary skill in the art.

In some embodiments, the data of (i) the level of expression of NT-proANP or ANP mRNA; and/or (ii) miR-425 expression level; and/or (iii) presence of an adenine "A" allele, or its complement thereof comprises a thymine "T" allele at the rs5068 SNP can be received from a memory, a storage device, or a database. The memory, storage device or database can be directly connected to the computer system retrieving the data, or connected to the computer through a wired or wireless connection technology and retrieved from a remote device or system over the wired or wireless connection. Further, the memory, storage device or database, can be located remotely from the computer system from which it is retrieved.

Examples of suitable connection technologies for use with the present invention include, for example parallel interfaces (e.g., PATA), serial interfaces (e.g., SATA, USB, Firewire,), local area networks (LAN), wide area networks (WAN), Internet, Intranet, and Extranet, and wireless (e.g., Blue Tooth, Zigbee, WiFi, WiMAX, 3G, 4G) communication technologies Storage devices are also commonly referred to in the art as "computer-readable physical storage media" which is useful in various embodiments, and can include any physical computer-readable storage medium, e.g., magnetic and optical computer-readable storage media, among others. Carrier waves and other signal-based storage or transmission media are not included within the scope of storage devices or physical computer-readable storage media encompassed by the term and useful according to the invention. The storage device is adapted or configured for having recorded thereon cytokine level information. Such information can be provided in digital form that can be transmitted and read electronically, e.g., via the Internet, on diskette, via USB (universal serial bus) or via any other suitable mode of communication.

As used herein, "stored" refers to a process for recording information, e.g., data, programs and instructions, on the storage device that can be read back at a later time. Those skilled in the art can readily adopt any of the presently known methods for recording information on known media to contribute to the data of (i) the level of expression of NT-proANP or ANP mRNA; (ii) miR-425 expression level; (iii) presence of an adenine "A" allele, or its complement thereof comprises a thymine "T" allele at the rs5068 SNP and generate a report of the presence or absence, or amount of (i) the expression of NT-proANP or ANP mRNA; (ii) miR-425 expression; (iii) an adenine "A" allele, or its complement thereof comprises a thymine "T" allele at the rs5068 SNP as disclosed in the methods herein.

A variety of software programs and formats can be used to store information on the storage device. Any number of data processor structuring formats (e.g., text file or database) can be employed to obtain or create a medium having recorded scorecard thereon.

In some embodiment, the system has a processor for running one or more programs, e.g., where the programs can include an operating system (e.g., UNIX, Windows), a relational database management system, an application program, and a World Wide Web server program. The application program can be a World Wide Web application that includes the executable code necessary for generation of database language statements (e.g., Structured Query Language (SQL) statements). The executables can include embedded SQL statements. In addition, the World Wide Web application can include a configuration file which contains pointers and addresses to the various software entities that provide the World Wide Web server functions as well as the various external and internal databases which can be accessed to service user requests. The Configuration file can also direct requests for server resources to the appropriate hardware devices, as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

In one embodiment, the system as disclosed herein can be used to compare the data of intensity of one or more of (i) the level of expression of NT-proANP or ANP mRNA; (ii) miR-425 expression level; (iii) presence of an adenine "A" allele, or its complement thereof comprises a thymine "T" allele at the rs5068 SNP and generate a report of the presence or absence, or amount of (i) the expression of NT-proANP or ANP mRNA; (ii) miR-425 expression; (iii) an adenine "A" allele, or its complement thereof comprises a thymine "T" allele at the rs5068 SNP with reference data (e.g., reference intensity values), as disclosed herein. By way of an example, but not as a limitation, reference data for NT-proANP can be the level of NT-proANP or ANP expression from a subject, or a representative pool of subjects who are heterozygous AG for rs5068 SNP. In some embodiments, reference data for expression of miR-425 is the level of miR-425 expression from a subject or a representative pool or cohort of subjects who are heterozygous AG for rs5068 SNP.

In some embodiments of this aspect and all other aspects of the present invention, the system can compare the data in a "comparison module" which can use a variety of available software programs and formats for the comparison operative to compare sequence information determined in the determination module to reference data. In one embodiment, the comparison module is configured to use pattern recognition techniques to compare levels of expression (e.g., mRNA levels and/or protein levels) as well as compare sequence information (e.g., identify the presence of an A allele at position 647 of SEQ ID NO: 12) from one or more entries to one or more reference data patterns. The comparison module may be configured using existing commercially-available or freely-available software for comparing patterns, and may be optimized for particular data comparisons that are conducted. The comparison module can also provide computer readable information related to the level or amount of intensity of expression of the level of expression of NT-proANP or ANP mRNA; or miR-425 expression level and the like as disclosed herein.

By providing data of the intensity of expression of (i) the level of expression of NT-proANP or ANP mRNA; and/or (ii) miR-425 expression level; and/or (iii) presence of an adenine "A" allele, or its complement thereof comprises a thymine "T" allele at the rs5068 SNP in computer-readable form, one can use the data to compare with data within the storage device. For example, search programs can be used to identify relevant reference data (i.e. data of appropriate reference cancer cell lines) that match the same type of cancer as the cancer of the test cancer cell population. The comparison made in computer-readable form provides computer readable content which can be processed by a variety of means. The content can be retrieved from the comparison module, the retrieved content.

In some embodiments, the comparison module provides computer readable comparison result that can be processed in computer readable form by predefined criteria, or criteria defined by a user, to provide a report which comprises content based in part on the comparison result that may be stored and output as requested by a user using a display module. In some embodiments, a display module enables display of a content based in part on the comparison result for the user, wherein the content is a report indicative of the results of the comparison of the intensity of expression of (i) the level of expression of NT-proANP or ANP mRNA; and/or (ii) miR-425 expression level; and/or (iii) presence of an adenine "A" allele, or its complement thereof comprises a thymine "T" allele at the rs5068 SNP respective reference values. For example, the data can be compared to representative reference values obtained from a cohort of subjects who are heterozygous AG or homozygous GG for the rs5068 SNP (e.g., negative controls), or homozygous AA for the rs5068 SNP (e.g., positive controls).

In some embodiments, the display module enables display of a report or content based in part on the comparison result for the end user, wherein the content is a report indicative of the results of the comparison of the intensity of expression of any one or more of (i) the level of expression of NT-proANP or ANP mRNA; and/or (ii) miR-425 expression level; and/or (iii) presence of at least two adenine "A" allele, or its complement thereof comprises a thymine "T" allele at the rs5068 SNP.

In some embodiments of this aspect and all other aspects of the present invention, the comparison module, or any other module of the invention, can include an operating system (e.g., UNIX, Windows) on which runs a relational database management system, a World Wide Web application, and a World Wide Web server. World Wide Web application can includes the executable code necessary for generation of database language statements [e.g., Standard Query Language (SQL) statements]. The executables can include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using an HTML interface provided by Web browsers and Web servers. In other embodiments of the invention, other interfaces, such as HTTP, FTP, SSH and VPN based interfaces can be used to connect to the Internet databases.

In some embodiments of this aspect and all other aspects of the present invention, a computer-readable media can be transportable such that the instructions stored thereon, such as computer programs and software, can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a processor to implement aspects of the present invention. The computer executable instructions can be written in a suitable computer language or combination of several languages. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The computer instructions can be implemented in software, firmware or hardware and include any type of programmed step undertaken by modules of the information processing system. The computer system can be connected to a local area network (LAN) or a wide area network (WAN). One example of the local area network can be a corporate computing network, including access to the Internet, to which computers and computing devices comprising the data processing system are connected. In one embodiment, the LAN uses the industry standard Transmission Control Protocol/Internet Protocol (TCP/IP) network protocols for communication. Transmission Control Protocol Transmission Control Protocol (TCP) can be used as a transport layer protocol to provide a reliable, connection-oriented, transport layer link among computer systems. The network layer provides services to the transport layer. Using a two-way handshaking scheme, TCP provides the mechanism for establishing, maintaining, and terminating logical connections among computer systems. TCP transport layer uses IP as its network layer protocol. Additionally, TCP provides protocol ports to distinguish multiple programs executing on a single device by including the destination and source port number with each message. TCP performs functions such as transmission of byte streams, data flow definitions, data acknowledgments, lost or corrupt data re-transmissions, and multiplexing multiple connections through a single network connection. Finally, TCP is responsible for encapsulating information into a datagram structure. In alternative embodiments, the LAN can conform to other network standards, including, but not limited to, the International Standards Organization's Open Systems Interconnection, IBM's SNA, Novell's Netware, and Banyan VINES.

In some embodiments, the computer system as described herein can include any type of electronically connected group of computers including, for instance, the following networks: Internet, Intranet, Local Area Networks (LAN) or Wide Area Networks (WAN). In addition, the connectivity to the network may be, for example, remote modem, Ethernet (IEEE 802.3), Token Ring (IEEE 802.5), Fiber Distributed Datalink Interface (FDDI) or Asynchronous Transfer Mode (ATM).

The computing devices can be desktop devices, servers, portable computers, hand-held computing devices, smart phones, set-top devices, or any other desired type or configuration. As used herein, a network includes one or more of the following, including a public internet, a private internet, a secure internet, a private network, a public network, a value-added network, an intranet, an extranet and combinations of the foregoing.

In one embodiment of the invention, the computer system can comprise a pattern comparison software can be used to determine whether the patterns of data of the intensity of expression of any one of (i) the level of expression of NT-proANP or ANP mRNA; and/or (ii) miR-425 expression level; and/or (iii) presence of at least two adenine "A" allele, or its complement thereof comprises a thymine "T" allele at the rs5068 SNP are indicative of that the subject is at risk of hypertension, or high blood pressure and/or a cardiovascular disease or disorder as disclosed herein. In this embodiment, the pattern comparison software can compare at least some of the data (e.g., one or more of data of (i) the level of expression of NT-proANP or ANP mRNA; and/or (ii) miR-425 expression level; and/or (iii) presence of at least two adenine "A" allele, or its complement thereof comprises a thymine "T" allele at the rs5068 SNP) with reference data (e.g., data of (i) the level of expression of NT-proANP or ANP mRNA from subjects homozygous AA for rs5068; and/or (ii) miR-425 expression level for subjects homozygous AA for rs5068; and/or (iii) presence of at least two adenine "A" allele at the rs5068 SNP) to determine how closely they match. The matching can be evaluated and reported in portions or degrees indicating the extent to which all or some of the pattern matches.

In some embodiments of this aspect and all other aspects of the present invention, a comparison module provides computer readable data that can be processed in computer readable form by predefined criteria, or criteria defined by a user, to provide a retrieved content that may be stored and output as requested by a user using a display module.

Output Module

In accordance with some embodiments of the invention, the computerized system can include or be operatively connected to an output module. In some embodiments, the output module is a display module, such as computer monitor, touch screen or video display system. The display module allows user instructions to be presented to the user of the system, to view inputs to the system and for the system to display the results to the user as part of a user interface. Optionally, the computerized system can include or be operative connected to a printing device for producing printed copies of information output by the system.

In some embodiments, the results can be displayed on a display module or printed in a report, e.g., a to indicate any one or more of (i) the level of expression of NT-proANP or ANP mRNA; and/or (ii) miR-425 expression level; and/or (iii) presence of at least two adenine "A" allele, or its complement thereof comprises a thymine "T" allele at the rs5068 SNP or any other report envisioned by the end user.

In some embodiments, the report is a hard copy printed from a printer. In alternative embodiments, the computerized system can use light or sound to report the result, e.g., to indicate any one or more of (i) the level of expression of NT-proANP or ANP mRNA; and/or (ii) miR-425 expression level; and/or (iii) presence of at least two adenine "A" allele, or its complement thereof at the rs5068 SNP. For example, in all aspects of the invention, the report produced by the methods, assays, systems and kits as disclosed herein can comprise a report which is color coded to signal or indicate any one or more of (i) the level of expression of NT-proANP or ANP mRNA; and/or (ii) miR-425 expression level; and/or (iii) presence of at least two adenine "A" alleles, or its complement thereof at the rs5068 SNP, or compared another "gold" standard of, for example, the level of NT-proANP or ANP, or miR-425 for a subject who is heterozygous AA for rs5068 (positive standard), or a subject who is heterozygous AG or homozygous GG for rs5068 (e.g., negative standard).

For example, a red color or other predefined signal can indicate that the subject has NT-proANP, or ANP or miR-425 levels, or a rs5068 profile indicative of the subject being homozygous AA for rs5068, and having a high risk of hypertension as disclosed herein, and is a suitable subject for treatment with anti-miR-425 agents as disclosed herein. In another embodiment, a green color or other predefined signal can indicate that the subject has NT-proANP, or ANP or miR-425 levels, or a rs5068 profile indicative of the subject being heterozygous AG, or homozygous GG for rs5068, and having a low risk of hypertension as disclosed herein, and not a suitable subject for treatment with anti-miR-425 agents as disclosed herein. Other color schemes and gradient schemes in the report are also encompassed.

In some embodiments, the report can display the normalized values of any one or more of the (i) the level of expression of NT-proANP or ANP mRNA; and/or (ii) miR-425 expression level; and/or (iii) presence of at least two adenine "A" allele, or its complement thereof at the rs5068 SNP, which can be normalized to the levels of a subject who is heterozygous AG or homozygous GG for rs5068 line (e.g., a selected "gold" standard of subjects at "low risk of hypertension" the investigators choice). Alternatively, the report can display the normalized values which are normalized to the levels of a subject who is homozygous AA for rs5068 line (e.g., a reference of subjects at "high risk for hypertension" as disclosed herein). Accordingly, a report can display the % difference, and/or the change in absolute number of the values measured as compared to values for homozygous AA ("high risk" category) and/or heterozygotes AG ("low risk" category) and/or homozygous GG ("very low risk" category) for rs5068 SNP.

In some embodiments, the report can also display one or more reference values for subjects who are homozygous AA ("high risk" category) and/or heterozygotes AG ("low risk" category) and/or homozygous GG ("very low risk" category) for rs5068 SNP. Such reference values can be used to compare with the values from the test cancer cell population.

In some embodiments, the report can also present text, either verbally or written, giving a recommendation of if a subject is amenable to treatment with an anti-miR-425 agent as disclosed herein. In other embodiments, the report provides just values or numerical scores for the presence of any one or more of the (i) the level of expression of NT-proANP or ANP mRNA; and/or (ii) miR-425 expression level; and/or (iii) presence of at least two adenine "A" allele, or its complement thereof at the rs5068 SNP which can be readily compared by a physician with reference values as disclosed herein.

In some embodiments of this aspect and all other aspects of the present invention, the report data from the comparison module can be displayed on a computer monitor as one or more pages of the printed report. In one embodiment of the invention, a page of the retrieved content can be displayed through printable media. The display module can be any device or system adapted for display of computer readable information to a user. The display module can include speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc.

In some embodiments of the present invention, a World Wide Web browser can be used to provide a user interface to allow the user to interact with the system to input information, construct requests and to display retrieved content. In addition, the various functional modules of the system can be adapted to use a web browser to provide a user interface. Using a Web browser, a user can construct requests for retrieving data from data sources, such as data bases and interact with the comparison module to perform comparisons and pattern matching. The user can point to and click on user interface elements such as buttons, pull down menus, scroll bars, etc. conventionally employed in graphical user interfaces to interact with the system and cause the system to perform the methods of the invention. The requests formulated with the user's Web browser can be transmitted over a network to a Web application that can process or format the request to produce a query of one or more database that can be employed to provide the pertinent information related to the tumor type, the retrieved content, process this information and output the results, e.g. at least one of any of the following: % invasion, % invasion under specific conditions (e.g., culture time, presence of drugs, tumor of different geometry, e.g., with or without hypoxic cells). In some embodiments, these values or their combination can exhibit strong correlation with invasive capacity of cells in the patients. In some embodiments, output information of the % invasion, % invasion under specific conditions (e.g., culture time, presence of drugs, tumor of different geometry, e.g., with or without hypoxic cells) can vary with different tumor types, and can be determined by one of ordinary skill in the art by comparing the numbers across a range of highly metastatic cancer cell lines as disclosed herein.

Kits

In another embodiment, this invention provides kits for the practice of the methods of this invention. The kits preferably include one or more containers containing an anti-miR-425 agent, e.g., an anti-miR complementary to the miRNA seed sequence SEQ ID NO:2 and a pharmaceutically acceptable excipient. The kit may optionally contain additional therapeutics to be co-administered with the anti-miR-425 agent. The kit may comprise instructions for administration of an anti-miR-425 agent to a subject with a cardiovascular disease or condition, e.g., but not limited to, hypertension, congestive heart failure (CHF), myocardial infarction etc. or a subject in need of elevating or increasing plasma ANP levels.

The kits may also optionally include appropriate systems (e.g. opaque containers) or stabilizers (e.g. antioxidants) to prevent degradation of the anti-miR-425 agent by light or other adverse conditions.

In another aspect of the invention provides kits including one or more containers containing an miR-425 agent as disclosed herein and a pharmaceutically acceptable excipient. The kit may optionally contain additional therapeutics to be co-administered with the anti-miR-425 agent. The kit may comprise instructions for administration of a subject with low blood pressure, or in need of decreasing plasma ANP levels. The kits may also optionally include appropriate systems (e.g. opaque containers) or stabilizers (e.g. antioxidants) to prevent degradation of the miR-425 agent by light or other adverse conditions.

Another aspect of the present invention relates to kit to detect the presence of a "G" allele at the rs5068 loci in a subject. In some embodiments, the kit can comprise probes, e.g., allele-specific oligonucleotide probes or allele specific primer probes for detecting the G allele at the rs5068 loci in a sample from a subject. In some embodiments, the kit can comprise probes, e.g., allele-specific oligonucleotide probes or allele specific primer probes for detecting the A allele at the rs5068 loci in a sample from a subject allele for the practice of the methods of this invention. Allele-specific probes are well known by persons of ordinary skill in the art, with oligonucleotides encompassed for use as probes, and refer to such as genomic DNA, mRNA, or other suitable sources of nucleic acid oligonucleotides. For such purposes, the oligonucleotides must be capable of specifically hybridizing to a target polynucleotide or DNA nucleic acid molecule. As used herein, two nucleic acid molecules are said to be capable of specifically hybridizing to one another if the two molecules are capable of forming an anti-parallel, double-stranded nucleic acid structure under hybridizing conditions.

The term "allele-specific oligonucleotide" or "ASO" refers to an oligonucleotide that is able to hybridize to a region of a target polynucleotide spanning the sequence, mutation, or polymorphism being detected and is substantially unable to hybridize to a corresponding region of a target polynucleotide that either does not contain the sequence, mutation, or polymorphism being detected or contains an altered sequence, mutation, or polymorphism. As will be appreciated by those in the art, allele-specific is not meant to denote an absolute condition. Allele-specificity will depend upon a variety of environmental conditions, including salt and formamide concentrations, hybridization and washing conditions and stringency. Depending on the sequences being analyzed, one or more allele-specific oligonucleotides can be employed for each target polynucleotide. Preferably, allele-specific oligonucleotides will be completely complementary to the target polynucleotide. However, departures from complete complementarity are permissible. In order for an oligonucleotide to serve as a primer oligonucleotide, however, it typically need only be sufficiently complementary in sequence to be able to form a stable double-stranded structure under the particular environmental conditions employed. Establishing environmental conditions typically involves selection of solvent and salt concentration, incubation temperatures, and incubation times.

In some embodiments, the kit can be used to perform a genotyping assay used to determine the allele of the rs5068 loci, where the genotyping assay is selected from any or a combination in the group consisting of: PCR-based assays, RT-PCR, nucleic acid hybridization, sequence analysis, Taq-Man SNP genotyping probes, microarrays, direct or indirect sequencing, restriction site analysis, hybridization based genotyping assays, gel migration assays, antibodies assays, fluorescent polarization, mass spectroscopy, allele-specific PCR, single-strand conformational polymorphism (SSCP) analysis, heteroduplex analysis, oligonucleotide ligation, PCR-RFLP, allele-specific amplification (ASA), single-molecule dilution (SMD), coupled amplification and sequencing (CAS), Restriction enzyme analysis, restriction fragment length polymorphism (RFLP), ligation based assays, single base extension (or minisequencing), MALDI-TOF, and homogenous assays.

In some embodiments, the genotyping assay detects a G-allele at position 647 of SEQ. ID NO: 12, or a C-allele in the complementary nucleic acid sequence of SEQ. ID NO: 12. In some embodiments, the kit comprises an allele-specific oligonucleotide (ASO) probe, or a pair of allele-specific primers which specifically hybridizes to a G-allele at position 647 of SEQ. ID NO: 12, or a C-allele in the complementary nucleic acid sequence of SEQ ID NO: 12. In some embodiments, the allele-specific oligonucleotide (ASO) probe is a nucleic acid probe and comprises a detectable signal or a means to generate a detectable signal.

In some embodiments, the genotyping assay detects a A-allele at position 647 of SEQ. ID NO: 12, or a T-allele in the complementary nucleic acid sequence of SEQ. ID NO: 12. In some embodiments, the kit comprises an allele-specific oligonucleotide (ASO) probe or a pair of allele-specific primers which specifically hybridizes to a A-allele at position 647 of SEQ. ID NO: 12, or a T-allele in the complementary nucleic acid sequence of SEQ ID NO: 12.

The kits may optionally include instructional materials containing directions (i.e., protocols) providing for the use of anti-miR-425 agents and/or miR-425 agents for the treatment of a disease in a mammal, e.g., for the treatment of hypertension or low blood pressure respectively. In particular the diseases related to hypertension can include any one or more of the disorders described herein including, but not limited to hypertension (end stage renal hypertension, pregnancy-related hypertension (e.g., preeclampsia), salt sensitivity hypertension, type II diabetes hypertension, alcohol abuse or obesity related hypertension, systolic hypertension in the elderly, and essential hypertension), ischemic and hemorrhagic stroke.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In some embodiments, the present invention may be defined in any of the following numbered paragraphs:

1. A method of inhibiting or preventing hypertension or a symptom thereof in a subject in need thereof, the method comprising administering to the subject an effective amount of an inhibitor of miRNA-425 activity.

2. A method of inhibiting or preventing hypertension or a symptom thereof in a subject in need thereof, the method comprising administering to a subject determined to homozygous (AA) or heterozygous (AG) for A allele for the single nucleotide polymorphism (SNP) rs5068 (A/G) an effective amount of an inhibitor of miRNA-425 activity.

3. The method of paragraphs 1 or 2, wherein the inhibitor is an oligonucleotide.

4. The method of paragraph 3, wherein the inhibitor is an anti-miR, antagomir, ribozyme, or siRNA.

5. The method of paragraph 4, wherein the inhibitor comprises a nucleotide sequence that is complementary to at least a portion of nucleic acid sequence GAAAGCGCUUUG-GAAUGACACGAUCACUCCCG-UUGAGUGGGCACCCGAGAAGCCAUCGGG AAU-GUCGUGUCCGCCCAGUGCUCUUUC (SEQ ID No: 13).

6. The method of paragraph 5, wherein the inhibitor comprises a nucleotide sequence that is complementary to at least a portion nucleic acid sequence AAUGACACGAUCACUC-CCGUUGA (SEQ ID NO: 1).

7. The method of paragraph 5, wherein the inhibitor comprises a nucleotide sequence that is complementary to nucleic acid sequence AUGACA (SEQ ID NO: 2).

8. The method of any of paragraphs 3-7, wherein the oligonucleotide comprises a modification selected from the group consisting of nucleobase modifications, sugar modifications, inter-sugar linkage modifications, backbone modifications, and any combinations thereof.

9. The method of any of paragraphs 3-8, wherein the oligonucleotide comprises a ligand.

10. The method of any of paragraphs 3-9, wherein the oligonucleotide is from about 11 to about 30 nucleotides in length.

11. The method of any of paragraphs 3-10, wherein the oligonucleotide is single-stranded.

12. The method of any of paragraphs 3-11, wherein the oligonucleotide is formulated in a lipid delivery vehicle. (liposomes, lipid particles, other compositions used for oligonucleotide delivery)

13. The method of any of paragraphs 3-12, wherein the oligonucleotide is encoded by an expression vector.

14. The method of any of paragraphs 1-13, wherein the inhibitor comprises the nucleotide sequence TTACTGTGCTAGTGAGGGCAACT (SEQ ID NO: 3).

15. The method of any of paragraphs 1-14, wherein the inhibitor decreases the amount of miRNA-425 in a cell relative to a control or reference level.

16. The method of any of paragraphs 1-15, wherein the inhibitor increases expression of atrial natriuretic peptide (ANP) or a nucleic acid encoding ANP in a cell relative to a control or reference level.

17. The method of paragraph 16, wherein said nucleic acid encoding ANP is mRNA.

18. The method of any of paragraphs 1-17, wherein the subject is homozygous for a single nucleotide polymorphism (SNP) of ANP gene, wherein the polymorphism is A allele of SNP rs5068 (A/G).

19. The method of any of paragraphs 1-18, further comprising selecting a subject for treatment for hypertension before onset of said administering, comprising assaying a biological sample from the subject for single nucleotide polymorphism of SNP rs5068 (A/G) and selecting the subject who is homozygous (AA) or heterozygous (AG) for A allele of SNP rs5068 (A/G).

20. The method of any of paragraphs 1-19, further comprising co-administering a therapeutic agent, wherein the therapeutic agent is for treatment of hypertension.

21. The method of paragraph 20, wherein the therapeutic agent is selected from the group consisting of statins, diuretics, adrenergic receptor antagonists, PDE5 inhibitors, calcium channel blockers, renin inhibitors, ACE inhibitors, angiotensin II receptor antagonists, aldosterone antagonists, vasodilators; alpha-2-agonists, and any combination thereof.

22. The method of paragraph 21, wherein the therapeutic agent is selected from the group consisting of bumetanide; ethacrynic acid; furosemide; torsemide; epitizide; hydrochlorothiazide; chlorothiazide; bendroflumethiazide; indapamide; chlorthalidone; metolazone; amiloride; triamterene; spironolactone; atenolol; metoprolol; nadolol; oxprenolol; pindolol; propranolol; timolol; doxazosin; phentolamine; indoramin; phenoxybenzamine; prazosin; terazosin; tolazoline; bucindolol; carvedilol; labetalol; amlodipine; felodipine; isradipine; lercanidipine; nicardipine; nifedipine; nimodipine; nitrendipine; diltiazem; verapamil; Aliskiren; captopril; enalapril; fosinopril; lisinopril; perindopril; quinapril; ramipril; trandolapril; benazepril; candesartan; eprosartan; irbesartan; losartan; olmesartan; telmisartan; valsartan; eplerenone; spironolactone; sodium nitroprusside; hydralazine; hydralazine derivatives; Clonidine; Guanabenz; Methyldopa; Moxonidine; Guanethidine; Reserpine; atorvastatin; fluvastatin; lovastatin; pitavastatin; pravastatin; rosuvastatin; simvastatin; and any combinations thereof.

23. An isolated oligonucleotide comprising a nucleotide sequence complementary to at least a portion of nucleic acid sequence GAAAGCGCUUUGGAAUGACACGAUCACUCCCGUUGAGUGGGCAC-CCGAGAAGCCAUCGGG AAUGUCGUGUCCGCCCAGUGCUCUUUC (SEQ ID NO: 13).

24. The isolated oligonucleotide of paragraph 23, wherein the isolated oligonucleotide comprises a nucleotide sequence that is complementary to at least a portion nucleic acid sequence AAUGACACGAUCACUCCCGUUGA (SEQ ID NO: 1).

25. The isolated oligonucleotide of paragraph 23 or 24, wherein the isolated oligonucleotide comprises a nucleotide sequence that is complementary to nucleic acid sequence AUGACA (SEQ ID NO: 2).

26. The isolated oligonucleotide of any of paragraphs 23-25, wherein the oligonucleotide is from about 10 to about 35 nucleotides in length.

27. The isolated oligonucleotide of any of paragraphs 23-25, wherein the oligonucleotide comprises a modification selected from the group consisting of nucleobase modifications, sugar modifications, inter-sugar linkage modifications, backbone modifications, and any combinations thereof.

28. The isolated oligonucleotide of any of paragraphs 23-27, wherein the oligonucleotide comprises a ligand.

29. The isolated oligonucleotide of any of paragraphs 23-28, wherein the oligonucleotide inhibits the activity of miRNA-425 in a cell.

30. The isolated oligonucleotide of any of paragraphs 23-29, wherein the oligonucleotide reduces the amount of miRNA-425 in a cell.

31. The isolated oligonucleotide of any of paragraphs 23-30, wherein the oligonucleotide increases the expression of atrial natriuretic peptide (ANP) or a nucleic acid encoding ANP in a cell.

32. The isolated oligonucleotide of paragraph 31, wherein said nucleic acid encoding ANP is mRNA.

33. The isolated oligonucleotide paragraph 31 or 32, wherein said nucleic acid encoding ANP comprises A allele of SNP rs5068 (A/G).

34. The isolated oligonucleotide of any paragraphs 23-33, wherein the isolated oligonucleotide comprises the nucleic acid sequence TTACTGTGCTAGTGAGGGCAACT (SEQ ID NO: 3) or a variant thereof.

35. A pharmaceutical composition comprising an isolated oligonucleotide of any of paragraphs 23-34 and a pharmaceutically acceptable carrier.

36. A kit comprising an isolated oligonucleotide of any of paragraphs 23-34.

37. A method of inhibiting angiogenesis or preventing or inhibiting low blood pressure (e.g., hypotension or orthostatic hypotension) or a symptom thereof in a subject in need thereof, the method comprising administering to the subject an effective amount of miRNA-425 agent, or a mimetic thereof.

38. A method of inhibiting angiogenesis or preventing or inhibiting low blood pressure (e.g., hypotension or orthostatic hypotension) or a symptom thereof in a subject in need thereof, the method comprising administering to a subject determined to heterozygous (AG) or homozygous (AA) for A allele for the single nucleotide polymorphism (SNP) rs5068 (A/G) an effective amount of a miRNA-425 agent, or a mimetic thereof.

39. The method of paragraph 37 or 38, wherein the miRNA-425 agent comprises a nucleotide sequence comprising at least a portion of nucleic acid sequence GAAAGCGCUUUGGAAUGACACGAUCACUCCCGUUGAGUGGGCACCCGAGAAGCCAUCGGG AAUGUCGUGUCCGCCCAGUGCUCUUUC (SEQ ID No. 13).

40. The method of paragraph 37 or 38, wherein the miRNA-425 agent comprises a nucleotide sequence that comprises at least a portion nucleic acid sequence AAUGACAC-GAUCACUCCCGUUGA (SEQ ID NO: 1).

41. The method of paragraph 37 or 38, wherein the miRNA-425 agent comprises a nucleotide sequence that comprises at least nucleic acid sequence AUGACA (SEQ ID NO:2).

42. The method of any of paragraphs 37-41, wherein the oligonucleotide comprises a modification selected from the group consisting of nucleobase modifications, sugar modifications, inter-sugar linkage modifications, backbone modifications, and any combinations thereof.

43. The method of any of paragraphs 37-42, wherein the oligonucleotide comprises a ligand.

44. The method of any of paragraphs 37-43, wherein the oligonucleotide is from about 11 to about 30 nucleotides in length.

45. The method of any of paragraphs 37-44, wherein the oligonucleotide is single-stranded.

46. The method of any of paragraphs 37-45, wherein the oligonucleotide is formulated in a lipid delivery vehicle. (liposomes, lipid particles, other compositions used for oligonucleotide delivery)

47. The method of any of paragraphs 37-46, wherein the oligonucleotide is encoded by an expression vector.

48. The method of any of paragraphs 37-47, wherein the miRNA-425 agent decreases the amount of NPPA mRNA in a cell relative to a control or reference level.

49. The method of any of paragraphs 37-48, wherein the miRNA-425 agent decrease expression of atrial natriuretic peptide (ANP) or a nucleic acid encoding ANP in a cell relative to a control or reference level.

50. The method of paragraph 49, wherein said nucleic acid encoding ANP is mRNA.

51. The method of any of paragraphs 37-50, wherein the subject is heterozygous for a single nucleotide polymorphism (SNP) of ANP gene, wherein the polymorphism is A allele of SNP rs5068 (A/G).

52. The method of any of paragraphs 37-51, wherein the subject is homozygous for a single nucleotide polymorphism (SNP) of ANP gene, wherein the polymorphism is A allele of SNP rs5068 (A/G).

53. The method of any of paragraphs 37-52, further comprising selecting a subject for treatment for inhibiting angiogenesis or preventing or inhibiting orthostatic hypotension before onset of said administering, comprising assaying a biological sample from the subject for single nucleotide polymorphism of SNP rs5068 (A/G) and selecting the subject who is heterozygous or homozygous for G allele of SNP rs5068 (A/G).

54. The method of any of paragraphs 37-53, further comprising co-administering a therapeutic agent, wherein the therapeutic agent is for treatment for inhibiting angiogenesis or orthostatic hypotension.

55. An assay to determine if a subject is at risk of a cardiovascular disease or disorder, the assay comprising: contacting a biological sample obtained from the subject with at least one probe to detect the levels or miR-425, wherein the level of miR-425 above a predefined reference miR-425 level identifies a subject who would be predicted to be at risk of a cardiovascular disease or disorder.

56. The assay of paragraph 55, wherein the probe comprises a detectable label or means of generating a detectable signal.

57. The assay of paragraph 55, wherein the probe is a nucleic acid probe which specifically hybridizes to miR-425.

58. An assay comprising:
   i. measuring or quantifying the amount of miR-425 in a biological sample obtained from a subject; and
   ii. comparing the measured or quantified amount of miR-425 with a reference value, and if the amount of miR-425 is increased relative to the reference value,
   iii. identifying the subject as having an increased probability of having high blood pressure, hypertension or cardiovascular disease.

59. An assay comprising:
   i. contacting a biological sample obtained from a subject with a detectable antibody specific for miR-425 or detectable nucleic acid for miR-425;
   ii. washing the sample to remove unbound antibody or unbound nucleic acid;
   iii. measuring the intensity of the signal from the bound, detectable antibody or bound detectable nucleic acid;
   iv. comparing the measured intensity of the signal with a reference value and if the measured intensity is increased relative to the reference value; and
   v. identifying the subject as having an increased probability of having high blood pressure or cardiovascular disease.

60. The assay of claims 58 and 59, wherein the subject has a cardiovascular disease or disorder.

61. The assay of claim 60, wherein the cardiovascular disease or disorder is selected from the group consisting of: heart failure, myocardial infarction or stable coronary artery disease.

62. An assay comprising:
   a. subjecting a test sample from a human subject diagnosed with having a cardiovascular disease or disorder to determine if treatment with an anti-miR-425 agent would be effective, to at least one genotyping assay that determines the genotype of the rs5068 loci;
   b. determining the genotype of the rs5038 loci;
   c. selecting a treatment regimen with an anti-miR-425 agent with at least on adenosine "A" allele at position 647 of SEQ ID NO: 12 is present, or when the subject is homozygous (AA) or heterozygous (AG) for the major allele at the rs5068 loci, and not selecting a treatment regimen with an anti-miR-425 agent where an adenosine "A" allele at position 647 of SEQ ID NO: 12 is absent, or where the subject is homozygous for the G allele (GG) at the rs5068 loci.

63. The assay of paragraph 62, wherein the subject has been diagnosed with high blood pressure or hypertension.

64. An assay comprising:
   a. subjecting a test sample from a human subject diagnosed with having low blood pressure to determine if treatment with an miR-425 agent would be effective, to at least one genotyping assay that determines the genotype of the rs5068 loci;
   b. determining the genotype of the rs5038 loci;
   c. selecting a treatment regimen with an miR-425 agent with at least on adenosine "A" allele at position 647 of SEQ ID NO: 12 is present, or when the subject is homozygous (AA) or heterozygous (AG) for the major allele at the rs5068 loci, and not selecting a treatment regimen with an miR-425 agent where an adenosine "A" allele at position 647 of SEQ ID NO: 12 is absent, or where the subject is homozygous for the G allele (GG) at the rs5068 loci.

65. A system for obtaining data from at least one test sample obtained from at least one subject, the system comprising:
   a. a determination module configured to receive said at least one test sample and perform at least one analysis on said at least one test sample to determine the presence or absence of at least one of the following conditions:
      i. an expression of NT-proANP or ANP mRNA is smaller than a pre-determined level;

ii. expression of miR-425 is greater than a pre-determined standard;
iii. at least one copy of a single nucleotide polymorphism (SNP) at position 647 of SEQ ID NO: 12 comprises an adenine "A" allele, or its complement thereof comprises a thymine "T" allele;
b. a storage device configured to store data output from said determination module; and
c. a display module for displaying a content based in part on the data output from said determination module, wherein the content comprises a signal indicative of the presence of at least one of these conditions determined by the determination module, or a signal indicative of the absence of at least one of these conditions determined by the determination module.

66. The system of paragraph 65, wherein the content displayed on said display module further comprises a signal indicative of the subject being recommended to receive a particular treatment regimen.

67. The system of paragraph 65, wherein the subject is recommended a treatment with a composition comprising an anti-miR-425 agent where the content from the display module produces a signal indicative of at least one of:
   i. the expression of NT-proANP or ANP mRNA is smaller than a pre-determined level;
   ii. the expression of miR-425 is at least the same as, or greater than a pre-determined standard;
   iii. the presence of at least one copy of single nucleotide polymorphism (SNP) at position 647 of SEQ ID NO: 12 comprises a adenine "A" allele, or its complement thereof comprises a thymine "T" allele (e.g., the subject is AA or AG); and wherein the subject is not recommended a treatment with a composition comprising an anti-miR-425 agent where the content from the display module produces a signal indicative of at least one of:
   iv. the expression of NT-proANP or ANP mRNA is at least the same as, or higher than a pre-determined level;
   v. the expression of miR-425 is lower than a pre-determined standard;
   vi. the presence of less than one copy of single nucleotide polymorphism (SNP) at position 647 of SEQ ID NO: 12 comprises an adenine "A" allele, or its complement thereof comprises a thymine "T" allele, or the presence of two copies of single nucleotide polymorphism (SNP) at position 647 of SEQ ID NO: 12 comprises an "G" allele, or its complement thereof comprises a thymine "C" allele (e.g., the subject is GG).

68. A method of treating a subject having a high blood pressure, hypertension, obesity or a cardiovascular disease, comprising administering a pharmaceutically effective amount of an anti-miR-425 agent to a subject having high blood pressure, hypertension or a cardiovascular disease and determined to show the plasma expression of miR-425 which is at least the same as or increased relative to a control level, and wherein the subject is not administered an anti-miR-425 agent if the plasma expression of miR-425 from the subject was determined to be less than the control level.

69. A method of determining if a subject is responsive to an anti-miR-425 agent comprising assaying a blood sample for at least one copy of the adenine (A) allele at rs5068 SNP (homozygotes), wherein the subject is responsive to an anti-miR-425 agent where at least one copy of the adenine (A) allele at rs5068 SNP is present.

70. The method of paragraph 69, further comprising administering an anti-miR-425 agent to the subject if two copies of the adenine (A) at rs5068 SNP is present.

71. An isolated oligonucleotide comprising a modified miR-425 nucleotide sequence which binds to the G allele miRNA target sequence of SEQ ID NO: 9.

72. The isolated oligonucleotide of claim 71 comprising the nucleic acid sequence A<u>G</u>UGACACGAUCACUCCCGUUGA (SEQ ID NO: 6) or a variant thereof 73. The isolated oligonucleotide of claim 71 or 72 for treatment of a subject with hypotension, wherein the subject has two copies of the "G" alleles at the single nucleotide polymorphism (SNP) at position 647 of SEQ ID NO: 12, or its complement thereof comprises a thymine "C" allele (e.g., the subject is GG).

74. A method of inhibiting angiogenesis or preventing or inhibiting low blood pressure (e.g., hypotension or orthostatic hypotension) or a symptom thereof in a subject in need thereof, the method comprising administering to the subject an effective amount of a modified miR-425 nucleotide sequence which binds to the G allele miRNA target sequence of SEQ ID NO: 9, or a mimetic thereof.

75. The method of claim 75, wherein the modified miR-425 nucleotide sequence comprises the nucleic acid sequence of A<u>G</u>UGACACGAUCACUCCCGUUGA (SEQ ID NO: 6) or a variant thereof 76. The method of claim 74 or 75, wherein the subject has two copies of the "G" alleles at the single nucleotide polymorphism (SNP) at position 647 of SEQ ID NO: 12, or its complement thereof comprises a thymine "C" allele (e.g., the subject is GG).

The technology described herein is further illustrated by the following examples which in no way should be construed as being further limiting, The contents of all cited references, including literature references, issued patents, published patent applications, and co-pending patent applications, cited throughout this application are hereby expressly incorporated by reference.

The technology described herein has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLES

Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods

Study Sample and Design.

The inventors recruited 699 healthy volunteers of European ancestry, aged 18 to 40 years, with normal body mass index and no history of hypertension (see Supplementary Appendix). Other enrollment criteria included blood pressure (BP) at two study visits ≤140/90 mm Hg, estimated creatinine clearance >60 cc/min, and willingness to comply with the study diet. All individuals were genotyped for rs5068 (where "A" is the major allele, and the "G" is the minor allele. The frequency of the minor G allele is 4%). 31 individuals were selected for further physiologic assessment based on genotype (attempting to recruit at least 1 heterozygous AG individual for every 3 AA individuals). Until completion of the protocol, only one study investigator (EM) had access to the unblinded genotype data. Thus, both subjects and study investigators involved in the protocol were blinded to genotype status. The study protocol was approved by the Partners Human Research Committee. All subjects provided written informed consent.

Subjects were randomly allocated to consume a high (200 mEq/day) or low (10 mEq/day) sodium diet for one week. Other micronutrients were standardized, including 100 (±2) mEq potassium and 1000 (±50) mg calcium per day. The macronutrient composition of both diets was the same (protein 10-20%, fat 20-35%, and carbohydrate 60-65%). All meals were made on-site at the Massachusetts General Hospital Clinical Research Center (MGH CRC). Subjects were instructed to drink only distilled water and use low-sodium toothpaste, both of which were provided. Compliance with the diet was assessed with a 24-hour urine collection beginning on day 5 of the study week.

After a week of standardized diet, subjects were admitted to the MGH CRC for an overnight visit. Subjects were kept supine overnight, and ambulatory BP monitoring was performed (every 20 minutes while awake and every 30 minutes while asleep) using a Space Labs system (Issaquah, Wash.). The following morning two intravenous catheters were placed for phlebotomy and infusion of 0.25 ml/kg/min normal (0.9 mEq/mL) saline over 2 hours. Venous blood was sampled hourly over 8 hours beginning immediately prior to the start of the infusion.

All subjects were subsequently assigned to one week of the alternate diet (e.g. the low-salt diet for individuals initially randomized to high salt, and vice versa). The second dietary intervention began on average 8 weeks following the initial diet. A second overnight visit for plasma sampling and saline infusion was performed following the second diet week. Women were studied during the first week of the menstrual cycle, corresponding to the early follicular phase.

Study Sample for Genotype-Directed Study.

Inclusion criteria for study subjects was age between 18 and 40 years old, with BP at two study visits ≤140/90, BMI<25 kg/m², estimated CrCl>60 cc/min, and willingness to comply with the study diet. Subjects were excluded if they had any of the following: history of hypertension; history of cardiovascular, renal, or liver disease; treated diabetes; use of vasoactive or diuretic medications; atrial fibrillation; anemia; abnormal serum sodium or potassium; urine human chorionic gonadotropin (HCG) level consistent with pregnancy; or abnormal liver function tests, current smokers, uses of stimulant medications in the past month, or inability to adhere to the study diet due to pre-existing dietary requirements (vegan, gluten-free, high-calorie athletic training diet).

Study Protocol.

Individuals were genotyped for rs5068 (A/G; minor allele frequency, 4%). From 699 individuals who were screened, 31 were selected for further physiologic assessment based on genotype (attempting to recruit at least 1 AG individual for every 3 AA individuals). Only the study statistician had access to the unblinded genotype data. The sodium contents of the high- and low-salt diets were 200 mEq/day and 10 mEq/day, respectively. Other micronutrients were standardized, including 100 (±2) mEq potassium and 1000 (±50) mg calcium per day. The macronutrient composition of both diets was the same (protein 10-20%, fat 20-35%, and carbohydrate 50-65%). All meals were prepared on site at the metabolic kitchen in the Massachusetts General Hospital Clinical Research Center (MGH CRC). Subjects picked up the prepared, frozen meals and snacks directly from the CRC. They were provided with bottled distilled water to consume while on the diet protocol and during the inpatient visits.

Subjects were also provided with low-sodium toothpaste during the low-sodium portion of the protocol. On day 5 of the diet, they performed a 24-hour urine collection (for urine sodium and creatinine) so that adherence to the study diet could be assessed. Women were studied during the first week of the menstrual cycle. After a week of standardized diet, subjects were admitted for an overnight visit. Subjects were kept supine overnight, and ambulatory BP monitoring was performed using a Space Labs system (Issaquah, Wash.). The following morning two intravenous catheters were placed for phlebotomy and infusion of 0.25 ml/kg/min normal saline (0.9 mEq/mL) over 2 hours. Venous blood was sampled hourly over 8 hours beginning immediately prior to the start of the infusion. Specifically, just prior to the initiation of the infusion, participants were asked to empty their bladder. Every 30 minutes during the infusion and afterwards up to 4 hours, the participants were asked to urinate. Urine volume and urine sodium concentration was measured. The protocol was subsequently repeated using the alternate diet for one week. The first 13 individuals were also studied in a separate echocardiographic investigation (Mak et al., Effects of subacute dietary salt intake and acute volume expansion on diastolic function in young normotensive individuals. 2013, Eur. Heart J. Cardiovasc. Imaging). On day 6 of the study week, subjects performed a 24-hour urine collection to confirm adherence to the study diet (Table 2).

Genotyping and Biomarker Assessment.

DNA was extracted from whole blood using the AutoGenFlex STAR system (AutoGen, Holliston, Mass.). A TaqMan assay (C_11644811_10) was used to genotype SNP rs5068 (Applied Biosystems, Foster City, Calif.). The genotyping call rate was 99.5%.

The N-terminal pro-peptides of ANP and BNP was measured, rather than the mature peptides, because the N-terminal pro-peptides have a longer half life in the circulation and higher assay reproducibility. Plasma N-terminal proANP (Nt-proANP) was measured by ELISA (proANP 1-98, Biomedica Medizinprodukte GmbH & Co K G, Austria). Plasma mature BNP was measured using CENTAUR immunoassay (Siemens, New York, N.Y.) and Nt-proBNP levels were measured using an electrochemiluminescence immunoassay (Elecsys proBNP, Roche, Indianapolis, Ind.). Plasma cyclic guanosine 3',5'-monophosphate (cGMP) levels were measured using an ELISA (Biomedical Technologies, Stoughton, Mass.)

Cultured Cells.

Epstein Barr virus (EBV)-transformed B lymphocytes from 5 individuals homozygous for the major allele of rs5068 (GM07019, GM07048, GM07349, GM10843, GM10850) and 4 individuals heterozygous for rs5068 (GM10852, GM10853, GM12864, GM07348) were obtained from Coriell Repositories (Coriell Institute for Medical Research, Camden, N.J.). The EBV-transformed B lymphoblasts were maintained in RPMI 1640 medium supplemented with 15% FBS. COS7 cell lines were purchased from American Type Culture Collection (ATCC, Manassas, Va.) and were maintained in Dulbecco's modified Eagle's medium (DMEM) supplemented with 10% FBS, penicillin, streptomycin, and 1-glutamine. The human hepatoma cell line (HepG2) was purchased from ATCC and maintained in Eagle's Minimum Essential Medium (EMEM) supplemented with 10% FBS, penicillin, streptomycin, and 1-glutamine. All cells were cultured at 37° C. in the presence of 5% $CO_2$. Human cardiomyocytes (97% purity) derived from iPS cells were purchased from Cellular Dynamics International (Madison, Wis.).

miRNAs.

Multiple microRNA databases (miRanda[14], TargetScan[15] and MicroSNiPer[16]) were screened to generate a list of microRNAs that are predicted in silico to interact with the ANP mRNA sequence containing the rs5068 major allele but not the minor allele. Chemically-modified, double-stranded RNAs designed to mimic the endogenous mature candidate miRNAs including miR-425 (AAUGACACGAUCACUCCCGUUGA, (SEQ ID NO: 1) underline denoting the location of rs5068), miR-4770 (UGAGAUGACACUGUAGCU) (SEQ ID NO: 4), and miR-196a*(CGGCAACAAGAAACUGCCUGAG) (SEQ ID NO: 5), as well as a negative control miRNA, were purchased from Applied Biosystems (Foster City, Calif.). A chemically-modified single-stranded RNA designed to inhibit the endogenous mature miR-425 and a single-stranded negative control microRNA were obtained from Applied Biosystems (Foster City, Calif.) for the anti-microRNA luciferase experiments. A modified miR-425 mimic, whose seed sequence matched the NPPA mRNA containing the minor G allele (AGUGACACGAUCACUCCCGUUGA (SEQ ID NO: 6), was purchased from Applied Biosystems.

RNA Extraction.

Total RNA was extracted from human tissues and cultured cells using TRIzol, according to the manufacturer's protocol (Life Technologies, Grand Island, N.Y.). Peripheral whole blood samples (2.5 ml) from fasting participants were collected in PAXgene™ tubes during Framingham Heart Study (FHS) offspring cohort examination 8 (2005-2008). Total RNA was isolated from frozen PAXgene blood tubes by Asuragen, Inc., according to the company's standard operating procedures for automated isolation of RNA. The RNA Integrity Number (RIN) for the RNA samples used in this study was 7.2±0.9 (mean and SD) indicating high RNA quality.

Measurement of mRNA and miRNA Levels.

NPPA mRNA levels in RNA extracted from FHS whole blood samples were measured using the Affymetrix Hu_Ex_1.0_st Exon array according to the manufacturer's instructions (Affymetrix, Santa Clara, Calif.). Log 2 expression levels, adjusted for technical covariates, were analyzed in relation to rs5068 genotype. Levels of NPPA mRNA and 18S ribosomal RNA in RNA extracted from extracted from lymphoblasts and cardiac myocytes were measured using quantitative RT-PCR and Taqman primers. Relative NPPA mRNA levels normalized to 18S ribosomal RNA levels were determined using the relative cycle threshold method. TaqMan microRNA reverse transcription and real-time assay kits were used to detect mature miR-425 and U6 snRNA (RNU6B). Differences in miR-425 levels normalized to RNU6B were determined using the relative Ct method (Applied Biosystems).

Evaluation of the Ability of miR-425 to Modulate NPPA 3' URR Function:

Luciferase-NPPA 3' UTR Reporter Constructs:

The NPPA 3' UTR sequences (299 bp) corresponding to the major A and minor G alleles of rs5068 were amplified by PCR from a de-identified human HapMap genomic DNA sample obtained from Coriell Repositories (Coriell Institute for Medical Research, Camden, N.J.). The NPPA 3'UTR was amplified from genomic DNA using the following primers (GCGGAGCTCAGATAACAGCCAGGGAGGACAAG (SEQ ID NO: 10) and GCTCTAGATTGTCTTCTGTC-CATGGTGCTGAAG (SEQ ID NO: 11)) The PCR products were digested with SacI and XbaI and cloned into the pISO vector. The 3' UTR NPPA sequences were cloned into the pISO vector (Addgene) 3' of the sequence encoding firefly luciferase to generate major (A) allele+luciferase (major-LUC) and minor (G) allele+luciferase (minor-LUC) constructs.

cDNA Expression Constructs:

A human NPPA major allele cDNA expression plasmid was purchased from OriGene (Rockville, Md., catalog # SC122740). A minor allele NPPA cDNA construct was created using site-directed mutagenesis, for example, a single base pair alteration in the NPPA cDNA expression construct was performed using QuickChange II XL site-directed mutagenesis kit (Stratagene, Santa Clara, Calif.) and synthetic forward and reverse oligonucleotides: GTCATCTTGT-TGCCATAGAGTTGTGATCATCCC (SEQ ID NO: 49) and GGGATGATCACAACTCTATGGCAACAAGATGAC (SEQ ID NO: 50), respectively, as per manufacturer's protocol.

Transient Transfection of Reporter Plasmids into COS, Hep2 and Human Cardiom**Yocyte Cells.

Luciferase Activity.

COS-7 cells were transfected with NPPA-luciferase (major-LUC and minor-LUC) or NPPA expression constructs, as well as a plasmid directing expression of renilla luciferase (as a transfection control), using FuGene 6 transfection reagent (Roche, Indianapolis, Ind.) according to the manufacturer's protocol. Twenty-four hours after plasmid DNA transfection, miRNA mimics or anti-miRNAs were transfected using RNAi Max (Life Technologies, Grand Island, N.Y.) at 5 nM. After an additional twenty four hours, cells were harvested, and firefly and renilla luciferase activities in cell extracts were measured using the Dual Luciferase Reporter Assay System (Promega, Madison, Wis.) according to the manufacturer's protocol. Forty-eight hours after transfection of NPPA expression plasmids, cells and media were collected for measurement of renilla luciferase activity (as above) and Nt-proANP levels by ELISA, respectively.

ANP Production:

NPPA expression plasmids and the plasmid specifying renilla luciferase (as a transfection efficiency control) were transfected into COS-7 cells, followed 24 hours later by transfection of miRNAs, as described above. Cells and media were collected 48 hours after plasmid transfection for measurement of Nt-proANP levels by ELISA and renilla luciferase activity.

Transfecting microRNAs into HepG2 Cells:

HepG2 cells were transfected with either miR-425 or a negative control miRNA using RNAi Max. Cells were harvested 48 hours later for RNA extraction. The relative expression of NPPA mRNA compared to 18S rRNA was determined by qRT-PCR.

Transfecting miRNAs into Human Cardiomyocytes:

Human cardiomyocytes were transfected with either miR-425 or a negative control miRNA using RNAi Max. After 24 hours, cells were washed and then incubated in serum-free medium for an additional 48 hours. Cells were harvested for RNA extraction and measurement of NPPA mRNA and 18S ribosomal RNA levels. Nt-proANP immunoreactivity in the culture media was measured using the Nt-proANP ELISA kit (as described above).

Statistical Analysis. Repeated measures ANOVA was used to assess the effect of genotype, diet, and intravenous saline on plasma Nt-proANP, Nt-proBNP, BNP, and cGMP levels. Gene expression data from the Framingham Heart Study have been deposited in dbGAP (National Center for Biotechnology Information, Bethesda, Md.), accession number phs000007.v19.p7. For relative luciferase activity, mRNA levels, and culture medium Nt-proANP concentrations, we performed 2-sample or paired t-tests, as appropriate. All analyses were conducted using SAS (Cary, N.C.). A two-sided p<0.05 was considered statistically significant. Data are presented as mean±SEM in the figures.

Example 1

Epidemiologic studies have shown differences in plasma natriuretic peptide concentrations between rs5068 genotypes (5), but these differences were identified in the context of random salt intake and other sources of variation inherent to community-based studies. To minimize this variation and provide mechanistic insights into the association of rs5068 with ANP levels and blood pressure, we undertook a high-resolution physiologic study of healthy subjects who were selected on the basis of their rs5068 genotype and maintained on defined low- and high-salt diets.

The inventors genotyped the rs5068 variant in 699 healthy, normotensive individuals of European ancestry between the ages of 18 and 40. Overall, 645 (92%) individuals were homozygous for the major A allele (AA), 51 (7%) were heterozygous (AG), and 3 were homozygous for the minor G allele (GG). Accordingly, 54 (8%) had at least one copy of the minor G allele (AG or GG). The inventors enrolled 23 AA individuals and 8 AG individuals for physiologic studies. Table 1 shows the characteristics of the individuals in the physiologic study sample, who had a mean age of 24±4 years, and 29 (94%) were men. Detailed characteristics of the 23 AA individuals and 8 AG individuals who participated in the physiologic study are shown in Table 1. By ascertainment, all individuals were normotensive with a mean systolic blood pressure of 115±10 mm Hg, and a mean diastolic blood pressure of 74±7 mmHg Body mass index ranged from 19.3 to 25.6 kg/m$^2$ (mean 22.9±1.7 kg/m$^2$).

TABLE 1

Baseline characteristics of the genotype-directed study sample

| Characteristics | All subjects (n = 31) | Major Homozygotes (AA) (n = 23) | Heterozygotes (AG) (n = 8) |
|---|---|---|---|
| Age (years) | 24 ± 4 | 21 ± 2 | 25 ± 6 |
| Male (%) | 94 | 95 | 88 |
| Body mass index (kg/m$^2$) | 23.1 ± 1.7 | 23.0 ± 1.6 | 23.5 ± 1.9 |
| Systolic blood pressure (mm Hg) | 114 ± 10 | 115 ± 9 | 114 ± 9 |
| Diastolic blood pressure (mm Hg) | 73 ± 7 | 74 ± 4 | 72 ± 8 |

Subjects were placed on a study diet for two weeks, consisting of one week on a high-sodium diet (200 mEq/day) and one week on a low-sodium diet (10 mEq/day), in random order. Mean 24-hour urine sodium was 22 mmol after a week on the low-sodium diet, and 142 mmol after a week on the high-sodium diet. AG individuals had higher plasma levels of N-terminal proANP (Nt-proANP) than did AA individuals after one week on either a low- or a high-salt diet (49% and 32%, respectively; P=0.016 for overall genotype effect). The transition from a low- to high-sodium diet was associated with a 55% increase in Nt-proANP levels (P<0.001), a difference that was similar in both genotype groups (diet-by-genotype interaction, P>0.8). AG individuals on a low-sodium diet had plasma Nt-proANP concentrations that were comparable to those of AA individuals on a high-sodium diet. These findings suggest that rs5068 influences the "set-point" of circulating ANP on both low- and high-sodium backgrounds. The magnitude of the genetic effect is similar to that of a marked (20-fold) change in salt intake.

Plasma Nt-proANP concentrations after the low- and high-salt diet weeks are shown according to genotype in FIG. 1A. AG individuals had significantly higher levels of Nt-proANP on both standardized diets, compared with major homozygotes (AA) (49% higher after the low-salt week, 32% higher after the high-salt week; p=0.016 for overall genotype effect, FIG. 1A). The transition from a low-salt to high-salt diet was associated with a 56% increase in Nt-proANP (p<0.001), a difference that was comparable in both genotype groups (diet-by-genotype interaction, p>0.8). Heterozygous individuals on a low-salt diet had plasma Nt-proANP concentrations that were comparable to those of major homozygote individuals on a high-salt diet.

Figure 1B:
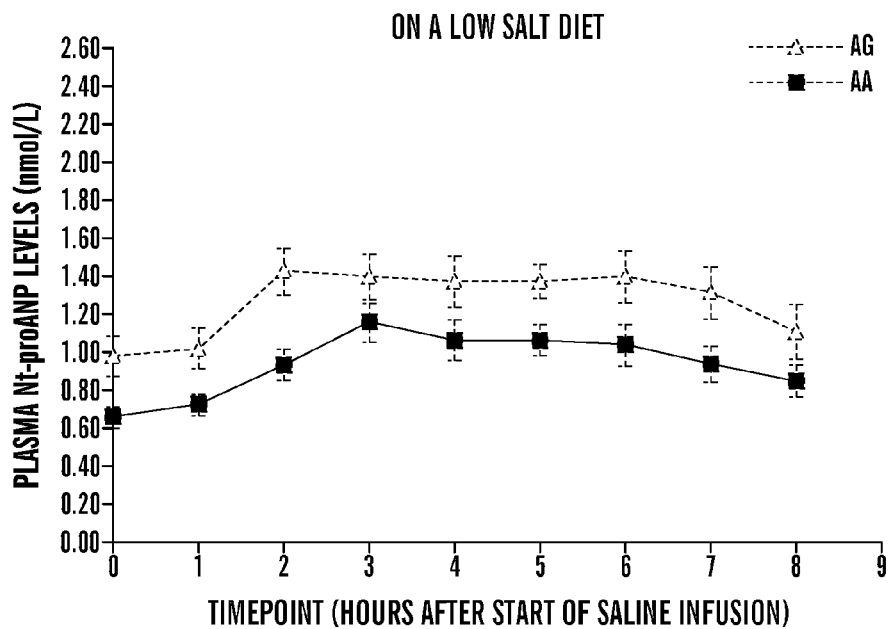
Figure 1C:
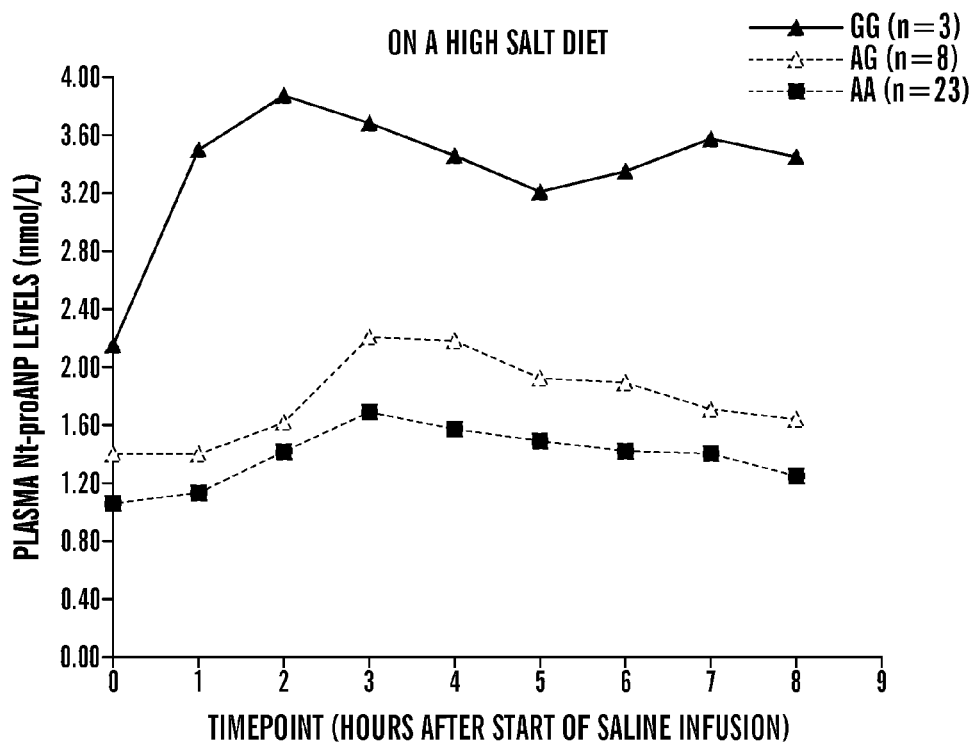

To ascertain whether rs5068 influences the ability of ANP levels to increase in response to intravascular volume expansion, plasma Nt-proANP levels were measured during and after a saline challenge. In the group as a whole, saline administration increased plasma Nt-proANP levels by 64% on a low-sodium diet background (FIG. 1B) and 59% on a high-sodium diet background (FIG. 1C). Mean plasma Nt-proANP concentrations at all time points during and after the saline infusion were higher in AG individuals than in AA individuals (P=0.018 for genotype effect), demonstrating that miR-425-mediated inhibition from the NPPA gene is greatest in the homozygous AA individuals as compared to the heterozygous AG individuals. The plasma levels of Nt-proANP at all time points were highest in GG homozygous individuals, demonstrating that miR-425 does not have an effect on decreasing gene expression from the NPPA gene from these individuals (FIG. 1C). There was no evidence of a saline-by-genotype interaction (P=0.84).

Figure 6A:
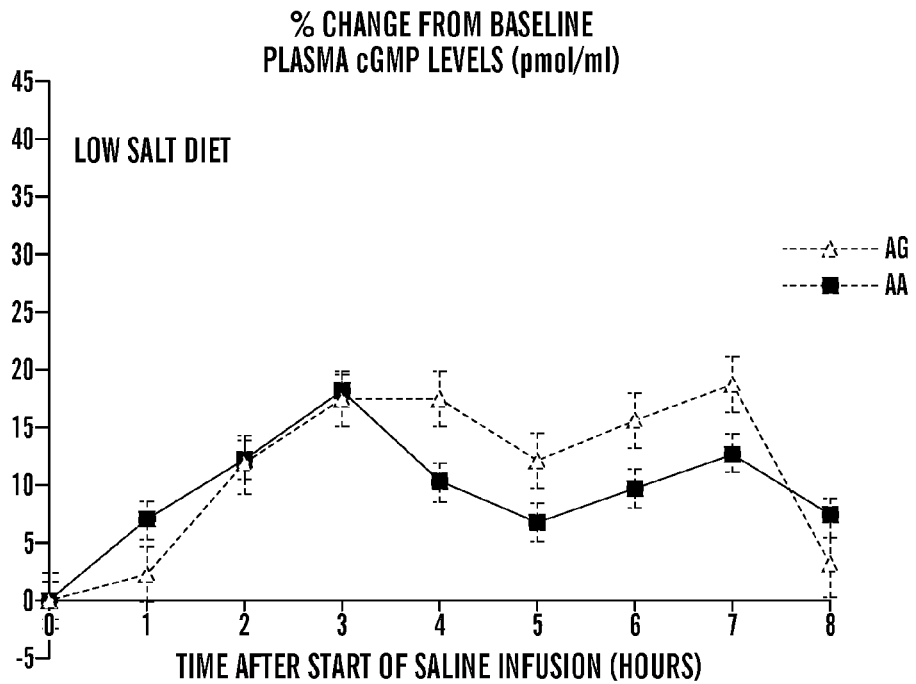
FIGS. 6A-6B show samples for measurement of plasma cGMP levels were obtained at baseline (time 0) and at 1, 2, 3, 4, 5, 6, 7 and 8 hours (h) after the start of saline infusion. AA denotes rs5068 major homozygote, and AG denotes rs5068 heterozygote.
Figure 6B:
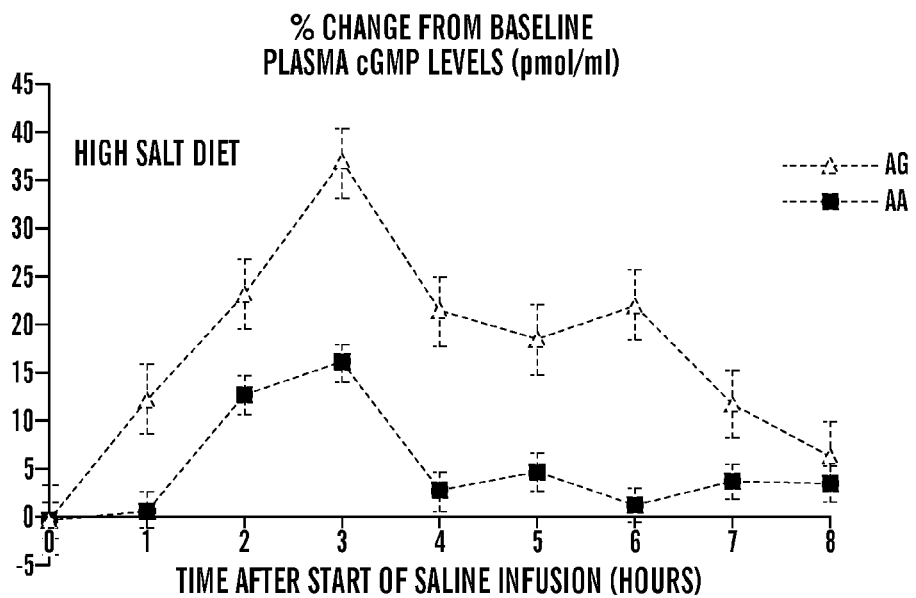
Figure 7A:
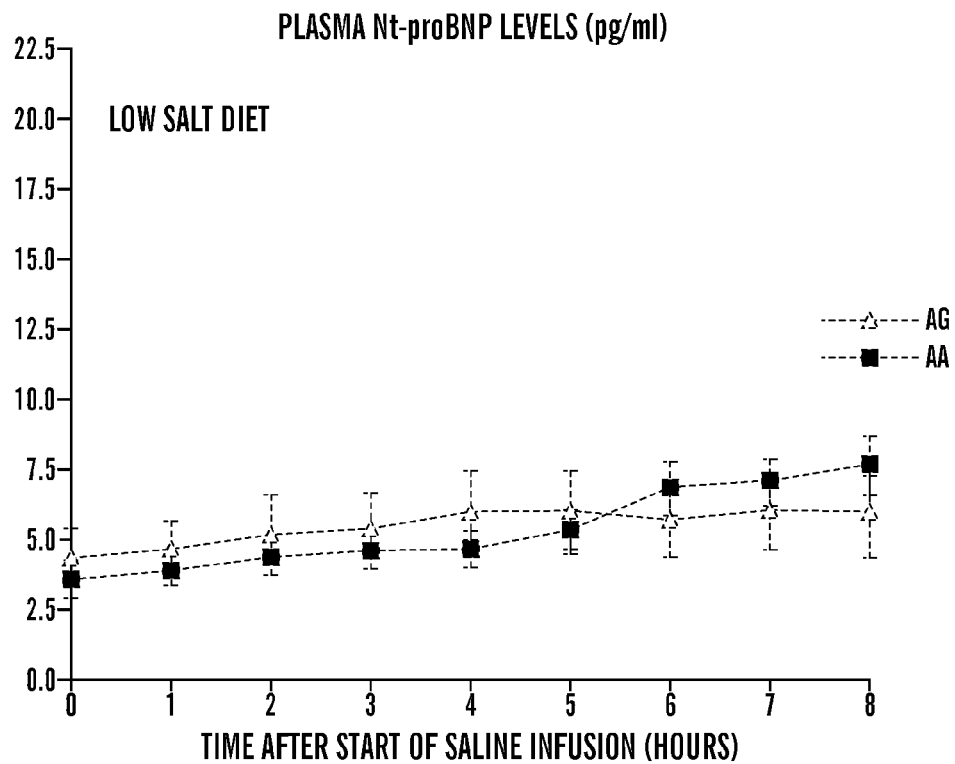
FIGS. 7A-7B show samples for measurement of plasma Nt-proBNP levels were obtained at baseline and at 1, 2, 3, 4, 5, 6, 7 and 8 hours (h) after the start of saline infusion. AA denotes rs5068 major homozygote, and AG denotes rs5068 heterozygote.
Figure 7B:
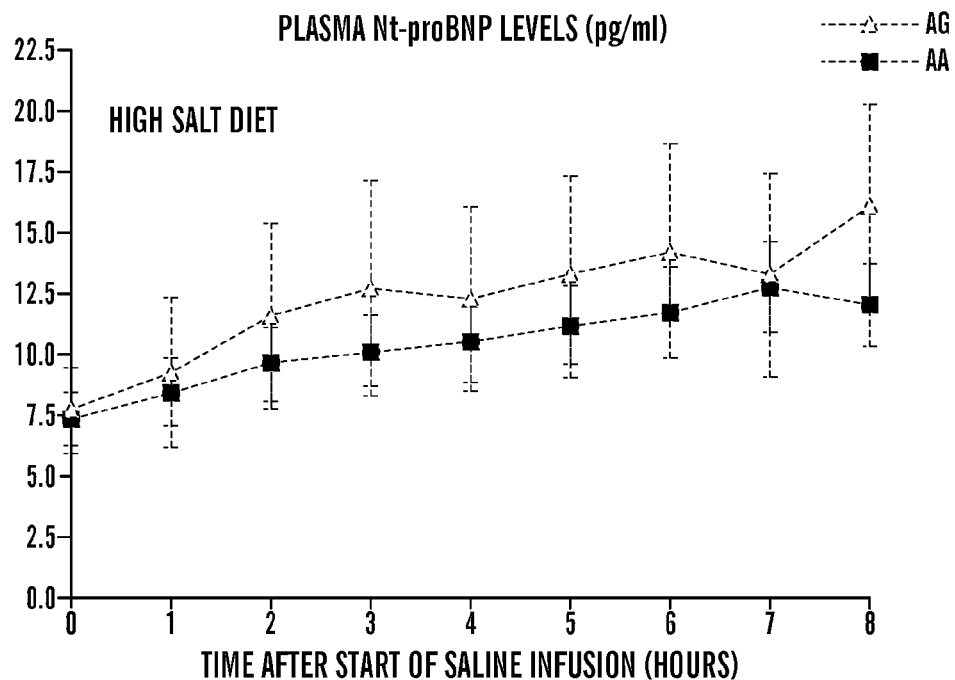
Figure 8A:
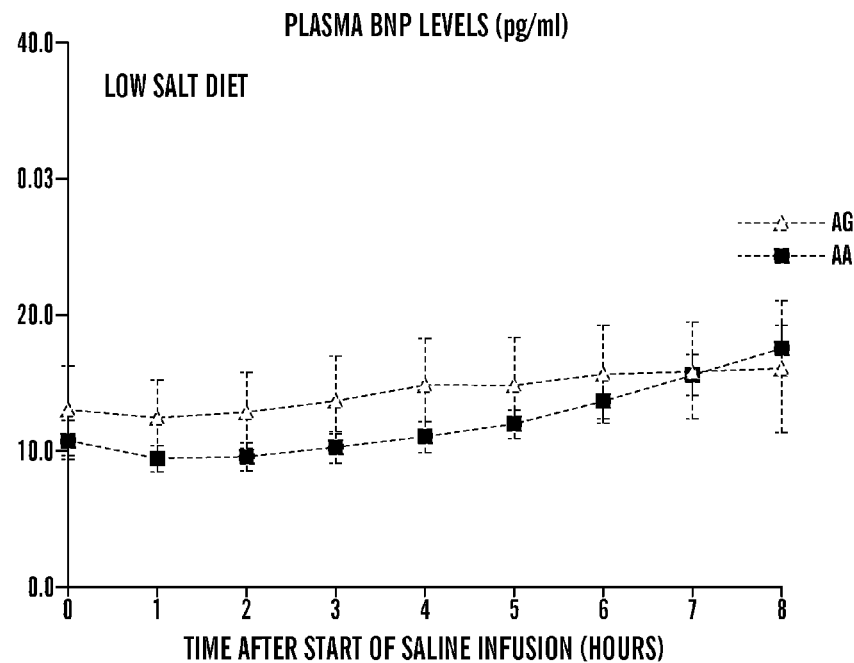
FIGS. 8A-8B show samples for measurement of plasma BNP levels were obtained at baseline and at 1, 2, 3, 4, 5, 6, 7 and 8 hours (h) after the start of saline infusion. AA denotes rs5068 major homozygote, and AG denotes rs5068 heterozygote.
Figure 8B:
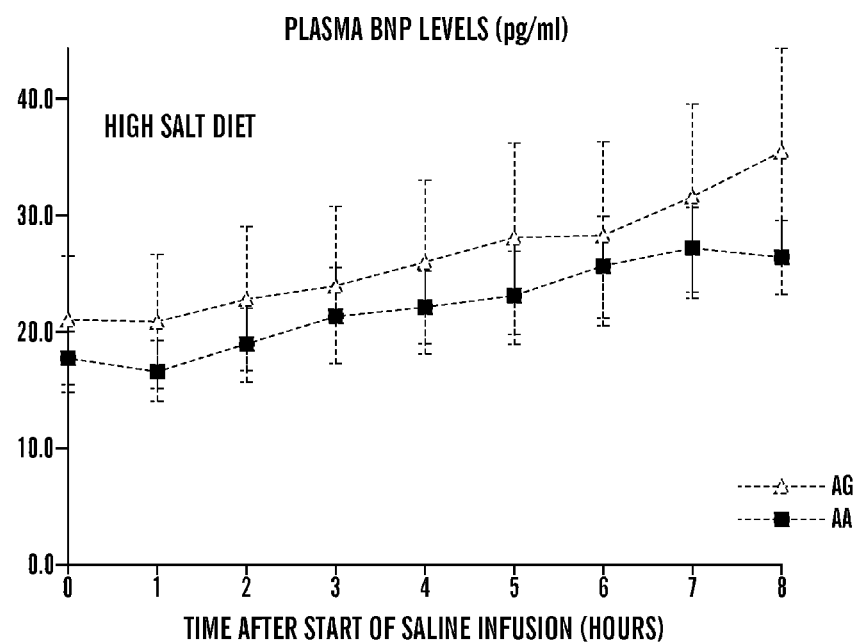

After one week on a low-sodium diet, saline administration increased plasma cGMP levels in both AG and AA individuals (FIG. 6A). After one week on a high-sodium diet, saline administration increased plasma cGMP levels by 37% in AG individuals and 16% in AA individuals (P=0.03 for genotype effect and P<0.001 for saline infusion; FIG. 6B). The associations of genotype and cGMP levels were consistent with those observed for circulating ANP levels.

In contrast to Nt-proANP, Nt-proBNP levels were not associated with rs5068 genotype and on either the low- or high-salt diet, at baseline, or after saline infusion (all p>0.37). Furthermore, in this healthy, normotensive cohort, no significant increases were noted in systolic or diastolic blood pressure with the transition from a low-salt diet to a high-salt diet, before or after saline infusion. However, there were trends toward lower systolic blood pressures in AG compared to AA individuals after the high-salt diet (112 mmHg vs. 117 mmHg, p=0.10) and after the saline infusion on a low-salt background (109 mmHg vs. 114 mmHg; p=0.06, Table 2).

The inventors did not detect an effect of the rs5068 genotype on urine volume or sodium excretion in response to saline infusion (p>0.3).

TABLE 2

Blood pressure and 24-hour urine measurements during the study (mean ± SD).

| Diet | Variable | AA (n = 23) | AG (n = 8) | p value |
|---|---|---|---|---|
| Low Salt | Overnight SBP (day 6) | 117 ± 10 | 117 ± 11 | 0.94 |
| | Overnight DBP (day 6) | 70 ± 6 | 71 ± 6 | 0.69 |
| | Post-Infusion SBP | 114 ± 5 | 109 ± 8 | 0.06 |
| | Post-Infusion DBP | 67 ± 8 | 65 ± 6 | 0.48 |
| | Total urine Na (mmol) | 22 ± 13 | 19 ± 19 | 0.62 |
| | Total urine creatinine (mg) | 1645 ± 459 | 1782 ± 1768 | 0.72 |
| High Salt | Overnight SBP (day 6) | 117 ± 8 | 112 ± 7 | 0.10 |
| | Overnight DBP (day 6) | 71 ± 7 | 68 ± 6 | 0.39 |
| | Post-Infusion SBP | 114 ± 6 | 111 ± 6 | 0.18 |
| | Post-Infusion DBP | 66 ± 6 | 65 ± 8 | 0.71 |
| | Total urine Na (mmol) | 146 ± 53 | 133 ± 49 | 0.54 |
| | Total urine creatinine (mg) | 1546 ± 413 | 1472 ± 569 | 0.69 |

Plasma N-terminal proBNP (Nt-proBNP) and mature BNP levels were higher on a high-than on a low-sodium diet and after saline infusion, but levels did not differ by rs5068 genotype (FIGS. 7A, 7B, 8A and 8B P>0.5). Thus the inventors have demonstrated the specificity of the effect of the rs5068 variant on ANP levels.

Although cardiac tissues are primarily responsible for ANP biosynthesis, the NPPA gene is expressed at low levels in a wide variety of cell types. The inventors assessed whether NPPA mRNA levels in the blood of 2,246 Framingham Heart Study (FHS) offspring participants varied by rs5068 genotype. NPPA expression was higher in individuals with at least one copy of the G allele (n=203) than in AA (n=2,043) individuals (P=$2\times10^{-18}$). The inventors also measured NPPA mRNA levels in lymphoblasts (Coriell Institute) with AG (n=4) and AA (n=5) genotypes. NPPA mRNA levels were 2-fold higher in the cells with the AG genotype (P=0.04). Thus the inventors have demonstrated that rs5068 acts by altering NPPA gene transcription or mRNA stability, rather than by altering secretory mechanisms or the clearance of the peptide from the circulation.

Figure 2:
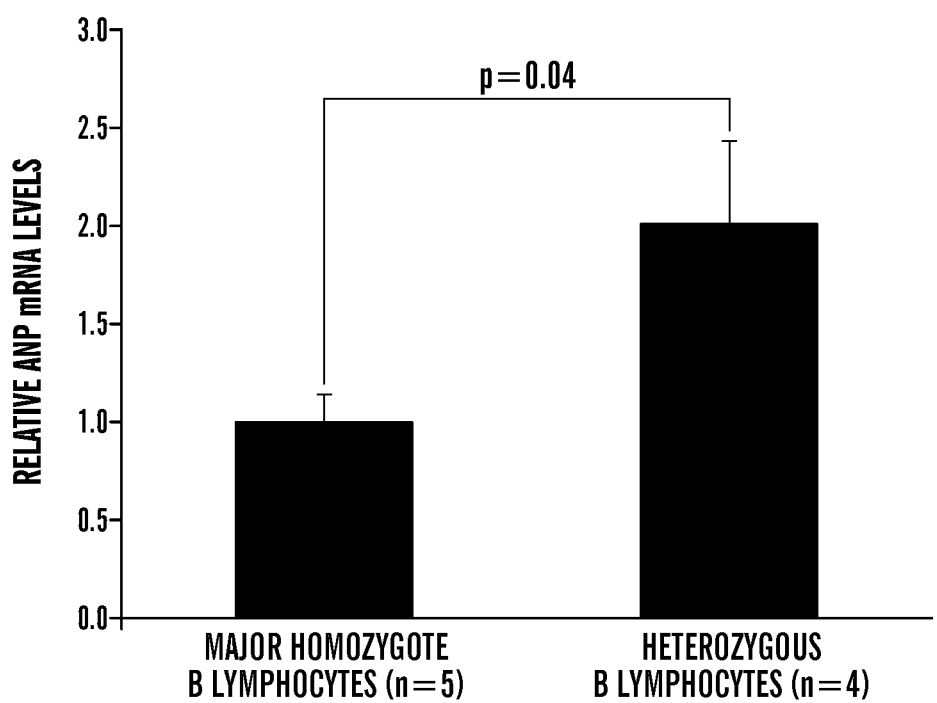
FIG. 2 shows the impact of rs5068 variant on NPPA mRNA levels in B lymphocyte cell lines. The B lymphocyte cell lines were obtained from 5 individuals homozygous for the major allele (AA) of rs5068 and 4 heterozygous individuals (AG), each of which express miR-425 which decrease the expression from the NPPA gene and/or the NPRA gene (which expresses the ANP receptor) and/or NPRB gene (which expresses the BNP receptor). Levels of NPPA mRNA and 18S ribosomal RNA in RNA extracted from lympoblasts were measured using quantitative RT-PCR and TaqMan primers. Relative NPPA mRNA levels normalized to 18S ribosomal RNA levels were determined using the relative cycle threshold method.

The inventors obtained transformed B lymphocyte cell lines with AG (n=4) and AA (n=5) genotypes. Using quantitative PCR, the inventors demonstrated that NPPA expression was significantly higher with the AG compared with the AA genotype (p=0.04; FIG. 2).

Example 2

Figure 3A:
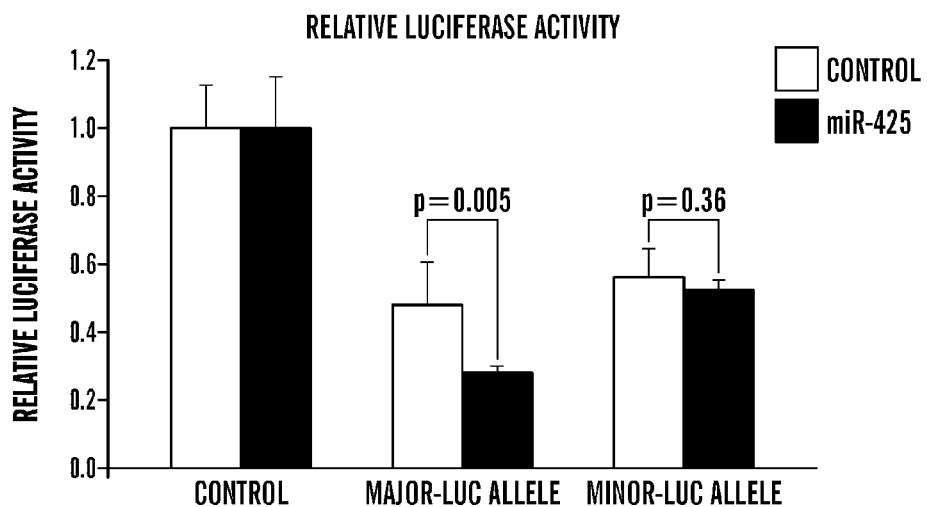
FIG. 3A-3D show allele-specific effects of miR-425, anti-miR-425, and a modified miR-425 on luciferase activity encoded by firefly luciferase-NPPA 3'UTR constructs. The ratio of firefly luciferase activity to renilla luciferase activity was normalized to that in cells transfected with a plasmid directing expression of luciferase without the NPPA 3'UTR (empty pISO vector). Data is presented as relative luciferase activity. Data are expressed as mean±SEM (n=6). Each experiment was repeated three times with similar results.
Figure 9:
FIG. 9 shows miRNAs that are predicted to target the major (A) but not minor allele (G) of the 3'UTR mRNA sequence of the NPPA gene which encompasses the rs5068 loci. The position of rs5068 is shown in red in a section of the mRNA sequence of SEQ ID NO: 7. The sequence complementary to the NPPA mRNA is shown in the figure to highlight the binding of the miRNAs to sequences around the rs5068 DNA variant. miR-196a* is shown as SEQ ID NO: 5, miR-425 is shown as SEQ ID NO: 1, miR-4770 is shown as SEQ ID NO: 4.
Figure 10:
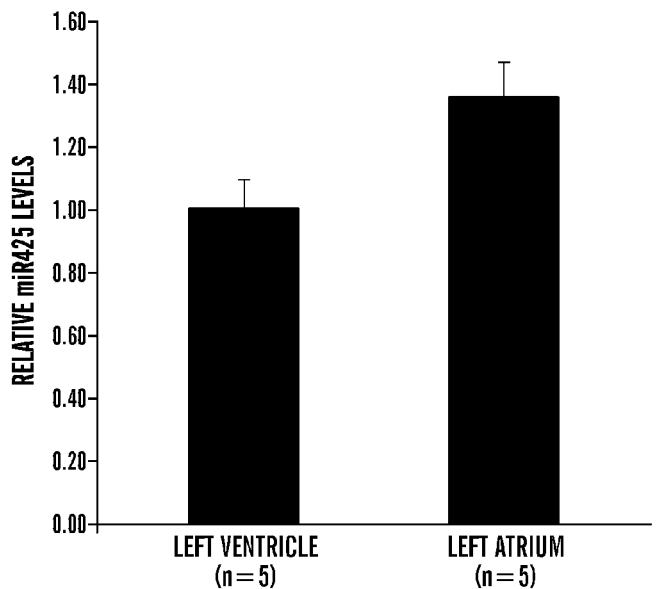
FIG. 10 shows the expression of miR-425 in the hearts of human donors. The TaqMan MicroRNA Assay for U6 RNA was used to normalize the relative abundance of microRNAs.
Figure 11:
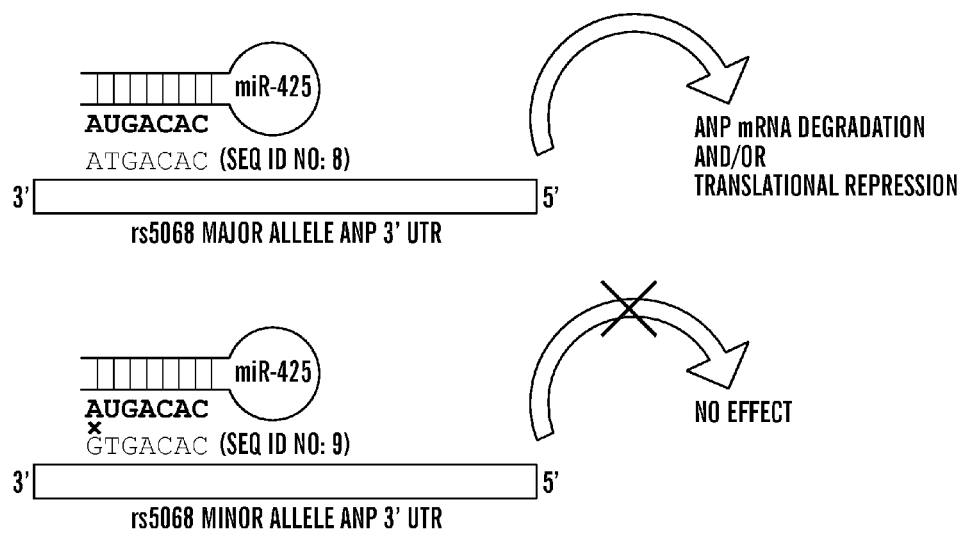
FIG. 11 is a schematic figure showing interaction of miR-425 with NPPA mRNA. The A (major) allele miRNA target sequence is shown as SEQ ID NO: 8, and the G (minor) allele miRNA target sequence is shown as SEQ ID NO: 9.

To identify an inhibitory miRNA that targets the NPPA rs5068 allele associated with lower plasma ANP levels, miRNA databases (miRanda (11), TargetScan (10) and MicroSNiPer (12)) were screened to generate a list of miRNAs predicted to interact with the NPPA 3' UTR containing the rs5068 A allele. The inventors identified 3 miRNAs that were predicted to bind at least 7 bases of the NPPA mRNA spanning the rs5068 A allele: miR-425, miR-4770, and miR-196a-3p (FIG. 9). Additionally, 8 other miRNAs that were predicted to bind to the NPPA mRNA spanning the rs5068 A allele were assessed: miR-139 UCUACAGUGCACGUGU-CUCCAGU (SEQ ID NO: 51); miR-151 UCGAGGAGCU-CACAGUCUAGU (SEQ ID NO: 52); miR-194 UGUAA-CAGCAACUCCAUGUGGA (SEQ ID NO: 53); miR-125a-3p ACAGGUGAGGUUCUUGGGAGCC (SEQ ID NO: 54); miR-143-3p UGAGAUGAAGCACUGUAGCUC (SEQ ID NO: 55); miR-155 UUAAUGCUAAUCGUGAUAGGGGU (SEQ ID NO: 56); miR-769 UGAGACCUCUGGGUU-CUGAGCU (SEQ ID NO: 57); and miR-224 CAAGUCAC-UAGUGGUUCCGUU (SEQ ID NO: 58). All were predicted to target the major but not the minor allele of rs5068. The inventors then assessed if the allele-specific different expression of ANP was mediated by one of these microRNAs. miR-425 and miR-4770, but not miR-196a-3p, were detected in cardiac tissues from heart transplant donors without cardiovascular disease (n=5). miR-425 levels were similar in left atrium and left ventricle (FIG. 10). In a separate study, miR-425 levels were detected in left atrial (n=3) and ventricular tissues (n=4) obtained from patients undergoing aortic valve replacement for aortic stenosis were similar to those in left ventricular tissues from heart transplant donors (n=3). miR-425 function was assessed in COS-7 cells transfected with luciferase reporter constructs containing the 3'UTR from NPPA major or minor alleles (major-LUC and minor-LUC, respectively). Surprisingly, transfection of miR-425 (but not the other miRNAs assessed) reduced relative luciferase activity in cells containing the major (A) allele construct (major-LUC construct) (p=0.005; FIG. 3A), but not in cells containing the minor (G) allele construct (minor-LUC construct). Transfection of miR-4770 and miR-196a* failed to alter relative luciferase activity (p=NS, data not shown). In addition, the inventors demonstrated that transfection with another 8 miRNAs (miR-139, miR-151, miR-194, miR-125a-3p, miR-143-3p, miR-155, miR-769 and miR-224) failed to alter relative luciferase activity in cell containing the major (A) allel construct. Surprisingly, in contrast to the other miRNA's assessed which are predicted to interact with the NPPA 3' UTR containing the rs5068 A allele, miR-425 was demonstrated to be specific and decreased the gene expression from the NPPA gene and thus decrease the production of ANP. Accordingly, the inventors thus focused the remaining work on miR-425. A schematic of the mechanism of miR-425 mediated reduction of ANP production is shown in FIG. 11.

Example 3

To establish that miR-425 was expressed in the human heart, the inventors obtained left atrial and left ventricular tissue from heart transplant donors without cardiovascular disease (n=5 donors). The inventors demonstrated that miR-425 expression was readily detectable in the left atrium and ventricle of human hearts in vivo (FIG. 10).

Figure 3B:
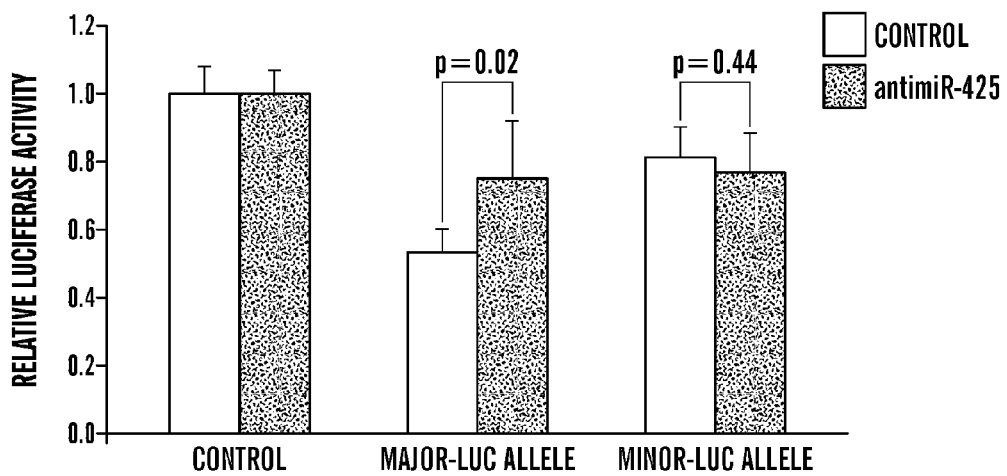
Figure 3C:
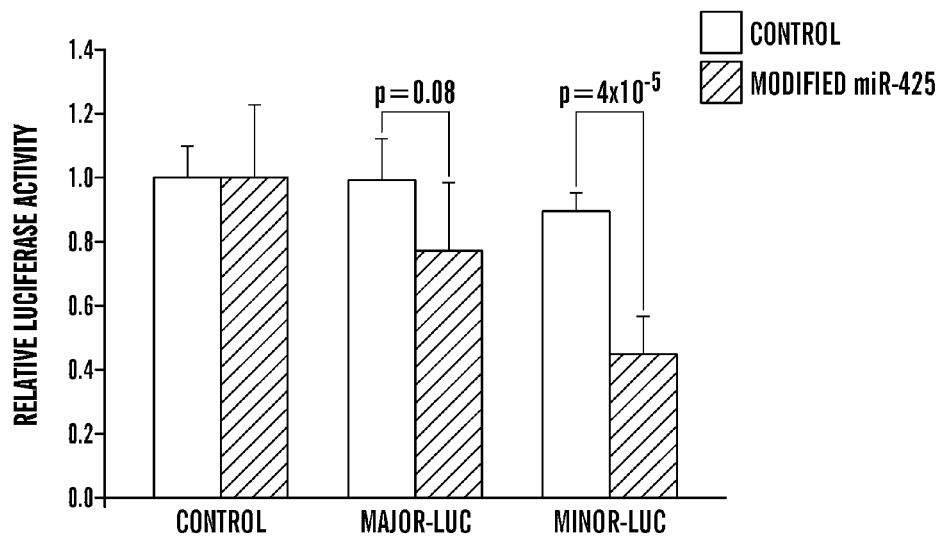

As miR-425 transfection was discovered to decrease the transcription from the NPPA gene and thus production of ANP in the presence of the A but not the G allele, the inventors next conducted transfection experiments to assess if endogenous miR-425 regulated the 3'UTR of NPPA. In particular, the inventors used an anti-miR-425 with a binding site for miR-425 (e.g., to function as an inhibitor to miR-425) to assess effect on endogenous NPPA levels. Transfection of the anti-miR-425 led to the opposite pattern induced by miR-425, i.e. increased expression of ANP by the NPPA gene in the presence of the A. but not G allele (FIG. 3B). Accordingly, the inventors demonstrated that transfection of the anti-miR-425 increased relative luciferase activity in cells containing the major (A) allele construct, but not in cells containing the minor (G) allele construct (FIG. 3B).

Figure 3D:
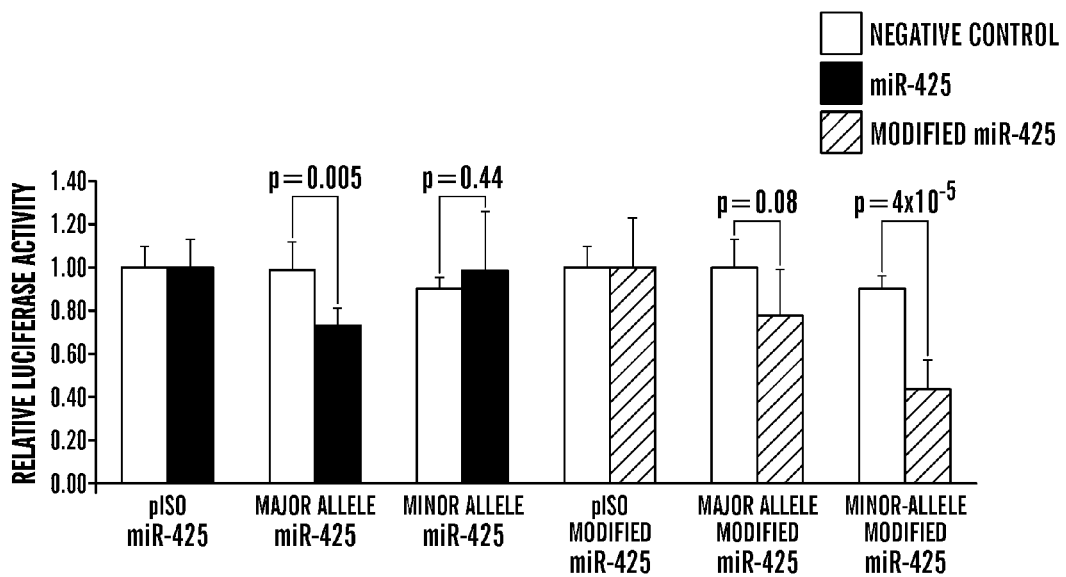

To confirm that the single base pair change at rs5068 was sufficient to account for its effect on NPPA expression, the inventors constructed a modified miR-425 in which a single base in the seed sequence was changed to match the minor G allele of rs5068, as opposed to the major A allele which matches the naturally-occurring miR-425. In contrast to miR- 425, the modified miR-425 selectively suppressed expression of the minor G allele (minor-LUC construct) (p=4×10⁻⁵) but not the major A allele (major-LUC construct) (FIG. 3D).

Example 4

Figure 4:
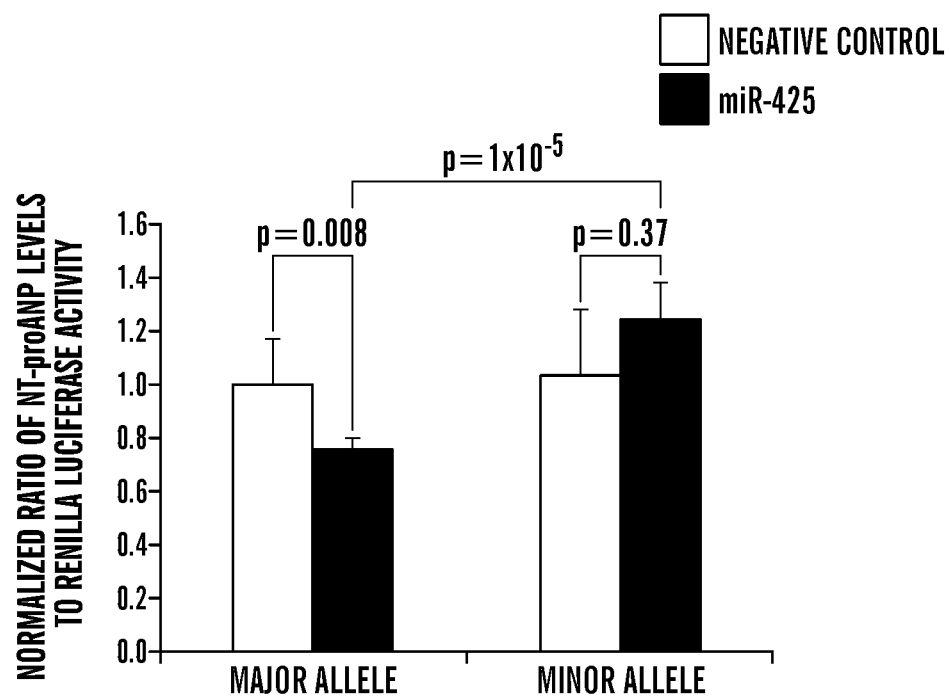
FIG. 4 shows miR-425 suppresses Nt-proANP production in cells with the AA major allele. Expression plasmids directing expression of the human NPPA cDNA (major and minor alleles) were transfected into COS-7 cells together with a plasmid directing expression of renilla luciferase (as a control for transfection efficiency). Media was collected for measurement of NT-proANP, and cells were collected for measurement of renilla luciferase.

The inventors next examined whether NPPA allele-specific effects of miR-425 leads to altered production of ANP peptide. Transfection of miR-425 into COS7 cells co-transfected with an NPPA cDNA expression plasmid containing the rs5068 major A allele reduced the release of Nt-proANP into the media (p=0.008, FIG. 4). In contrast, transfection of miR-425 did not alter Nt-proANP release from cells co-transfected with the NPPA expression plasmid containing the rs5068 minor G allele (p=0.40; p for genotype effect=1×10⁻⁵).

To further determine whether miR-425 could regulate endogenous NPPA gene expression in cardiac cells, the inventors transfected the miR-425 into human cardiomyocytes derived from induced pluripotent stem (iPS) cells. Compared with a negative control miRNA, transfection of miR-425 into cardiomyocytes reduced NPPA mRNA levels by 66% (P=0.0005, FIG. 5A) and secretion of Nt-proANP by 56% (P=0.00001, FIG. 5B). The inventors have previously demonstrated that transfection of cardiomyocytes with anti-miR-425 increased NPPA mRNA levels (data not shown).

Taken together, the inventors have demonstrated herein that rs5068 is the causal variant underlying the previously-reported blood pressure association, clarify the molecular mechanism by which rs5068 acts on ANP levels, and identify miR-425 as a novel regulator of the natriuretic peptide system.

Although NPPA gene expression is expressed at high levels in the heart, low levels of NPPA mRNA have been detected in a variety of cell types, including HepG2 hepatoma cells. The inventors assessed if miR-425 could modulate endogenous NPPA gene expression in vitro. The inventors demonstrated that transfection of miR-425 into HepG2 cells (rs5068 A/A) reduced NPPA mRNA levels as compared to a negative control miRNA. In particular, the inventors demonstrated a 40-50% reduction of NPPA mRNA levels in HepG2 cells having the major A rs5068 allele (major-LUC) when transfected with miR-425 as compared to negative control miRNA (p=0.01, FIG. 3B).

Example 5

Figure 12:
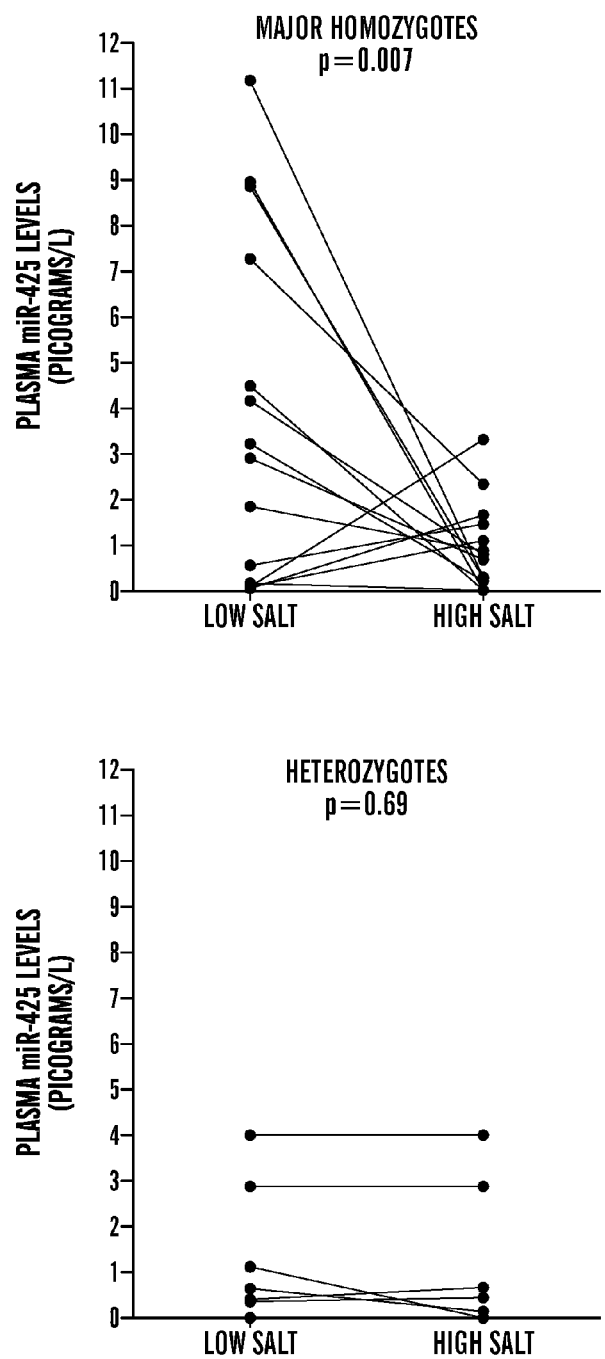
FIG. 12 shows the impact of dietary sodium and genotype on plasma miR-425 levels. RT-PCR assay for miR-425 was used to detect plasma levels of miR-425 in subjects after a week of low salt and high salt diet.
Figure 13:
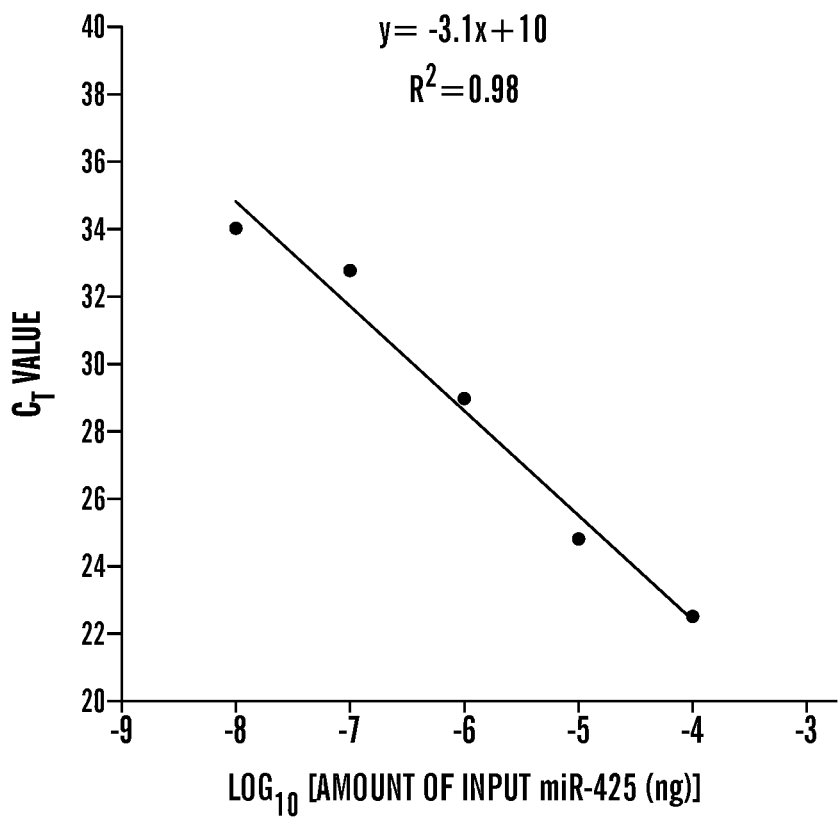
FIG. 13 shows construction of miR-425 standard curve. A series of 10-fold dilutions (from $1\times10^{-4}$ to $1\times10^{-8}$ ng) of a miR-425 mimic were reverse-transcribed and amplified by real-time PCR. A blank (no template control) was also included in the assay. The $C_T$ values obtained were converted to the linear form by the equation $2^{-CT}$. The linearized $C_T$ value of the blank was subtracted from each of the linearized $C_T$ values of the standards, and the $\log_{10}$ of the resulting values [$\log_{10}(2^{-CT})$] were plotted against the $\log_{10}$ of the amount of input miR-425.

MicroRNAs have been detected in plasma of subjects and have been proposed to exert effects at a distance. The inventors herein detected miR-425 in plasma in the study population using RT-PCR. In 31 subjects homozygous for the major allele (AA), plasma miR-425 levels were 0.8 pg/L after a week of high-salt diet and 2.8 pg/L after a week of low-salt diet (p=0.007) (FIG. 12). Plasma miR-425 levels were essentially not effected with a variation of high, and low-salt diet with subjects which are heterozygous for the major allele (e.g., AG) (p=0.69) (FIG. 12).

Figure 14:
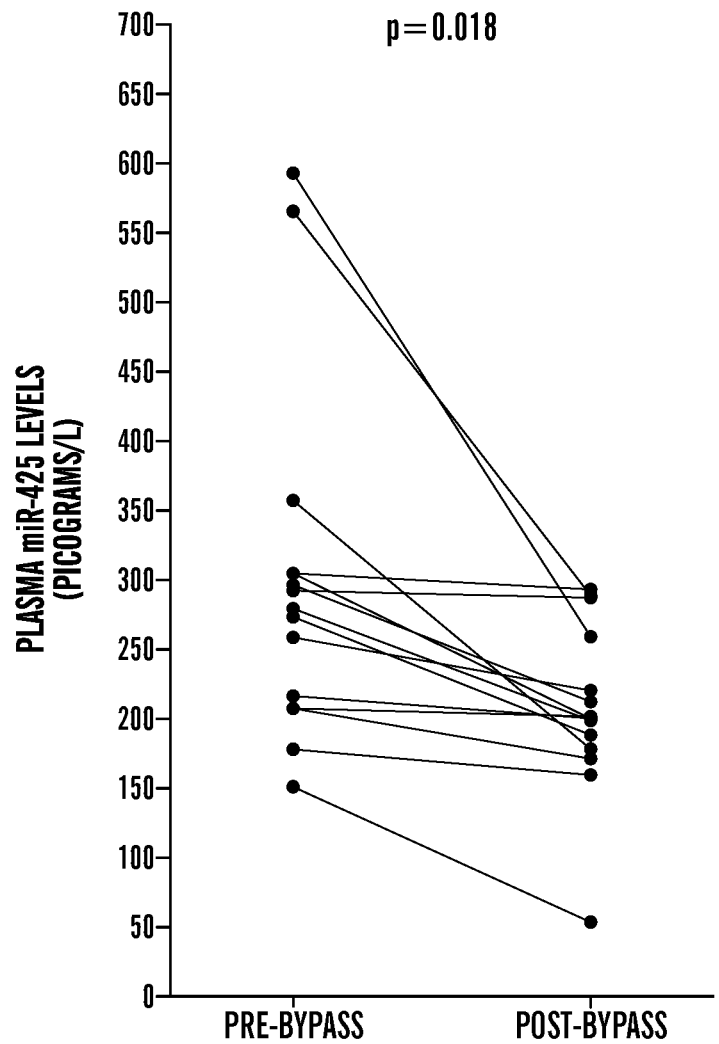
FIG. 14 shows the plasma miR-425 levels before, and 6 months after, gastric bypass surgery. miR-425 levels were detected by RT-PCR which shows lower mean circulating miR-425 plasma levels in subjects post-bypass as compared to pre-bypass (290 pg/L pre-bypass vs. 209 pg/L post-bypass, p=0.018).
Figure 15A:
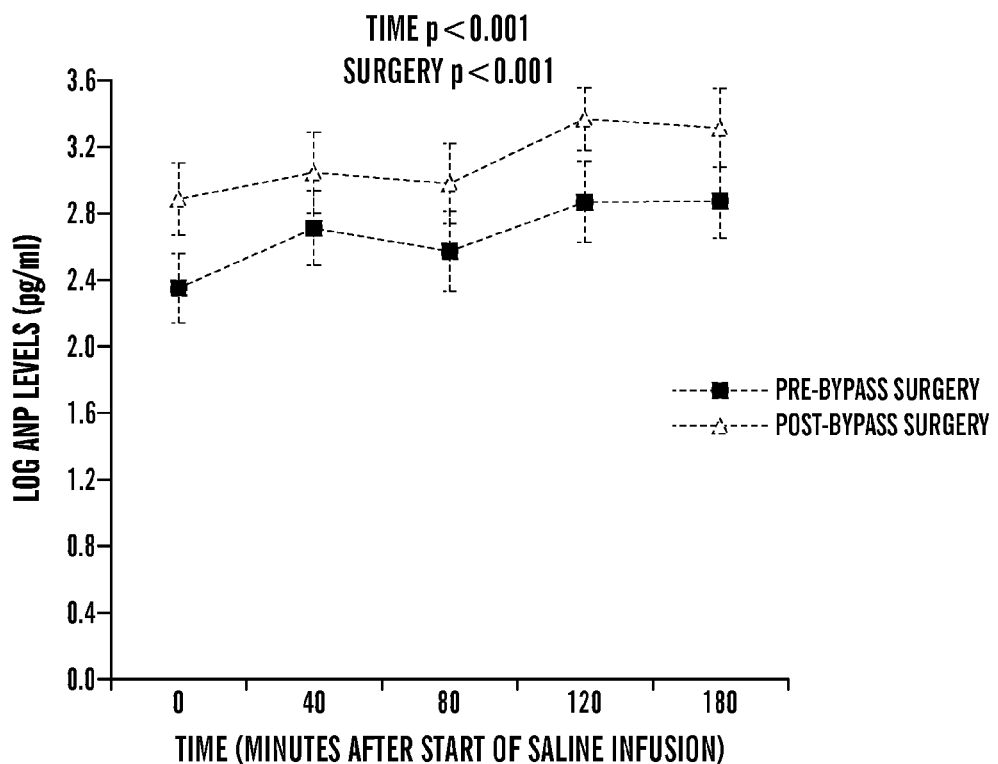
FIG. 15A-15B shows the levels of ANP and Nt-proANP after saline infusion in subject's pre- and post-gastric bypass.
Figure 15B:
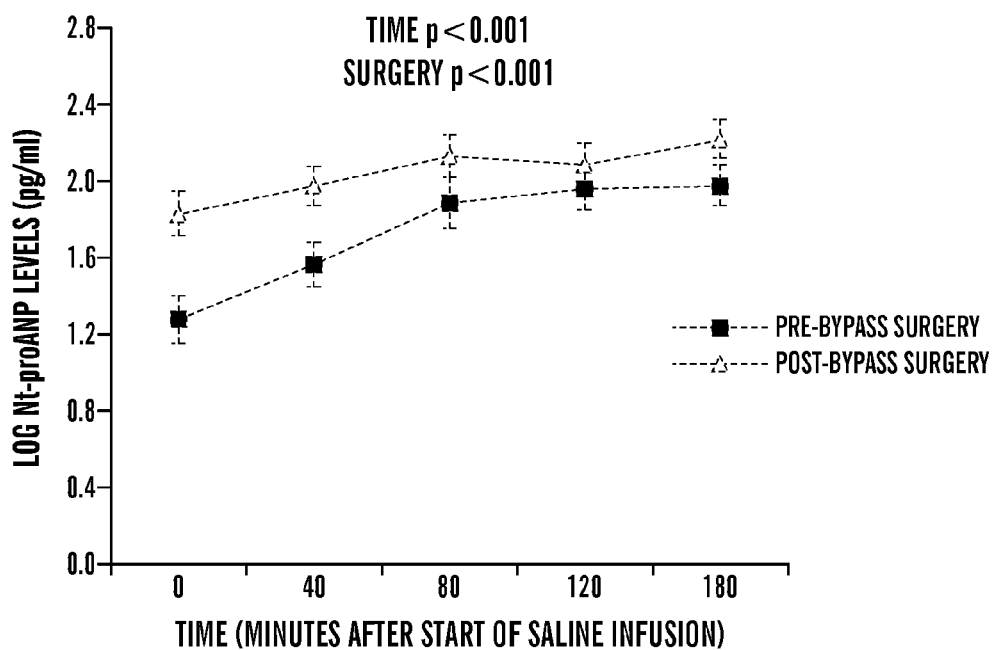

The inventors assessed whether miR-425 was reproducibly detectable in plasma before, and 6 months after, gastric bypass surgery using qRT-PCR. As demonstrated in FIG. 14, a 38% reduction in mean circulating miR-425 plasma levels was detected between pre- and post-bypass, with the levels for post-bypass being lower than the levels for pre-bypass (290 pg/L pre-bypass vs. 209 pg/L post-bypass, p=0.015). The inventors also detected a concurrent increase in plasma Nt-proANP levels (FIG. 15B) observed for post-bypass. Accordingly, the inventors have discovered that "circulating miR-425" in the plasma can be used as an important diagnostic tool as a risk determinator to stratify patients in different cardiovascular diseases with elevated natriuretic peptide concentrations, e.g., cardiovascular disease such as but not limited to, heart failure, myocardial infarction and stable coronary artery disease.

Example 6

Approximately 7% of individuals of European ancestry have a single base pair difference (e.g., G allele) in the 3' UTR of the NPPA gene associated with a lower risk of hypertension. In a genotype-directed physiologic study, the inventors demonstrate herein that individuals with at least one copy of the G allele (minor allele) in the 3' UTR have circulating Nt-proANP concentrations up to 50% higher than that of individuals with the more common A allele form. This genotype-related change in natriuretic peptide (ANP) levels is comparable to that induced by a 20-fold difference in dietary sodium intake. In addition, the inventors demonstrate that miR-425 modulates (e.g., decreases) ANP expression in human cell lines, and that the minor G allele of rs5068 is resistant to the negative regulatory effect of miR-425 on NPPA expression. Taken together, the inventors have demonstrated that that rs5068 is a causal genetic variant for blood pressure, and also demonstrate the molecular mechanism of ANP expression is regulated by miRNA, and identify miR-425 as a novel regulator of the natriuretic peptide system (e.g., subjects with two copies of the major A allele express miR-425 and consequently have decreased ANP levels), and that miR-425 is both expressed in the heart and is present in the peripheral circulation of subjects with two copies of the major A allele of rs5068.

Although numerous common polymorphisms in specific gene regions have been associated with blood pressure[17], little is known about the physiological or molecular mechanisms underlying these associations. The presence of multiple correlated variants at many loci and the lack of a recognizable biologic intermediate for the genes in many of these loci are challenges to identifying causal variants and functional mechanisms. Herein the inventors have discovered that the rs5068 variant in the 3' UTR of NPPA plays an important role of the natriuretic peptide system in salt homeostasis. Large, observational epidemiologic cohort studies have confirmed differences in natriuretic peptide (ANP) concentrations between rs5068 genotypes[9], but these differences were identified in the context of random salt intake and other sources of variation inherent to large community-based studies.

The inventors demonstrate herein the importance of interactions among miRNAs, polymorphisms in non-coding regions of the genome, and responses to environmental factors such as salt intake. It has been postulated that interference with miRNA binding is an important mechanism by which non-coding genetic variants identified by GWAS may exert their actions. However, to our knowledge, the present study provides the first example of this phenomenon for a validated blood pressure association. Interestingly, rs5068 had a substantial effect on the ANP "set-point," without altering the responsiveness of ANP to salt loading. This observation could have implications for future therapies based on miR-425, as it might be desirable to shift basal plasma ANP levels without changing the ability of the system to respond to stimuli.

Aside from elucidating the role of the rs5068 SNP, the inventors herein have demonstrated a novel mechanism for regulation of ANP, in particular miRNA's which negatively regulate (e.g., decrease) ANP levels. MicroRNAs are small, noncoding RNAs that inhibit the expression of protein-encoding genes in multiple tissues. Specific microRNAs have emerged as regulators of lipid metabolism and vascular function.[18] However, there are few data linking microRNAs to blood pressure regulation or salt homeostasis:[9,20] Using two reporter systems and a cell line expressing the human NPPA gene, the inventors have demonstrated herein that one microRNA, miR-425, suppresses NPPA expression and reduces the amount of secreted ANP.

Herein, the inventors demonstrate that the allele-specific nature of the miR-425/NPPA interaction contributes to a physiologic action of miR-425 in vivo. Specifically, the inventors have demonstrated that individuals with the minor rs5068 G allele, in whom miR-425 binding affinity to the 3'UTR of the NPPA gene is reduced, have increased ANP levels and lower blood pressure, and thus demonstrate that miR-425 plays an important physiologic role as a microRNA regulating the expression of the NPPA gene in salt and blood pressure homeostasis. Importantly, the inventors also demonstrated that miR-425 is expressed in the human heart, the principal site of synthesis of the natriuretic peptides. Interestingly, the inventors also demonstrated that miR-425 is present in the circulation in healthy individuals. It has been proposed that circulating microRNAs may function as hormones, allowing them to regulate target transcripts at a distance.[21]

Several extra-cardiac factors are known to alter natriuretic peptide synthesis, including age, gender, and body mass index.

Accordingly, the inventors have demonstrated the importance of interactions among microRNAs, polymorphisms in non-coding regions of the genome, and responses to environmental factors such as salt intake. It has been postulated that interference with microRNA binding is an important mechanism by which non-coding genetic variants identified by GWASs may exert their actions. The inventors herein have demonstrated that the G allele of rs5068 is a blood pressure variant, and effects microRNA regulation of ANP levels. In particular, the inventors have demonstrated that miR-425 has reduced binding ability to the 3'UTR for the NPPA gene in subject with at least one copy of the G allele of rs5068 (e.g., AG or GG), thus preventing miR-425 induced gene silencing of the NPPA transcription and downstram reduction in ANP levels. Accordingly, the inventors herein have demonstrated that miR-425 is a target for inhibition, e.g., with an anti-miR, in subjects homozygous for the major A allele (e.g., AA), thus preventing miR-425 downregulation of ANP production.

It is likely that differences in blood pressure and hypertension of subjects who are major homozygotes (AA) would be greater with those subjects with 2 copies of the minor G allele (GG homozygotes) as compared to subjects that are heterozygotes (AG) for the G allele. The inventors were unable to administer miR-425 in in vivo in experimental models, because although miR-425 is expressed in the hearts of mice and rats (data not shown), the 3' UTR of rodent ANP mRNAs does not have a recognition site for miR-425. Accordingly, one of ordinary skill in the art could use a transgenic mouse model with the rodent or human NPPA gene under the control of the human 3'UTR of the NPPA gene to demonstrate that miR-425 regulates NPPA expression in vivo.

In conclusion, the inventors have demonstrated a mechanism linking a common single base pair change in the 3'UTR of the NPPA gene to salt homeostasis and blood pressure. Herein, the inventors have demonstrated that common genetic variants can have a large influence on physiologic responses, even if their association with clinical traits is more modest, presumably due to the multifactorial determination of these traits and compensatory mechanisms. Indeed, the genetic effect of rs5068 on circulating natriuretic peptides (ANP) is comparable to the environmental change induced by switching from an extremely low-salt diet (230 mg/day) to a diet with the salt content of a typical western diet (4600 mg/day).

In summary, the inventors have discovered a mechanism underlying blood pressure regulation and salt homeostasis by way of a common single base pair change in the NPPA gene that prevents binding of miR-425 and results in higher ANP levels. The inventors demonstrated that common genetic variants can have a relatively large influence on physiologic responses, even if their association with clinical traits is more modest, presumably due to the multifactorial determination of these traits and compensatory mechanisms. Indeed, the genetic effect of rs5068 on circulating Nt-proANP levels is comparable to the environmental change induced by switching from an extremely low-salt diet (230 mg/day) to a diet with salt content typical of a western diet (4600 mg/day).

In some embodiments, knowledge of rs5068 genotype could facilitate tailored strategies for the prevention and treatment of hypertension. The discovery as disclosed herein also permits strategies using antagonists of miR-425-mediated suppression of NPPA expression (e.g., anti-miR-425) to treat disorders of salt overload, including hypertension and its complications.

Additionally, herein the inventors have demonstrated that screening a subject to identify them as homozygous for the major allele (AA) for the rs5068 genotype, or screening subjects to identify the presence of levels of miR-425 in a subject is useful in methods for tailored strategies for preventing and/or treating hypertension, high blood pressure and other cardiovascular diseases. Additionally, the inventors have demonstrated that administration of an anti-miR-425 agent in subjects comprising at least one major allele (e.g., A allele) for rs5068 (e.g., subjects who are homozygous for the major allele (e.g., AA) or heterozygous (e.g., AG) for rs5068) has therapeutic utility in methods for the treatment of hypertension, high blood pressure and other cardiovascular diseases and disorders, and prevent their complications.

REFERENCES

The cited references and publications in the specification and Examples section are incorporated herein in their entirety by reference.

1. McGuire S. Institute of Medicine. 2010. Strategies to Reduce Sodium Intake in the United States. Washington, D.C.: The National Academies Press. Adv Nutr; 1:49-50.
2. Application of lower sodium intake recommendations to adults—United States, 1999-2006. MMWR Morb Mortal Wkly Rep 2009; 58:281-3.
3. Vollmer W M, Sacks F M, Ard J, et al. Effects of diet and sodium intake on blood pressure: subgroup analysis of the DASH-sodium trial. Ann Intern Med 2001; 135:1019-28.
4. He F J, MacGregor G A. Salt reduction lowers cardiovascular risk: meta-analysis of outcome trials. Lancet; 378: 380-2.
5. Sacks F M, Svetkey L P, Vollmer W M, et al. Effects on blood pressure of reduced dietary sodium and the Dietary Approaches to Stop Hypertension (DASH) diet. DASH-Sodium Collaborative Research Group. N Engl J Med 2001; 344:3-10.
6. Bibbins-Domingo K, Chertow G M, Coxson P G, et al. Projected effect of dietary salt reductions on future cardiovascular disease. N Engl J Med 2010; 362:590-9.
7. John S W, Krege J H, Oliver P M, et al. Genetic decreases in atrial natriuretic peptide and salt-sensitive hypertension.

[erratum appears in Science 1995 Mar. 24; 267(5205): 1753]. Science 1995; 267:679-81.
8. Oliver P M, Fox J E, Kim R, et al. Hypertension, cardiac hypertrophy, and sudden death in mice lacking natriuretic peptide receptor A. Proceedings of the National Academy of Sciences 1997; 94:14730-5.
9. Newton-Cheh C, Larson M G, Vasan R S, et al. Association of common variants in NPPA and NPPB with circulating natriuretic peptides and blood pressure. Nat Genet 2009; 41:348-53.
10. Newton-Cheh C, Johnson T, Gateva V, et al. Genome-wide association study identifies eight loci associated with blood pressure. Nat Genet 2009; 41:676.
11. Lifton R P, Gharavi A G, Geller D S. Molecular mechanisms of human hypertension. Cell 2001; 104:545-56.
12. Bartel D P. MicroRNAs: genomics, biogenesis, mechanism, and function. Cell 2004; 116:281-97.
13. Pasquinelli A E. MicroRNAs and their targets: recognition, regulation and an emerging reciprocal relationship. Nat Rev Genet; 13:271-82.
14. John B, Enright A J, Aravin A, Tuschl T, Sander C, Marks D S. Human MicroRNA targets. PLoS Biol 2004; 2:e363.
15. Lewis B P, Burge C B, Bartel D P. Conserved seed pairing, often flanked by adenines, indicates that thousands of human genes are microRNA targets. Cell 2005; 120:15-20.
16. Barenboim M, Zoltick B J, Guo Y, Weinberger D R. MicroSNiPer: a web tool for prediction of SNP effects on putative microRNA targets. Hum Mutat 2010; 31:1223-32.
17. Ehret G B, Munroe P B, Rice K M, et al. Genetic variants in novel pathways influence blood pressure and cardiovascular disease risk. Nature; 478:103-9.
18. Rayner K J, Suarez Y, Davalos A, et al. MiR-33 contributes to the regulation of cholesterol homeostasis. Science 2010; 328:1570-3.
19. Liang M, Liu Y, Mladinov D, et al. MicroRNA: a new frontier in kidney and blood pressure research. Am J Physiol Renal Physiol 2009; 297:F553-8.
20. Yang Z, Kaye D M. Mechanistic insights into the link between a polymorphism of the 3'UTR of the SLC7A1 gene and hypertension. Hum Mutat 2009; 30:328-33.
21. Creemers E E, Tijsen A J, Pinto Y M. Circulating microRNAs: novel biomarkers and extracellular communicators in cardiovascular disease? Circ Res 2012; 110:483-95.
Weinberger, M. H., Salt sensitivity of blood pressure in humans. Hypertension, 1996, 27; 481-490.
Go, A. S., Mozaffarian, D., Roger, V. L., Benjamin, E. J., Berry, J. D., Borden, W. B., Bravata, D. M., Dai, S., Ford, E. S., Fox, C. S., et al. 2013. Executive summary: heart disease and stroke statistics—2013 update: a report from the American Heart Association. *Circulation* 127:143-152.
Roger, V. L., Go, A. S., Lloyd-Jones, D. M., Benjamin, E. J., Berry, J. D., Borden, W. B., Bravata, D. M., Dai, S., Ford, E. S., Fox, C. S., et al. 2012. Heart disease and stroke statistics—2012 update: a report from the American Heart Association. *Circulation* 125:e2-e220.
Heidenreich, P. A., Trogdon, J. G., Khavjou, O. A., Butler, J., Dracup, K., Ezekowitz, M. D., Finkelstein, E. A., Hong, Y., Johnston, S. C., Khera, A., et al. 2011. Forecasting the future of cardiovascular disease in the United States: a policy statement from the American Heart Association. *Circulation* 123:933-944.

What is claimed is:

1. A method for treating a subject with hypertension, the method comprising administering to the subject an effective amount of nucleic acid inhibitor of miRNA-425 activity, wherein the subject is determined to be homozygous (AA) or heterozygous (AG) for A allele for the single nucleotide polymorphism (SNP) rs5068 (A/G).

2. The method of claim 1, wherein the nucleic acid inhibitor comprises a nucleotide sequence that is at least 75% complementary to the nucleic acid sequence GAAAGCGCUUUGGAAUGACAC-GAUCACUCCCGUUGAGUGGGCAC-CCGAGAAGCCAUCGGGAA UGUCGUGUCCGC-CCAGUGCUCUUUC (SEQ ID No: 13).

3. The method of claim 1, wherein the nucleic acid inhibitor comprises a nucleotide sequence that is at least 75% complementary to the nucleic acid sequence AAUGACAC-GAUCACUCCCGUUGA (SEQ ID NO: 1).

4. The method of claim 1, wherein the nucleic acid inhibitor comprises a nucleotide sequence that is complementary to nucleic acid sequence AUGACA (SEQ ID NO: 2).

5. The method of claim 1, wherein the nucleic acid inhibitor comprises the nucleotide sequence TTACTGTGCTAGT-GAGGGCAACT (SEQ ID NO: 3).

6. The method of claim 1, further comprising selecting the subject for treatment for hypertension before onset of said administering, comprising assaying a biological sample from the subject for single nucleotide polymorphism of SNP rs5068 (A/G) and selecting the subject who is homozygous for A allele of SNP rs5068 (A/G).

7. The method of claim 1, further comprising co-administering a therapeutic agent, wherein the therapeutic agent is for treatment of hypertension.

8. A method of treating a subject with hypotension, the method comprising administering to the subject an effective amount of a miR-425 miRNA or RNAi molecule effective at binding to the miRNA target sequence of 5'ATGACAC-3' (SEQ ID NO: 8) or 5'GTGACAC-3' (SEQ ID NO: 9) in the 3'UTR of the NPPA gene, and wherein the subject is determined to heterozygous or homozygous for A allele for the single nucleotide polymorphism (SNP) rs5068 (A/G).

9. The method of claim 8, wherein the miR-425 miRNA comprises a nucleotide sequence that has at least 85% sequence identity to the nucleic acid sequence of: GAAAGCGCUUUGGAAUGACAC-GAUCACUCCCGUUGAGUGGGCAC-CCGAGAAGCCAUCGGGAA UGUCGUGUCCGC-CCAGUGCUCUUUC (SEQ ID No. 13).

10. The method of claim 8, wherein the miR-425 miRNA comprises a nucleotide sequence that has at least 85% sequence identity to the nucleic acid sequence of: AAUGA-CACGAUCACUCCCGUUGA (SEQ ID NO: 1).

11. The method of claim 8, wherein the miR-425 miRNA comprises the nucleic acid sequence AUGACA (SEQ ID NO:2).

12. The method of claim 8, further comprising selecting the subject for treatment for inhibiting angiogenesis or preventing or inhibiting orthostatic hypotension before onset of said administering, comprising assaying a biological sample from the subject for single nucleotide polymorphism of SNP rs5068 (A/G) and selecting the subject who is heterozygous or homozygous for A allele of SNP rs5068 (A/G).

13. The method of claim 8, further comprising co-administering a therapeutic agent, wherein the therapeutic agent is for treatment for inhibiting angiogenesis or orthostatic hypotension.

* * * * *

SEQUENCE LISTING

<160> NUMBER OF SEQ ID NOS: 58

<210> SEQ ID NO 1
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aaugacacga ucacucccgu uga                                              23

<210> SEQ ID NO 2
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2 augaca                                                                  6

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttactgtgct agtgagggca act                                              23

-continued

```
<210> SEQ ID NO 4
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ugagaugaca cuguagcu                                                       18

<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cggcaacaag aaacugccug ag                                                  22

<210> SEQ ID NO 6
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
agugacacga ucacucccgu uga                                                 23

<210> SEQ ID NO 7
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
aucacaacuc cauggcaaca agaugacaca aaugcagcag agacc                         45

<210> SEQ ID NO 8
<211> LENGTH: 7
<212> TYPE: DNA
<213> ORGANISM: Homo sapiens

<400> SEQUENCE: 8 atgacac                                                                    7

<210> SEQ ID NO 9
<211> LENGTH: 7
<212> TYPE: DNA
<213> ORGANISM: Homo sapiens

<400> SEQUENCE: 9 gtgacac                                                                    7

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 10
gcggagctca gataacagcc agggaggaca ag                          32

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gctctagatt gtcttctgtc catggtgctg aag                         33

<210> SEQ ID NO 12
<211> LENGTH: 858
<212> TYPE: DNA
<213> ORGANISM: Homo sapiens

<400> SEQUENCE: 12
gagacaggga cagacgtagg ccaagagagg ggaaccagag aggaaccaga ggggagagac    60
agagcagcaa gcagtggatt gctccttgac gacgccagca tgagctcctt ctccaccacc   120
accgtgagct tcctcctttt actggcattc cagctcctag gtcagaccag agctaatccc   180
atgtacaatg ccgtgtccaa cgcagacctg atggatttca agaatttgct ggaccatttg   240
gaagaaaaga tgcctttaga agatgaggtc gtgccccac aagtgctcag tgagccgaat    300
gaagaagcgg gggctgctct cagcccctc cctgaggtgc ctccctggac cggggaagtc    360
agcccagccc agagagatgg aggtgccctc gggcggggcc cctgggactc ctctgatcga   420
tctgccctcc taaaaagcaa gctgagggcg ctgctcactg cccctcggag cctgcggaga   480
tccagctgct tcgggggcag gatggacagg attggagccc agagcggact gggctgtaac   540
agcttccggt actgaagata acagccaggg aggacaagca gggctgggcc tagggacaga   600
ctgcaagagg ctcctgtccc ctggggtctc tgctgcattt gtgtcatctt gttgccatgg   660
agttgtgatc atcccatcta agctgcagct tcctgtcaac acttctcaca tcttatgcta   720
actgtagata aagtggtttg atggtgactt cctcgcctct cccaccccat gcattaaatt   780
ttaaggtaga acctcacctg ttactgaaag tggtttgaaa gtgaataaac ttcagcacca   840
tggacagaag acaaaaaa                                                858

<210> SEQ ID NO 13
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gaaagcgcuu uggaaugaca cgaucacucc cguugagugg gcacccgaga agccaucggg    60
aaugucgugu ccgcccagug cucuuuc                                       87

<210> SEQ ID NO 14
<211> LENGTH: 29
<212> TYPE: PRT
<213> ORGANISM: Unknown
<220> FEATURE:
<223> OTHER INFORMATION: Description of Unknown: GALA
      peptide
```

```
<400> SEQUENCE: 14

Ala Ala Leu Glu Ala Leu Ala Glu Ala Leu Ala Glu Ala Leu Ala Glu Ala
1               5                   10                  15

Leu Glu Ala Leu Ala Glu Ala Ala Ala Gly Gly Cys
            20                  25

<210> SEQ ID NO 15
<211> LENGTH: 30
<212> TYPE: PRT
<213> ORGANISM: Unknown
<220> FEATURE:
<223> OTHER INFORMATION: Description of Unknown: EALA
      polypeptide

<400> SEQUENCE: 15

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Gly Gly Cys
            20                  25                  30

<210> SEQ ID NO 16
<211> LENGTH: 15
<212> TYPE: PRT
<213> ORGANISM: Unknown
<220> FEATURE:
<223> OTHER INFORMATION: Description of Unknown: Exemplary
      endosomolytic/fusogenic peptide

<400> SEQUENCE: 16

Ala Leu Glu Ala Leu Ala Glu Ala Leu Glu Ala Leu Ala Glu Ala
1               5                   10                  15

<210> SEQ ID NO 17
<211> LENGTH: 22
<212> TYPE: PRT
<213> ORGANISM: Unknown
<220> FEATURE:
<223> OTHER INFORMATION: Description of Unknown: INF-7
      peptide

<400> SEQUENCE: 17

Gly Leu Phe Glu Ala Ile Glu Gly Phe Ile Glu Asn Gly Trp Glu Gly
1               5                   10                  15

Met Ile Trp Asp Tyr Gly
            20

<210> SEQ ID NO 18
<211> LENGTH: 23
<212> TYPE: PRT
<213> ORGANISM: Unknown
<220> FEATURE:
<223> OTHER INFORMATION: Description of Unknown: Inf HA-2
      peptide

<400> SEQUENCE: 18

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 19
<211> LENGTH: 48
<212> TYPE: PRT
<213> ORGANISM: Unknown
```

```
<220> FEATURE:
<223> OTHER INFORMATION: Description of Unknown: diINF-7
      polypeptide

<400> SEQUENCE: 19

Gly Leu Phe Glu Ala Ile Glu Gly Phe Ile Glu Asn Gly Trp Glu Gly
1               5                   10                  15

Met Ile Asp Gly Trp Tyr Gly Cys Gly Leu Phe Glu Ala Ile Glu Gly
                20                  25                  30

Phe Ile Glu Asn Gly Trp Glu Gly Met Ile Asp Gly Trp Tyr Gly Cys
            35                  40                  45

<210> SEQ ID NO 20
<211> LENGTH: 44
<212> TYPE: PRT
<213> ORGANISM: Unknown
<220> FEATURE:
<223> OTHER INFORMATION: Description of Unknown: diINF-3
      polypeptide

<400> SEQUENCE: 20

Gly Leu Phe Glu Ala Ile Glu Gly Phe Ile Glu Asn Gly Trp Glu Gly
1               5                   10                  15

Met Ile Asp Gly Gly Cys Gly Leu Phe Glu Ala Ile Glu Gly Phe Ile
                20                  25                  30

Glu Asn Gly Trp Glu Gly Met Ile Asp Gly Gly Cys
            35                  40

<210> SEQ ID NO 21
<211> LENGTH: 35
<212> TYPE: PRT
<213> ORGANISM: Unknown
<220> FEATURE:
<223> OTHER INFORMATION: Description of Unknown: GLF
      polypeptide

<400> SEQUENCE: 21

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
                20                  25                  30

Gly Ser Cys
        35

<210> SEQ ID NO 22
<211> LENGTH: 34
<212> TYPE: PRT
<213> ORGANISM: Unknown
<220> FEATURE:
<223> OTHER INFORMATION: Description of Unknown: GALA-INF3
      polypeptide

<400> SEQUENCE: 22

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
                20                  25                  30

Ser Cys

<210> SEQ ID NO 23
<211> LENGTH: 41
<212> TYPE: PRT
<213> ORGANISM: Unknown
```

```
<220> FEATURE:
<223> OTHER INFORMATION: Description of Unknown: INF-5
      polypeptide
<220> FEATURE:
<221> NAME/KEY: MOD_RES
<222> LOCATION: (17)..(17)
<223> OTHER INFORMATION: Norleucine
<220> FEATURE:
<221> NAME/KEY: MOD_RES
<222> LOCATION: (38)..(38)
<223> OTHER INFORMATION: Norleucine

<400> SEQUENCE: 23

Gly Leu Phe Glu Ala Ile Glu Gly Phe Ile Glu Asn Gly Trp Glu Gly
1               5                   10                  15

Leu Ile Asp Gly Lys Gly Leu Phe Glu Ala Ile Glu Gly Phe Ile Glu
            20                  25                  30

Asn Gly Trp Glu Gly Leu Ile Asp Gly
        35                  40

<210> SEQ ID NO 24
<211> LENGTH: 19
<212> TYPE: PRT
<213> ORGANISM: Unknown
<220> FEATURE:
<223> OTHER INFORMATION: Description of Unknown: JTS-1
      peptide

<400> SEQUENCE: 24

Leu Phe Glu Ala Leu Leu Glu Leu Leu Glu Ser Leu Trp Glu Leu Leu
1               5                   10                  15

Leu Glu Ala

<210> SEQ ID NO 25
<211> LENGTH: 20
<212> TYPE: PRT
<213> ORGANISM: Unknown
<220> FEATURE:
<223> OTHER INFORMATION: Description of Unknown: ppTG1
      peptide

<400> SEQUENCE: 25

Gly Leu Phe Lys Ala Leu Leu Lys Leu Leu Lys Ser Leu Trp Lys Leu
1               5                   10                  15

Leu Leu Lys Ala
            20

<210> SEQ ID NO 26
<211> LENGTH: 20
<212> TYPE: PRT
<213> ORGANISM: Unknown
<220> FEATURE:
<223> OTHER INFORMATION: Description of Unknown: ppTG20
      peptide

<400> SEQUENCE: 26

Gly Leu Phe Arg Ala Leu Leu Arg Leu Leu Arg Ser Leu Trp Arg Leu
1               5                   10                  15

Leu Leu Arg Ala
            20

<210> SEQ ID NO 27
<211> LENGTH: 30
<212> TYPE: PRT
<213> ORGANISM: Unknown
```

```
<220> FEATURE:
<223> OTHER INFORMATION: Description of Unknown: KALA
      polypeptide

<400> SEQUENCE: 27

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 28
<211> LENGTH: 22
<212> TYPE: PRT
<213> ORGANISM: Unknown
<220> FEATURE:
<223> OTHER INFORMATION: Description of Unknown: HA
      peptide

<400> SEQUENCE: 28

Gly Leu Phe Phe Glu Ala Ile Ala Glu Phe Ile Glu Gly Gly Trp Glu
1               5                   10                  15

Gly Leu Ile Glu Gly Cys
            20

<210> SEQ ID NO 29
<211> LENGTH: 26
<212> TYPE: PRT
<213> ORGANISM: Unknown
<220> FEATURE:
<223> OTHER INFORMATION: Description of Unknown: Melittin
      peptide

<400> SEQUENCE: 29

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 30
<211> LENGTH: 8
<212> TYPE: PRT
<213> ORGANISM: Unknown
<220> FEATURE:
<223> OTHER INFORMATION: Description of Unknown: Exemplary
      endosomolytic/fusogenic peptide

<400> SEQUENCE: 30

His His His His His Trp Tyr Gly
1               5

<210> SEQ ID NO 31
<211> LENGTH: 10
<212> TYPE: PRT
<213> ORGANISM: Unknown
<220> FEATURE:
<223> OTHER INFORMATION: Description of Unknown: Exemplary
      endosomolytic/fusogenic peptide

<400> SEQUENCE: 31

Cys His Lys Lys Lys Lys Lys Lys His Cys
1               5                   10

<210> SEQ ID NO 32
<211> LENGTH: 16
<212> TYPE: PRT
<213> ORGANISM: Unknown
```

```
<220> FEATURE:
<223> OTHER INFORMATION: Description of Unknown: Penetratin
      peptide

<400> SEQUENCE: 32

Arg Gln Ile Lys Ile Trp Phe Gln Asn Arg Arg Met Lys Trp Lys Lys
1               5                   10                  15

<210> SEQ ID NO 33
<211> LENGTH: 14
<212> TYPE: PRT
<213> ORGANISM: Human immunodeficiency virus

<400> SEQUENCE: 33

Gly Arg Lys Lys Arg Arg Gln Arg Arg Arg Pro Pro Gln Cys
1               5                   10

<210> SEQ ID NO 34
<211> LENGTH: 27
<212> TYPE: PRT
<213> ORGANISM: Unknown
<220> FEATURE:
<223> OTHER INFORMATION: Description of Unknown: Signal
      peptide

<400> SEQUENCE: 34

Gly Ala Leu Phe Leu Gly Trp Leu Gly Ala Ala Gly Ser Thr Met Gly
1               5                   10                  15

Ala Trp Ser Gln Pro Lys Lys Arg Lys Val
            20                  25

<210> SEQ ID NO 35
<211> LENGTH: 18
<212> TYPE: PRT
<213> ORGANISM: Unknown
<220> FEATURE:
<223> OTHER INFORMATION: Description of Unknown: PVEC
      peptide

<400> SEQUENCE: 35

Leu Leu Ile Ile Leu Arg Arg Arg Ile Arg Lys Gln Ala His Ala His
1               5                   10                  15

Ser Lys

<210> SEQ ID NO 36
<211> LENGTH: 26
<212> TYPE: PRT
<213> ORGANISM: Unknown
<220> FEATURE:
<223> OTHER INFORMATION: Description of Unknown: Transportan
      peptide

<400> SEQUENCE: 36

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 37
<211> LENGTH: 18
<212> TYPE: PRT
<213> ORGANISM: Unknown
<220> FEATURE:
<223> OTHER INFORMATION: Description of Unknown: Amphiphilic
      model peptide
```

-continued

```
<400> SEQUENCE: 37

Lys Leu Ala Leu Lys Leu Ala Leu Lys Ala Leu Lys Ala Ala Leu Lys
1               5                   10                  15

Leu Ala

<210> SEQ ID NO 38
<211> LENGTH: 9
<212> TYPE: PRT
<213> ORGANISM: Unknown
<220> FEATURE:
<223> OTHER INFORMATION: Description of Unknown: Exemplary
      cell permeation peptide

<400> SEQUENCE: 38

Arg Arg Arg Arg Arg Arg Arg Arg Arg
1               5

<210> SEQ ID NO 39
<211> LENGTH: 10
<212> TYPE: PRT
<213> ORGANISM: Unknown
<220> FEATURE:
<223> OTHER INFORMATION: Description of Unknown: Bacterial
      cell wall permeating peptide

<400> SEQUENCE: 39

Lys Phe Phe Lys Phe Phe Lys Phe Phe Lys
1               5                   10

<210> SEQ ID NO 40
<211> LENGTH: 37
<212> TYPE: PRT
<213> ORGANISM: Unknown
<220> FEATURE:
<223> OTHER INFORMATION: Description of Unknown: LL-37
      polypeptide

<400> SEQUENCE: 40

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
        35

<210> SEQ ID NO 41
<211> LENGTH: 31
<212> TYPE: PRT
<213> ORGANISM: Unknown
<220> FEATURE:
<223> OTHER INFORMATION: Description of Unknown: Cecropin
      P1 polypeptide

<400> SEQUENCE: 41

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
                20                  25                  30

<210> SEQ ID NO 42
<211> LENGTH: 30
<212> TYPE: PRT
<213> ORGANISM: Unknown
```

```
<220> FEATURE:
<223> OTHER INFORMATION: Description of Unknown: Alpha-defensin
      polypeptide

<400> SEQUENCE: 42

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 43
<211> LENGTH: 36
<212> TYPE: PRT
<213> ORGANISM: Unknown
<220> FEATURE:
<223> OTHER INFORMATION: Description of Unknown: Beta-defensin
      polypeptide

<400> SEQUENCE: 43

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
            35

<210> SEQ ID NO 44
<211> LENGTH: 42
<212> TYPE: PRT
<213> ORGANISM: Unknown
<220> FEATURE:
<223> OTHER INFORMATION: Description of Unknown: PR-39
      polypeptide

<400> SEQUENCE: 44

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
            35                  40

<210> SEQ ID NO 45
<211> LENGTH: 13
<212> TYPE: PRT
<213> ORGANISM: Unknown
<220> FEATURE:
<223> OTHER INFORMATION: Description of Unknown: Indolicidin
      peptide

<400> SEQUENCE: 45

Ile Leu Pro Trp Lys Trp Pro Trp Trp Pro Trp Arg Arg
1               5                   10

<210> SEQ ID NO 46
<211> LENGTH: 16
<212> TYPE: PRT
<213> ORGANISM: Unknown
<220> FEATURE:
<223> OTHER INFORMATION: Description of Unknown: RFGF
      peptide

<400> SEQUENCE: 46

Ala Ala Val Ala Leu Leu Pro Ala Val Leu Leu Ala Leu Leu Ala Pro
1               5                   10                  15
```

```
<210> SEQ ID NO 47
<211> LENGTH: 11
<212> TYPE: PRT
<213> ORGANISM: Unknown
<220> FEATURE:
<223> OTHER INFORMATION: Description of Unknown: RFGF
      analogue peptide

<400> SEQUENCE: 47

Ala Ala Leu Leu Pro Val Leu Leu Ala Ala Pro
1               5                   10

<210> SEQ ID NO 48
<211> LENGTH: 12
<212> TYPE: PRT
<213> ORGANISM: Unknown
<220> FEATURE:
<223> OTHER INFORMATION: Description of Unknown: Bactenecin
      peptide

<400> SEQUENCE: 48

Arg Lys Cys Arg Ile Val Val Ile Arg Val Cys Arg
1               5                   10

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gtcatcttgt tgccatagag ttgtgatcat ccc                               33

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gggatgatca caactctatg gcaacaagat gac                               33

<210> SEQ ID NO 51
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ucuacagugc acgucucc agu                                            23

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ucgaggagcu cacagucuag u                                            21
```

```
<210> SEQ ID NO 53
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uguaacagca acuccaugug ga                                              22

<210> SEQ ID NO 54
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
acaggugagg uucuugggag cc                                              22

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ugagaugaag cacuguagcu c                                               21

<210> SEQ ID NO 56
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uuaaugcuaa ucgugauagg ggu                                             23

<210> SEQ ID NO 57
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
ugagaccucu ggguucugag cu                                              22

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
caagucacua gugguuccgu u                                               21
```